(12) United States Patent
Selnick et al.

(10) Patent No.: US 6,515,011 B2
(45) Date of Patent: Feb. 4, 2003

(54) THROMBIN INHIBITORS

(75) Inventors: Harold G. Selnick, Ambler, PA (US); James C. Barrow, Harleysville, PA (US); Philippe G. Nantermet, Lansdale, PA (US); Peter D. Williams, Harleysville, PA (US); Kenneth J. Stauffer, Souderton, PA (US); Philip E. Sanderson, Philadelphia, PA (US); Kenneth E. Rittle, Green Lane, PA (US); Matthew M. Morrissette, Pottstown, PA (US); Catherine M. Wiscount, Allentown, PA (US); Lekhanh O. Tran, Norristown, PA (US); Terry A. Lyle, Lederach, PA (US); Donnette D. Staas, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/023,776

(22) Filed: Dec. 18, 2001

(65) Prior Publication Data

US 2002/0119992 A1 Aug. 29, 2002

Related U.S. Application Data

(60) Provisional application No. 60/256,304, filed on Dec. 18, 2000, and provisional application No. 60/323,184, filed on Sep. 18, 2001.

(51) Int. Cl.[7] ........................ A61K 31/40; C07D 207/08
(52) U.S. Cl. ........................ 514/423; 548/538; 548/528; 548/518; 546/111; 546/279.1; 514/422; 514/343; 514/290
(58) Field of Search ................... 514/423, 290, 514/343, 422; 548/538, 528, 518; 546/111, 279.1

(56) References Cited

U.S. PATENT DOCUMENTS 2,277,409 A   3/1942   Murray (List continued on next page.)

FOREIGN PATENT DOCUMENTS

EP   0 185 210       6/1986
EP   0 195 212 A2    9/1986

(List continued on next page.)

OTHER PUBLICATIONS

Henriksen, D. B. et al., *Int. J. Peptide Protein Res.*, "Peptide amidation by enzymatic transacylation and photolysis" Vo. 41, pp. 169–180 (1993).

(List continued on next page.)

*Primary Examiner*—Charanjit S. Aulakh
(74) *Attorney, Agent, or Firm*—Richard S. Parr; Melvin Winokur; Valerie J. Camara

(57) ABSTRACT

Compounds of the invention are useful in inhibiting thrombin and associated thrombotic occlusions having the following structure:

1)

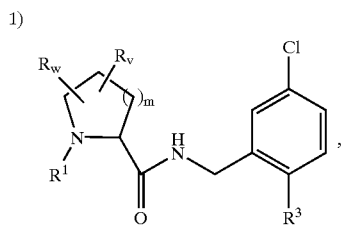

2)

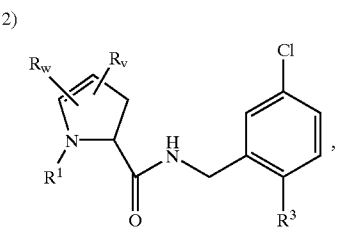

3)

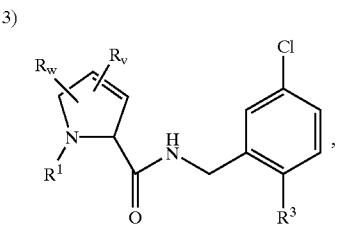

4)

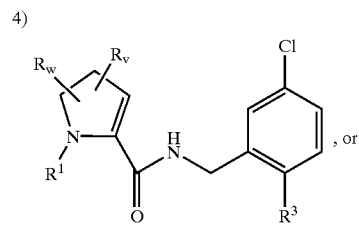

5)

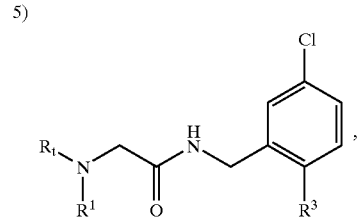

or a pharmaceutically acceptable salt thereof, e.g. where $R^3$ is $-CH_2NH_2$, $-CH_2CH_2NH_2$, or $-CH_2NHC(O)OC(CH_3)_3$.

23 Claims, No Drawings

U.S. PATENT DOCUMENTS

| | | |
|---|---|---|
| 4,346,078 A | 8/1982 | Bajusz et al. |
| 4,703,036 A | 10/1987 | Bajusz et al. |
| 4,804,743 A | 2/1989 | Kaltenbronn et al. |
| 5,252,566 A | 10/1993 | Shuman |
| 5,332,726 A | 7/1994 | Klein et al. |
| 5,380,713 A | 1/1995 | Balasubramanian et al. |
| 5,416,093 A | 5/1995 | Shuman |
| 5,510,369 A | 4/1996 | Lumma et al. |
| 5,691,356 A | 11/1997 | Das et al. |
| 5,792,779 A | 8/1998 | Sanderson et al. |
| 5,798,377 A | 8/1998 | Lumma et al. |
| 5,866,573 A | 2/1999 | Sanderson et al. |
| 5,869,487 A | 2/1999 | Coburn et al. |
| 6,004,976 A | 12/1999 | Coburn |
| 6,011,038 A | 1/2000 | Dorsey et al. |
| 6,017,934 A | 1/2000 | Sanderson et al. |
| 6,087,373 A | 7/2000 | Coburn et al. |
| 6,147,078 A | 11/2000 | Sanderson et al. |
| 6,239,132 B1 | 5/2001 | Coburn et al. |

FOREIGN PATENT DOCUMENTS

| | | |
|---|---|---|
| EP | 0 363 284 A2 | 4/1990 |
| EP | 0 471 651 A2 | 2/1992 |
| EP | 0 479 489 A2 | 4/1992 |
| EP | 0 601 459 A2 | 6/1994 |
| EP | 603112 A1 | 6/1994 |
| EP | 0 648 780 A1 | 4/1995 |
| EP | 0 672 658 A1 | 9/1995 |
| WO | WO 92/07869 | 5/1992 |
| WO | WO 92/14750 | 9/1992 |
| WO | WO 94/29336 | 12/1994 |
| WO | WO 96/31504 | 10/1996 |
| WO | WO 96/32110 | 10/1996 |
| WO | WO99/29664 | 6/1999 |
| WO | WO00/35869 | 6/2000 |
| WO | WO 00/75134 A1 | 12/2000 |
| WO | WO 01/38323 | 5/2001 |
| WO | WO 02/09711 A1 | 2/2002 |

OTHER PUBLICATIONS

Bajusz, S. et al., *J. Med. Chem.*, "Highly Active and Selective Anticoagulants: D–Phe–Pro–Arg–H, a Free Tripeptide Aldehyde Prone to Spontaneous Inactivation, and Its Stable N–Methyl Derivative, D–MePhe–Pro–Arg–H" vol. 33, pp. 1729–1735 (1990).

Berndt, M. C. et al., *Gordon(ed) Platelets in Biology and Pathology–2*, "Platelet membrane proteins: composition and receptor function", pp. 43–75 (1981).

Martin, B. M. et al., *Biochemistry*, "Platelet Stimulation by Thrombin and Other Proteases", Vo. 14, No. 6, pp. 1308–1314 (1975).

Greco, N.J. et al., *Blood*, "PPACK–Thrombin Inhibits Thrombin–Induced Platelet Aggregation and Cytoplasmic Acidification but Does Not Inhibit Platelet Shape Change", vol. 75, No. 10 (May 15), pp. 1983–1990 (1990).

Bode, W. et al, *The EMBO Journal*, "The refined 1.9 A crystal structure of human a–thrombin: interaction with D–Phe–Pro–Arg chloromethylketone and significance of the Tyr–Pro–Pro–Trp insertion segment", vol. 8, No. 11, pp. 3467–3475 (1989).

Workman, E. F. et al., *The Journal of Biological Chemistry*, "Structure–Function Relationships in the Interaction of a–Thrombin with Blood Platelets", vol. 252, No. 20, pp. 7118–7123 (1992).

Hui, K. Y. et al, *Biochemical and Biophysical Research Communications*, "Minimal Sequence Requirement of Thrombin Receptor Agonist Pepride", vol. 184, No. 2, pp. 790–796 (1992).

Scarborough, R. M. et al., *The Journal of Biological Chemistry*, "Tethered Ligand Agonist Peptides—Structural Requirements for Thrombin Receptor Activation Reveal Mechanism of Proteolytic Unmasking of Agonist Function", vol. 267, No. 19, pp. 13146–13149 (1992).

Vassallo Jr, R.R. et al., *The Journal of Biological Chemistry*, "Structure–Function Relationships in the Activation of Platelet Thrombin Receptor by Receptors–derived Peptides", Vo. 267, No. 9, pp. 6081–6085 (1992).

Iwanowicz, E.J. et al., *Organic and Medicinal Chemistry Letters*, "a–Hydroxy–and a–Ketoester Functionalized Thrombin Inhibitors", vol. 2, No. 12, pp. 1607–1612 (1992).

Okumura, T. et al, *The Journal of Biological Chemistry*, "Platelet Glycocalicin—Interaction with Thrombin and Role as Thrombin Receptor of the Platelet Surface", vol. 263, No. 10, pp. 3435–3443 (1978).

Tollefsen, D. M. et al., *The Journal of Biological Chemistry*, "The BInding of Thrombin to the Surface of Human Platelets", vol. 249, No. 8, pp. 2646–2651 (1974).

Vu et al., *Cell*, "Molecular Cloning of a functional Thrombin Receptor Reveals a Novel Proteolytic Mechanism of Receptor Activation", vol. 64, pp. 1057–1068 (1991).

Gronke, R.S. et al., *The Journal of Biological Chemistry*, "Thrombin Interaction with Platelets—Influence of a Platelet Protease Nexin", vol. 262, No. 7, pp. 3030–3036 (1987).

Phillips, *Thrombos. Diathes. haemorrh.* (*Stuttg.*), "Thrombin interaction with Human PLatelets Potentiation of Thrombin–Induced Aggregation and Release by Imactivated Thrombin", vol. 32, pp. 207–215 (1974).

Balasubramanian, N. et al., *J. Med. Chem.*, "Active Site–Directed Synthetic Thrombin Inhibitors: Synthesis, in Vitro and in Vivo Activity Profile of BMY 44621 and Analogs. An Examination of the Role of the Amino Group in the D–Phe–Pro–Arg–H Series", vol. 36, pp. 300–303 (1993).

Kettner, C. et al., *The Journal of Biological Chemistry*, "The Selective Inhibition of Thrombin by Peptides of Boroarginine", vol. 265, No. 30, pp. 18289–18297 (1990).

Shuman, R. T. et al., *Journal of Medicinal Chem.*, "Highly Selective Tripeptide Thrombin Inhibitors", vol. 36, No. 3, pp. 314–319 (1993).

Hussain, M. A. et al., *Peptides*, "Anticoagulant Activity of a Peptide Boronic Acid Thrombin Inhibitor by Various Routes of Administration in Rats", vol. 12, pp. 1153–1154 (1991).

Vencill, C. F. et al., *Chemical Abstracts*, vol. 103, Abstract No. 18900 (1986).

Edwards, P. D. et al., *J. Am. Chem. Soc.*, "Design Synthesis, and Kinetic Evaluation of a Unique Class of Elastase Inhibitors, the Peptidyl a–Ketobenzoxazoles, and the X–ray Crystal Structure of the Covalent Complex between Porcine Pancreatic Elastae and Ac–Ala–Pro–Val–2–Benzoxazole", vol. 114, pp. 1854–1863 (1992).

Banner, D. et al., *Perspect. Med. Chem.*, "Serine Proteases: 3DStructures, Mechanisms of Action and Inhibitors", Chapter 3, pp. 29–43 (1993).

Tapparelli, C. et al., *TiPS*, "Synthenic low–molecular weight thrombin inhibitors: molecular design and pharmacological profile" vol. 14, pp. 366–376 (1993).

THROMBIN INHIBITORS

CROSS-REFERENCE TO RELATED APPLICATIONS

This application claims priority to provisional applications Ser. No. 60/256,304, filed Dec. 18, 2000 and Ser. No. 60/323,184, filed Sep. 18, 2001.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc., (1992) vol. 114, pp. 1854–63, describes peptidyl a-ketobenzoxazoles which are reversible inhibitors of the serine proteases human leukocyte elastase and porcine pancreatic elastase. European Publication 363 284 describes analogs of peptidase substrates in which the nitrogen atom of the scissile amide group of the substrate peptide has been replaced by hydrogen or a substituted carbonyl moiety. Australian Publication 86245677 also describes peptidase inhibitors having an activated electrophilic ketone moiety such as fluoromethylene ketone or a-keto carboxyl derivatives. R. J. Brown et al., J. Med. Chem., Vol. 37, pages 1259–1261 (1994) describes orally active, non-peptidic inhibitors of human leukocyte elastase which contain trifluoromethylketone and pyridinone moieties. H. Mack et al., J. Enzyme Inhibition, Vol. 9, pages 73–86 (1995) describes rigid amidino-phenylalanine thrombin inhibitors which contain a pyridinone moiety as a central core structure. U.S. Pat. Nos. 5,536,708, 5,672,582, 5,510,369 and 5,741,485 describe proline-based thrombin inhibitors having cyclohexylamino end groups. The present invention includes proline-based thrombin inhibitors having phenyl ring end groups substituted with ammonioethyl or ammoniomethyl moieties, which have been found to provide therapeutically effective thrombin inhibitors having desirable potency and pharmacokinetic properties.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention are useful as thrombin inhibitors and have therapeutic value in for example, preventing coronary artery disease.

This invention includes compounds of the general formula

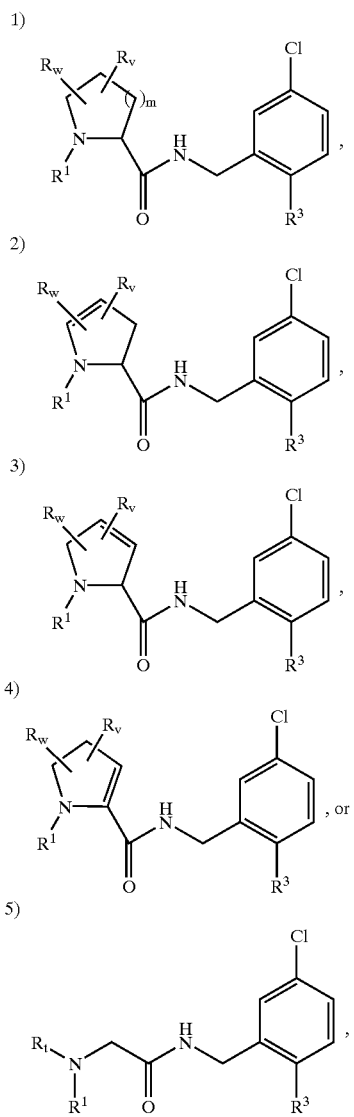

or a pharmaceutically acceptable salt thereof, wherein m is 0, 1, or 2;

$R_w$ and $R_v$ are independently selected from the group consisting of hydrogen, $C_{1-4}$ alkyl, and halogen;

$R_t$ is $C_{1-6}$ alkyl or $C_{3-7}$ cycloalkyl;
$R^1$ is selected from the group consisting of
1)

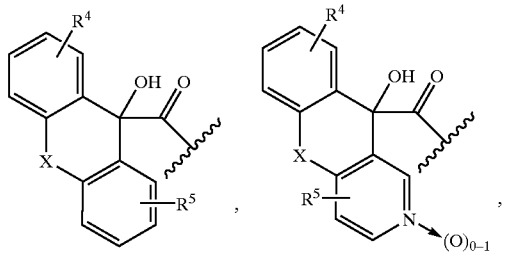

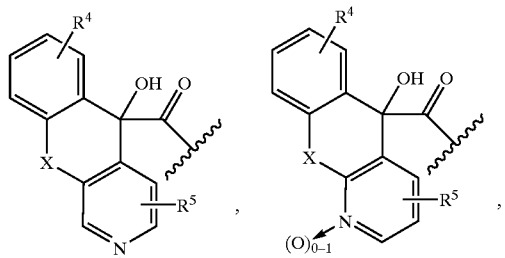

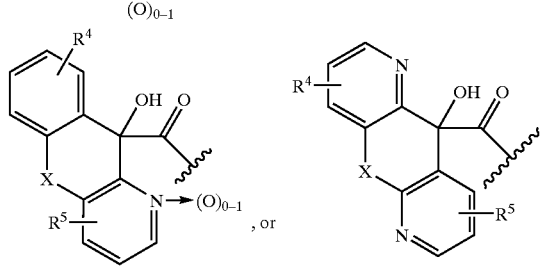

wherein
   $R^4$ and $R^5$ are independently selected from the group consisting of hydrogen, halogen, $C_{1-4}$ alkoxy, $C_{1-6}$ alkyl, —OH, and cyano, and
   X is a bond, O, or S, and 2) 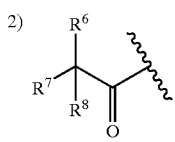

wherein
   $R^6$ is selected from the group consisting
   a) hydrogen,
   b) $C_{1-6}$ alkyl,
   c) —OH,
   d) —$NR^{24}R^{25}$, where $R^{24}$ and $R^{25}$ are independently hydrogen, or $C_{1-6}$ alkyl unsubstituted or substituted with one or more of —OH, —COOH, $C_{3-7}$ cycloalkyl, or $COOR^{17}$, where $R^{17}$ is $C_{1-6}$ alkyl,
   e) $NHC(O)OR^{18}$,
   f) $NHC(O)R^{18}$,
   g) $NHC(O)NHR^{18}$,
   h) $NHSO_2R^{18}$,
   i) $NHC(O)NH_2$, and
   j) NHCN,
      wherein $R^{18}$ is selected from the group consisting of $C_{1-6}$ alkyl, aryl, and $C_{3-7}$ cycloalkyl;
$R^7$ and $R^8$ are independently selected from the group consisting of a) hydrogen,
b) —$CF_3$,
c) $C_{1-6}$ alkyl,
d) phenyl, unsubstituted or substituted with $C_{1-6}$ alkyl, $COOR^{26}$ or halogen, where $R^{26}$ is $C_{1-6}$ alkyl or hydrogen, e) 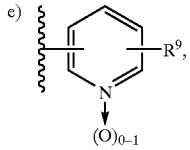

f) $C_{3-7}$ cycloalkyl, g) 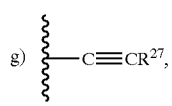

where $R^{27}$ is $C_{1-6}$ alkyl or $C_{3-7}$ cycloalkyl, h) 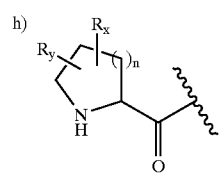

wherein $R_x$ and $R_y$ are independently selected from the group consisting of hydrogen, $C_{1-6}$ alkyl, $C_{3-7}$ cycloalkyl, unsubstituted phenyl or phenyl substituted with halogen, $C_{1-4}$ alkyl, OH, or $C_{1-4}$ alkoxy, and
wherein n is 0, 1, 2 or 3, i) $C_{1-6}$ alkyl substituted with one or two of the group consisting of
   i) $C_{3-7}$ cycloalkyl, either unsubstituted or substituted with $C_{1-4}$ alkyl,
   ii) —COOH,
   iii) —OH,

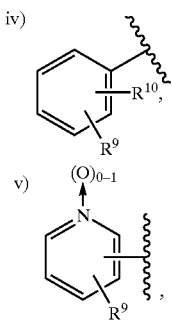

wherein $R^9$ and $R^{10}$ are independently selected from the group consisting of
   aa) hydrogen,
   bb) halogen,
   cc) $C_{1-4}$ alkoxy,
   dd) $C_{1-4}$ alkyl,
   ee) hydroxy,
   ff) $CF_3$,
   gg) cyano,
   hh) $COOR^{28}$, where $R^{28}$ is $C_{1-6}$ alkyl or hydrogen;

or $R^7$ and $R^8$ are joined to form a $C_{3-7}$ carbocyclic ring which is unsubstituted or independently substituted with one or two $C_{1-6}$ alkyl groups;

$R^3$ is selected from the group consisting of
1) $-C(R^{11})(R^{12})C(R^{13})(R^{14})N(R^{15})(R^{16})$,
2) $-C(R^{13})(R^{14})N(R^{15})(R^{16})$, and 3) 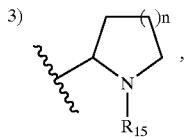

where n is 0, 1 or 2,
wherein
$R^{11}$ and $R^{12}$ are independently selected from the group consisting of
a) hydrogen,
b) F,
c) $C_{1-4}$ alkyl,
d) $CF_3$,
e) $CHF_2$,
f) $C_{3-7}$ cycloalkyl,
or $R^{11}$ and $R^{12}$ together form a 3–7 membered carbocyclic ring,
$R^{13}$ and $R^{14}$ are independently selected from the group consisting of
a) hydrogen,
b) $C_{1-4}$ alkyl
c) $-CF_3$,
d) $-CHF_2$,
e) $-CH_2OH$,
f) $C_{3-6}$cycloalkyl, or $R^{13}$ and $R^{14}$ together form a 3–7 membered carbocyclic ring,
$R^{15}$ and $R^{16}$ are independently selected from the group consisting of
a) hydrogen,
b) $C_{1-6}$ alkyl, unsubstituted or substituted with $-OH$, $C_{3-7}$ cycloalkyl, or $C(O)OR^{19}$, wherein $R^{19}$ is selected from the group consisting of hydrogen and $C_{1-6}$ alkyl,
c) $C_{3-7}$ cycloalkyl, and
d) $-C(O)R^{20}$, wherein $R^{20}$ is selected from the group consisting of $C_{1-6}$ alkyl, $-OR^{21}$ and $-NHR$, and wherein $R^{21}$ is hydrogen, $C_{1-6}$ alkyl or benzyl,
or $R^{15}$ and $R^{16}$ are joined to form a 4–7 membered heterocyclic ring which is unsubstituted or substituted with hydroxyl or halogen.

In a class of these compounds or pharmaceutically acceptable salts thereof, the compound has the formula

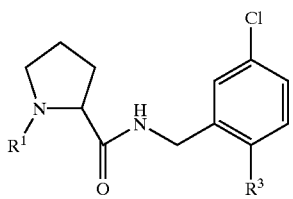

and $R^3$ is $-C(R^{11})(R^{12})C(R^{13})(R^{14})N(R^{15})(R^{16})$ or $-C(R^{13})(R^{14})N(R^{15})(R^{16})$.

In a subclass of this class, $R^3$ is $-C(R^{11})(R^{12})C(R^{13})(R^{14})N(R^{15})(R^{16})$.

In a group of this subclass, $R^3$ is $-C(R^{11})(R^{12})C(R^{13})(R^{14})NH_2$.

In a subgroup of this group, $R^3$ is $-CH_2CH_2NH_2$, $-CH_2CH(CHF_2)NH_2$, or $-CH_2CH(CF_3)NH_2$.

In a family of this subgroup,
x is a bond;
$R^6$ is hydrogen, $-OH$, $-CH_3$ or $-NH_2$;
$R^7$ is hydrogen, $-CH_3$, phenyl, 3-chlorophenyl, cyclopropyl or $-CH_2CH_3$; and
$R^8$ is phenyl, 3-chlorophenyl, cyclohexyl, $-CH_3$, $-CF_3$, $-CH_2CH_3$, $-CH(CH_3)_2$, $-CH(CH_3)(CH_2CH_3)$, $-C(CH_3)_3$, 2-pyridyl, 3-pyridyl,

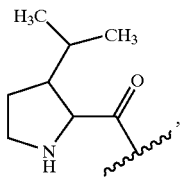

or $C_{1-6}$ alkyl substituted with

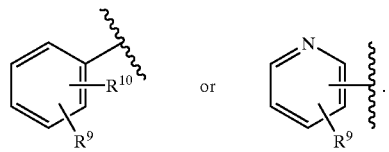

In a subfamily of this family, $R^9$ is hydrogen or Cl and $R^{10}$ is hydrogen.

In a collection of this subfamily, $R^1$ is selected from the group consisting of

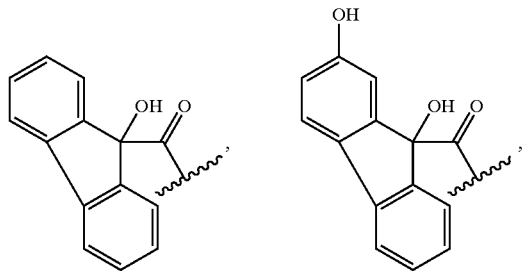

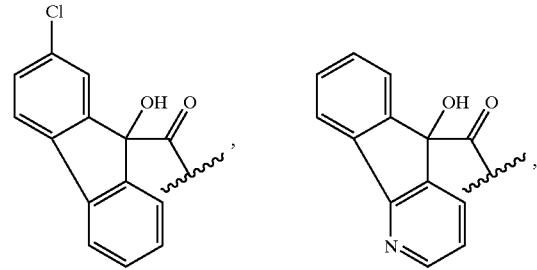

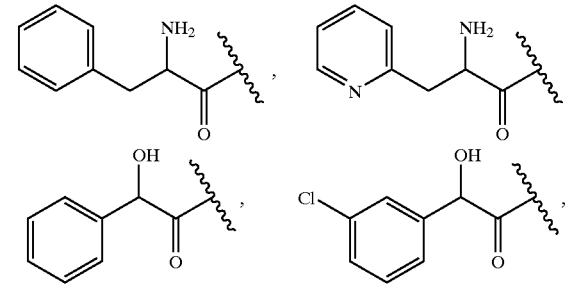

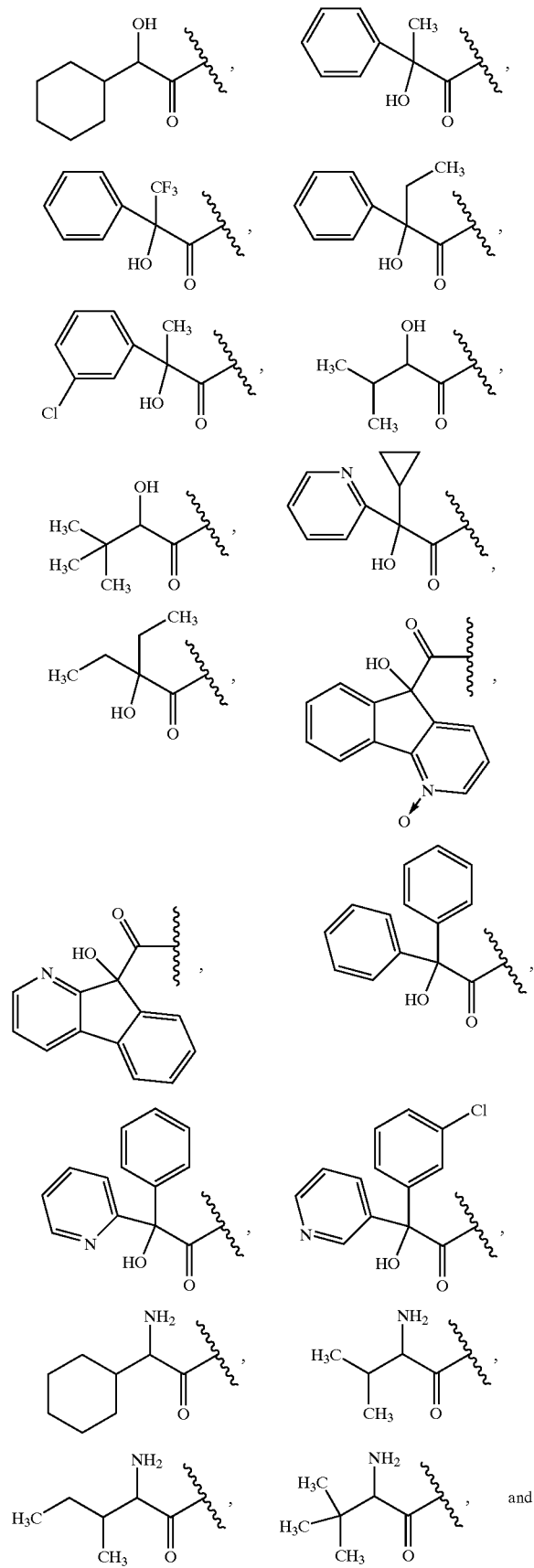
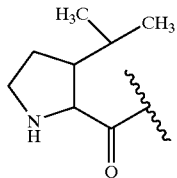
Examples of this collection are selected from the group consisting of
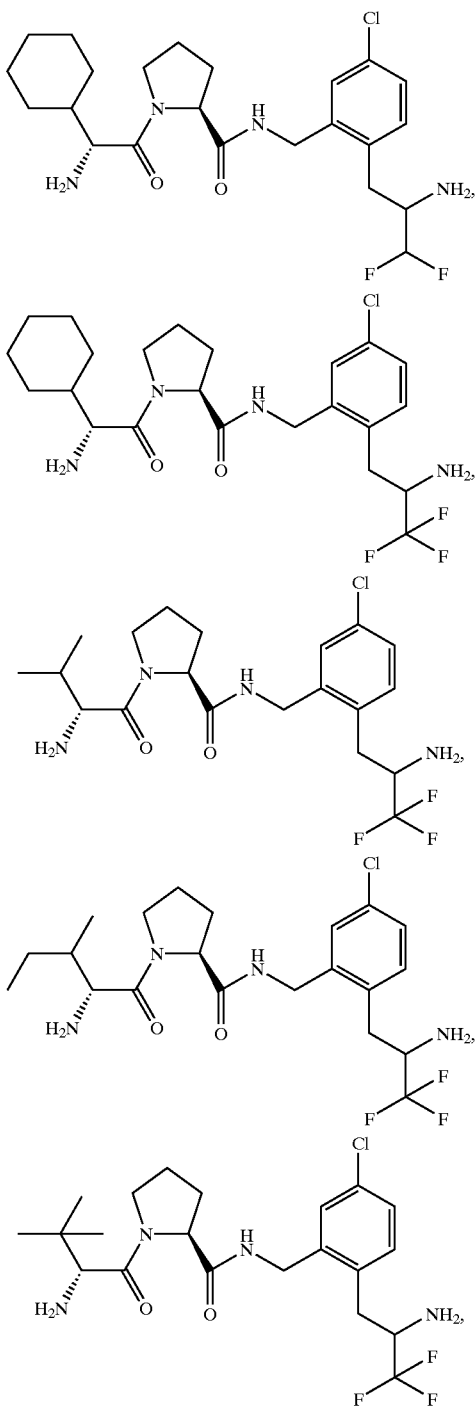

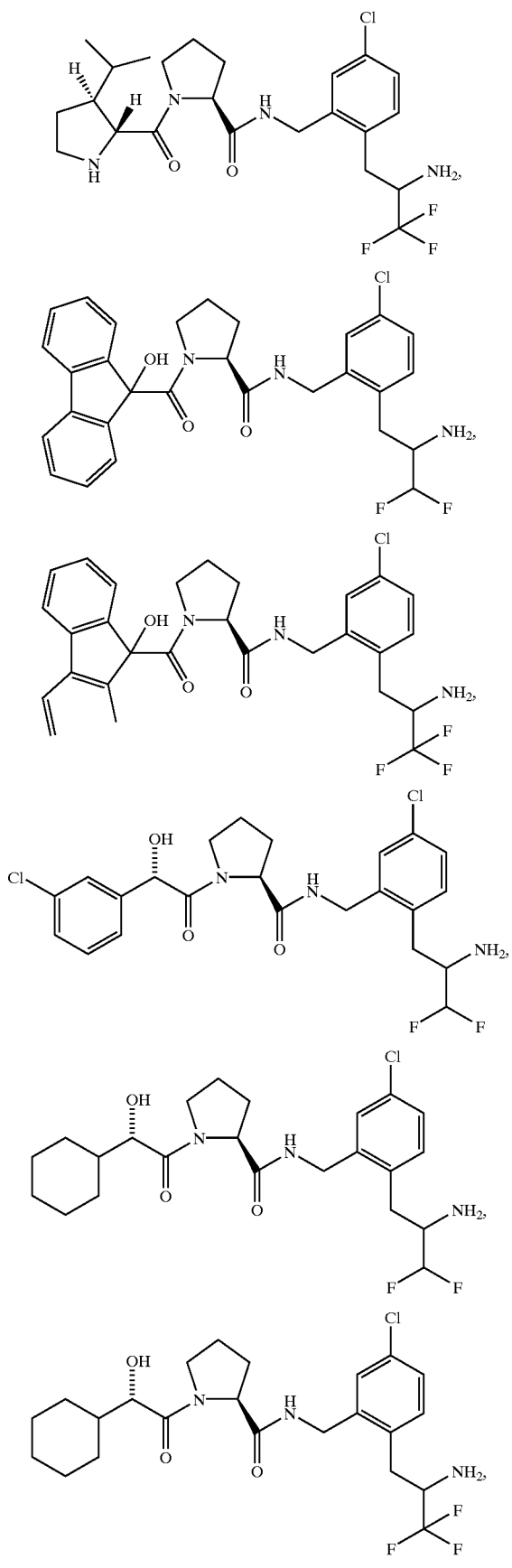
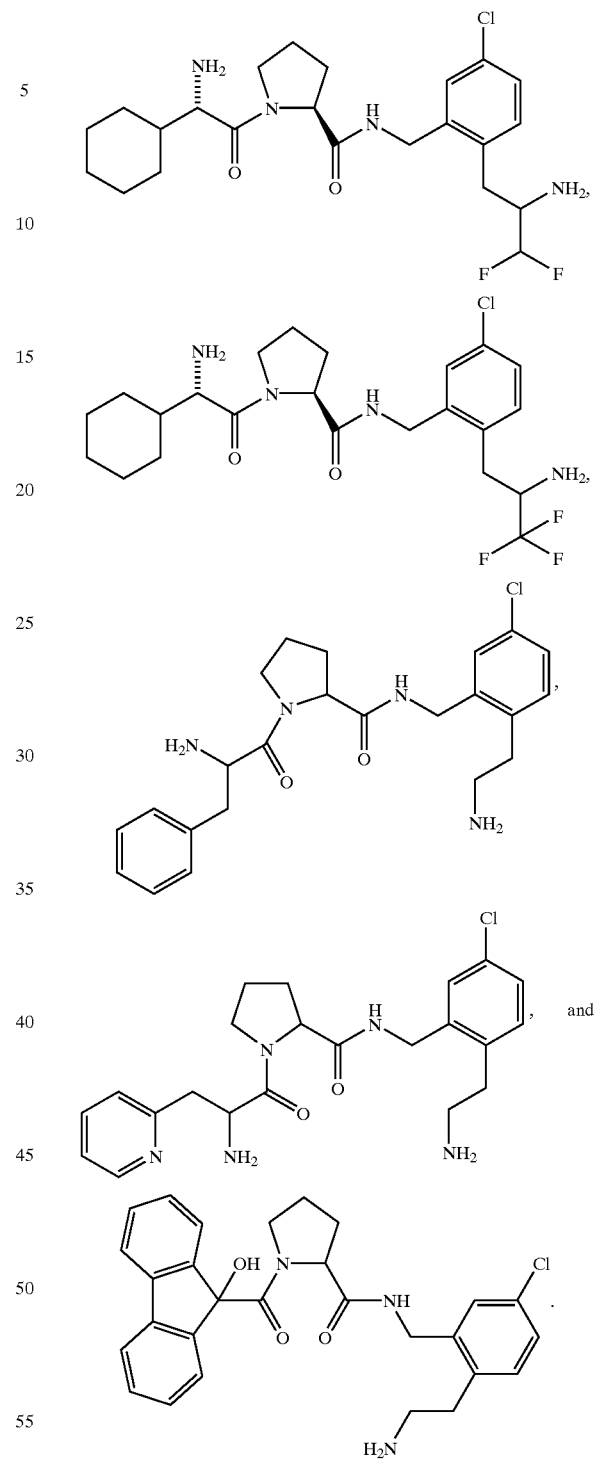
In a second subclass of the class, $R^3$ is —C($R^{13}$)($R^{14}$)N($R^{15}$)($R^{16}$).
In a group of the second subclass, $R^3$ is —CH$_2$N($R^{15}$)($R^{16}$), —CH(CHF$_2$)N($R^{15}$)($R^{16}$), —CH(CH$_2$OH)N($R^{15}$)($R^{16}$), or —CH(CH$_3$)N($R^{15}$)($R^{16}$).
In a subgroup of this group, $R^3$ is —CH$_2$NH$_2$, —CH$_2$NHC(O)OC(CH$_3$)$_3$, —CH(CHF$_2$)NH$_2$, —CH(CH$_2$OH)NH$_2$, or —CH(CH$_3$)NH$_2$.

In a family of this subgroup, x is a bond;

$R^6$ is hydrogen, —OH or —$NH_2$;

$R^7$ is hydrogen, —$CH_3$, phenyl, 3-chlorophenyl, cyclopropyl or —$CH_2CH_3$; and $R^8$ is phenyl, 3-chlorophenyl, cyclohexyl, —$CH_3$, —$CF_3$, —$CH_2CH_3$, —$CH_2C(CH_3)_3$, 2-pyridyl, 3-pyridyl, or $C_{1-6}$ alkyl substituted with

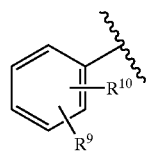 or 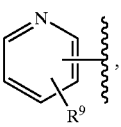,

In a subfamily of this family, $R^9$ is hydrogen or Cl and $R^{10}$ is hydrogen.

In a collection of this subfamily, $R^1$ is selected from the group consisting of

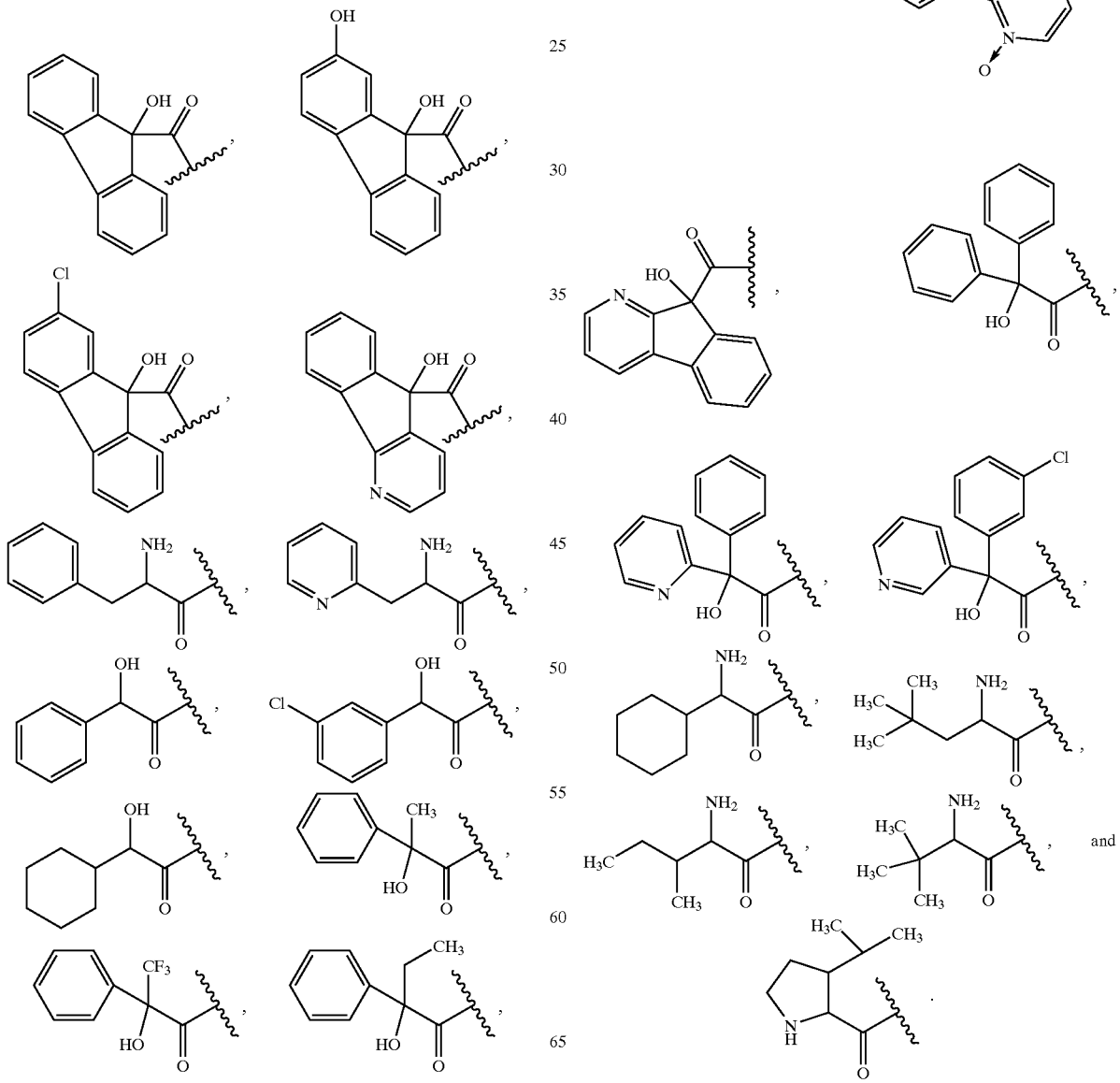

Examples of this collection are selected from the group consisting of
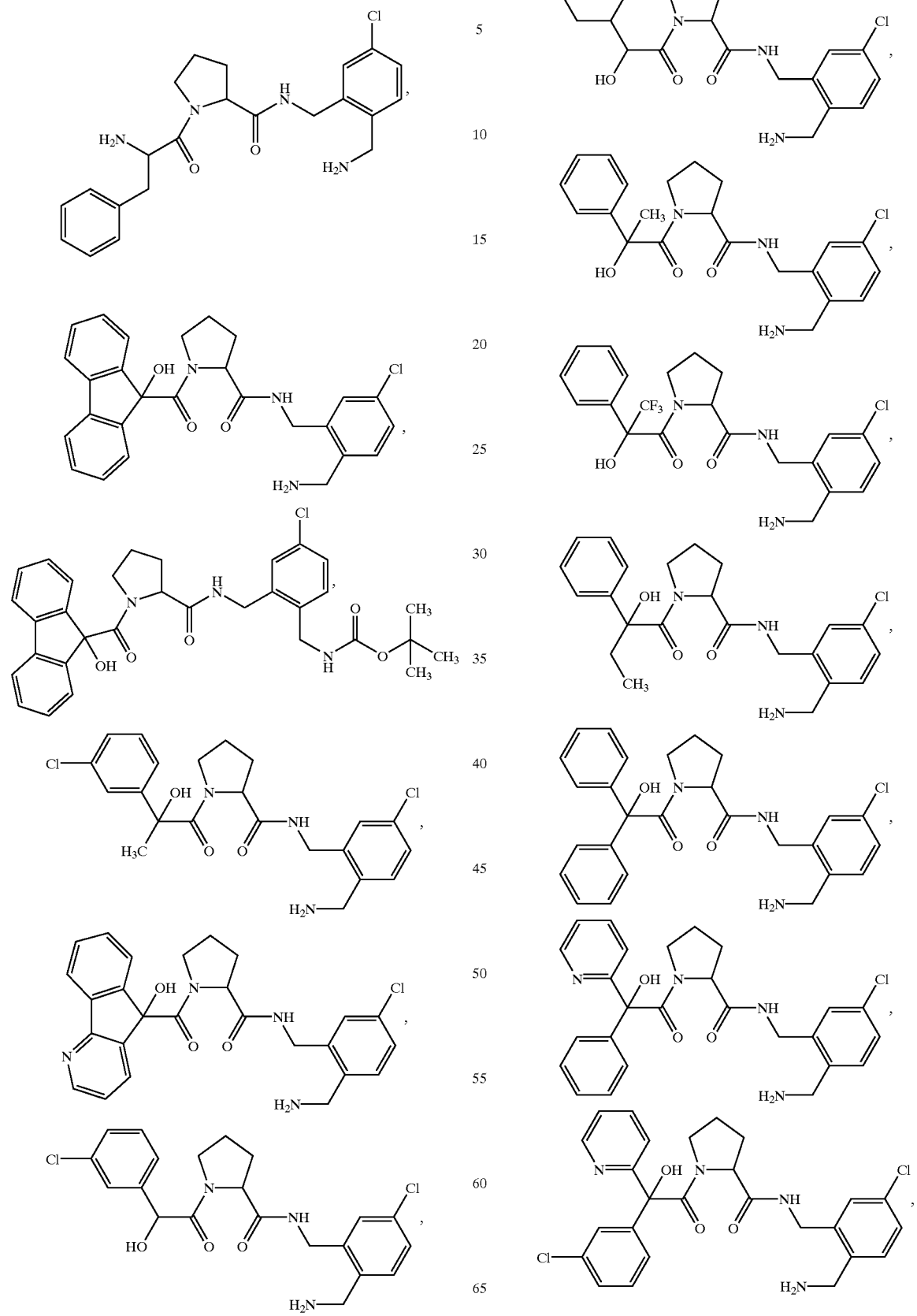

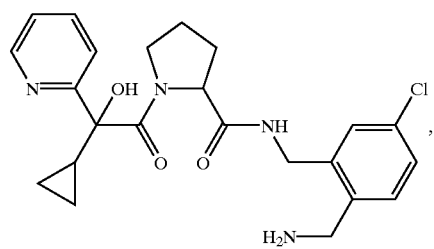
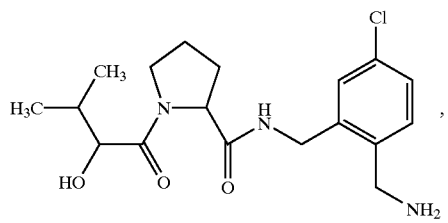
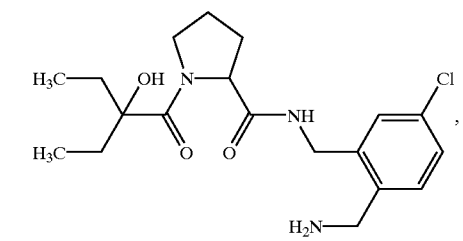
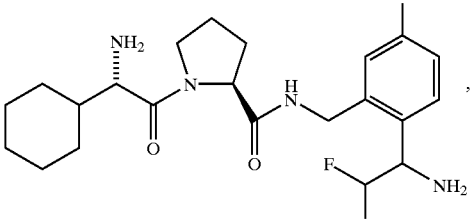
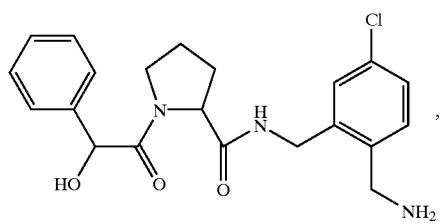
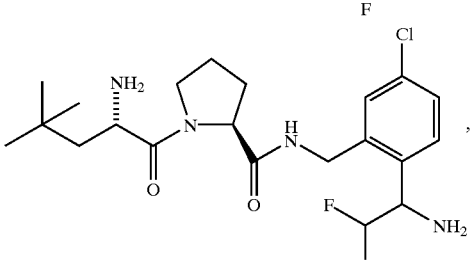
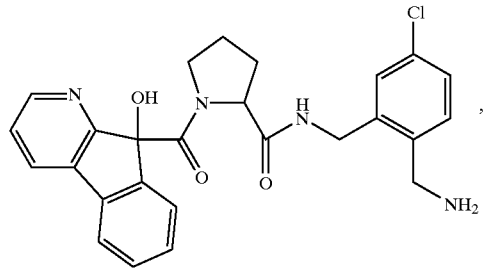
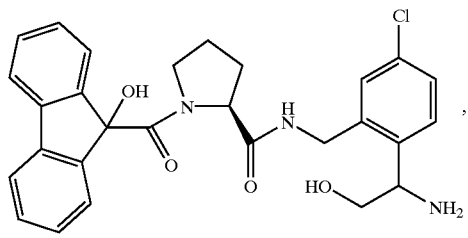
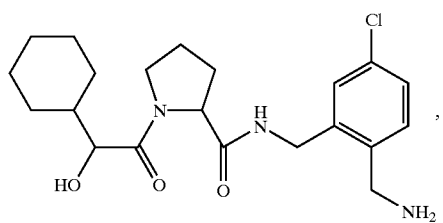
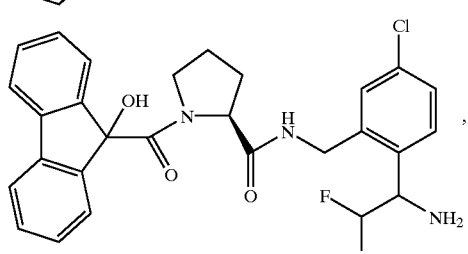
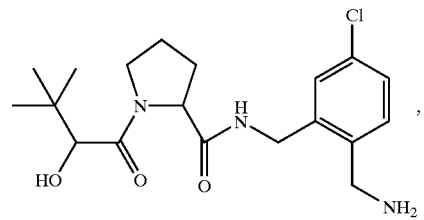
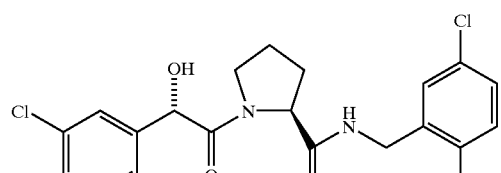
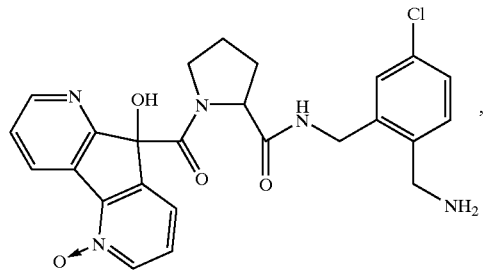
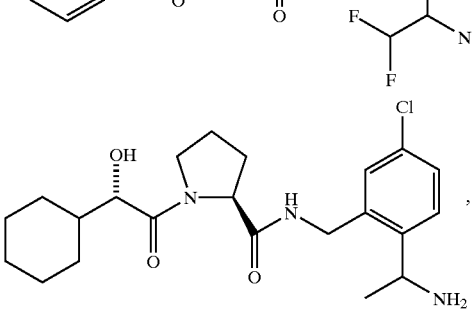

-continued

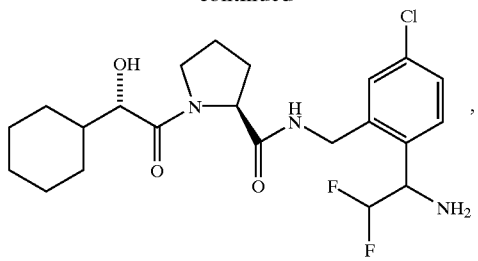

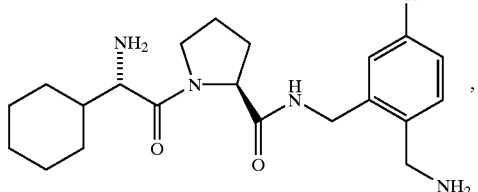

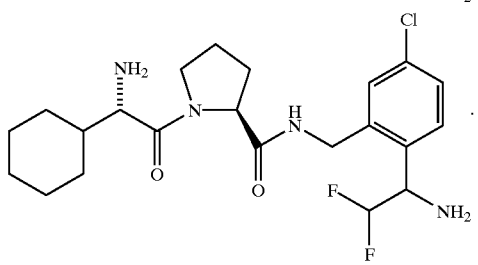

Particular examples of these examples are selected from the group consisting of

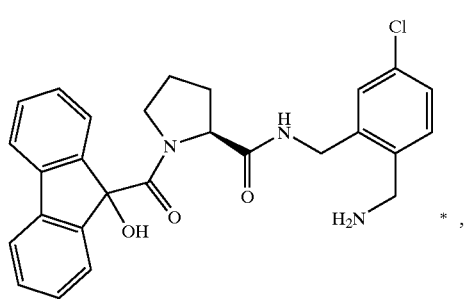

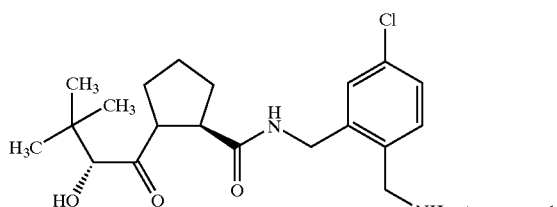

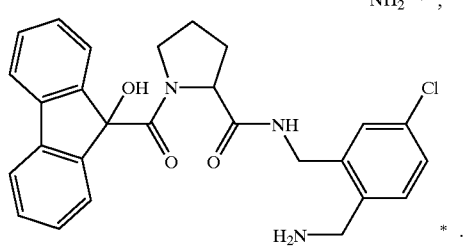

Compounds marked with "*" have a Ki of less than or equal to 2.0.

Compounds of the invention are useful as thrombin inhibitors and have therapeutic value in for example, preventing coronary artery disease. The invention includes compounds having the following structure:

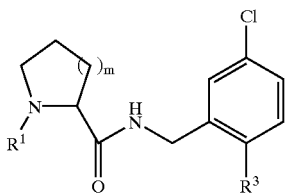

wherein m is 0, 1, or 2;

$R^1$ is selected from the group consisting of

1)

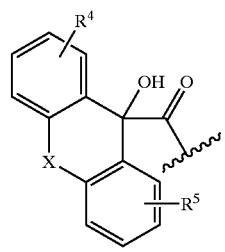

wherein $R^4$ and $R^5$ are independently selected from the group consisting of hydrogen, halogen, $C_{1-4}$ alkoxy, $C_{1-4}$ alkyl, —OH, and cyano, and X is a bond or O, and

2)

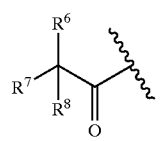

wherein $R^6$ is selected from the group consisting
 a) —OH,
 b) —NH$_2$,
 c) $C_{1-6}$ alkyl, unsubstituted or substituted with one or more of —OH, —COOH, $C_{3-7}$ cycloalkyl, or COOR$^{17}$, where R$^{17}$ is $C_{1-4}$ alkyl,
 d) $C_{3-7}$ cycloalkyl,
 e) C(O)OR$^{18}$,
 f) C(O)R$^{18}$,
 g) C(O)NHR$^{18}$,
 h) SO$_2$R$^{18}$,
 i) C(O)NH$_2$, and
 j) CN,
  wherein R$^{18}$ is selected from the group consisting of $C_{1-4}$ alkyl and $C_{3-7}$ cycloalkyl;

$R^7$ and $R^8$ are independently selected from the group consisting of
 a) hydrogen,
 b) —CF$_3$,
 c) unsubstituted $C_{1-6}$ akyl,
 d) $C_{3-6}$ cycloalkyl, and
 e) $C_{1-6}$ alkyl substituted with one of the group consisting of i) $C_{3-6}$ cycloalkyl,
ii) —COOH,
iii) —OH, iv) 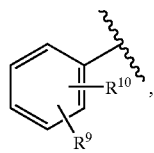, v) 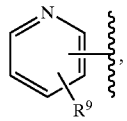, vi) 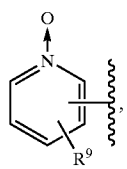, wherein $R^9$ and $R^{10}$ are independently selected from the group consisting of
aa) hydrogen,
bb) halogen,
cc) $C_{1-4}$ alkoxy,
dd) $C_{1-4}$ alkyl,
ee) hydroxy,
ff) $CF_3$ and
gg) cyano;

$R^3$ is selected from the group consisting of

1) 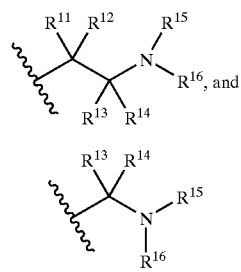

2)

wherein
$R^{11}$ and $R^{12}$ are independently selected from the group consisting of
a) hydrogen,
b) F
c) $C_{1-4}$ alkyl
d) $CF_3$,
e) $CHF_2$,
f) $C_{3-6}$ cycloalkyl,
 or $R^{11}$ and $R^{12}$ together form a 3–6 membered carbocyclic ring,
$R^{13}$ and $R^{14}$ are independently selected from the group consisting of
a) hydrogen,
b) $C_{1-4}$ alkyl
c) $CF_3$,
d) $CHF_2$,
e) $C_{3-6}$ cycloalkyl,
 or $R^{11}$ and $R^{12}$ together form a 3–6 membered carbocyclic ring, $R^{15}$ and $R^{16}$ are independently selected from the group consisting of
a) hydrogen,
b) $C_{1-4}$ alkyl, unsubstituted or substituted with —OH, $C_{3-7}$ cycloalkyl, or $C(O)OR^{19}$, wherein $R^{19}$ is selected from the group consisting of hydrogen and $C_{1-4}$ alkyl,
c) $C_{3-7}$ cycloalkyl,
d) —$C(O)R^{20}$, wherein $R^{20}$ is selected from the group consisting of —$OR^{21}$ and —$NHR^{21}$, and wherein $R^{21}$ is hydrogen, $C_{1-4}$ alkyl or benzyl, and
e) —$CO_2R^{22}$, where $R^{22}$ is $C_{1-4}$ alkyl.

In a subclass of compounds and pharmaceutically acceptable salts thereof, m is 1, X is a bond, $R^6$ is $NH_2$, $R^7$ is hydrogen, and $R^8$ is $C_{1-6}$ alkyl substituted with

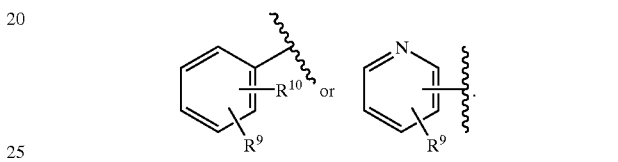

In a subgroup of this subclass of compounds and pharmaceutically acceptable salts thereof, $R^1$ is selected from the group consisting of

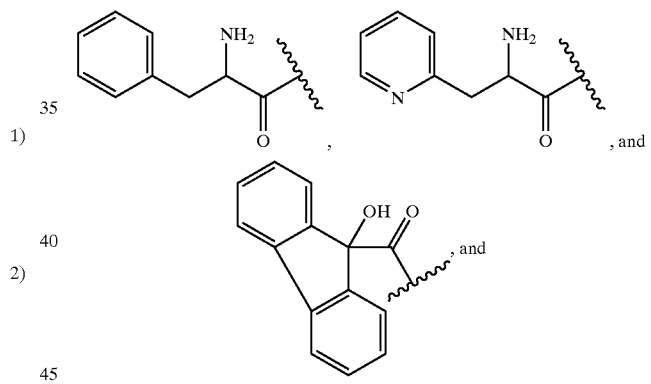

$R^3$ is —$CH_2NH_2$, —$CH_2CH_2NH_2$, or —$CH_2NHC(O)OC(CH_3)_3$.

Examples of this subgroup include

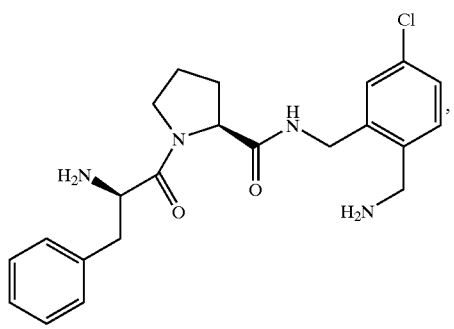

-continued

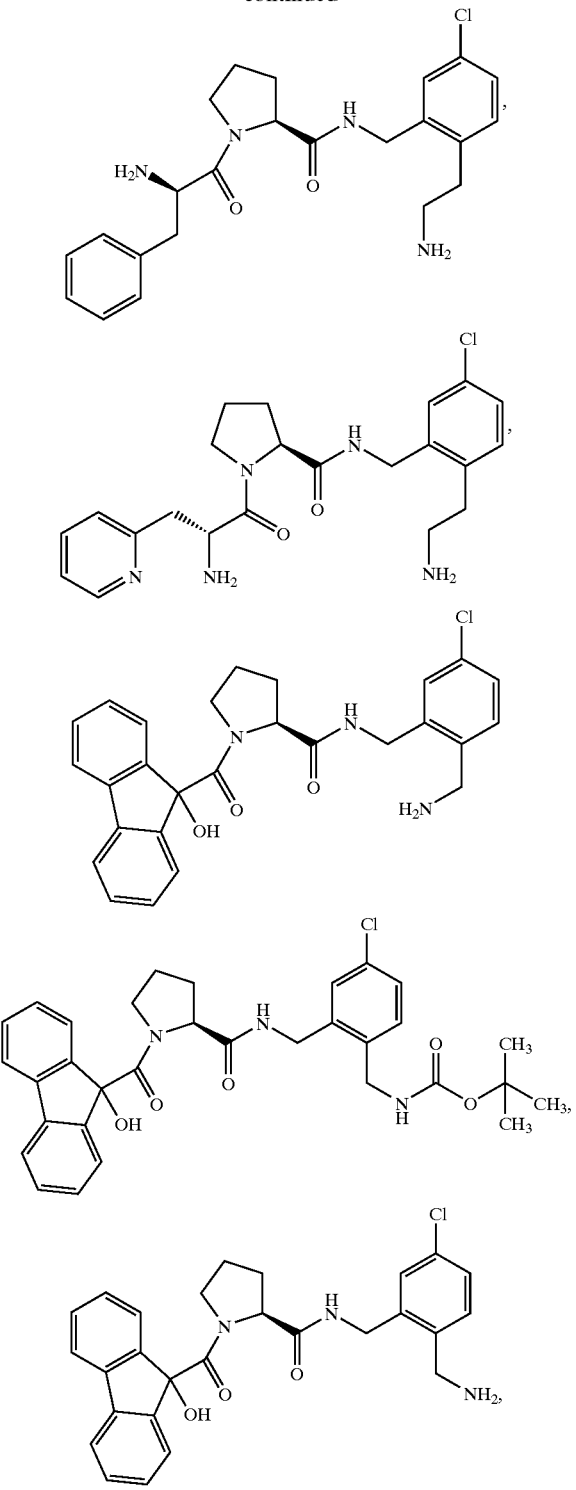

and pharmaceutically acceptable salts thereof.

Compounds of the invention are useful as thrombin inhibitors and have therapeutic value in for example, preventing coronary artery disease. The invention includes compounds having the following structure:

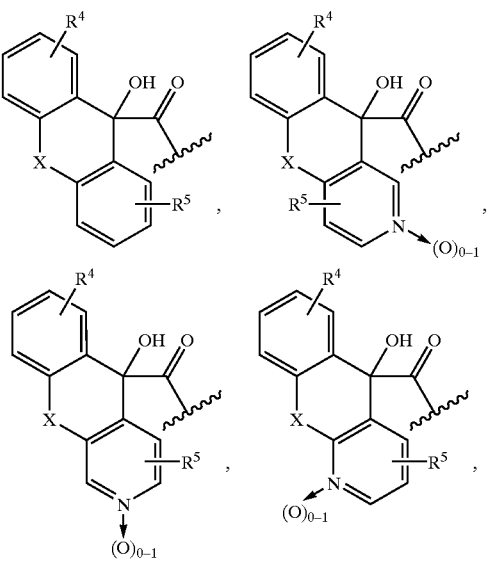

or a pharmaceutically acceptable salt thereof, wherein
m is 0, 1, or 2;
$R^1$ is selected from the group consisting of
1)

[structures shown]

wherein
$R^4$ and $R^5$ are independently selected from the group consisting of hydrogen, halogen, $C_{1-4}$ alkoxy, $C_{1-6}$ alkyl, —OH, and cyano, and
X is a bond, O, or S, and 2) 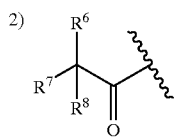

wherein
$R^6$ is selected from the group consisting
a) hydrogen,
b) $C_{1-6}$ alkyl,
c) —OH,
d) —NR$^{24}$R$^{25}$, where $R^{24}$ and $R^{25}$ are independently hydrogen, or $C_{1-6}$ alkyl unsubstituted or substituted with one or more of —OH, —COOH, $C_{3-7}$ cycloalkyl, or COOR$^{17}$, where $R^{17}$ is $C_{1-6}$alkyl, e) NHC(O)OR$^{18}$,
f) NHC(O)R$^{18}$,
g) NHC(O)NHR$^{18}$,
h) NHSO$_2$R$^{18}$,
i) NHC(O)NH$_2$, and
j) NHCN,
   wherein R$^{18}$ is selected from the group consisting of C$_{1-6}$ alkyl, aryl, and C$_{3-7}$ cycloalkyl;

R$^7$ and R$^8$ are independently selected from the group consisting of
a) hydrogen,
b) —CF$_3$,
c) C$_{1-6}$ alkyl,
d) phenyl, unsubstituted or substituted with C$_{1-6}$ alkyl, COOR$^{26}$ or halogen,
   where R$^{26}$ is C$_{1-4}$ alkyl or hydrogen, e) 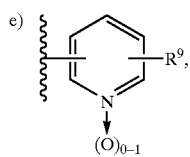

f) C$_{3-7}$ cycloalkyl, g) 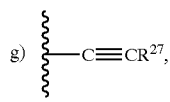

where R$^{27}$ is C$_{1-6}$ alkyl or C$_{3-7}$ cycloalkyl,
h) C$_{1-6}$ alkyl substituted with one or two of the group consisting of
   i) C$_{3-7}$ cycloalkyl,
   ii) —COOH,
   iii) —OH, iv) 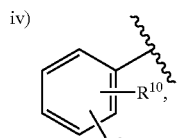

v) 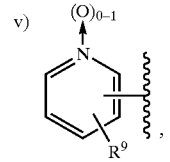

wherein R$^9$ and R$^{10}$ are independently selected from the group consisting of
aa) hydrogen,
bb) halogen,
cc) C$_{1-4}$ alkoxy,
dd) C$_{1-4}$ alkyl,
ee) hydroxy,
ff) CF$_3$,
gg) cyano,
hh) COOR$^{28}$, where R$^{28}$ is C$_{1-4}$ alkyl or hydrogen;

or R$^7$ and R$^8$ are joined to form a C$_{3-7}$ carbocyclic ring which is unsubstituted or independently substituted with one or two C$_{1-6}$ alkyl groups;

R$^3$ is selected from the group consisting of
1) —C(R$^{11}$)(R$^{12}$)C(R$^{13}$)(R$^{14}$)N(R$^{15}$)(R$^{16}$),
2) —C(R$^{13}$)(R$^{14}$)N(R$^{15}$)(R$^{16}$), and 3) 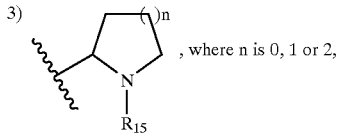, where n is 0, 1 or 2, wherein
R$^{11}$ and R$^{12}$ are independently selected from the group consisting of
a) hydrogen,
b) F,
c) C$_{1-4}$ alkyl,
d) CF$_3$,
e) CHF$_2$,
f) C$_{3-7}$ cycloalkyl,
   or R$^{11}$ and R$^{12}$ together form a 3–7 membered carbocyclic ring, R$^{13}$ and R$^{14}$ are independently selected from the group consisting of
a) hydrogen,
b) C$_{1-4}$ alkyl
c) —CF$_3$,
d) —CHF$_2$,
e) —CH$_2$OH,
f) C$_{3-6}$ cycloalkyl,
   or R$^{13}$ and R$^{14}$ together form a 3–7 membered carbocyclic ring, R$^{15}$ and R$^{16}$ are independently selected from the group consisting of
a) hydrogen,
b) C$_{1-6}$ alkyl, unsubstituted or substituted with —OH, C$_{3-7}$ cycloalkyl, or C(O)OR$^{19}$, wherein R$^{19}$ is selected from the group consisting of hydrogen and C$_{1-6}$ alkyl,
c) C$_{3-7}$ cycloalkyl, and
d) —C(O)R$^{20}$, wherein R$^{20}$ is selected from the group consisting of —OR$^{21}$ and —NHR$^{21}$, and wherein R$^{21}$ is hydrogen, C$_{1-6}$ alkyl or benzyl,
   or R$^{15}$ and R$^{16}$ are joined to form a 4–7 membered heterocyclic ring which is unsubstituted or substituted with hydroxyl or halogen.

In a class of these compounds or pharmaceutically acceptable salts thereof, R$^3$ is —C(R$^{11}$)(R$^{12}$)C(R$^{13}$)(R$^{14}$)N(R$^{15}$)(R$^{16}$) or —C(R$^{13}$)(R$^{14}$)N(R$^{15}$)(R$^{16}$).

In a subclass of this class, R$^3$ is —C(R$^{11}$)(R$^{12}$)C(R$^{13}$)(R$^{14}$)N(R$^{15}$)(R$^{16}$).

In a group of this subclass, R$^3$ is —C(R$^{11}$)(R$^{12}$)C(R$^{13}$)(R$^{14}$)NH$_2$.

In a subgroup of this group, R$^3$ is —CH$_2$CH$_2$NH$_2$.

In a family of this subgroup, x is a bond;

R$^6$ is hydrogen, —OH, —CH$_3$ or —NH$_2$;

R$^7$ is hydrogen, —CH$_3$, phenyl, 3-chlorophenyl, cyclopropyl or —CH$_2$CH$_3$; and R$^8$ is phenyl, 3-chlorophenyl, cyclohexyl, —CH$_3$, —CF$_3$, —CH$_2$CH$_3$, 2-pyridyl, 3-pyridyl, or C$_{1-6}$ alkyl substituted with

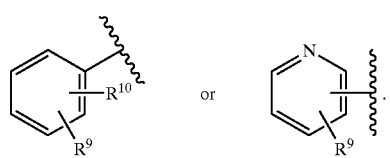 or 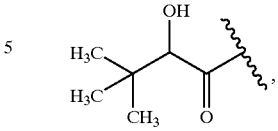.
In a subfamily of this family, $R^9$ is hydrogen or Cl and $R^{10}$ is hydrogen.
In a collection of this subfamily, $R^1$ is selected from the group consisting of
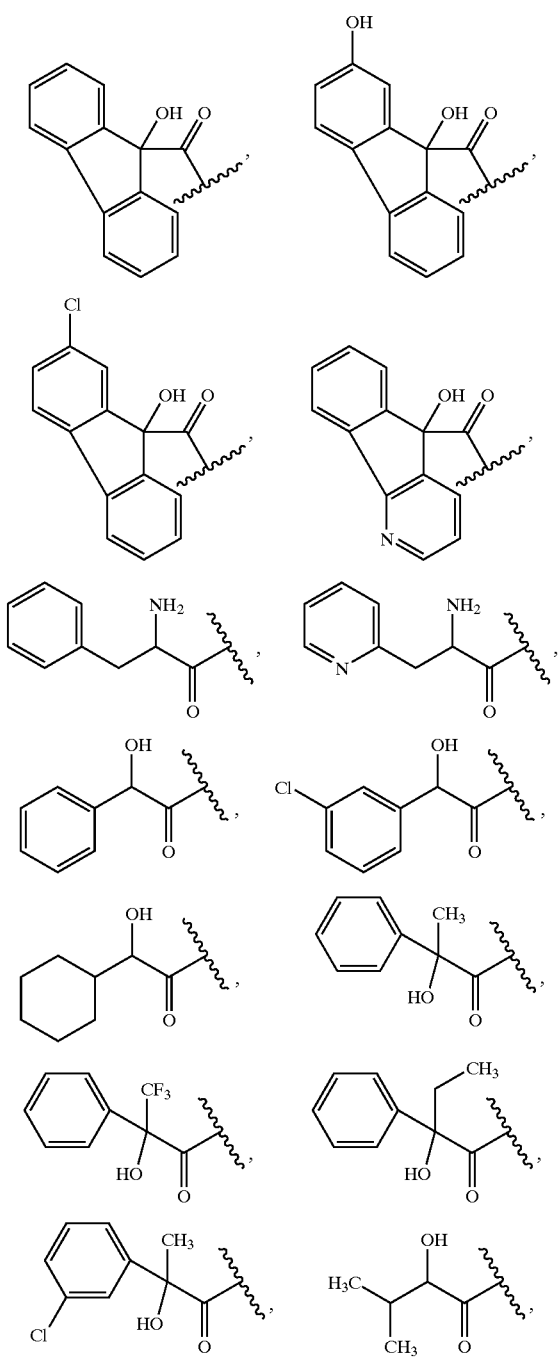
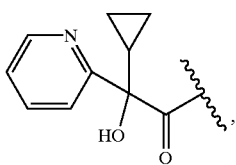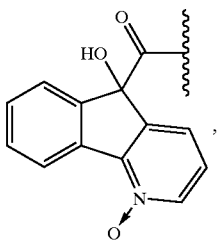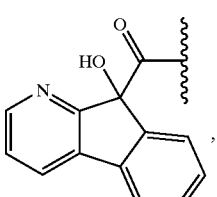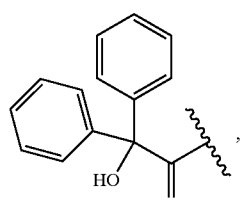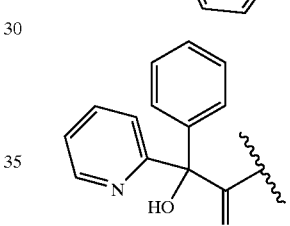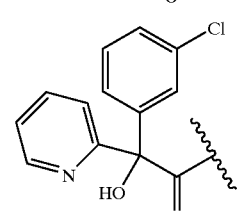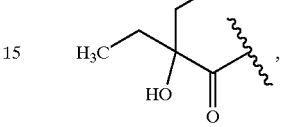
Examples of this collection are selected from the group consisting of
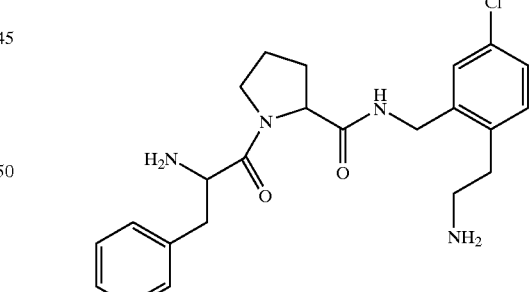
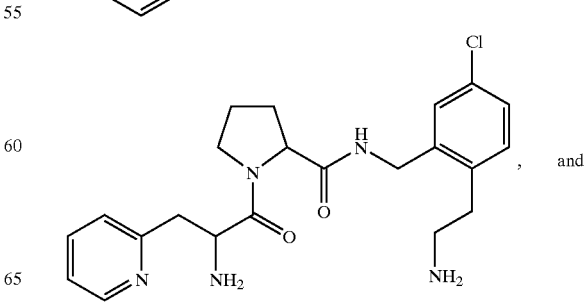, and

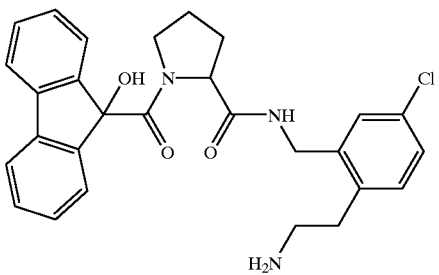

In a second subclass of the class, $R^3$ is —C($R^{13}$)($R^{14}$)N($R^{15}$)($R^{16}$).

In a group of the second subclass, $R^3$ is —CH$_2$N($R^{15}$)($R^{16}$).

In a subgroup of this group, $R^3$ is —CH$_2$NH$_2$ or —CH$_2$NHC(O)OC(CH$_3$)$_3$.

In a family of this subgroup, x is a bond;

$R^6$ is hydrogen, —OH, —CH$_3$ or —NH$_2$; $R^7$ is hydrogen, —CH$_3$, phenyl, 3-chlorophenyl, cyclopropyl or —CH$_2$CH$_3$; and $R^8$ is phenyl, 3-chlorophenyl, cyclohexyl, —CH$_3$, —CF$_3$, —CH$_2$CH$_3$, 2-pyridyl, 3-pyridyl, or C$_{1-6}$ alkyl substituted with

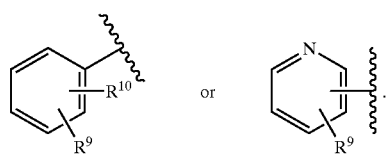

In a subfamily of this family, $R^9$ is hydrogen or Cl and $R^{10}$ is hydrogen.

In a collection of this subfamily, $R^1$ is selected from the group consisting of

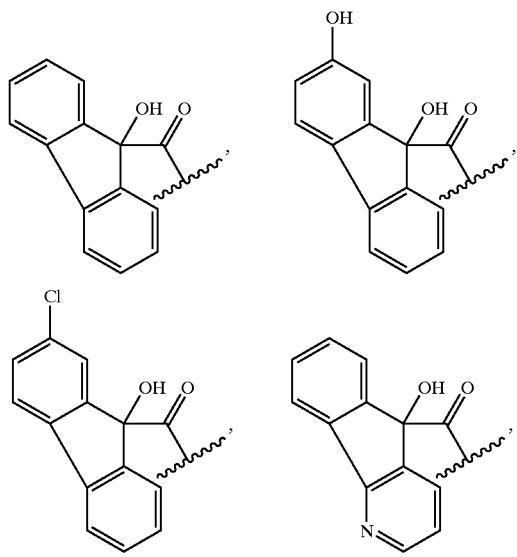

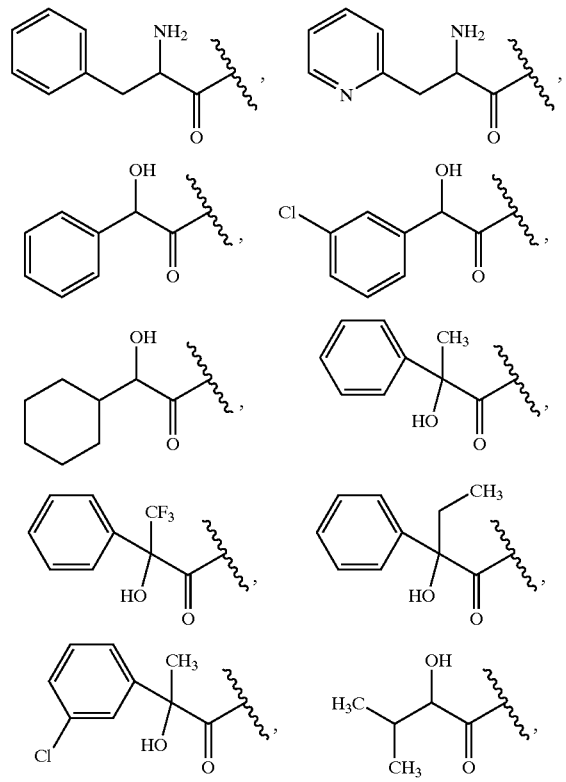

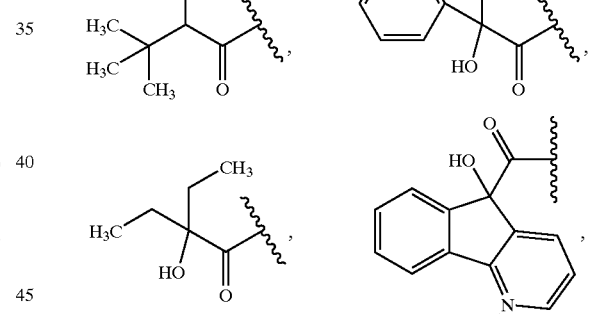

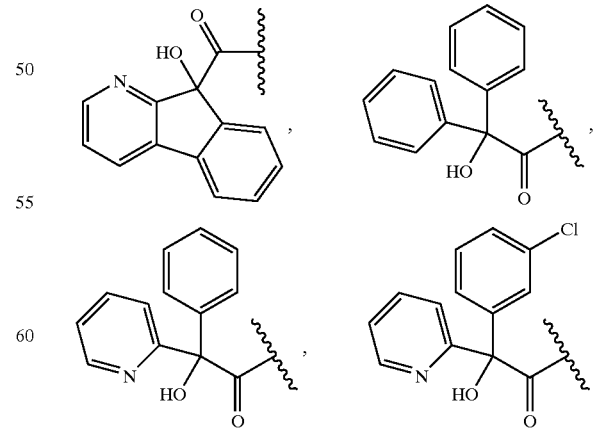

Examples of this collection are selected from the group consisting of

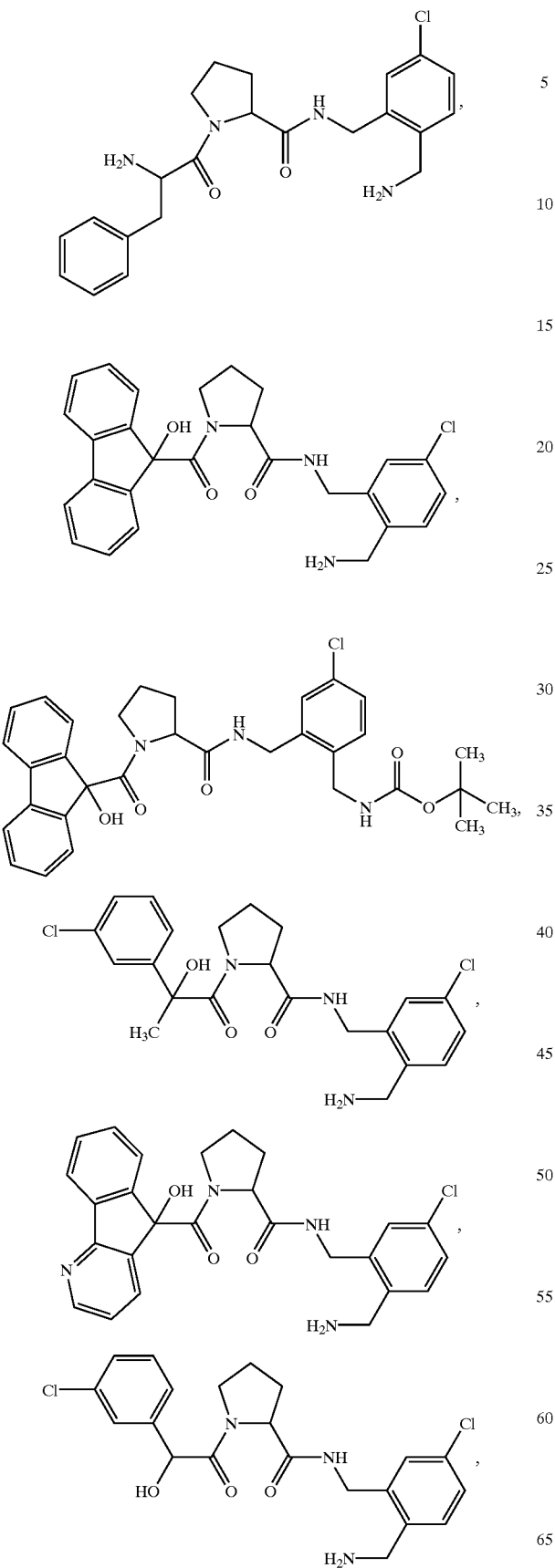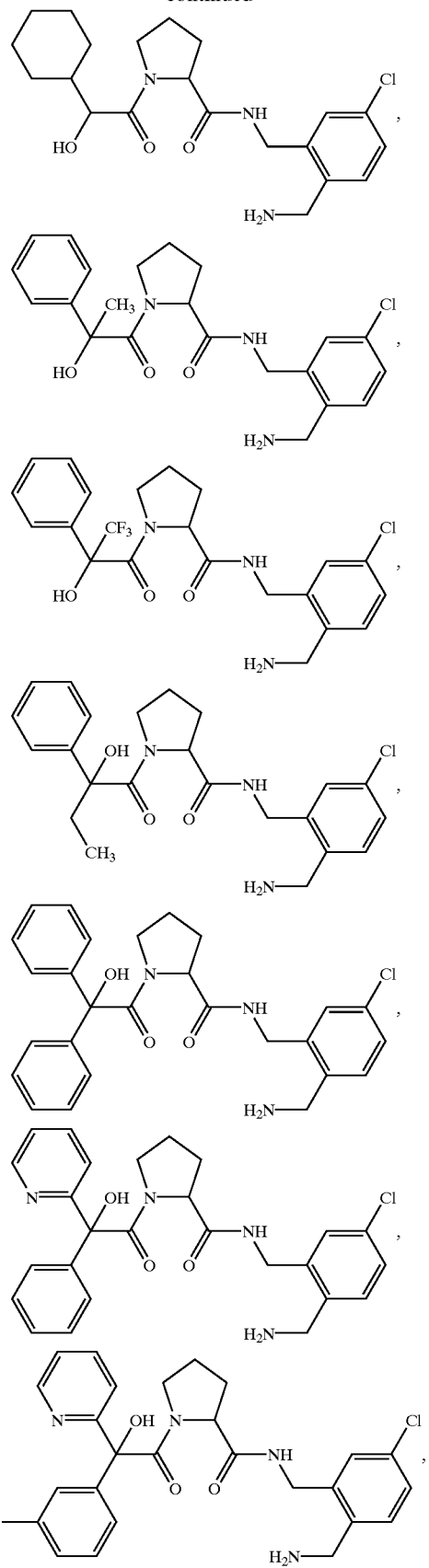

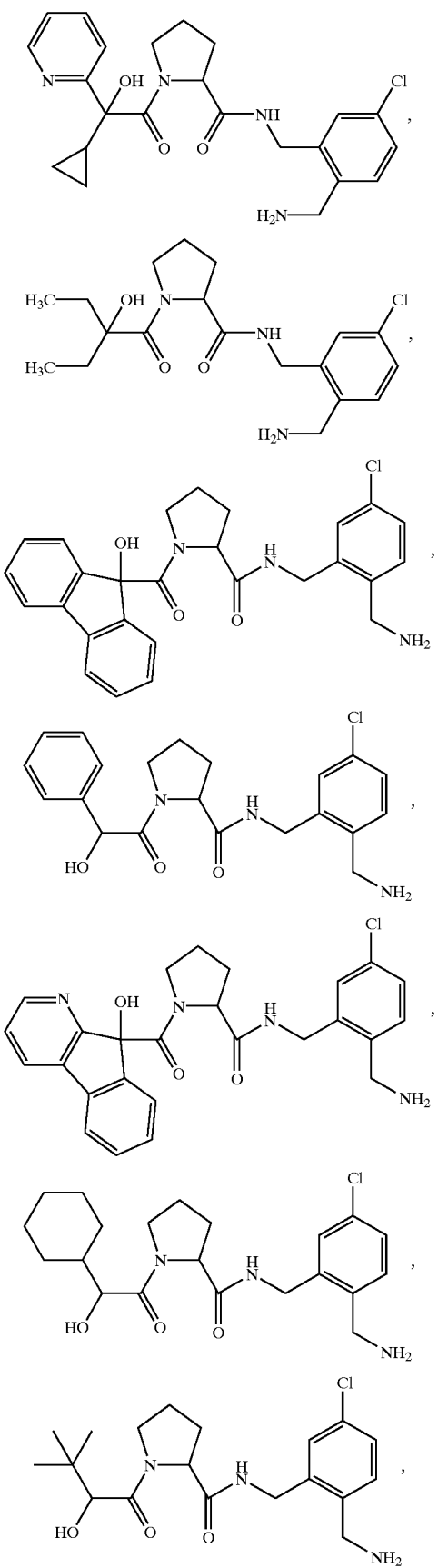
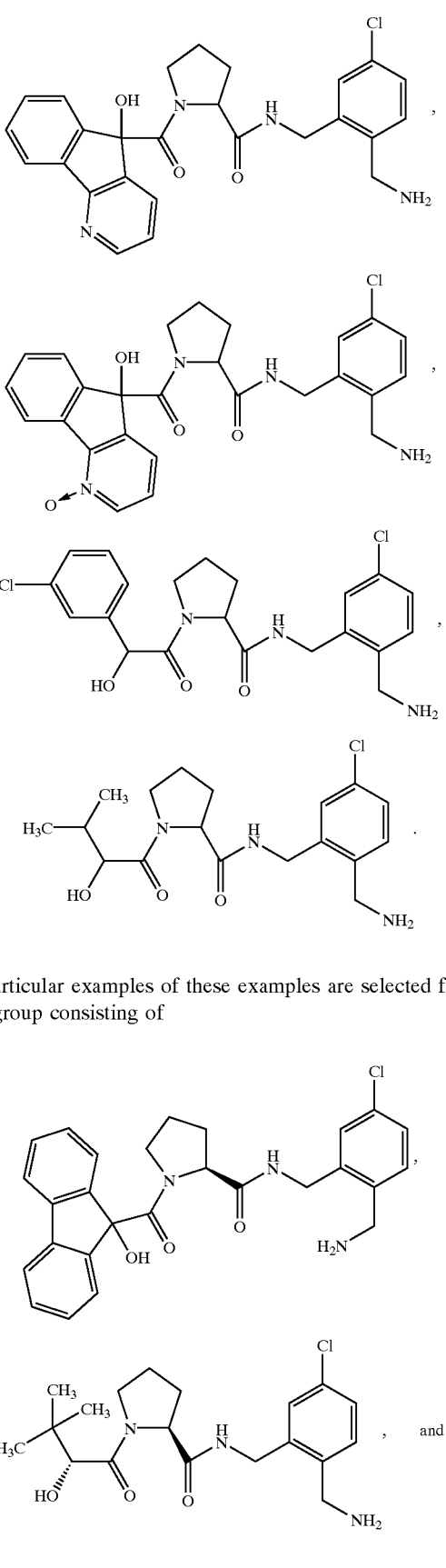
Particular examples of these examples are selected from the group consisting of

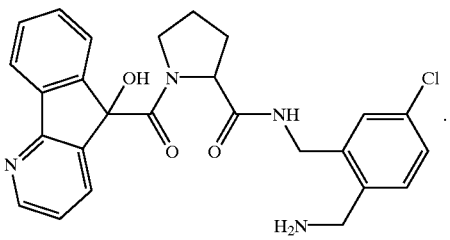

The compounds of the present invention, may have chiral centers and occur as racemates, racenuc mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows:

| ABBREVIATIONS | |
|---|---|
| Designation | |
| AcOH | acetic acid |
| Boc | tert-butyloxycarbonyl |
| (Boc)$_2$O | di-t-butyl dicarbonate |
| BOP reagent | benzotriazol-1-yloxy-tris(dimethylamino)phosphonium hexafluorophosphate |
| CAN | ceric ammonium nitrate |
| DAST | diethylaminosulfurtrifluoride |
| DBU | 1,8-diazabicyclo[5.4.0]undec-7-ene |
| DCE | 1,2-dichloroethane |
| DIEA | N,N-diisopropylethylamine |
| DMAP | dimethylaminopyridine |
| DMF | dimethylformamide |
| DPPA | diphenylphosphoryl azide |
| EDC | 1-ethyl-3-(3-dimethylaminopropyl)carbodiimide hydrochloride |
| EtOAc | ethyl acetate |
| Et$_2$O | diethyl ether |
| Fmoc | 9-fluorenylmethoxycarbonyl |
| HATU | (O-7-azabenzotriazol-1-y)-1,1,3,3-tetramethyluronium hexafluorophosphate |
| HCl | hydrochloric acid |
| HOAc | acetic acid |
| HOAT | 1-hydroxy-7-azabenzotriazole |
| HOBT | 1-hydroxybenzotriazole |
| HPLC | high pressure liquid chromatography |
| IPrOH | 2-propanol |
| KOH | potassium hydroxide |
| LAH | lithium aluminum hydride |
| LCMS | liquid chromatography mass spectrum |
| MCPBA | m-chloroperoxybenzoic acid |
| MeOH | methanol |
| MgSO$_4$ | magnesium sulfate |
| n-BuLi | n-butyllithium |
| N$_3$PO(Ph)$_2$ | diphenyl phosphoryl azide |
| NaBH$_4$ | sodium borohydride |
| NaHCO$_3$ | sodium hydrogen carbonate |
| NaN$_3$ | sodium azide |
| Na$_2$SO$_4$ | sodium sulfate |
| Na$_2$S$_2$O$_3$ | sodium thiosulfate |
| NCS | N-chlorosuccinimide |
| NH$_4$Cl | ammonium chloride |

| ABBREVIATIONS | |
|---|---|
| Designation | |
| NMM | N-methylmorpholine |
| PMP | para-methoxyphenyl |
| PPh$_3$ | triphenyl phosphine |
| Pd-C | palladium on activated carbon catalyst |
| Pd(PPh$_3$)$_4$ | tetrakis triphenylphosphine palladium |
| PhCH$_3$ | toluene |
| POBr$_3$ | phosphorous oxybromide |
| TEA | triethylamine |
| Tf$_2$O | trifluoromethane sulfonic anhydride |
| THF | tetrahydrofuran |
| TLC | thin layer chromatography |
| SiO$_2$ | silicon oxide |
| Zn(CN)$_2$ | zinc cyanide |

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "halogen", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "cycloC$_{3-7}$alkyl" is intended to include cyclopropyl, cyclobutyl, cyclopentyl, cyclohexyl and cycloheptyl, and the like.

The term "aryl" as used herein except where noted, represents a stable 6- to 10-membered mono- or bicyclic ring system such as phenyl, or naphthyl. The aryl ring can be unsubstituted or substituted with one or more of C$_{1-4}$ lower alkyl; hydroxy; alkoxy; halogen; amino.

The pyridyl N-oxide portion of the compounds of the invention are structurally depicted using conventional representations

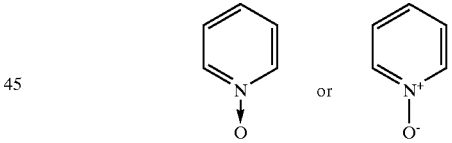

which have equivalent meanings.

In this specification methyl substituents may be represented by

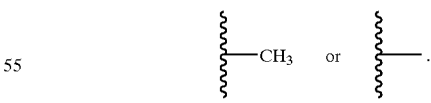

For example, the structures

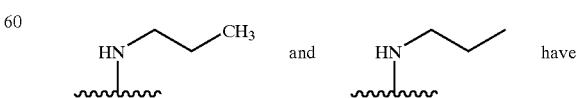

equivalent meanings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activatormediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulafion agents, or thrombolytic agents, or may be substantially less that those doses of thrombin inhibitors administered without coadministration of additional anti-platelet agents, anticoagulation agents, or thrombolytic agents, depending on a patient's therapeutic needs.
Unless otherwise stated, all NMR determinations were made using 400 MHz field strength.
SCHEME 1
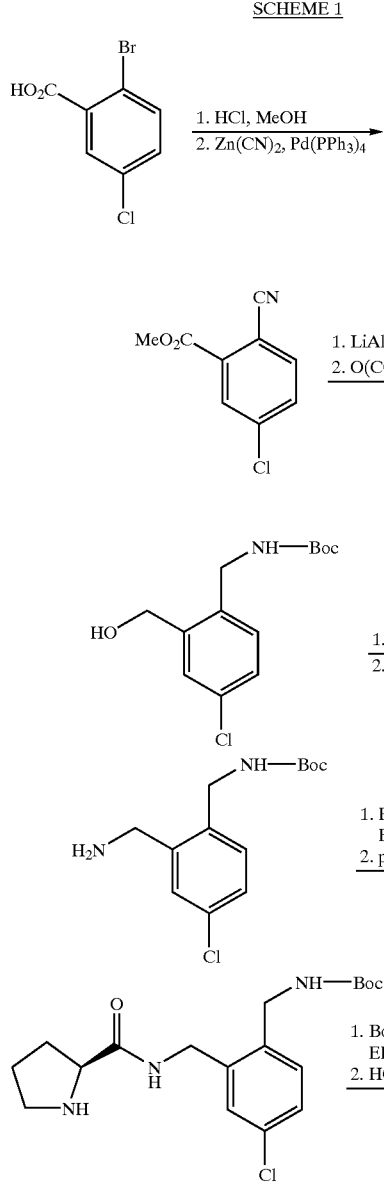
SCHEME 2
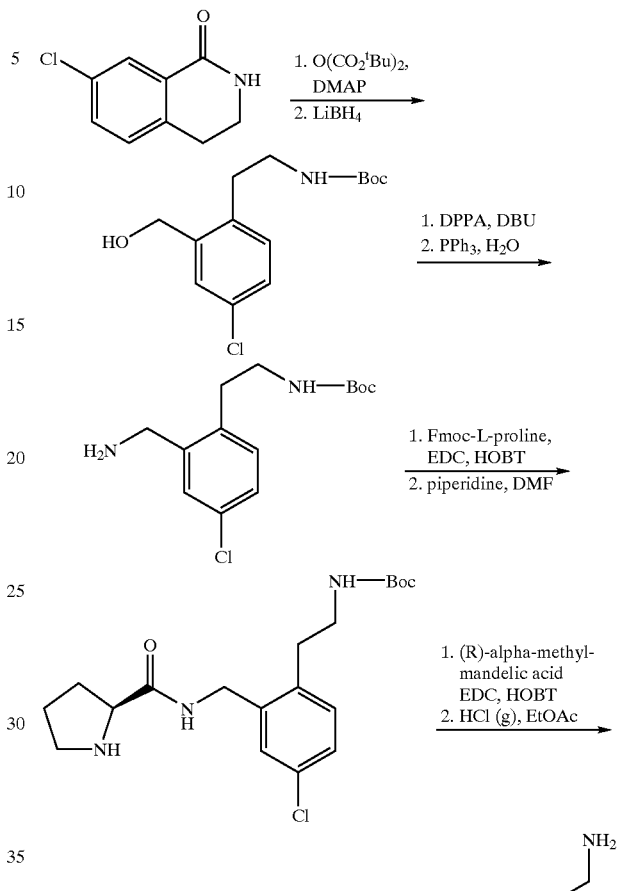
SCHEME 3
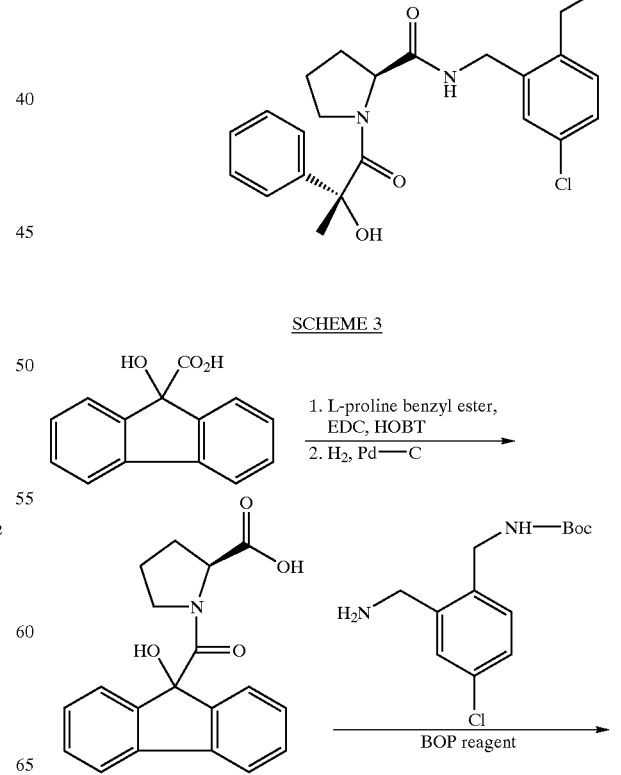
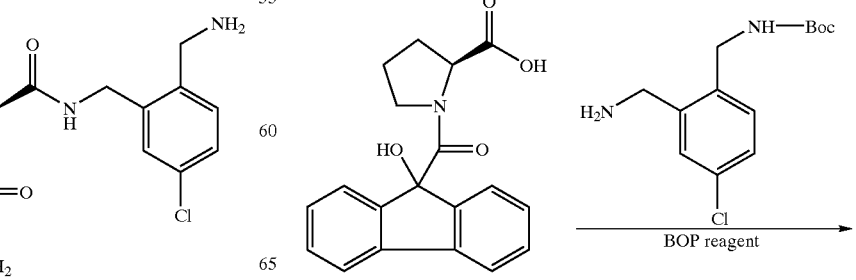

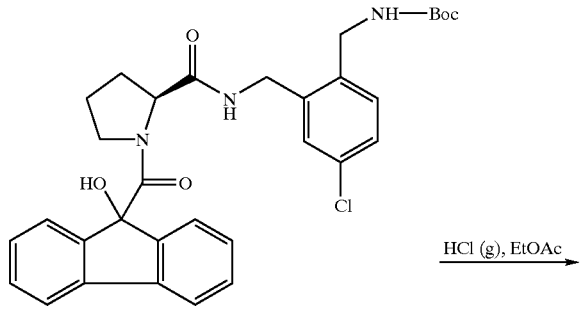
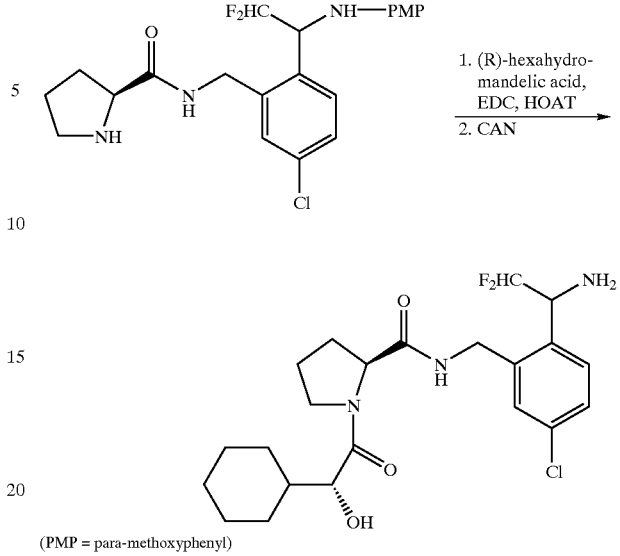
(PMP = para-methoxyphenyl)
SCHEME 4
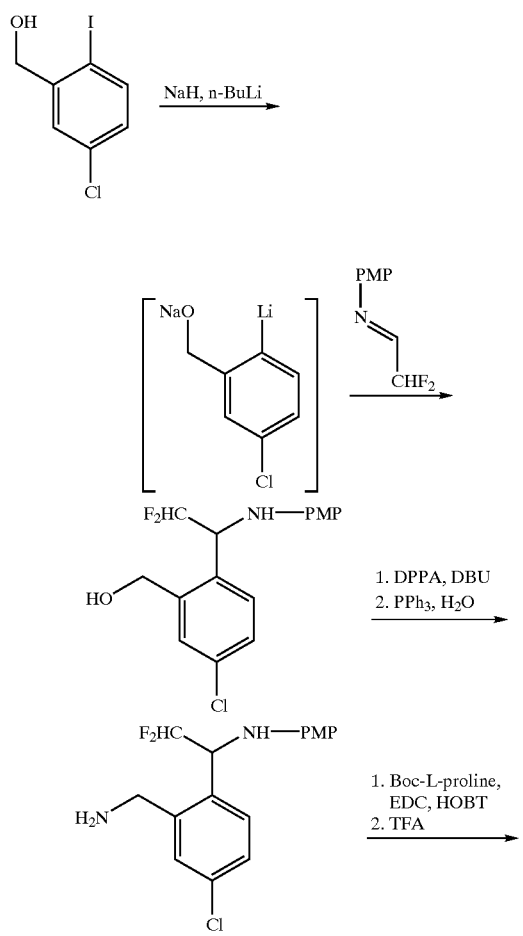
SCHEME 5
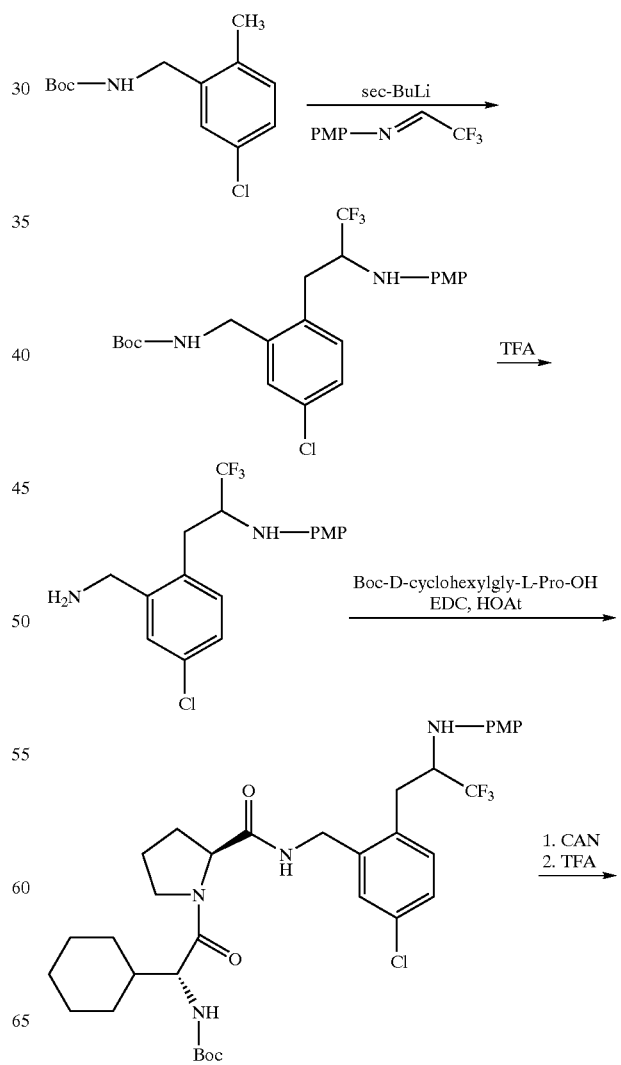

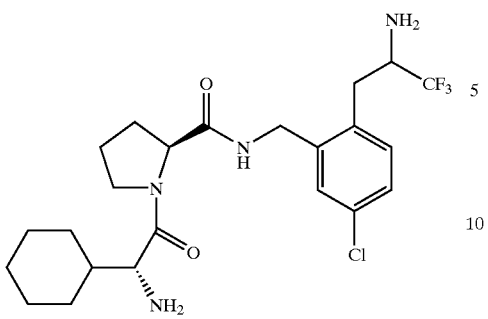
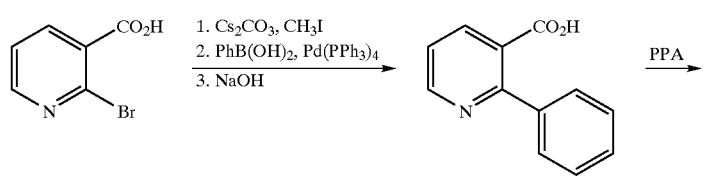
SCHEME 6
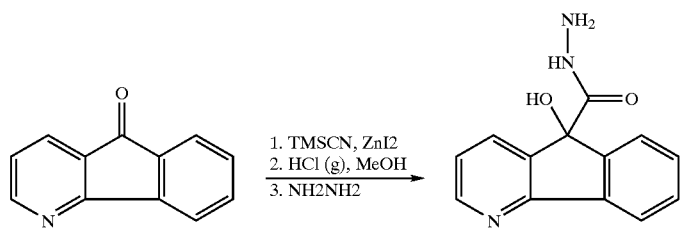
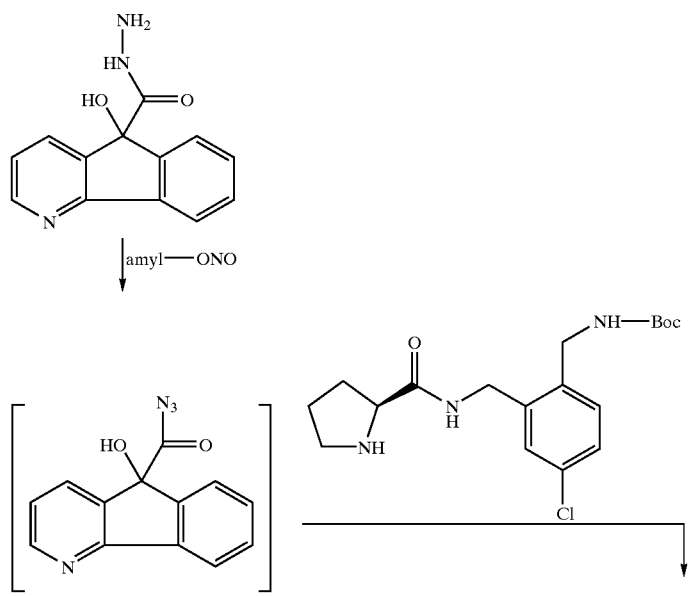

-continued
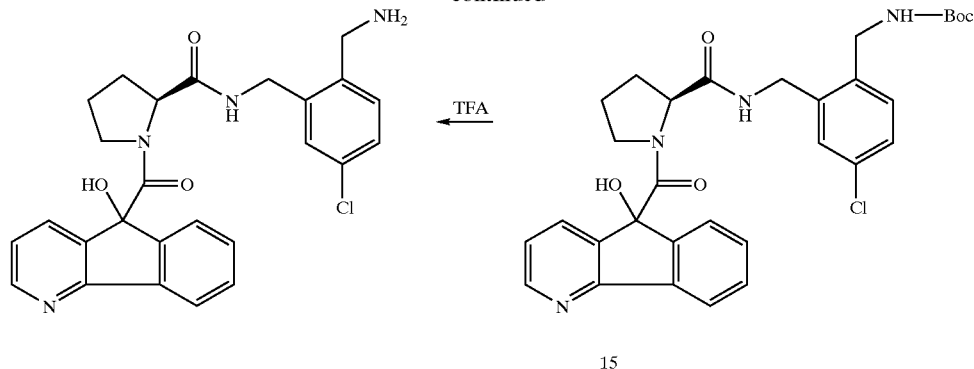
SCHEME 7
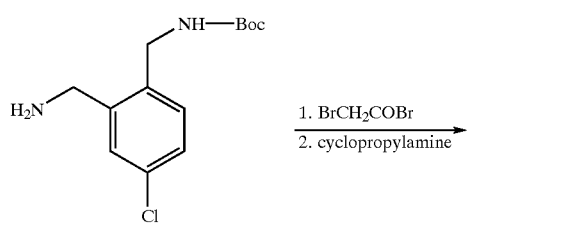
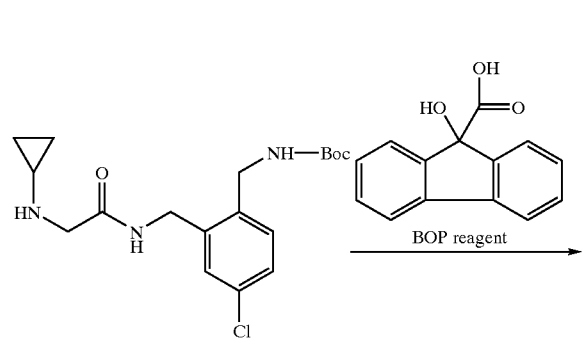
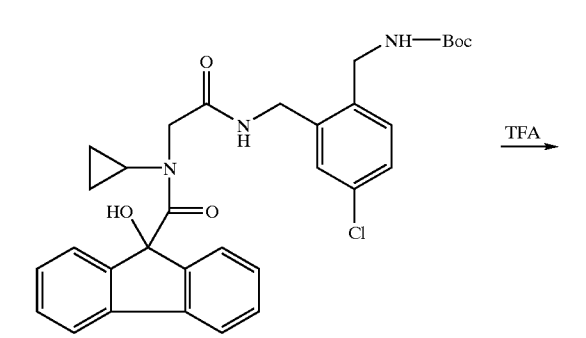
Scheme 8
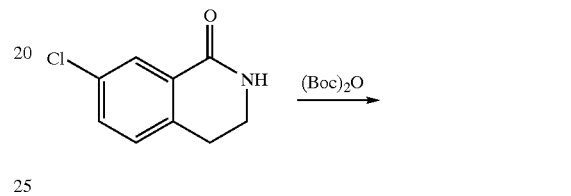
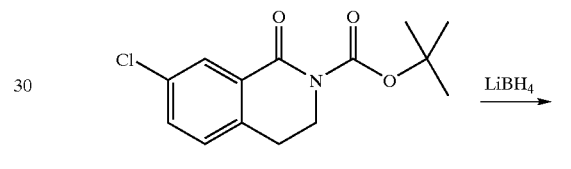
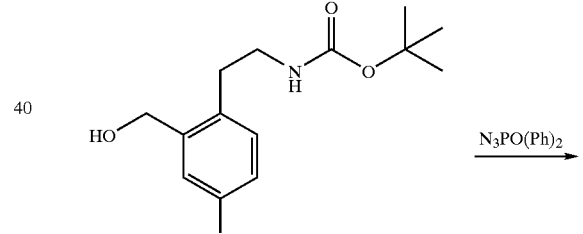
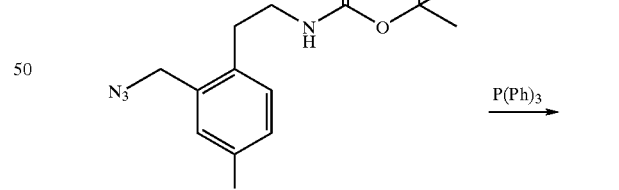

Step A: 2-(tert-Butoxycarbonyl)-7-chloro-3,4-dihydro-2H-isoquinolin-1-one

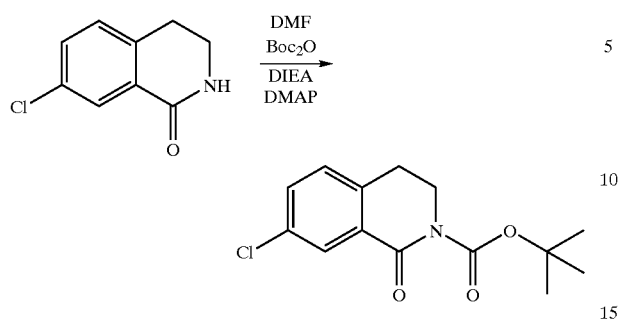

Into a stirred solution of 7-chloro-3,4-dihydroisoquinolin-1-one (11.6 g, 12.6 mMol) in 50 mL of anhydrous N,N-dimethylformamide under inert atmosphere at ambient temperature was added diisopropylethylamine (17.0 mL, 95.8 mmol, 1.5eq), di-tert-butyl dicarbonate (15.33 g, 70.26 mMol, 1.1 eq), and a catalytic amount of 4-(dimethylamino)pyridine. This was stirred at ambient temperature for 2 hours, concentrated in vacuo, then partitioned between methylene chloride and water. The organics were dried (Na$_2$SO$_4$) and concentrated in vacuo. The residue was purified by flash silica gel chromatography using methylene chloride as an eluent. Desired fractions were concentrated in vacuo to afford 2-(tert-butoxycarbonyl)-7-chloro-3,4-dihydro-2H-isoquinolin-1-one (2) as a clear colorless oil (hplc rt=3.55 min, method A; mass spec m/z=282.1).

Step B: 2-(tert-Butoxycarbonylaminoethyl)-5-chlorobenzyl Alcohol

Into a stirred solution of 2-(tert-butoxycarbonyl)-7-chloro-3,4-dihydro-2H-isoquinolin-1-one (18.4 g, 64.38 mMol) in 50 mL of anhydrous tetrahydrofuran under inert atmosphere at 0° C. was added 2.0M LiBH4 in tetrahydrofuran (64.38 mL, 128.76 mMol, 2eq). This was stirred at 0° C. for 1.5 hours, quenched with saturated ammonium chloride solution, then partitioned between ethyl acetate and water. The organics were dried(Na$_2$SO$_4$) and concentrated in vacuo. This afforded 2-(tert-butoxycarbonylaminoethyl)-5-chlorobenzyl alcohol as a clear colorless oil (hplc rt=3.21 min, method A; mass spec m/z=286.2).

Scheme 9

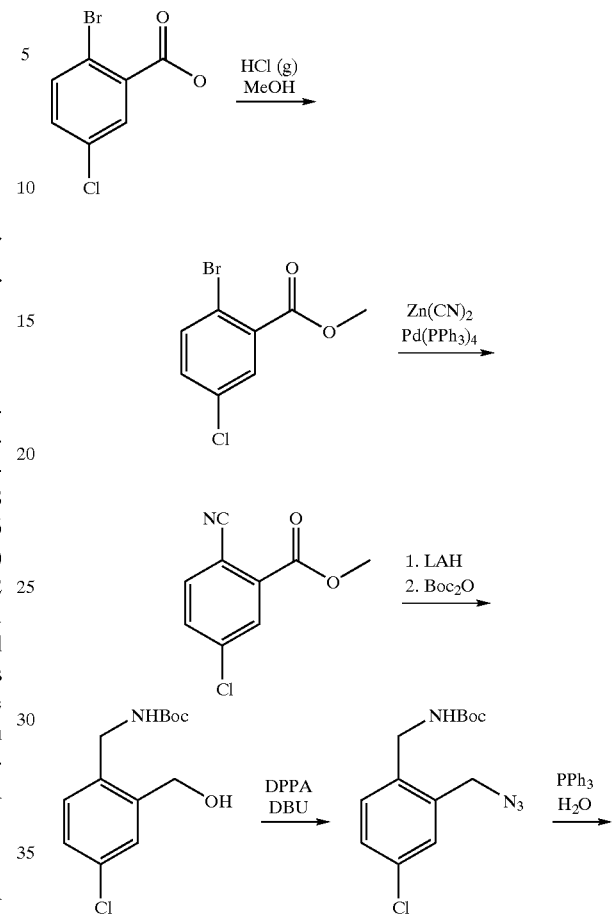

Scheme 10

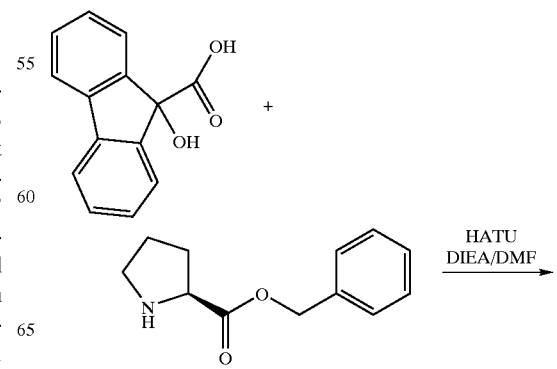

-continued
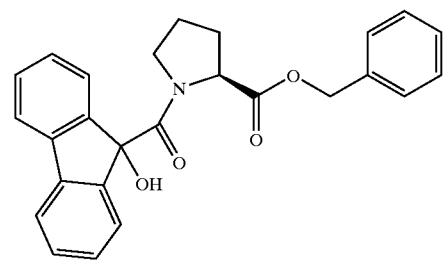
Scheme 11
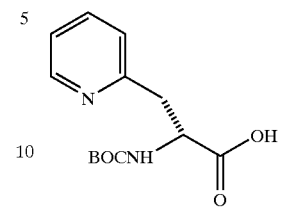
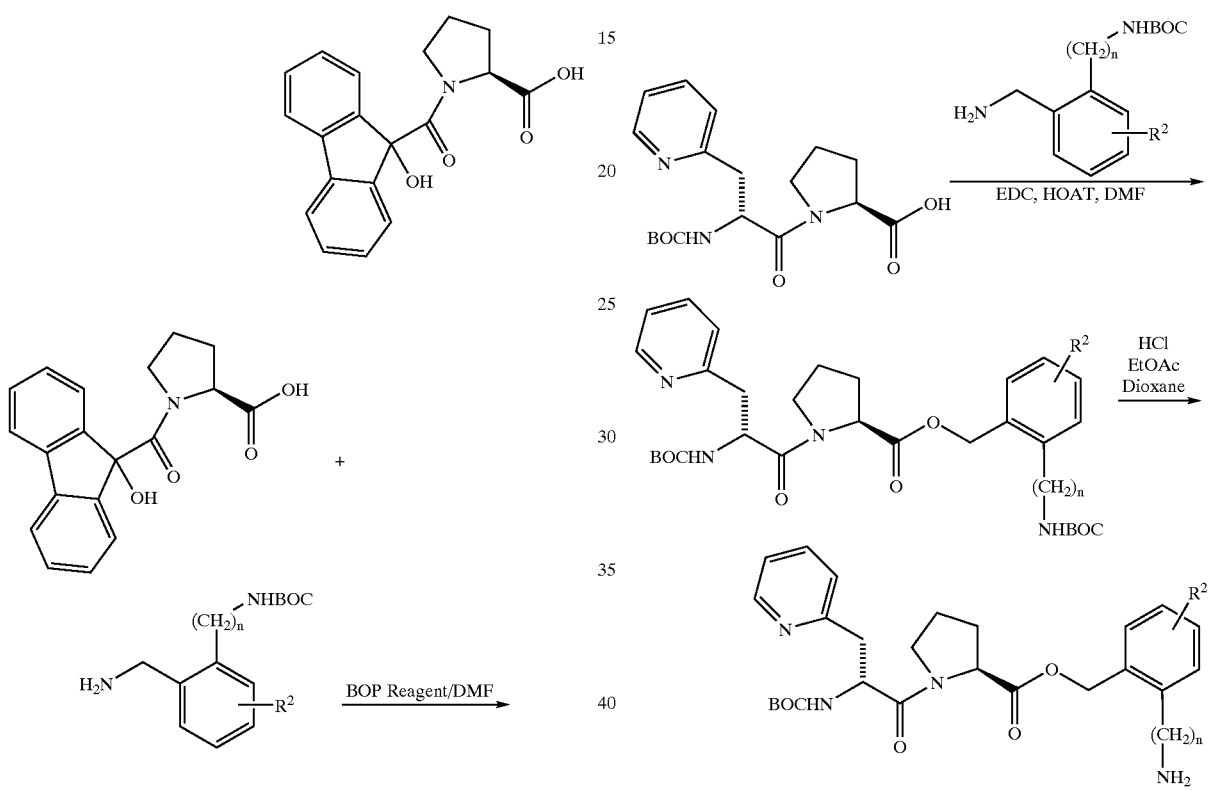
Scheme 12
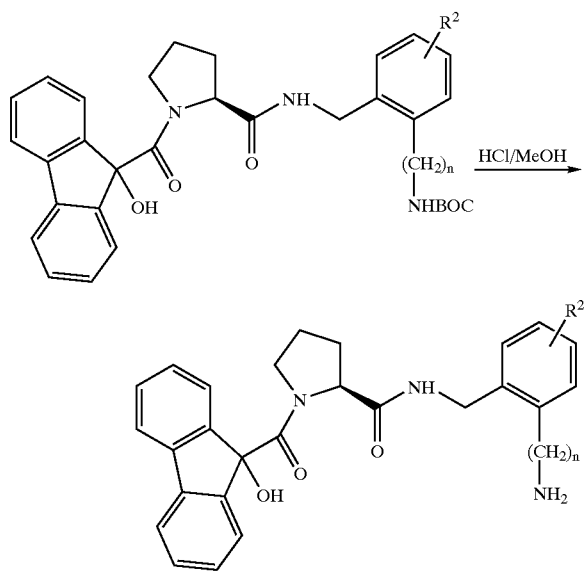

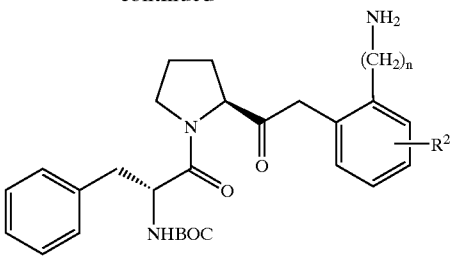

Compounds of the present invention are synthesized using procedures and chemical intermediates which are well known to those of ordinary skill in the art. The compounds of the present invention are essentially comprised of three subunits, referred to as the P1, P2 and P3 subunits, which are connected together by two amide bonds. The central subunit, the P2 subunit, is an amino acid. This P2 amino acid is connected at its carboxy end via an amide bond to the P1 subunit, and this P2 amino acid is connected at its amino end via an amide bond to the P3 subunit. Standard amino acid coupling procedures and protecting group chemistry enables synthesis of the final compounds in either direction, i.e., the P2-P1 amide bond may be formed first (as exemplified in Schemes 1, 2, 4, 6, and 7), followed by formation of the P3-P2 amide bond, or the P3-P2 amide bond may be formed first (as exemplified in Scheme s 3 and 5), followed by formation of the P2-P1 amide bond. Standard protecting group chemistry may be employed, if necessary, in the P1 and P3 subunits to allow selective amide bond formation between the various subunits. After the subunits have been connected via the two amide bonds to give a P3-P2-P1 structure, any additional protecting groups that may present in the P1 and or P3 subunits can be removed using standard procedures to give final compounds. Schemes 1, 2, 4, and 5 show the synthesis of several specific examples of P1 subunits contained in the present invention. These P1 subunits are comprised of a 5-chlorobenzylamine, the amino group of which is connected to the carboxyl end of the P2 amino acid via an amide bond. The 5-chlorobenzylamine P1 subunit is additionally substituted at the 2 position with aminomethyl (Schemes 1, 3, 4, 6, and 7) or aminoethyl groups (Schemes 2 and 5) which may be additionally substituted on the carbon and or nitrogen atoms. The range of aminomethyl and aminoethyl substituent types are fully described in the broadest genus of the present invention, and additional specific substituent types are found in the Experimental Section. The central P2 amino acid subunit can be derived from a cyclic amino acid such as proline (Schemes 1, 2, 3, 4, 5, and 7) or an N-substituted glycine (Scheme 6). The P2 subunit may also be derived from cyclic amino acids of different ring sizes, and the cyclic amino acid P2 subunit may also be substituted with a variety of groups and or contain a double bond as described in the broadest genus of the present invention. For example, proline derivatives substituted with alkyl groups, fluorines, hydroxyl groups, or which contain a double bond in the ring are well known in the literature (for example, see Demange, L., et al. *Tetrahedron Lett.* 1998, 39(10), 1169–1172; Robinson, J., et al. *Tetrahedron* 1998, 54(5), 981–996; Shumacher, K., et al. *Tetrahedron Asymmetry* 1998, 9(1), 47–53; Sibi, M., et al. *Tetrahedron Lett*. 1995, 36(35), 6213–6216; Mack, H., et al. DE 19630082; Moody, C., et al. *Tetrahedron Lett.* 1994, 35(39), 7277–7280; Pedregal, C., et al. *Tetrahedron Lett.* 1994, 35(13), 2053–2056; Soucy, F., et a *Chem. Soc., Perk I* 1991, (11), 2885–2887; U.S. Pat. No. 4,060,603; Holladay, M., et al. *J. Medicinal Chem.* 1991, 34(1), 455–457; Chung, J., et al. *J. Org. Chem.* 1990, 55(1), 270–275; Esch, P., et *Tetrahedron* 1992, 48(22), 4659; Sasaki, A., et al. *J. Org. Chem.* 1997, 62(3), 765–770; Mulzer, J., et al. *Synthesis* 1996, 123) and or are available from commercial sources. Any of these P2 variations, as described in the broadest genus, may be employed for preparing compounds of the present invention. The P3 subunit is a carboxylic acid which is used to acylate the amino end of the central P2 amino acid subunit. Many of these P3 subunits are derived from alpha-amino acids (Schemes 1 and 5) or alpha-hydroxy acids (Schemes 2, 3, 4, 6, and 7). A wide range of P3 subunits may be employed to produce potent thrombin inhibitors as described in the broadest genus of the present invention and as exemplified with additional specific compounds in the Experimental Section.

EXAMPLE 1

3-Pyridin-2-yl-D-alanyl-N-(2-(2-aminoethyl)-5-chlorobenzyl)-L-prolinamide

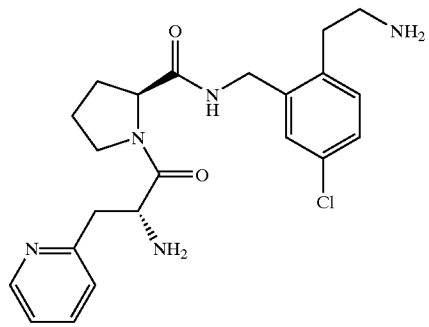

Step 1. Into a stirred solution of 7-chloro-3,4-dihydroisoquinolin-1-one (11.6 g, 12.6 mmol) in 50 mL of anhydrous N,N-dimethylformamide under inert atmosphere at ambient temperature was added diisopropylethylamine (17.0 mL, 95.8 mmol, 1.5 eq), di-tert-butyl dicarbonate (15.33 g, 70.26 mmol, 1.1 eq), and a catalytic amount of 4-(dimethylamino)pyridine. This solution was stirred at ambient temperature for 2 hours, concentrated in vacuo, then partitioned between methylene chloride and water. The organics were dried ($Na_2SO_4$) and concentrated in vacuo. The residue was purified by flash silica gel chromatography using methylene chloride as an eluent. Desired fractions were concentrated in vacuo to afford 2-(tert-butoxycarbonyl)-7-chloro-3,4-dihydro-2H-isoquinolin-1-one as a clear colorless oil (HPLC RT=3.55 min, method A; LC-MS m/z=282.1).

Step 2. Into a stirred solution of 2-(tert-butoxycarbonyl)-7-chloro-3,4-dihydro-2H-isoquinolin-1-one (18.4 g, 64.3 8 mMol) from the previous step in 50 mL of anhydrous tetrahydrofuran under inert atmosphere at 0° C. was added 2.0 M $LiBH_4$ in tetrahydrofuran (64.38 mL, 128.76 mmol, 2 eq). This solution was stirred at 0° C. for 1.5 hours, quenched with saturated ammonium chloride solution, then partitioned between ethyl acetate and water. The organics were dried ($Na_2SO_4$) and concentrated in vacuo. This afforded 2-(2-(tert-butoxycarbonylamino) ethyl)-5-chlorobenzyl alcohol as a clear colorless oil (HPLC RT=3.21 min, method A; LC-MS m/z=286.2).

Step 3. To a solution of 649 mg (2.27 mmol) 2-(2-(tert-butoxycarbonylamino)ethyl)-5-chlorobenzyl alcohol from the previous step in 5.0 mL THF at 0° C. was added 0.674 mL (3.13 mmol) of DPPA and 0.468 mL (3.13 mmol) of DBU and the reaction was stirred at 0° C. for 10 min, then at room temperature. After 3 h the reaction was treated with saturated aqueous sodium carbonate and extracted with ethyl acetate (3×). The organic extracts were combined, washed with brine, dried over sodium sulfate, filtered and concentrated to dryness in vacuo to give 963 mg of a crude oil. Flash chromatography on silica gel (15% ethyl acetate in hexane) gave tert-butyl 2-(2-(tert-butoxycarbonylamino)ethyl)-5-chlorobenzyl azide as a colorless oil: $^1$H NMR (DMSO-d$_6$, 400 MHz): δ 7.44 (d, 1H, J=1.8 Hz), 7.36 (dd, 1H, J=2.0 and 8.2 Hz), 7.26 (d, 1H, J=8.1 Hz), 6.92 (br t, 1H, J=5.5 Hz), 4.53 (s, 2H), 3.10 (dt, 2H, J=6.3 and 7.6 Hz), 2.73 (t, 2H, J=7.3 Hz), 1.36 (s, 9H); MS (Electrospray): M+Na=333.0; TLC R$_f$=0.32 (15% ethyl acetate in hexane).

Step 4. To a solution of 629 mg (2.02 mmol) 2-(2-(tert-butoxycarbonylamino)ethyl)-5-chlorobenzyl azide from the previous step in 30.0 mL THF containing 3.1 mL water was added 1.06 g (4.05 mmol) triphenylphosphine and the reaction was stirred at room temperature overnight. The THF was removed in vacuo and the residual aqueous phase extracted with methylene chloride (3×). The organics were combined, washed with brine, dried over sodium sulfate, filtered and concentrated to dryness in vacuo. Flash chromatography on silica gel (linear gradient from 266/10/1 to 200/10/1 of methylene chloride/methanol/concentrated ammonium hydroxide) gave 2-(2-(tert-butoxycarbonylamino)ethyl)-5-chlorobenzyl amine as a colorless oil: $^1$H NMR (DMSO-d$_6$, 400 MHz): δ 7.45 (d, 1H, J=1.7 Hz), 7.18 (dd, 1H, J=2.1 and 8.2 Hz), 7.12 (d, 1H, J=8.2 Hz), 7.01 (br t, 1H, J=5.2 Hz), 3.73 (s, 2H), 3.07 (dt, 2H, J=6.5 and 7.3 Hz), 2.68 (t, 2H, J=7.4 Hz), 1.36 (s, 9H); MS (Electrospray): M+H=285.1; TLC R$_f$=0.33 (160/10/1 of methylene chloride/methanol/concentrated ammonium hydroxide).

Step 5. To a solution of 1.0 g (3.8 mmol) N-(tert-butoxycarbonyl)-3-pyridin-2-yl-D-alanine in 7 ml DMF was added 0.62 g (3.8 mmol) L-proline methyl ester hydrochloride, 0.52 mL (3.8 mmol) triethylamine, 0.51 g (0.38 mmol) HOAt, and 1.1 g (5.7 mmol) EDC. After 3 h at room temperature, the reaction mixture was diluted with 300 ml EtOAc, washed with 200 ml each of saturated NaHCO$_3$ solution, water, and brine. The organic layer was dried over Na$_2$SO$_4$, filtered and concentrated in vacuo. Purification by automated flash chromatography (ISCO combiflash, 70 g silica gel, linear gradient 50–100% EtOAc:hexane 30 min then 2–10% MeOH/EtOAc at 60 mL/min) afforded 0.9 g N-(tert-butoxycarbonyl)-3-pyridin-2-yl-D-alanyl-L-proline methyl ester of which 0.44 g (1.2 mmol) was dissolved in 7 mL MeOH. To this was added 1.2 mL (1.2 mmol, 1M aqueous solution) LiOH and the reaction mixture stirred 6 hours, then another 0.12 mL (0.12 mmol, 1M aqueous solution) portion of LiOH was added and the reaction mixture stirred an additional 16 hrs before addition of 0.12 mL conc. HCl (1.44 mmol, 12M aqueous solution) was added and the reaction concentrated to give N-(tert-butoxycarbonyl)-3-pyridin-2-yl-D-alanyl-L-proline as a foam. $^1$H NMR (CD$_3$OD, 400 MHz) δ 8.47 (m, 1H); 7.78 (m, 1H); 7.34 (m, 2H,); 4.31 (dd, 1H, J=4.21, 8.8 Hz); 3.78 (br m, 1H); 3.54 (br m, 1H); 3.17 (dd, 1H, J=6.23 and 13.5 Hz); 3.02 (m, 2H); 2.3–1.8 (br m, 4H); 1.35 (s, 9H); electrospray mass spectrum 364.

Step 6. The title compound was prepared from 2-(2-(tert-butoxycarbonylamino)ethyl)-5-chlorobenzyl amine from Step 4 and N-(tert-butoxycarbonyl)-3-pyridin-2-yl-D-alanyl-L-proline from Step 5 using a similar coupling, deprotection, and purification procedures as described in Steps 7 and 8 of Example 15: $^1$H NMR (DMSO-d$_6$, 400 MHz): δ 8.84 (t, 1H, J=5.8 Hz), 8.72–8.62 (br m, 4H), 8.12–8.00 (br m, 4H), 7.54 (d, 2H, J=7.9 Hz), 7.33–7.19 (m, 4H), 4.58 (br s, 1H), 4.40–4.20 (m, 3H), 3.88–3.80 (m, 2H), 3.43–3.28 (m, 3H), 2.96 (br s, 4H), 1.90–1.75 (br m, 2H); MS (Electrospray): M+H=430.2; TLC R$_f$=0.13 (80/10/1 of methylene chloride/methanol/concentrated ammonium hydroxide).

EXAMPLE 2

1-((2R)-2-Hydroxy-2-phenylpropanoyl)-N-(2-(2-aminoethyl)-5-chlorobenzyl)-L-prolinamide

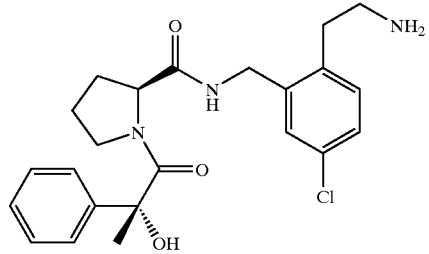

Step 1. To a stirred solution of 2-(2-(tert-butyloxycarbonylamino)ethyl)-5-chlorobenzylamine (0.38 g, 1.4 mmol), Fmoc-L-Proline (0.49 g, 1.4 mmol), and HOBT hydrate (0.22 g, 1.5 mmol) in DMF (6 mL) was added EDC (0.35 g, 1.8 mmol). The pH of the solution was slowly raised to pH 6 (as measured on wetted E. Merck pH indicator strips) by the gradual addition of diisopropylethylamine (~0.2 mL). At 3 hours reaction time, HPLC analysis indicated complete consumption of the benzylamine starting material. The solvent was removed on a rotary evaporator (bath temp 30° C., ~0.5 torr) and the residue was partitioned between EtOAc and water. The organic phase was dried (MgSO$_4$), filtered, and the solvent was removed on a rotary evaporator. The residue purified by flash silica gel column chromatography using 1:1, 3:1, 1:0 EtOAc:hexanes as eluant. Product-containing fractions were combined and the solvent was removed under reduced pressure to give 1-fluroenylmethoxycarbonyl-N-(2-(2-(tert-butyloxycarbonylamino)ethyl)-5-chlorobenzyl)-L-prolinamide as a foam (0.75 g; 90%; TLC R$_f$=0.5 (1:1 EtOAc:hexanes); HPLC RT=3.95 min, method A; LC-MS m/z=604).

Step 2. To a stirred solution of 1-fluroenylmethoxycarbonyl-N-(2-(2-(tert-butyloxycarbonylamino)ethyl)-5-chlorobenzyl)-L-prolinamide from the previous step (0.70 g, 1.2 mmol) in DMF (10 mL) was added piperidine (2 mL). At 15 min reaction time, HPLC analysis indicated complete consumption of the starting material. The solvent and excess piperidine were removed on a rotary evaporator (bath temp 40° C., ~0.5 torr). The residue was purified by flash chromatography using a gradient elution of 95:5 to 90:10 to 85:15 CH$_2$Cl$_2$:A (A=95:5 MeOH:NH$_4$OH). L-Prolin-N-(2-(2-(tert-butyloxycarbonylamino)ethyl)-5-chlorobenzyl)amide was obtained as a gum (0.35 g; TLC R$_f$=0.3 (90:10:0.5 CH$_2$Cl$_2$:MeOH:NH$_4$OH; iodine visualization); HPLC RT=2.83 min, method A; LC-MS m/z=382).

Step 3. To a solution of L-prolin-N-(2-(2-(tert-butyloxycarbonylamino)ethyl)-5-chlorobenzyl)amide (0.50 g, 1.31 mmol), 1-hydroxybenzotriazole hydrate (0.215 g, 1.4), and 2R-hydroxy-2-phenylpropionic acid (0.215 g, 1.3 mmol) in DMF (15 mL) was added EDC (0.29 g, 1.5 mmol). To the stirred solution was added DIEA (approximately 0.14 mL) until the solution measured pH 6 on wetted E. Merck pH indicator strips. The mixture was stirred for 18 h at ambient temperature. The solvent was removed under reduced pressure and the residue was partitioned between EtOAc (100 mL) and saturated aqueous sodium bicarbonate solution (50 mL). The organic phase was separated, dried (MgSO$_4$), filtered, and concentrated under reduced pressure. The residue was purified by flash silica gel column chromatography using 98:2 CH$_2$Cl$_2$:MeOH as eluant. The product-containing fractions were combined and removal of the solvent under reduced pressure gave 1-((2R)-2-hydroxy-2-phenylpropanoyl)-N-(2-(2-(tert-butyloxycarbonylamino)ethyl)-5-chlorobenzyl)-L-prolinamide as a gum (0.62 g; TLC R$_f$=0.3 (98:2 CH$_2$Cl$_2$:MeOH); HPLC RT=3.46 min, method A; LC-MS m/z=530).

Step 4. Into a stirred solution of 1-((2R)-2-hydroxy-2-phenylpropanoyl)-N-(2-(2-(tert-butyloxycarbonylamino)ethyl)-5-chlorobenzyl)-L-prolinamide from the previous step (0.62 g, 1.2 mmol) in EtOAc (20 mL) at 0° C. was bubbled HCl gas for 15 min. The mixture was stirred at 0° C. for 2 h, then the solvent and excess HCl were removed under reduced pressure. The residue was purified by flash silica gel column chromatography using a gradient elution of 5% to 10% to 15% A:CH$_2$Cl$_2$ (A=95:5 MeOH:NH$_4$OH). The product-containing fractions were combined to give the title compound as an amorphous solid after removal of solvents under reduced pressure (TLC R$_f$=0.3 (90:10:0.5 CH$_2$Cl$_2$:MeOH:NH$_4$OH); HPLC RT=2.66 min, method A; LC-MS m/z=430).

EXAMPLE 3

1-((2R)-2-Hydroxy-2-phenylpropanoyl)-N-(2-(2-(methylsulfonylamino)ethyl)-5-chlorobenzyl)-L-prolinamide

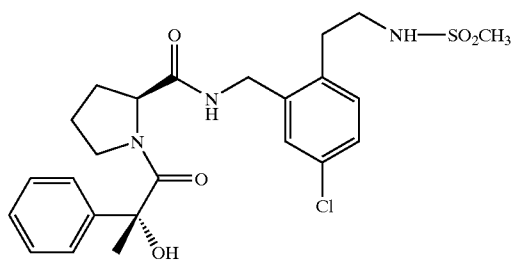

To a stirred solution of 1-((2R)-2-hydroxy-2-phenylpropanoyl)-N-(2-(2-aminoethyl)-5-chlorobenzyl)-L-prolinamide (90 mg, 0.21 mmol) in CH$_2$Cl$_2$ (2 mL) was added triethylamine (50 microliters, 0.35 mmol) and methanesulfonyl chloride (16 microliters, 0.21 mmol). The mixture was stirred at ambient temperature for 30 min. The mixture was diluted with CH$_2$Cl$_2$ (20 mL) and washed with saturated aqueous sodium bicarbonate solution (10 mL). The organic phase was separated, dried (MgSO$_4$), filtered, and the solvent was removed under reduced pressure to give the title compound as an amorphous solid (TLC R$_f$=0.2 (98:2 CH$_2$Cl$_2$:MeOH); HPLC RT=3.05 min, method A; LC-MS m/z=508).

EXAMPLE 4

1-((2R)-2-Hydroxy-2-phenylpropanoyl)-N-(2-(2-(ethoxycarbonylethylamino)ethyl)-5-chlorobenzyl)-L-prolinamide

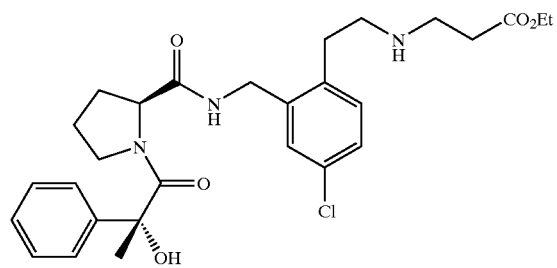

To a stirred solution of 1-((2R)-2-hydroxy-2-phenylpropanoyl)-N-(2-(2-aminoethyl)-5-chlorobenzyl)-L-prolinamide (90 mg, 0.21 mmol) in EtOH (2 mL) was added ethyl acrylate (25 microliters, 0.22 mmol). The mixture was stirred at ambient temperature for 48 h. The solvent was removed under reduced pressure and the residue was purified by flash silica gel column chromatography using a gradient elution of 5% to 7.5% MeOH in CH$_2$Cl$_2$. The product-containing fractions were combined to give the title compound as an amorphous solid upon removal of the solvents in vacuo (TLC R$_f$=0.4 (95:5 CH$_2$Cl$_2$:MeOH); HPLC RT=2.95 min, method A; LC-MS m/z=530).

EXAMPLE 5

1-((2R)-2-Hydroxy-2-phenylpropanoyl)-N-(2-(2-(carboxyethylamino)ethyl)-5-chlorobenzyl)-L-prolinamide

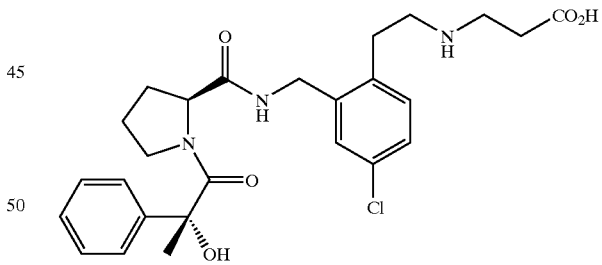

To a stirred solution of 1-((2R)-2-hydroxy-2-phenylpropanoyl)-N-(2-(2-(ethoxycarbonylethylamino)ethyl)-5-chlorobenzyl)-L-prolinamide (60 mg, 0.11 mmol) in EtOH (2 mL) was added aqueous NaOH (45 microliters of a 3.0 molar solution, 0.135 mmol). The mixture was stirred at ambient temperature for 48 h. The solvent was removed under reduced pressure and the residue was purified by preparative reverse-phase HPLC using an acetonitrile:water: 0.1% TFA gradient. The product-containing fractions were combined and lyophilized to give the TFA salt of the title compound as a gum (HPLC RT=2.72 min, method A; LC-MS m/z=502).

EXAMPLE 6

1-((2R)-2-Cyclohexyl-2-hydroxyethanoyl)-N-(2-(1-amino-2,2,2-trifluoroethyl)-5-chlorobenzyl)-L-prolinamide

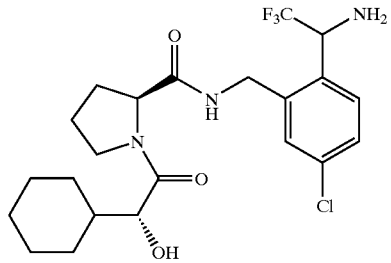

Preparation of N-(4-methoxyphenyl)-N-(-2,2,2-trifluoroethylidene)amine: Ingrassia, Laurent; Mulliez, Michel. Expedient synthesis of perhalo aldehyde N-acyl hemiaminals. Synthesis (1999), (10), 1731–1738.

Step 1. A solution of 2-chloro-5-iodobenzyl alcohol (0.537 g, 2.0 mmol) in THF (10 mL) was added to sodium hydride (88 mg of a 60% dispersion in mineral oil, 2.2 mmol) at 0° C. with stirring under nitrogen. After 5 min the mixture was cooled to −78° C. and n-butyl-lithium (2.5 M in hexanes, 1.66 mL, 4.15 mmol) was added over 6 min. After a further 5 min a solution of N-(4-methoxyphenyl)-N-(-2,2,2-trifluoroethylidene)amine (0.406 g, 2.0 mmol) in THF (2 mL) was added over 5 min. After a further 5 min the reaction was quenched with saturated ammonium chloride solution and the mixture was warmed to ambient temperature and partitioned between ethyl acetate and brine. The organic layer was dried ($Na_2SO_4$) and evaporated to a gum which was purified by chromatography on silica (eluting with 2% methanol/chloroform) to give N-{1-[4-chloro-2-(hydroxymethyl)phenyl]-2,2,2-trifluoroethyl}-N-(4-methoxyphenyl)amine as a 1:1.7 mixture with 3-chlorobenzyl alcohol (0.38 g) as a gum: MS 346.4 (M+1).

Step 2. DBU (0.483 mL, 3.23 mmol) was added to a stirred solution of N-{1-[4-chloro-2-(hydroxymethyl)phenyl]-2,2,2-trifluoroethyl}-N-(4-methoxyphenyl)amine (0.46 g of a 1:1.7 mixture with 3-chlorobenzyl alcohol) and DPPA (0.696 mL, 3.23 mmol) in THF (4 mL) at 0° C. The mixture was warmed to ambient temperature and after 3 h was partitioned between ether and water. The organic layer was washed with 1 M sodium hydroxide solution and brine, dried ($Na_2SO_4$) and evaporated to an oil which was purified by flash column chromatography on silica (eluting with 5% methylene chloride, 0–15% ethyl acetate/hexanes) to give N-{1-[2-(azidomethyl)-4-chlorophenyl]-2,2,2-trifluoroethyl}-N-(4-methoxyphenyl)amine (0.199 g) as an oil: $^1$H NMR ($CDCl_3$, 400 MHz) δ 3.72 (s, 3H), 3.97 (d, J=7.3 Hz, 1H), 4.37 (d, J=14.1 Hz, 1H), 4.48 (d, J=14.1 Hz, 1H), 5.20 (pentet, J=7.1 Hz, 1H), 6.63 (d, J=9.0 Hz, 2H), 6.75 (d, J=9.0 Hz, 2H), 7.37 (m, 2H), 7.55 (d, J=8.2 Hz, 1H).

Step 3. Triphenylphosphine (0.157 mg, 0.60 mmol) was added to a stirred solution of N-{1-[2-(azidomethyl)-4-chlorophenyl]-2,2,2-trifluoroethyl}-N-(4-methoxyphenyl)amine (0.199 mg, 0.538 mmol) in water (1 mL) and water (30 μL). After 16 h the volatiles were evaporated in vacuo, the residue was dissolved in methanol (1 mL), potassium hydroxide (1 pellet) was added and the mixture was stirred at 60° C. for 15 min. The reaction mixture was then cooled and partitioned between ether and water. The organic layer was dried ($Na_2SO_4$) and evaporated to a gum. EDC (154.7 mg, 0.81 mmol) was added to a stirred mixture of this crude amine, N-Boc-L-proline (115.8 mg, 0.54 mmol) and HOAT (36.6 mg, 0.27 mmol) in DMF (3 mL). After 16 h, the mixture was concentrated and the residue was partitioned between EtOAc and 10% $NaHCO_3$ solution. The organic layer was washed with water and brine, dried ($Na_2SO_4$) and evaporated to a gum. This was purified by chromatography on silica gel (eluting with $EtOAc/CHCl_3$, 1:5) to give N-(5-chloro-2-{1-[(4-methoxyphenyl)amino]-2,2,2-trifluoroethyl}benzyl)-1-(tert-butoxycarbonyl)-L-prolinamide (196 m g) as a glass: MS: 542.3 (M+1).

Step 4. TFA (2.5 mL) was added to a stirred solution of N-(5-chloro-2-{[(4-methoxyphenyl)amino]-2,2,2-trifluoroethyl}benzyl)-1-(tert-butoxycarbonyl)-L-prolinamide (196 mg, 0.36 mmol) in $CH_2Cl_2$ (1.5 ml) at 0° C. After 1 h the solution was concentrated and the residue was partitioned between $CH_2Cl_2$ and 10% $NaHCO_3$ solution. The organic layer was washed with water and brine, dried ($Na_2SO_4$) and evaporated to give N-(5-chloro-2-{1-[(4-methoxyphenyl)amino]-2-trifluoroethyl}benzyl)-L-prolinamide (136 mg) as a glass: $^1$H NMR ($CDCl_3$, 400 MHz) δ 1.67 (m, 2H), 1.82–1.94 (m, 3H), 2.16 (m, 1H), 2.81 (m, 1H), 2.95 (m, 1H), 3.65 (m, 0.5H), 3.72 (s, 3H), 3.77 (m, 0.5H), 3.98 (d, J=7.2 Hz, 0.5H), 4.03 (d, J=7.6 Hz, 0.5H), 4.36 (m, 1H), 4.62 (m, 1H), 5.26 (m, 1H), 6.65–6.77 (m, 4H), 7.33 (m, 2H), 7.49 (d, J=8.4 Hz, 0.5H), 7.51 (d, J=8.3 Hz, 0.5H), 7.94 (br s, 0.5H), 8.05 (br s, 0.5H).

Step 5. EDC (44.0 mg, 0.23 mmol) was added to a stirred mixture of N-(5-chloro -2-{1-[(4-methoxyphenyl)amino]-2,2,2-trifluoroethyl}benzyl)-L-prolinamide (68 mg, 0.15 mmol), (R)-(−)-hexahydromandelic acid (24.2 mg, 0.15 mmol) and HOAT (10.4 mg, 0.076 mmol), in DMF (2 mL). After 16 h, the mixture was concentrated and the residue was partitioned between EtOAc and 10% $NaHCO_3$ solution. The organic layer was washed with water and brine, dried ($Na_2SO_4$) and evaporated. The residue was purified by chromatography on silica (eluting with $EtOAc/CHCl_3$, 1:2) to give N-(5-chloro-2-{1-[(4-methoxyphenyl)amino]-2,2,2-trifluoroethyl)}benzyl)-1-[(2R)-2-cyclohexyl-2-hydroxyethanoyl]-L-prolinamide (44.4 mg) as a glass: MS: 582.4 (M+1).

Step 6. A solution of CAN (83.6 mg, 0.15 mmol) in (1.5 mL) was added to a stirred solution of N-(5-chloro-2-{1-[(4-methoxyphenyl)amino]-2,2,2-trifluoroethyl}benzyl)-1-[(2R)-2-cyclohexyl-2-hydroxyethanoyl]-L-prolinamide (44.4 mg, 0.076 mmol) in $CH_3CN$ (2 mL) at 0° C. After 1 hr the reaction mixture was partitioned between water and $CH_2Cl_2$. The aqueous layer was adjusted to pH=8.5 with 1M NaOH solution and then was saturated with NaCl. The resulting mixture was extracted with $CH_2Cl_2$ and organic layer was washed with brine, dried ($Na_2SO_4$) and evaporated. The residue was purified by chromatography on silica (ammonia saturated $CHCl_3$/MeOH, 98:2) to give the title compound as a glass: HRMS (FAB) calcd $C_{22}H_{30}ClF_3N_3O_3$ (M+1) 476.1922, found 476.1926.

EXAMPLE 7

1-((2R)-2-Cyclohexyl-2-hydroxyethanoyl)-N-(2-(1-amino-2,2-difluoroethyl)-5-chlorobenzyl)-L-prolinamide

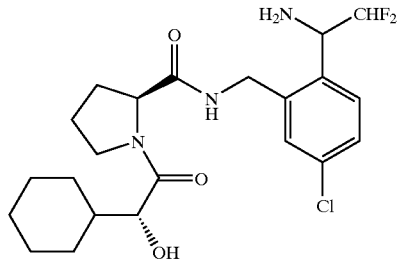

N-(4-methoxyphenyl)amine was prepared from difluoroacetaldehyde ethyl hemiacetal by the method described for the synthesis of N-(4-methoxyphenyl)-N-(2,2,2-tifluoroethylidene)amine: $^1$H NMR (CDCl$_3$, 400 MHz) δ 3.83 (s, 3H), 6.16 (dt, J=5.3 and 54.9 Hz, 1H), 6.93 (m, 2H), 7.23 (m, 2H), 7.85 (dt, J=2.6 and 5.3 Hz, 1H).

Step 1. A solution of 5-chloro-2-iodobenzylalcohol (0.948 g, 3.53 mmol) in dry THF (27 mL) was added, rinsing with dry THF, to a stirred suspension of NaH (0.155 g, 3.89 mmol) in dry THF (9 mL) at 0° C. After 5 min the mixture was cooled to −78° C. and n-butyl-lithium (2.5 M in hexanes, 2.97 mL, 7 mmol) was added dropwise over 5 minutes. After a further 10 min, a solution of N-(2,2-difluoroethylidene)-N-(4-methoxyphenyl)amine (0.654 g, 3.53 mmol) in dry THF (9 mL) was added. After 1 h the mixture was quenched with excess saturated aqueous NH$_4$Cl at −78° C. then was stirred at ambient temperature for 15 min. The solution was partitioned between EtOAc and brine. The EtOAc layer was dried (Na$_2$SO$_4$) and evaporated in vacuo and the residue was purified by flash column chromatography on silica (eluting with 5% methylene chloride, 5–30% ethyl acetate/hexanes gradient) to give (5-chloro-2-{2,2-difluoro-1-[(4-methoxyphenyl)amino]ethyl}phenyl)methanol (0.439 g) as an oil: MS 328.4 (M+1); $^1$H NMR (CDCl$_3$, 400 MHz) δ 2.00 (br s, 1H), 3.70 (s, 3H), 4.14 (br s, 1H), 4.82 (m, 2H), 5.02 (m, 1H), 6.08 (dt, J=3.0 Hz, 56.0 Hz, 1H), 6.57 (d, J=9.0 Hz, 2H), 6.71 (d, J=9.0 Hz), 2H), 7.29 (dd, J=2.2 and 8.4 Hz, 1H), 7.40 (d, J=2.2 Hz, 1H), 7.47 (d, J=8.4 Hz, 1H).

Step 2. DBU (0.20 mL, 1.34 mmol) was added to a stirred solution of (5-chloro-2-{2,2-difluoro-1-[(4-methoxyphenyl)amino]ethyl}phenyl)methanol (0.439 g, 1.34 mmol) and DPPA (0.29 mL, 1.34 mmol) in THF (1.7 mL) at 0° C. and the mixture was warmed to ambient temperature. After 3 h the solution was partitioned between EtOAc (20 mL) and water (10 mL). The EtOAc layer was washed with 1M NaOH (10 mL) and brine (10 mL), dried (Na$_2$SO$_4$) and reduced in vacuo to give N-{1-[2-(azidomethyl)-4-chlorophenyl]-2,2-difluoroethyl}-N-(4-methoxyphenyl)amine (0.463 g) as an oil: MS 353.5 (M+1).

Step 3. Triphenylphosphine (0.344 g, 1.31 mmol) was added to a stirred solution of N-{1-[2-(azidomethyl)-4-chlorophenyl]-2,2-difluoroethyl}-N-(4-methoxyphenyl)amine (0.463 g, 1.31 mmol) and water (0.02 mL, 1.31 mmol) in THF (2.6 mL). The solution was stirred at ambient temperature for 2 h and the solvent was removed under reduced pressure. The residue was dissolved in MeOH (5 mL). One KOH pellet was added and the mixture was refluxed for 5 min. The solvent was removed under reduced pressure and the residue was partitioned between EtOAc and 1M HCl. The aqueous layer was basicified with 1M NaOH and the solution was extracted with diethyl ether. The organic phase was dried (Na$_2$SO$_4$) and reduced in vacuo and the residue was purified by column chromatography on silica (eluting with ammonium hydroxide/methanol/chloroform, 1:9:90) to give N-{1-[2-(aminomethyl)-4-chlorophenyl]-2,2-difluoroethyl}-N-(4-methoxyphenyl)amine (0.314 g) as an oil: MS 327.5 (M+1).

Step 4. EDC (0.171 g, 1.25 mmol) was added to a stirred mixture of N-{1-[2-(aminomethyl)-4-chlorophenyl]-2,2-difluoroethyl}-N-(4-methoxyphenyl)amine (0.314 g, 0.96 mmol), N-BOC-L-proline (0.207 g, 0.96 mmol) and HOAT (0.171, 1.25 mmol) in DMF (2.0 mL). After 18 h the mixture was partitioned between EtOAc and water. The organic layer was washed with 1M citric acid, saturated aqueous NaHCO$_3$ and brine, dried (Na$_2$SO$_4$) and reduced in vacuo and the residue was purified by flash column chromatography on silica (eluting with 5% methylene chloride, 10–50% ethyl acetate/hexanes gradient) to give N-(5-chloro-2-{2,2-difluoro-1-[(4-methoxyphenyl)amino]ethyl}benzyl)-1-(tert-butoxycarbonyl)-L-prolinamide (0.256 g) as a foam; LC-MS m/z=524.3.

Step 5. TFA (2.50 mL) was added to a stirred solution of N-(5-chloro-2-{2,2-difluoro-1[(4-methoxyphenyl)amino]ethyl}benzyl)-1-(tert-butoxycarbonyl)-L-prolinamide (0.256 g, 0.49 mmol) in CH$_2$Cl$_2$ (5.0 mL). After 1 h the solvent was evaporated in vacuo and the residue was partitioned between EtOAc and saturated aqueous Na$_2$CO$_3$. The organic layer was dried (Na$_2$SO$_4$) and evaporated in vacuo to give the N-(5-Chloro-2-{2,2-difluoro-1-[(4-methoxyphenyl)amino]ethyl}benzyl)-L-prolinamide (0.207 g) as a gum.

Step 6. EDC (0.0469 g, 0.24 mmol was added to a stirred mixture of N-(5-chloro-2-{2,2-difluoro-1-[(4-methoxyphenyl)amino]ethyl}benzyl)-L-prolinamide (0.0691 g, 0.16 mmol), (R)-hexahydromandelic acid (0.0258 g, 0.16 mmol) and HOAT (0.0111 g, 0.08 mmol) in DMF (2.0 mL). After 2 h the mixture was partitioned between EtOAc and water. The organic layer was washed with brine, dried (Na$_2$SO$_4$) and evaporated in vacuo and the residue was purified by flash column chromatography on silica (eluting with 5% methylene chloride, 10–70% ethyl acetate/hexanes gradient) to give N-(5-chloro-2-{2,2-difluoro-1-[(4-methoxyphenyl)amino]ethyl}benzyl)-1-[(2R)-$^2$-cyclohexyl-2-hydroxyethanoyl]-L-prolinamide (0.0332 g) as a white solid; LC-MS m/z=564.4.

Step 7. A solution of CAN (0.0647 g, 0.12 mmol) in water (0.4 mL) was added to a stirred solution of N-(5-chloro-2-{2,2-difluoro-1-[(4-methoxyphenyl)amino]ethyl}benzyl)-1-[(2R)-2-cyclohexyl-2-hydroxyethanoyl]-L-prolinamide (0.0332 g, 0.06 mmol) in CH$_3$CN (1.5 mL) at 0° C. and the solution was warmed to ambient temperature. After 4 h the solution was partitioned between EtOAc and 10% aqueous NH$_4$OH. The resulting two phase suspension was filtered and the EtOAc layer was washed with 10% sodium sulfite solution and brine, dried (Na$_2$SO$_4$) and evaporated in vacuo. The residue was purified by column chromatography on silica (eluting with 1–10% of 10% ammonium hydroxide in methanol/chloroform gradient) to give the title compound as a gum: LC-MS m/z=458.4.

EXAMPLE 8

N-(5-Chloro-2-((3,3-difluoroazetidin-1-yl)methyl)benzyl)-1-((2R)-cyclohexyl-2-hydroxyethanoyl)-L-prolinamide

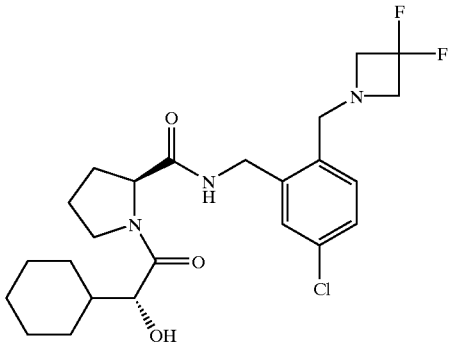

Preparation of 3,3-difluoroazetidine hydrochloride: Carling, William Robert; Mitchinson, Andrew; Russell, Michael Geoffrey Neil; Street, Leslie Joseph. Preparation of triazolylmethoxy-triazolopyridazines as GABAA receptor ligands. PCT Int. Appl. (2000), WO 0047582 A1 20000817.

Preparation of 2-bromomethyl-5-chlorobenzonitrile: Nannini, G.; Giraldi, P. N.; Molgora, G.; Biasoli, G.; Spinelli, F.; Logemann, W.; Dradi, E.; Zanni, G.; Buttinoni, A.; Tommasini, R. New analgesic-antiinflammatory drugs. 1-Oxo-2-substituted isoindoline derivatives. Arzneim.-Forsch. (1973), 23(8), 1090–100.

Step 1. DIEA (0.196 mL, 1.12 mmol) was added to a stirred mixture of 3,3-difluoroazetidine hydrochloride (64.8 mg, 0.50 mmol) and 2-bromomethyl-5-chlorobenzonitrile (121.0 mg, 0.52 mmol) in $CH_2Cl_2$ (7 mL). After 16 h the reaction was partitioned between EtOAc and water. The organic layer was washed with water and brine, dried ($Na_2SO_4$) and evaporated. The residue was partitioned between 1N HCl and ether. The aqueous layer was made neutral with $NaHCO_3$ and was extracted with $CH_2Cl_2$. The organic layer was dried with $Na_2SO_4$ and then evaporated to give 5-chloro-2-[(3,3-difluoroazetidin-1-yl)methyl]benzonitrile (67.8 mg) as a glass: $^1H$ NMR ($CDCl_3$, 400 MHz) δ 3.68 (t, J=11.9 Hz, 4H), 3.93 (s, 2H), 7.54 (m, 2H), 7.63 (d, J=2.2 Hz, 1H).

Step 2. 1M LAH in ether (0.42 mL, 0.42 mmol) was added to a stirred solution of 5-chloro-2-[(3,3-difluoroazetidin-1-yl)methyl]benzonitrile (67.8 mg, 0.28 mmol) in ether (5 ml) at 0° C. After 1 h the reaction was treated successively with water (16 μL), 15% NaOH (16 μL), and water (32 μL). After stirring for 15 min the mixture was filtered and the filtrate was evaporated. The residue was partitioned between 1N HCl and ether. The aqueous layer was made neutral with $NaHCO_3$ and was extracted with $CH_2Cl_2$. The organic layer was dried with $Na_2SO_4$ and evaporated to give 5-chloro-2-[(3,3-difluoroazetidin-1-yl)methyl]benzylamine (61 mg) as a glass: $^1H$ NMR ($CDCl_3$, 400 MHz) δ 3.56 (t, J=11.9 Hz, 4H), 3.73 (s, 2H), 3.85 (s, 2H), 7.26 (m, 3H).

Step 3. EDC (80.2 mg, 0.42 mmol) was added to a stirred mixture of 5-chloro-2-[(3,3-difluoroazetidin-1-yl)methyl]benzylamine (68.8 mg, 0.28 mmol), N-BOC-L-proline (60.0 mg, 0.28 mmol) and HOAT (19.0 mg, 0.14 mmol) in DMF (2.5 mL). After 66 h the reaction mixture was concentrated and the residue was partitioned between EtOAc and 10% $NaHCO_3$. The organic layer was washed with water and brine, dried ($Na_2SO_4$) and evaporated. The residue was purified by chromatography on silica (eluting with EtOAc/$CHCl_3$, 1:5) to give N-{5-chloro-2-[(3,3-difluoroazetidin-1-yl)methyl]benzyl}-1-(tert-butoxycarbonyl)-L-prolinamide (64.2 mg) as a glass: MS: 444.4 (M+1).

Step 4. TFA (1 mL) was added to a stirred solution of N-{5-chloro-2-[(3,3-difluoroazetidin-1-yl)methyl]benzyl}-1-(tert-butoxycarbonyl)-L-prolinamide (64.2 mg, 0.14 mmol) in $CH_2Cl_2$ (2 ml) at 0° C. After 3 h, another 0.3 mL TFA was added. After 30 additional min the reaction mixture was concentrated and the residue was partitioned between $CH_2Cl_2$ and 10% $NaHCO_3$. The $CH_2Cl_2$ layer was washed with water and brine, dried ($Na_2SO_4$) and evaporated to give N-{5-chloro-2-[(3,3-difluoroazetidin-1-yl)methyl]benzyl}-L-prolinamide (45.0 mg) as a glass: $^1H$ NMR ($CDCl_3$, 400 MHz) δ 1.70 (m, 2H), 1.90 (m, 2H), 2.16 (m, 1H), 2.85–3.04 (m, 2H), 3.58 (t, J=12.1 Hz, 4H), 3.73 (m, 3H), 4.37–4.52 (m, 2H), 7.19 (m, 2H), 7.32 (d, J=2.19 Hz, 1H), 8.45 (br s, 1H).

Step 5. EDC (37.6 mg, 0.20 mmol) was added to a stirred mixture of N-{5-chloro-2-[(3,3-difluoroazetidin-1-yl)methyl]benzyl}-L-proline (45.0 mg, 0.13 mmol), (R)-(-)-hexahydromandelic acid (21.7 mg, 0.14 mmol) and HOAT (8.9 mg, 0.65 mmol) in DMF (2 mL). After 4 h the reaction mixture was concentrated and the residue was partitioned between EtOAc and 10% $NaHCO_3$. The organic layer was washed with water and brine, dried ($Na_2SO_4$) and evaporated. The residue was purified by chromatography on silica (eluting with $CHCl_3$/MeOH, 98:2), to give the title compound as a glass: HRMS (FAB) calcd $C_{24}H_{33}ClF2N_3O_3$ (M+1) 484.2173, found 484.2140.

EXAMPLE 9

1-((2R)-2-Amino-2-cyclohexylethanoy)-N-(2-(2-amino-3,3-difluoropropyl)-5-chlorobenzyl)-L-prolinamide

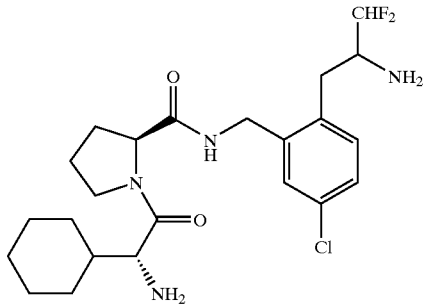

Step 1. A solution of LAH (1 M in ether, 40 mL) was added to a stirred solution of 5-chloro-2-methylbenzonitrile (3.03 g, 20.0 mmol) in $Et_2O$ (10 mL) at 0° C. and the resulting solution was warmed to ambient temperature. After 30 min the solution was cooled to 0° C. and water (1.52 mL), 15% NaOH (1.52 mL) and water (4.56 mL) were added successively. The solids were removed by filtration and the filtrate was evaporated in vacuo to give 5-chloro-2-methylbenzylamine (3.11 g) as an oil.

Step 2. $Boc_2O$ (5.24 g, 24.0 mmol) was added to a stirred solution of 5-chloro-2-methylbenzylamine (3.11 g, 20.0 mmol) in $CH_2Cl_2$ (20 mL). After 30 min the solution was evaporated in vacuo and the residue was purified by flash column chromatography on silica (eluting with 5% methylene chloride, 5–15% ethyl acetate/hexanes gradient) to give tert-butyl 5-chloro-2-methylbenzylcarbamate (1.78 g) as a solid; $^1$H NMR (CDCl$_3$, 400 MHz) δ 1.47 (s, 9H), 2.27 (s, 3H), 4.28 (d, J=5.3 Hz, 1H), 4.73 (br s, 1H), 7.08 (d, J=8.2 Hz, 1H), 7.15 (dd, J=2.0 and 8.2 Hz, 1H), 7.22 (s, 1H).

Step 3. sec-Butyl-lithium (1.3 M in cyclohexane, 10.72 mL) was added to a stirred solution of tert-butyl 5-chloro-2-methylbenzylcarbamate (1.781 g, 6.96 mmol) in THF (14 mL) at −78° C. under nitrogen to give a deep red solution. After 10 min N-(-2,2-difluoroethylidene)-N-(4-methoxyphenyl)amine (1.29 g, 6.96 mmol) was added and after a further 5 min the solution was quenched with excess saturated aqueous NH$_4$Cl and warmed to ambient temperature. The solution was partitioned between EtOAc and brine. The organic layer was dried (Na$_2$SO$_4$) and evaporated in vacuo. The residue was purified by flash column chromatography on silica (eluting with 5% methylene chloride, 5–15% ethyl acetate/hexanes gradient) to give tert-butyl 5-chloro-2-{3,3-difluoro-2-[(4-methoxyphenyl)amino]propyl}benzylcarbamate (0.516 g) as a foam; MS m/z=441.1.

Step 4. TFA (5.2 mL) was added to a stirred solution of tert-butyl 5-chloro-2-{3,3-difluoro-2-[(4-methoxyphenyl)amino]propyl}benzylcarbamate (0.516 g, 1.17 mmol) in CH$_2$Cl$_2$ (5.2 mL). After 1 h the solvent was evaporated in vacuo and the residue was partitioned between EtOAc and saturated aqueous Na$_2$CO$_3$. The EtOAc layer was dried (Na$_2$SO$_4$) and evaporated in vacuo to give N-{1-[2-(aminomethyl)-4-chlorobenzyl]-2,2-difluoroethyl}-N-(4-methoxyphenyl)amine (0.550 g) as a foam; MS m/z=341.1.

Step 5. EDC (0.402 g, 2.10 mmol) was added to a stirred mixture of N-{1-[2-(aminomethyl)-4-chlorobenzyl]-2,2-difluoroethyl}-N-(4-methoxyphenyl)amine (0.550 g, 1.61 mmol), N-Boc-L-proline (0.347 g, 1.61 mmol) and HOAT (0.286 g, 2.10 mmol) in DMF (2.8 mL). After 18 h the mixture was partitioned between EtOAc and water. The organic phase was washed with 1 M citric acid, saturated aqueous NaHCO$_3$ and brine, dried (Na$_2$SO$_4$) and evaporated in vacuo to give N-(5-Chloro-2-{3,3-difluoro-2-[(4-methoxyphenyl)amino]propyl}benzyl)-1-tert-butoxycarbonyl-L-prolinamide (0.626 g) as an oil; MS m/z=538.4.

Step 6. TFA (5.3 mL) was added to a stirred solution of N-(5-chloro-2-{3,3-difluoro-2-[(4-methoxyphenyl)amino]propyl}benzyl)-1-tert-butoxycarbonyl-L-prolinamide (0.626 g, 1.20 mmol) in CH$_2$Cl$_2$ (5.3 mL). After 1 h the solvent was evaporated in vacuo and the residue was partitioned between EtOAc and saturated aqueous Na$_2$CO$_3$. The EtOAc layer was dried (Na$_2$SO$_4$) and evaporated in vacuo to give N-(5-chloro-2-{3,3-difluoro-2-[(4-methoxyphenyl)amino]propyl}benzyl)-L-prolinamide (0.439 g) as a foam; MS m/z=438.4.

Step 7. EDC (0.0656 g, 0.34 mmol) was added to a stirred mixture of N-(5-chloro-2-{3,3-difluoro-2-[(4-methoxyphenyl)amino]propyl}benzyl)-L-prolinamide (0.100 g, 0.23 mmol), N-(tert-butoxycarbonyl)-D-cyclohexylglycine (0.0587 g, 0.23 mmol) and HOAT (0.0155 g, 0.11 mmol) in DMF (2.8 mL). After 2 h the mixture was partitioned between EtOAc and water. The organic layer was washed with brine, dried (Na$_2$SO$_4$) and evaporated in vacuo to give 1-{(2R)-2-[(tert-butoxycarbonyl)amino]-2-cyclohexylglycyl}-N-(5-chloro-2-{3,3-difluoro-2-[(4-methoxyphenyl)amino]-propyl}benzyl)-L-prolinamide (0.1845 g) as an oil; MS m/z=677.4.

Step 8. A solution of CAN (0.274 g, 0.50 mmol) in water (2.0 mL) was added to a stirred solution of 1-{(2R)-2-[(tert-butoxycarbonyl)amino]-2-cyclohexylglycyl}-N-(5-chloro-2-{3,3-difluoro-2-[(4-methoxyphenyl)amino]propyl}benzyl)-L-prolinamide (0.168 g, 0.25 mmol) in CH$_3$CN (3.0 mL) at 0° C. and the resulting solution was warmed to ambient temperature. After 18 h the solution was partitioned between EtOAc(20 mL) and 10% aqueous NH$_4$OH (10 mL). The resulting two phase suspension was filtered and the organic layer was washed with 10% sodium sulfite and brine, dried (Na$_2$SO$_4$) and evaporated in vacuo. The residue was purified by flash chromatography (eluting with 5% methylene chloride, 70% ethyl acetate/hexanes followed by ammonium hydroxide/methanol/chloroform, 1:9:90) to give N-[2-(2-amino-3,3-difluoropropyl)-5-chlorobenzyl]-1-{(2R)-2-[(tert-butoxycarbonyl)amino]2-cyclohexylethanoyl}-L-prolinamide (0.0801 g) as an oil; MS m/z=571.4.

Step 9. TFA (0.65 mL) was added to a stirred solution of N-[2-(2-amino-3,3-difluoropropyl)-5-chlorobenzyl]-1-{(2R)-2-[(tert-butoxycarbonyl)amino]-2-cyclohexylethanoyl}-L-prolinamide (0.080 g, 0.14 mmol) in CH$_2$Cl$_2$ (0.7 mL). After 1 h the solvent was evaporated in vacuo and the residue was partitioned between EtOAc and saturated aqueous Na$_2$CO$_3$. The organic layer was dried (Na$_2$SO$_4$) and evaporated in vacuo. The residue was partitioned between EtOAc and 1M HCl. The aqueous layer was evaporated in vacuo to give the HCl salt of the title compound as an off white solid; MS m/z=471.5.

EXAMPLE 10

1-[(2R)-2-Amino-2-cyclohexylethanoyl]-N-[2-(2-amino-3,3,3-trifluoropropyl)-5-chlorobenzyl]-L-prolinamide

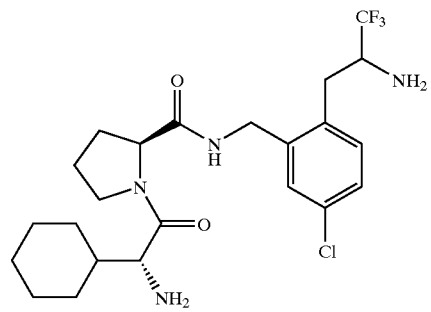

Step 1. sec-Butyl-lithium (1.3 M in cyclohexane, 21.72 mL) was added to a stirred solution of tert-butyl 5-chloro-2-methylbenzylcarbamate (3.61 g, 14.12 mmol) in THF (30 mL) at −78° C. under nitrogen to give a deep red solution. After 10 min N-(4-methoxyphenyl)-N-(2,2,2-trifluoroethylidene)amine (3.01 g, 14.12 mmol) was added and after a further 5 min the solution was quenched with excess saturated aqueous NH$_4$Cl and warmed to ambient temperature. The solution was partitioned between EtOAc and brine. The organic layer was dried (Na$_2$SO$_4$) and evaporated in vacuo. The residue was purified by flash column chromatography on silica (eluting with 5% methylene chloride, 5–20% ethyl acetate/hexanes gradient) to give tert-butyl 5-chloro-2-{2-[(4-methoxyphenyl)amino]-3,3,3-trifluoropropyl}benzylcarbamate (2.69 g) as a gum; $^1$H NMR (CDCl$_3$ 400 MHz) δ 1.47 (s, 9H), 2.90 (dd, J=10.7 and 14.7 Hz, 1H), 3.16 (dd, J=3.4 and 14.7 Hz, 1H), 3.62 (br d, J=8.2 Hz, 1H), 3.71 (s, 3H), 4.03 (br m, 1H), 4.29 (dd, J=5.6 and 14.7 Hz, 1H), 4.34 (br dd, 1H), 4.87 (br s, 1H), 6.47 (d, J=8.9 Hz, 2H), 6.69 (d, J=8.9 Hz, 2H), 7.14 (d, J=8.2 Hz, 1H), 7.19 (dd, J=8.2 and 2.0 Hz, 1H), 7.23 (s, 1H).

Step 2. TFA (1 mL) was added to a stirred solution of tert-butyl 5-chloro-2-{2-[(4-methoxyphenyl)amino]-3,3,3-trifluoropropyl}benzylcarbamate (0.205 g, 0.447 mmol) in CH₂Cl₂ (2 mL). After 1 h the solvent was evaporated in vacuo and the residue was partitioned between EtOAc and saturated aqueous Na₂CO₃. The organic layer was dried (Na₂SO₄) and evaporated in vacuo to give N-{1-[2-(aminomethyl)-4-chlorobenzyl]-2,2,2-trifluoroethyl}-N-(4-methoxyphenyl)amine (0.182 a solid; ¹H NMR (CDCl₃, 400 MHz) δ 3.02 (dd, J=10.9 and 14.2 Hz, 1H), 3.11 (dd, J=3.4 and 14.2 Hz, 1H), 3.69 (s, 3H), 3.86 (d, J=12.9 Hz, 1H), 3.97 (d, J=12.9 Hz, 1H), 3.98 (obscured m, 1H), 6.44 (d, J=8.8 Hz, 2H), 6.66 (d, J=8.8 Hz, 2H), 7.19 (s, 2H), 7.22 (s, 1H).

Step 3. EDC (0.229 g, 1.19 mmol) was added to a stirred mixture of N-Boc-D-cyclohexylglycyl-L-proline (0.325 g, 0.92 mmol), N-{1-[2-(aminomethyl)-4-chlorobenzyl]-2,2,2-trifluoroethyl}-N-(4-methoxyphenyl)amine (0.329 g, 0.92 mmol) and HOAT (0.162 g, 1.19 mmol) in DMF (2 mL). After 2 h the solution was partitioned between EtOAc and water. The organic layer was washed with brine, dried (Na₂SO₄) and evaporated in vacuo to give 1-{(2R)-2-[(tert-butoxycarbonyl)amino]-2-cyclohexylethanoyl}-N-(5-chloro-2-{3,3,3-trifluoro-2-[(4-methoxyphenyl)amino]propyl}benzyl)-L-prolinamide (0.798 g) as an oil; MS m/z=695.4.

Step 4. A solution of CAN (1.259 g, 2.30 mmol) in water (12 mL) was added to a stirred solution of 1-{(2R)-2-[(tert-butoxycarbonyl)amino]-2-cyclohexylglycyl}-N-(5-chloro-2-{3,3,3-trifluoro-2-[(4-methoxyphenyl)amino]propyl}benzyl)-L-prolinamide (0.798 g, 1.15 mmol) in CH₃CN (20 mL) at 0° C. and the resulting solution was warmed to ambient temperature. The solution was partitioned between EtOAc and 10% aqueous NH₄OH and the resulting two phase suspension was filtered and the organic layer was washed with 10% sodium sulfite and brine, dried (Na₂SO₄) and evaporated in vacuo. The residue was purified by flash column chromatography on silica (eluting with 1–10% of 10% ammonium hydroxide in methanol/chloroform gradient) to give N-[2-(2-amino-3,3,3-trifluoropropyl)-5-chlorobenzyl]-1-{(2R)-2-[(tert-butoxycarbonyl)amino]-2-cyclohexylethanoyl}-L-prolinamide (0.282 g) as a foam; MS m/z=589.6.

Step 5. TFA (2.5 mL) was added to a stirred solution of N-[2-(2-amino-3,3,3-trifluoropropyl)-5-chlorobenzyl]-1-{(2R)-2-[(tert-butoxycarbonyl)amino]-2-cyclohexylethanoyl}-L-prolinamide (0.282 g, 0.48 mmol) in CH₂Cl₂ (5 mL) and after 1 h the solvent was evaporated in vacuo and the residue was partitioned between EtOAc and saturated aqueous Na₂CO₃. The organic layer was dried (Na₂SO₄) and evaporated in vacuo to give the title compound as a foam; MS m/z=489.6.

EXAMPLE 11

1-((2R)-2-Amino-2-cyclohexylethanoyl)-N-(2-(azetidin-1-ylmethyl)-5-chlorobenzyl)-L-prolinamide

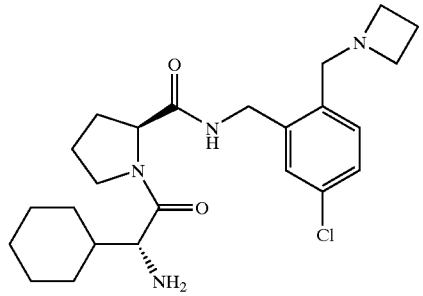

Step 1. DPPA (0.442 mL, 2.05 mmol) followed by DBU (0.306 mL, 2.05 mmol) were added to a stirred solution of 5-chloro-2-iodobenzyl alcohol (500 mg, 1.86 mmol) in DMF (10 mL) at 0° C. and the reaction mixture was warmed to room temperature. After 16 h the mixture was warmed to 70° C. for 2 hr. The reaction was then concentrated and the residue was partitioned between EtOAc and 10% NaHCO₃. The organic layer was washed with water and brine, dried (Na₂SO₄) and evaporated to give 5-chloro-2-iodobenzylazide (588 mg): ¹H NMR (CDCl₃, 400 MHz) δ 4.43 (s, 2H), 7.03 (dd, J=2.6, 8.4 Hz, 1H), 7.39 (d, J=2.6, 1H), 7.78 (d, J=8.4 Hz, 1H).

Step 2. PPh₃ (1.46 g, 5.58 mmol) was added to a stirred solution of 5-chloro-2-iodobenzylazide (0.55 g, 1.86 mmol) in THF (17.5 mL), and water (3.5 mL) were combined and stirred at room temperature. After 16 hr, the mixture was warmed to 80° C. for 3 h. The reaction was then concentrated and the residue was partitioned between ether and 1N HCl. The aqueous layer was adjusted to pH=8 with NaHCO₃, saturated with NaCl and then extracted into CH₂Cl₂. The CH₂Cl₂ layer was washed with brine, dried (Na₂SO₄) and evaporated to give 5-chloro-2-iodobenzylamine (428 mg): ¹H NMR (CDCl₃, 400 MHz) δ 3.83 (s, 2H), 6.95 (dd, J=2.6, 8.4 Hz, 1H), 7.40 (d, J=2.4 Hz, 1H), 7.72 (d, J=8.2 Hz, 1H).

Step 3. EDC (509 mg, 2.66 mmol) was added to a stirred mixture of 5-chloro-2-iodobenzylamine (428 mg, 1.60 mmol), Boc-D-cyclohexylglycyl-L-proline, (627 mg, 1.77 mmol), HOAT (121 mg, 0.88 mmol) in DMF (5.0 mL). After 16 h the reaction mixture was concentrated and the residue was partitioned between EtOAc and 10% NaHCO₃. The organic layer was washed with water and brine, dried (Na₂SO₄) and evaporated. The residue was purified by chromatographed on silica (eluting with EtOAc/CHCl₃, 1:3) to give Boc-D-Cyclohexylglycyl-N-(5-chloro-2-iodobenzyl)-L-prolinamide (745 mg) as a glass; ¹H NMR (CDCl₃, 400 MHz) δ 1.05–1.24 (m, 6H), 1.26 (d, J=2.9 Hz, 9H), 1.68–1.80 (m, 6H), 1.89 (d, J=12.6 Hz, 1H), 2.00–2.07 (obscured) (m, 1H), 2.41 (m, 1H), 3.57 (dd, J=9.2, 16.5 Hz, 1H), 3.97–4.09 (m, 2H), 4.28 (dd, J=5.7, 16.1 Hz, 1H), 4.40 (dd, J=6.6, 16.3 Hz, 1H), 4.70 (d, J=6.4 Hz, 1H), 5.08 (d, J=6.6 Hz, 1H), 6.93 (dd, J=2.6, 8.4 Hz, 1H), 7.29 (d, J=2.6 Hz, 1H), 7.61 (br s, 1H), 7.68 (d, J=8.4 Hz, 1H).

Step 4. A solution of tri-n-butyl tin hydride (388 mg, 1.33 mmol) in THF (9 mL) was added over 3 h to a stirred solution of Boc-D-cyclohexylglycyl-N-(5-chloro-2-iodobenzyl)-L-prolinamide (670 mg, 1.11 mmol), palladium (II) acetate (10 mg, 0.04 mmol) and PPh₃ (46.6 mg, 0.17 mmol) in THF (3 mL) under a carbon monoxide atmosphere. After 16 h at room temperature the reaction was concentrated and the residue was partitioned between EtOAc and 10% NaHCO₃. The organic layer was washed with water and brine, dried (Na₂SO₄) and evaporated and the residue was purified by chromatography on silica (eluting with CHCl₃/MeOH, 97:3) to give Boc-D-Cyclohexylglycyl-N-(5-chloro-2-formylbenzyl)-L-prolinamide (221 mg) as a glass: MS: 506.5 (M+1).

Step 5. TEA (221 mg, 2.18 mmol) was added to a stirred mixture of azetidine hydrochloride (204 mg, 2.18 mmol) and 1,2-dichloroethane (7 mL). After 2 min, Boc-D-cyclohexylglycyl-N-(5-chloro-2-formylbenzyl)-L-prolinamide (221 mg, 0.44 mmol), sodium triacetoxy borohydride (463 mg, 2.18 mmol) and acetic acid (30 μL, 0.52 mmol) were added and after another 16 h the reaction mixture was partitioned between CH₂Cl₂ and 10% NaHCO₃. The organic layer was washed with water and brine, dried (Na₂SO₄) and evaporated. The residue was partitioned between cold 1N HCl and ether. The aqueous layer was adjusted to pH=8 with NaHCO₃ solution saturated with NaCl and then was extracted into CH₂Cl₂. The CH₂Cl₂ layer was then washed with brine, dried (Na₂SO₄) and evaporated to give Boc-D-Cyclohexylglycyl-N-[2-(azetidin-1-ylmethyl)-5-chlorobenzyl]-L-prolinamide (105 mg) as a glass: ¹H NMR (CDCl₃, 400 MHz) δ 1.02–2.30 (m, 26H), 3.19 (m, 4H), 3.46–3.66 (m, 3H), 3.92 (m, 1H), 4.15 (m, 1H), 4.47 (m, 2H), 4.78 (d, J=8.6 Hz, 1H), 5.14 (d, J=7.3 Hz, 1H), 7.16 (s, 1H), 7.21 (dd, J=2.0, 8.1 Hz, 1H), 7.29 (s, 1H), 8.05 (br s, 1H).

Step 6. TFA (1 mL) was added to a stirred solution of Boc-D-cyclohexylglycyl-N-[2-(azetidin-1-ylmethyl)-5-chlorobenzyl]-L-prolinamide (105 mg, 0.19 mmol) in CH₂Cl₂ (2 mL) at 0° C. After the reaction mixture was concentrated and the residue was taken up in a solution of CHCl₃ saturated with ammonia. This mixture was then filtered and concentrated. The residue was purified by chromatography on silica (ammonia saturated CHCl₃/MeOH, 96:4) to give the title compound as glass. HRMS (FAB) C₂₄H₃₆ClN₄O₂ (M+1) calcd: 447.2521 Found: 447.2513.

EXAMPLE 12

N-(2-Azetidin-2-yl-5-chlorobenzyl)-1-((2R)-2-hydroxy-3,3-dimethylbutanoyl)-L-prolinamide

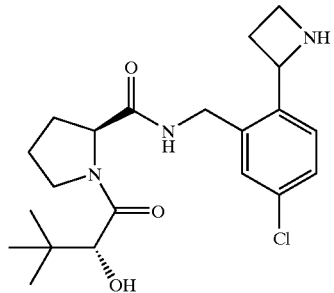

Step 1. Borane methylsulfide (7.3 mL, 73 mmol) was added to a stirred solution of 5-chloro-2-iodobenzoic acid (17.17 g, 60.79 mmol) in THF (40 mL) and trimethylborate (20 mL), maintaining the internal temperature at 20–25° C. After 16 h methanol (8.87 mL, 0.219 mol) was added cautiously and the solution was evaporated in vacuo, azeotroping with methanol (3×50 mL). The resulting solid was recrystallized (hexanes/ethyl acetate, 5:1, 120 mL) to give 5-chloro-2-iodobenzyl alcohol (12.2 g): ¹H NMR (CDCl₃, 400 MHz) δ 2.00 (br s, 1H), 4.64 (s, 2H), 7.00 (dd, J=2.6, 8.4 Hz, 1H), 7.49 (d, J=2.4, 1H), 7.72 (d, J=8.2 Hz, 1H).

Step 2. Triisopropylsilylchloride (14.59 mL, 68.16 mmol) was added to a stirred solution of 5-chloro-2-iodobenzyl alcohol (12.2 g, 45.44 mmol) and imidazole (4.64 g, 68.16 mmol) in DMF (45 mL). After 1 h the mixture was partitioned between hexanes and water. The organic layer was dried (Na₂SO₄) and evaporated in vacuo to an oil which was purified by flash column chromatography on silica (eluting with 5% methylene chloride/hexanes) to give [(5-chloro-2-iodobenzyl)oxy](triisopropyl)silane as an oil (1611 g): ¹H NMR (CDCl₃, 400 MHz) δ 1.11 (d, J=6.8 Hz, 18H), 1.20 (septet, J=6.8 Hz, 3H), 4.65 (s, 2H), 6.96 (dd, J=2.6, 8.4 Hz, 1H), 7.56 (d, J=2.8 Hz, 1H), 7.66 (d, J=8.2 Hz, 1H).

Step 3. n-Butyl-lithium (2.5 M solution in hexanes, 3.6 mL) was added to stirred solution of [(5-chloro-2-iodobenzyl)oxy](triisopropyl)silane (3.82 g, 9.0 mmol) in ether (18 mL) at −78° C. under nitrogen. After 10 min a solution of copper(I) bromide-dimethylsulfide complex (0.925 g, 4.5 mmol) in dimethylsulfide (36 mL) was added and the solution was warmed to −50° C. A solution of 4-acetoxy-2-azetidinone (0.291 g, 2.25 mmol) in THF (2 mL) was added and the solution was warmed to −30° C. After a further 1 h the reaction was poured into 10% ammonium chloride solution basicified with ammonium hydroxide and extracted into ether. The organic layer was dried (Na₂SO₄) and evaporated in vacuo to an oil which was purified by flash column chromatography on silica (eluting with 5% methylene chloride/0–50% ethyl acetate/hexanes gradient) to give 4-(4-chloro-2-{[(triisopropylsilyl)oxy]methyl}phenyl)azetidin-2-one (0.712 g) as a heavy oil: ¹H NMR (CDCl₃, 400 MHz) δ 1.08 (d, J=6.4 Hz, 18H), 1.16 (septet, J=6.4 Hz, 3H), 2.78 (dd, J=2.6, 14.8 Hz, 1H), 3.45 (dq, J=14.8, 2.6 Hz, 1H), 4.72 (d, J=13.1 Hz, 1H), 4.78 (d, J=13.1 Hz, 1H), 4.94 (q, J=2.6 Hz, 1H), 6.06 (br s, 1H), 7.30 (dd, J=2.1, 8.4 Hz, 1H), 7.43 (m, 2H).

Step 4. LAH (1 M solution in ether, 7.74 mL) was added to a stirred solution of 4-(4-chloro-2-{[(triisopropylsilyl)oxy]methyl}phenyl)azetidin-2-one (0.7122 g, 1.935 mmol) in ether (2 mL) at 0° C. The solution was heated to reflux and after 2 h was cooled to 0° C. and quenched with water (0.294 mL), 15% sodium hydroxide solution (0.294 mL) and water (0.881 mL). The mixture was sonicated to give a uniform precipitate, filtered and evaporated in vacuo to an oil. The oil was dissolved in ethanol (10 mL) and concentrated HCl (0.167 mL, 2 mmol) was added with stirring at 0° C. The reaction was warmed to ambient temperature and after 30 min was evaporated in vacuo, azeotroping with ethanol to give (2-azetidin-2-yl-5-chlorophenyl)methanol hydrochloride (0.453 g) as a crystalline solid: ¹H NMR (CD₃OD, 400 MHz) δ 2.79 (m, 1H), 3.14 (m, 1H), 3.87 (dt, J=4.5 and 10.0 Hz, 1H, 4.18 (q, J=9.3 Hz, 1H), 4.61 (d, J=13.1 Hz, 1H), 4.68 (d, J=13.1 Hz, 1H), 5.93 (t, J=9.0 Hz, 1H), 7.49 (m, 2H), 7.69 (d, J=8.2 Hz, 1H).

Step 5. Aqueous sodium hydroxide (1 M, 2.67 mL) was added to a stirred solution of (2-azetidin-2-yl-5-chlorophenyl)methanol hydrochloride (0.312 g, 1.33 mmol) and trichloroethoxycarbonyl chloride (0.184 mL, 1.33 mmol) in dioxane (8 mL) and water (0.4 mL) at 0° C. The reaction was warmed to ambient temperature and after 1 h was acidified with 1 M HCl solution, extracted into ether, dried (Na₂SO₄) and evaporated in vacuo to an oil. The crude product was purified by flash column chromatography on silica (eluting with 5% methylene chloride/10–50% ethyl acetate/hexanes gradient) to give 2,2,2-trichloroethyl 2-[4-chloro-2-(hydroxymethyl) phenyl]azetidine-1-carboxylate (283 mg a colorless gum: ¹H NMR (CDCl₃, 400 MHz) δ 2.24 (br m, 1H), 2.78 (m, 1H), 4.20 (br s, 2H), 4.61 (br m, 2H), 4.68 (br m, 2H), 5.66 (dd, J=8.6, 6.4 Hz, 1H), 7.34 (m, 2H), 7.56 (d, J=8.1 Hz, 1H).

Step 6. DBU (0.209 mL, 1.40 mmol) was added to a stirred solution of 2,2,2-trichloroethyl 2-[4-chloro-2-(hydroxymethyl)phenyl]azetidine-1-carboxylate (0.346 g, 0.927 mmol) and DPPA (0.302 mL, 1.40 mmol) in THF (2 mL) at 0° C. After 2 h the reaction was partitioned between ether and water and the organic layer was washed with 1 M sodium hydroxide solution (2 times) and 1 M HCl solution, dried (Na₂SO₄) and evaporated in vacuo to an oil. Triphenylphosphine (0.262 g, 1.00 mmol) was added to a stirred solution of this oil in THF (2 mL) and water (4 drops). After 16 h methanol (2 mL), water (1 mL) and sodium hydroxide (1 pellet) were added, the mixture was stirred for a further 15 min and then was partitioned between ether and water. The organic layer was extracted into dilute aqueous acetic acid which was basicified with sodium hydroxide and extracted with ether. This organic layer was dried (Na₂SO₄) and evaporated in vacuo to an oil which was purified by flash column chromatography on silica (eluting with a chloroform/10% ammonium hydroxide in methanol gradient, 1–4% ammonium hydroxide/methanol) to give 2,2,2-trichloroethyl 2-[2-(aminomethyl)-4-chlorophenyl]azetidine-1-carboxylate (275 mg) as an oil: ¹H NMR (CDCl₃, 400 MHz) δ 2.11 (m, 1H), 2.78 (m, 1H), 3.77 (br d, J=14.4 Hz, 1H), 3.87 (br d, J=14.4 Hz, 1H), 4.16 (br m, 2H), 4.64 (br m, 2H), 5.63 (br s, 1H), 7.27 (obscured m, 1H), 7.35 (s, 1H), 7.50 (br s, 1H).

Step 7. N-Fmoc-L-proline (0.249 g, 0.739 mmol) was added to a stirred mixture of 2,2,2-trichloroethyl 2-[2-(aminomethyl)-4-chlorophenyl]azetidine-1-carboxylate (0.275 g, 0.739 mmol), EDC (0.213 g, 1.11 mmol) and HOAT (50 mg, 0.37 mmol) in DMF (2 mL). After 16 h the reaction mixture was partitioned between ethyl acetate and dilute HCl solution. The organic layer was washed with water and brine, dried (Na₂SO₄) and evaporated in vacuo to a foam. This material was dissolved in DMF (2 mL) and piperidine (0.5 mL) and stirred for 30 min. The solution was poured into water (50 mL) and the precipitated solids were removed by filtration, washing with water (5×10 mL, which was collected and set aside) and methanol. The methanol was evaporated in vacuo and the residue was purified by flash column chromatography on silica (eluting with ethyl acetate followed by chloroform/methanol/ammonium hydroxide, 90:9:1) to give 2,2,2-trichloroethyl 2-{4-chloro-2-[(L-prolylamino)methyl]phenyl}azetidine-1-carboxylate (66 mg) as a gum. The milky aqueous washings were extracted into ethyl acetate (adding brine to dispel the emulsion) and the organic layer was washed with water and brine, dried (Na₂SO₄) and evaporated in vacuo to give more of the desired compound (0.206 g) as a gum: MS 468.5 (M+1) with an isotope distribution consistent with four chlorines.

Step 8. EDC (28.8 mg, 0.15 mmol) was added to a stirred mixture of 2,2,2-trichloroethyl 2-{4-chloro-2-[(L-prolylamino)methyl]phenyl}azetidine-1-carboxylate (46.9 mg, 0.10 mmol) and HOAT (6.8 mg, 0.05 mmol) in DMF (0.5 mL). After 2 h the mixture was partitioned between dilute HCl/brine and ethyl acetate and the organic layer was washed with sodium carbonate solution and brine, dried (Na₂SO₄) and evaporated in vacuo to a glass. This material was dissolved in glacial acetic acid (1 mL), zinc dust (100 mg) was added and the resulting mixture was stirred for 16 h. The mixture was filtered through celite, washing with THF and ethanol and the filtrate was evaporated in vacuo. The residue was partitioned between ether and water and the aqueous layer was basicified with sodium hydroxide and extracted into ethyl acetate (2×). The combined organic layers were washed with brine, dried (Na₂SO₄) and evaporated in vacuo to a gum which was purified by flash column chromatography on silica (eluting with a chloroform/10% ammonium hydroxide in methanol gradient, 1–16% ammonium hydroxide/methanol) to give the title compound as a glass: MS 408.3 (M+1); ¹H NMR (CDCl₃, 400 MHz) sets of signals consistent with a 1:1 mixture of diastereomers: δ 1.96 (m, 2H), 2.12 (m, 1H), 2.39 (m, 2H), 2.62 (m, 1H), 3.37 (m, 0.5H), 3.45 (m, 0.5H), 3.55–3.76 (m, 2H), 3.80 (q, J=8.2 Hz, 1H), 3.97 (s, 0.5H), 4.01 (s, 0.5H), 4.29 (dd, J=5.0 and 14.8 Hz, 1H), 4.38 (m, 1H), 4.56 (m, 1H), 5.14 (t, J=8.1 Hz, 1H), 7.24–7.32 (obscured m, 2H), 7.52 (br m, 1H), 7.59 (d, J=8.3 Hz, 0.5H), 7.64 (d, J=8.2 Hz, 0.5H).

EXAMPLE 13

1-((2R)-2-Hydroxy-2-cyclohexylethanoyl)-N-(2-(1-aminoethyl)-5-chlorobenzyl)-L-prolinamide

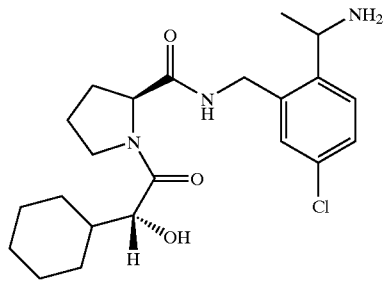

Step 1. To a stirred solution of (S)-(−)-2-methyl-2-propanesulfinamide (1.0 g, 8.25 mmol) and acetaldehyde (2.0 mL, 35.61 mmol) in dichloromethane (20 mL) at ambient temperature under nitrogen atmosphere was added CuSO₄ (2.9 g, 18.15 mmol). The mixture was stirred at ambient temperature for 18 h. The reaction was filtered through celite and the filtrate solvent was removed under reduced pressure. N-ethylidene-2-methyl-2-propanesulfinamide was obtained as a clear colorless oil (1.18 g; ¹H NMR, 400 MHz, CDCl₃, 8.8 ppm (q, 11H), 2.24 ppm (d, 3H), 1.2 ppm (s, 9H)).

Step 2. To a stirred solution of iPr₂NH (0.31 mL, 2.24 mmol) in THF (10 mL) at −78° C. under nitrogen atmosphere was added 2.5M n-BuLi in THF solution (0.75 mL, 1.86 mmol). The solution was stirred for 15 min at −78° C. and added to it in one portion was 2-iodo-5-chlorobenzyl alcohol (0.5 g, 1.86 mmol). This solution was stirred for 30 min at −78° C. then was concentrated in vacuo and placed under high vacuum for 1 h. The residue, under nitrogen atmosphere, was dissolved in THF (20 mL), cooled to −78° C., and 2.5M n-BuLi in THF solution (0.75 mL, 1.86 mmol) was added. This solution was stirred for 15 min at −78° C. and added drop wise was N-ethylidene- 2-methyl-2-propanesulfinamide from the previous step (0.274 g, 1.86 mmol) dissolved in THF (5 mL). This solution was stirred for 30 min at −78° C. then was allowed to equilibrate to ambient temperature over 1 h. Saturated NH$_4$Cl was added (3 mL), and the mixture was partitioned between EtOAc and water. The EtOAc layer was separated, dried over anhydrous Na$_2$SO$_4$, and filtered. The filtrate solvent was removed under reduced pressure and the residue was purified by flash silica gel chromatography eluting with a methanol in dichloromethane gradient (1% to 3% MeOH in 0.5% increments). After concentration of desired fractions in vacuo, the separate isomers of 2-(1-tert-butylsulfinamidylethyl)-5-chlorobenzyl alcohol were obtained as a yellow oils (isomer 1(less polar) 120 mg; HPLC RT=2.93 min, method A; LC-MS m/z=290.1; $^1$H NMR, 400 MHz, CDCl$_3$, 7.38 ppm (s, 1H), 7.36 ppm (d, 1H), 7.28 ppm (dd, 1H), 4.86 ppm (d, 1H), 4.82 ppm (m, 1H), 4.54 ppm (d, 1H), 4.3 ppm (br s, 1H), 3.94 ppm (d, 1H), 1.54 ppm (d, 3H), 1.2 ppm (s, 9H); isomer 2(more polar) 38 mg; HPLC RT=2.69 min; LC-MS m/z=290.1; $^1$H NMR, 400 MHz, CDCl$_3$ 7.4 ppm (d, 1H), 7.365 ppm (d, 1H), 7.28 ppm (dd, 1H), 4.86 ppm (m, 1H), 4.78 ppm (dd, 1H), 4.64 ppm (dd, 1H), 3.67 ppm (br s, 1H), 3.65 ppm (d, 1H), 1.52 ppm (d, 3H), 1.18 ppm (s, 9H)).

Step 3. To a stirred solution of 2-(1-tert-butylsulfinamidylethyl)-5-chlorobenzyl alcohol from the previous step (isomer 1, 0.410 g, 1.42 mmol) in MeOH (5 mL) at ambient temperature was added 4M HCl in dioxane (0.71 mL, 2.8 mmol). The resulting solution was stirred at ambient temperature for 0.5 h, then concentrated in vacuo. The residue was partitioned between EtOAc and water basicified to pH=8 with saturated NaHCO$_3$ solution. The EtOAc layer was separated, dried over anhydrous Na$_2$SO$_4$, and filtered. The filtrate solvent was removed under reduced pressure. 2-(1-aminoethyl)-5-chlorobenzyl alcohol was obtained as a pink oil that crystallized on sitting (0.2 g; HPLC RT=2.06 min, method A; $^1$H NMR, 400 MHz, CDCl$_3$, 7.3 ppm (s, 1H), 7.28 ppm (d, 1H), 7.22 ppm (d, 1H), 4.73 ppm (d, 1H), 4.45 ppm (d, 1H), 4.3 ppm (m, 1H), 1.52 ppm (d, 3H).

Step 4. To a stirred solution of 2-(1-aminoethyl)-5-chlorobenzyl alcohol from the previous step (0.2 g, 1.1 mmol) in DMF (5.0 mL) at ambient temperature under nitrogen atmosphere was added Boc$_2$O (0.25 g, 1.15 mmol). The mixture was stirred at ambient temperature for 18 h. The reaction was concentrated in vacuo and the residue was purified by flash silica gel chromatography using dichloromethane as an eluent. 2-(1-(tert-butyloxycarbonylamino)ethyl)-5-chlorobenzyl alcohol was obtained as a yellow oil after concentration of desired fractions in vacuo (0.272 g; HPLC RT=3.24 min, method A; $^1$H NMR, 400 MHz, CDCl$_3$, 7.33 ppm (d, 1H), 7.26 ppm (dd, 2H), 5.12 ppm (br s, 1H), 5.0 ppm (m, 1H), 4.9 ppm (d, 1H), 4.46 ppm (m, 1H), 4.22 ppm (br s, 1H), 1.42 ppm (d, 3H), 1.36 ppm (s, 9H)).

Step 5. To a stirred solution of 2-(1-tert-butyloxycarbonylaminoethyl)-5-chlorobenzyl alcohol from the previous step (0.272 g, 0.96 mmol) in toluene (20.0 mL) at ambient temperature under nitrogen atmosphere was added DBU (0.15 mL g, 1.0 mmol) and DPPA (0.25 mL, 1.14 mmol). The mixture was stirred at ambient temperature for 18 h. The reaction was partitioned between EtOAc and water. The EtOAc layer was separated, dried over anhydrous Na$_2$SO$_4$, and filtered. The filtrate solvent was removed under reduced pressure and the residue purified by flash silica gel chromatography using dichloromethane as an eluent. 2-(1-(tert-butyloxycarbonylamino)ethyl)-5-chloro-benzylazide was obtained as a yellow oil after concentration of desired fractions in vacuo (0.28 g; HPLC RT 3.71 min, method A).

Step 6. To a stirred solution 2-(1-tert-butyloxycarbonylaminoethyl)-5-chlorobenzylazide from the previous step (0.28 g, 0.90 mmol) in THF (10.0 mL) and water (1 mL) at ambient temperature was added Ph$_3$P (0.29 mg, 1.1 mmol). The mixture was refluxed for 3 h. The reaction was partitioned between Et$_2$O and diluted 1N HCl. The Et$_2$O layer was removed, and the aqueous layer basicified with saturated NaHCO$_3$ solution. The aqueous layer was extracted with Et$_2$O which was separated, dried over anhydrous Na$_2$SO$_4$, and filtered. The filtrate solvent was removed under reduced pressure. 2-(1-(tert-butyloxycarbonylamino)ethyl)-5-chlorobenzylamine was obtained as a pink oil (0.205 g; HPLC RT=2.76 min, method A; $^1$H NMR, 400 MHz, CDCl$_3$, 7.33 ppm (s, 1H), 7.22 ppm (dd, 2H), 5.2 ppm (br s, 1H), 5.0 ppm (br s, 1H), 4.0 ppm (d, 1H), 3.85 ppm (d, 1H), 1.7 (br s, 1H), 1.4 ppm (s, 12H)).

Step 7. To a stirred solution under nitrogen atmosphere at ambient temperature of 2-(1-tert-butyloxycarbonylaminoethyl)-5-chlorobenzylamine (0.105 g, 0.37 mmol), Fmoc-L-Proline (0.124 g, 0.37 mmol), and HOBT hydrate (0.055 g, 0.41 mmol) in DMF (5 mL) was added iPr$_2$NEt (64 μL, 0.37 mmol), and EDC (0.106 g, 0.55 mmol). The reaction was stirred at ambient temperature for 1 h. The reaction was concentrated in vacuo and the residue was partitioned between EtOAc and water. The EtOAc layer was separated, dried over anhydrous Na$_2$SO$_4$, and filtered. The filtrate solvent was removed under reduced pressure. 1-Fluroenylmethoxycarbonyl-N-(2-(1-(tert-butyloxycarbonylamino)ethyl)-5-chlorobenzyl)-L-prolinamide was obtained as a yellow foam (0.237 g; HPLC RT=3.93 min, method A; LC-MS m/z=604.0).

Step 8. To a solution of 1-fluroenylmethoxycarbonyl-N-(2-(1-(tert-butyloxycarbonylamino)ethyl)-5-chlorobenzyl)-L-prolinamide from the previous step (0.237 g, 0.39 mmol) in DMF (3 mL) at ambient temperature was added piperidine (1 mL). The reaction was stirred at ambient temperature for 1 h. The reaction was concentrated in vacuo and the residue was partitioned between EtOAc and water. The EtOAc layer was separated, dried over anhydrous Na$_2$SO$_4$, and filtered. The filtrate solvent was removed under reduced pressure and the residue purified by flash silica gel chromatography using 10% MeOH in dichloromethane as an eluent. L-Prolin-N-(2-(1-(tert-butyloxycarbonylamino)ethyl)-5-chlorobenzyl)amide was obtained as a orange-red oil after concentrating desired fractions in vacuo (0.107 g; HPLC RT=2.85 min, method A; LC-MS m/z=382.1; $^1$H NMR, 400 MHz, CDCl$_3$, 8.9 ppm (br s, 1H), 7.25 ppm (s, 3H), 5.18 ppm (br s, 1H), 4.83 ppm (m, 1H), 4.6 ppm (dd, 1H), 4.38 ppm (m, 1H), 3.36 ppm (m, 4H), 2.35 ppm (m, 1H), 1.96 ppm (m, 4H), 1.36 ppm (s, 12H)).

Step 9. To a stirred solution of L-prolin-N-(2-(1-tert-butyloxycarbonylaminoethyl)-5-chlorobenzyl)amide from the previous step (54.6 mg, 0.143 mmol), R-(−)-hexahydromandelic acid(22.62 mg, 0.143 mmol), and NMM (16 μL, 0.143 mmol) in DMF (5 mL) at ambient temperature under nitrogen atmosphere was added BOP reagent (76 mg, 0.172 mmol). The mixture was stirred at ambient temperature for 3 h. The solvent was removed under reduced pressure. The residue was partitioned between EtOAc and saturated aqueous NaHCO$_3$. The EtOAc layer was separated, dried over anhydrous Na$_2$SO$_4$, and filtered. The filtrate solvent was removed under reduced pressure and the residue was purified by preparative thick layer silica gel plate chromatography (2000 μM×20 cm×20 cm) developed with 7.5% MeOH in dichloromethane. Desired bands were removed and eluted with 5% MeOH in dichloromethane which were concentrated in vacuo to obtain 1-((2R)-2-hydroxy-2-cyclohexylethanoyl)-N-(2-(1-(tert-butyloxycarbonylamino)ethyl)-5-chlorobenzyl)-L-prolinamide as a clear colorless oil (40 mg; HPLC RT=3.51 min, method A; LC-MS m/z=522.1).

Step 10. 1-((2R)-2-Hydroxy-2-cyclohexylethanoyl)-N-(2-(1-(tert-butyloxycarbonylamino)ethyl)-5-chlorobenzyl)-L-prolinamide from the previous step (0.40 g, 0.077 mmol) was dissolved in EtOAc (10 mL) and cooled with stirring to 0° C. Into this solution was bubbled in HCl gas for 5 min. The resulting solution was stirred at 0° C. for 30 min, then concentrated in vacuo. The solid which had formed was triturated with Et$_2$O and collected by filtration and washed with several portions of ether. The hydrochloride of the title compound was obtained as a white solid after drying under high vacuum (HPLC RT=2.72 min, method A; LC-MS m/z=422.1; $^1$H NMR, 400 MHz, CD$_3$OD, 7.65 ppm (d, 1H), 7.35 ppm (s, 1H), 7.25 ppm (d, 1H), 4.81 ppm (dd, 2H), 4.24 ppm (q, 1H), 4.1 ppm (m, 2H), 3.74 ppm (m, 1H), 3.64 ppm (m, 1H), 2.2 ppm (m, 2H), 2.08 ppm (m, 2H), 1.94 ppm (m, 4H), 1.16 ppm (d, 3H), 1.2 ppm (m, 7H)).

EXAMPLE 14

1-((2R)-2-Hydroxy-2-cyclohexylethanoyl)-N-(2-(1-aminoethyl)-5-chlorobenzyl)-L-prolinamide

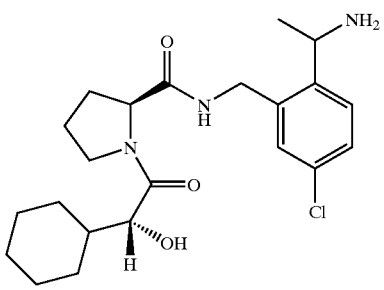

Step 1. To a stirred solution of 2-(1-tert-butylsulfinamidylethyl)-5-chlorobenzyl alcohol from step 2 of the L-519,502 synthesis (isomer 2, 0.654 g, 2.23 mmol) in MeOH (10 mL) at ambient temperature was added 4M HCl in dioxane (1.12 mL, 4.46 mmol). The resulting solution was stirred at ambient temperature for 0.5 h, then concentrated in vacuo. The residue was partitioned between EtOAc and water basified to pH=8 with saturated NaHCO$_3$ solution. The EtOAc layer was separated, dried over anhydrous Na$_2$SO$_4$, and filtered. The filtrate solvent was removed under reduced pressure. 2-(1-aminoethyl)-5-chlorobenzyl alcohol was obtained as a pink oil that crystallizes on sitting (0.3 g; HPLC RT=2.07 min, method A; $^1$H NMR, 400 MHz, CDCl$_3$, 7.32 ppm (d, 1H), 7.29 ppm (d, 1H), 7.24 ppm (dd, 1H), 4.76 ppm (d, 1H), 4.65 ppm (d, 1H), 4.34 ppm (q, 1H), 3.4 ppm (br s, 3H), 1.7 ppm (d, 3H).

Step 2. To a stirred solution of 2-(1-aminoethyl)-5-chlorobenzyl alcohol from the previous step (0.3 g, 1.62 mmol) in DMF (5.0 mL) at ambient temperature under nitrogen atmosphere was added Boc$_2$O (0.4 g, 1.83 mmol). The mixture was stirred at ambient temperature for 18 h. The reaction was concentrated in vacuo and the residue was partitioned between EtOAc and water. The EtOAc layer was separated, dried over anhydrous Na$_2$SO$_4$, and filtered. The filtrate solvent was removed under reduced pressure. 2-(1-(tert-butyloxycarbonylamino)ethyl)-5-chlorobenzyl alcohol was obtained as a yellow oil (0.475 g; HPLC RT=3.22 min, method A; $^1$H NMR, 400 MHz, CDCl$_3$, 7.33 ppm (d, 1H), 7.26 ppm (dd, 2H), 5.12 ppm (br s, 1H), 5.0 ppm (m, 1H), 4.9 ppm (d, 1H), 4.46 ppm (m, 1H), 4.22 ppm (br s, 1H), 1.42 ppm (d, 3H), 1.36 ppm (s, 9H)).

Step 3. To a stirred solution of 2-(1-(tert-butyloxycarbonylamino)ethyl)-5-chlorobenzyl alcohol from the previous step (0.475 g, 1.67 mmol) in toluene (20.0 mL) at ambient temperature under nitrogen atmosphere was added DBU (0.26 mL g, 1.74 mmol) and DPPA (0.43 mL, 2.0 mmol). The mixture was stirred at ambient temperature for 72 h. The reaction was concentrated in vacuo then partitioned between EtOAc and water. The EtOAc layer was separated, dried over anhydrous Na$_2$SO$_4$, and filtered. The filtrate solvent was removed under reduced pressure and the residue purified by flash silica gel chromatography using dichloromethane as an eluent. 2-(1-(tert-butyloxycarbonylamino)ethyl)-5-chlorobenzylazide was obtained as a yellow oil after concentration of desired fractions in vacuo (0.53 g; HPLC RT=3.71 min, method A).

Step 4. To a stirred solution 2-(1-(tert-butyloxycarbonylamino)ethyl)-5-chlorobenzylazide from the previous step (0.53 g, 1.7 mmol) in THF (10.0 mL) and water (1 mL) at ambient temperature was added Ph$_3$P (0.536 g, 2.05 mmol). The mixture was stirred at ambient temperature for 18 h. The reaction was concentrated in vacuo then partitioned between Et$_2$O and diluted 1N HCl. The Et$_2$O layer was removed, and the aqueous layer basicified with saturated NaHCO$_3$ solution. The aqueous layer was extracted with Et$_2$O which was separated, dried over anhydrous Na$_2$SO$_4$, and filtered. The filtrate solvent was removed under reduced pressure. 2-(1-(tert-butyloxycarbonyamino)ethyl)-5-chlorobenzylamine was obtained as a clear colorless oil that crystallizes on sitting (0.366 g; HPLC RT=2.77 min, method A; LC-MS m/z= 285.1; $^1$H NMR, 400 MHz, CDCl$_3$, 7.33 ppm (s, 1H), 7.22 ppm (dd, 2H), 5.2 ppm (br s, 1H), 5.0 ppm (br s, 1H), 4.0 ppm (d, 1H), 3.85 ppm (d, 1H), 1.62 (br s, 1H), 1.4 ppm (s, 12H)).

Step 5. To a stirred solution under nitrogen atmosphere at ambient temperature of 2-(1-(tert-butyloxycarbonylamino)ethyl)-5-chlorobenzylamine (0.155 g, 0.54 mmol), Fmoc-L-Proline (0.184 g, 0.54 mmol), and HOBT hydrate (0.081 g, 0.60 mmol) in DMF (5 mL) was added iPr$_2$NEt (95 μL, 0.54 mmol), and EDC (0.156 g, 0.82 mmol). The reaction stirred at ambient temperature for 1 h. The reaction was concentrated in vacuo and the residue was partitioned between EtOAc and water. The EtOAc layer was separated, dried over anhydrous Na$_2$SO$_4$, and filtered. The filtrate solvent was removed under reduced pressure and the residue purified by flash silica gel chromatography using 1% MeOH in dichloromethane as an eluent. After concentration of desired fractions in vacuo, 1-fluroenylmethoxycarbonyl- N-(2-(1-(tert-butyloxycarbonylamino)ethyl)-5-chlorobenzyl)-L-prolinamide was obtained as a clear colorless oil that crystallizes on sitting (0.298 g; HPLC RT=3.93 min, method A; LC-MS m/z=604.1).

Step 6. To a solution of, 1-fluroenylmethoxycarbonyl-N-(2-(1-(tert-butyloxycarbonylamino)ethyl)-5-chlorobenzyl)-L-prolinamide from the previous step (0.298 g, 0.49 mmol) in DMF (3mL) at ambient temperature was added piperidine (1 mL). The reaction stirred at ambient temperature for 2 h. The reaction was concentrated in vacuo and the residue was partitioned between EtOAc and water. The EtOAc layer was separated, dried over anhydrous $Na_2SO_4$, and filtered. The filtrate solvent was removed under reduced pressure and the residue purified by flash silica gel chromatography using 10% MeOH in dichloromethane as an eluent. After concentrating desired fractions in vacuo, L-prolin-N-(2-(1-(tert-butyloxycarbonylamino)ethyl)-5-chlorobenzyl)amide was obtained as a clear colorless oil (0.150 g; HPLC RT=2.84 min, method A; LC-MS m/z=382.1; $^1$H NMR, 400 MHz, $CDCl_3$, 8.2 ppm (br s, 1H), 7.22–7.28 ppm (m, 3H), 5.02 ppm (br s, 1H), 4.88 ppm (m, 1H), 4.58 ppm (dd, 1H), 4.42 ppm (m, 1H), 3.84 ppm (q, 1H), 3.36 ppm (m, 1H), 2.2 ppm (m, 1H), 1.96 ppm (m, 1H), 1.78 ppm (m, 2H), 1.38 ppm (s, 12H)).

Step 7. To a stirred solution of L-prolin-N-(2-(1-(tert-butyloxycarbonylamino)ethyl)-5-chlorobenzyl)amide from the previous step (75 mg, 0.196 mmol), R-(–)-hexahydro-mandelic acid(34.2 mg, 0.22 mmol), and NMM (22 µL, 0.196 mmol) in DMF (5 mL) at ambient temperature under nitrogen atmosphere was added BOP reagent (104 mg, 0.24 mmol). The mixture was stirred at ambient temperature for 5 h. The solvent was removed under reduced pressure and the residue was purified by preparative thick layer silica gel plate chromatography (2000 µM×20 cm×20 cm) developed with 7.5% MeOH in dichloromethane. Desired bands were removed and eluted with 5% MeOH in dichloromethane which were concentrated in vacuo to obtain 1-((2R)-2-hydroxy-2-cyclohexylethanoyl)-N-(2-(1-(tert-butyloxycarbonylamino)ethyl)-5-chlorobenzyl)-L-prolinamide as a clear colorless oil (85 mg; HPLC RT 3.51 min, method A; LC-MS m/z=522.2).

Step 8. 1-(2R)-2-hydroxy-2-cyclohexylethanoyl)-N-2 (tertbutyloxycarbonylamino)ethyl)-5-chlorobenzyl)-L-prolinamide from the previous step (0.85 mg, 0.163 mmol) was dissolved in EtOAc (10 mL) and cooled with stirring to 0° C. Into this solution was bubbled in HCl gas for 5 min. The resulting solution was stirred at 0° C. for 30 min, then concentrated in vacuo. The solid which had formed was triturated with $Et_2O$ and collected by filtration and washed with several portions of ether. The hydrochloride of the title compound was obtained as a white solid after drying under high vacuum (HPLC RT=2.71 min, method A; LC-MS m/z=422.2; $^1$H NMR, 400 MHz, $CD_3OD$, 7.52 ppm (d, 1H), 7.46 ppm (d, 1H), 7.43 ppm (dd, 1H), 4.44 ppm (dd, 2H), 4.32 ppm (dd, 1H), 4.06 ppm (d,1H), 3.74 ppm (m, 1H), 3.64 ppm (m, 1H), 2.2 ppm (m, 2H), 2.08 ppm (m, 2H), 1.94 ppm (m, 4H), 1.6 ppm (d, 3H), 1.2 ppm (m, 7H)).

EXAMPLE 15

D-Phenylalanyl-N-(2-aminomethyl-5-chlorobenzyl)-L-prolinamide

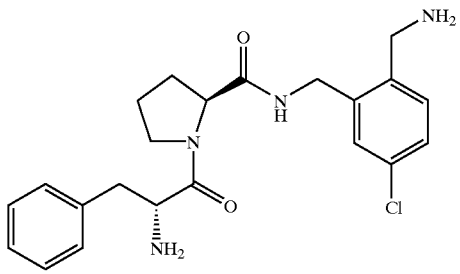

Step 1. Into a stirred solution of 2-bromo-5-chlorobenzoic acid (11 g, 46.7 mmol, HPLC RT=2.99 min) in methanol (250 mL) at 0° C. was bubbled HCl gas. The reaction was allowed to warm to room temperature and stirred overnight. The reaction mixture was concentrated in vacuo to give an orange oil, which was purified by flash chromatography using hexanes as eluant to give methyl 2-bromo-5-chlorobenzoate as a colorless oil (10.7 g, 92% yield). TLC $R_f$=0.6 (5% EtOAc-hexanes); HPLC RT=3.48 min, method A; $^1$H NMR ($CDCl_3$, 400MHz) 7.78 ppm (d, 1H, J=2.6 Hz); 7.59 ppm (d, 1H, J=12.81 Hz); 7.30 ppm (dd, 1H, J=8.6, 2.5 Hz); 3.94 ppm (s, 3H).

Step 2. To a stirred solution of methyl 2-bromo-5-chlorobenzoate from the previous step (11.5 g, 46 mmol) in degassed DMF (50 mL) was added zinc cyanide (2.82 g, 24.0 mmol) and palladium tetrakis-triphenylphosphine (1.0 g, 0.86 mmol) and the mixture was heated to 90° C. for 18 h. The reaction was partitioned between EtOAc (200 mL) and water (100 mL). The organic phase was concentrated in vacuo and the residue was purified by flash chromatography eluting with a gradient of 10%, 15%, 20% ethyl acetate in hexane yielding methyl 5-chloro-2-cyanobenzoate as a white solid (8.0 g, 88% yield). TLC $R_f$=0.4 (15% EtOAc-hexanes); HPLC RT=3.13 min, method A; $^1$H NMR ($CDCl_3$, 400 MHz) 8.13 ppm (d, 1H, J=1.83 Hz); 8.09 ppm (d, 1H, J=8.24 Hz); 7.29 ppm (dd, I H, J=8.34, 2.10 Hz); 4.02 ppm (s, 3H).

Step 3. To a stirred solution of lithium aluminum hydride (104 mL of a 1.0 molar solution in ether, 104 mmol) in anhydrous THF (200 mL) at 0° C. was added methyl 5-chloro-2-cyanobenzoate from the previous step (9.28 g, 47 mmol) in anhydrous THF (15 mL). After 1 h, the reaction was quenched at 0° C. with water (3.9 mL), 3.0 N aqueous NaOH (4.0 mL, 12 mmol) and water (3.9 mL). Ether (200 mL) was added and the thick precipitate which had formed was removed by filtration and washed with THF. The filtrate was concentrated in vacuo and the crude product, 2-aminomethyl-5-chlorobenzyl alcohol, was used immediately in the next step. $^1$H NMR ($CDCl_3$, 400 MHz) 7.17–7.36 ppm (m, 3H); 4.60 ppm (s, 2H); 3.98 ppm (s, 2H).

Step 4. To a stirred solution of crude 1-hydroxymethyl-2-aminomethyl-5-chlorobenzene from the previous step in dichloromethane (200 mL) was added di-tert-butyl dicarbonate (11.38 g, 52.18 mmol) at room temperature. After one hour, the reaction was partitioned with water (200 mL). The organic layer was concentrated in vacuo and the residue was purified by flash chromatography eluting a gradient of 20%, 30%, 40% EtOAc in hexane. The brown oil which resulted was taken up in dichloromethane (500 mL) and treated with activated charcoal to give 2-(tert-butyloxycarbonylaminomethyl)-5-chlorobenzyl alcohol as an off-white solid (9.2 g, 72% yield over two steps). TLC R$_f$=0.3 (25% EtOAc-hexanes); HPLC RT=3.15 min, method A; LC-MS m/z=272; $^1$H NMR (CDCl$_3$, 400 MHz) 7.36 ppm (s, 1H); 7.2–7.5 ppm (m, 2H); 4.69 ppm (b s, 2H); 4.32 ppm (d, 2H, J=6.04 Hz); 1.43 ppm (s, 9H).

Step 5. To a stirred solution of 2-(tert-butyloxycarbonyl-aminomethyl)-5-chlorobenzyl alcohol from the previous step (10 g, 36.8 mmol) in anhydrous THF (100 mL) at 0° C. was added DPPA (8.3 mL, 38.6 mmol) and DBU (5.79 mL, 38.6 mmol). The mixture was stirred for 1 h at 0° C. and then for 18 h at ambient temperature. The mixture was partitioned between EtOAc (250 mL) and water (100 mL). The organic layer was washed with brine and was concentrated in vacuo. The residue was purified by flash chromatography, eluting with a gradient of 10%, 15%, 20% EtOAc in hexane to give 1-azidomethyl-2-(tert-butyloxycarbonylaminomethyl)-5-chlorobenzene as an oil (9.2 g, 85% yield). HPLC RT=3.65 min, method A; LC-MS m/z=152 (parent ion not observed); $^1$H NMR (CDCl$_3$, 400 MHz) 7.25–7.39 ppm (m, 3H); 4.41 ppm (s, 2H), 4.32 ppm (d, 2H, J=5.86 Hz); 1.45 ppm (s, 9H).

Step 6. To a stirred solution of 1-azidomethyl-2-(tert-butyloxycarbonylaminomethyl)-5-chlorobenzene from the previous step (10.9 g, 36.73 mmol) in THF (60 mL) and water (6 mL) was added triphenylphospine (10.59 g, 40.40 mmol). The reaction was heated to 50° C. and stirred for 18 h. The reaction was concentrated in vacuo and the residue was purified by flash chromatography using a gradient elution of 2%, 3%, 4%, 5% A in dichloromethane (A=95:5 MeOH:NH$_4$OH). Concentration of product-containing fractions in vacuo gave 2-(tert-butyloxycarbonylaminomethyl)-5-chlorobenzylamine as a solid (8.8 g, 88% yield). TLC R$_f$=0.3 (95:5:0.25 CH$_2$Cl$_2$:MeOH:NH$_4$OH); HPLC RT=2.64 min, method A; LC-MS m/z=271; $^1$H NMR (CDCl$_3$, 400 MHz) 7.21–7.52 ppm (m, 3H); 4.32 ppm (b d, 2H); 3.90 ppm (s, 2H); 1.44 ppm (s, 9H).

Step 7. To a solution of 2-(tert-butyloxycarbonylaminomethyl)-5-chlorobenzylamine from the previous step (0.14 mmol, 37 mg), EDC (0.21 mmol, 40 mg), and Boc-D-Phe-L-Pro-OH (0.14 mmol, 50 mg), in 0.5 mL dimethylformamide, was added HOAT (0.15 mmol, 21 mg). The solution was stirred overnight and purified by preparative reverse phase HPLC using an acetonitrile:water gradient containing 0.1% TFA to give N-(tert-buyloxycarbonyl)-D-phenylalanyl-N-(2-(tert-butyloxycarbonylaminomethyl)-5-chlorobenzyl)-L-prolinamide. Mass Spec ES (M+1)=615.2.

Step 8. HCl gas was bubbled through a 0° C. solution of N-(tert-buyloxycarbonyl)-D-phenylalanyl-N-(2-(tert-butyloxycarbonylaminomethyl)-5-chlorobenzyl)-L-prolinamide from the previous step (0.073 mmol, 45 mg) in 1 mL ethyl acetate for 2 min. The mixture was stirred for 1 h and concentrated in vacuo to give the hydrochloride salt of the title compound as a solid. Mass Spec ES (M+1)=415.1.

EXAMPLE 16

1-((2R)-3,3-Dimethyl-2-hydroxybutanoyl)-N-(2-aminomethyl-5-chlorobenzyl)-L-prolinamide

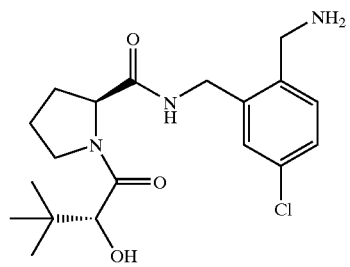

Step 1. To a stirred solution of 2-(tert-butyloxycarbonylaminomethyl)-5-chlorobenzylamine (3.80 g, 14.1 mmol, HPLC RT=2.63 min), Fmoc-L-Proline (4.98 g, 14.8 mmol, HPLC RT=3.26 min), and HOBT hydrate (2.15 g, 14.1 mmol) in DMF (30 mL) was added EDC (3.51 g, 18.3 mmol). The pH of the solution was slowly raised to pH 6 (as measured on wetted E. Merck pH indicator strips) by the gradual addition of diisopropylethylamine (~2 mL). At 2 hours reaction time, HPLC analysis indicated complete consumption of the benzylamine starting material. The solvent was removed on a rotary evaporator (bath temp 30° C., ~0.5 torr) and the residue was partitioned between EtOAc (200 mL) and water (100 mL). The organic phase was dried (MgSO$_4$), filtered, and the solvent was removed on a rotary evaporator. The residue was stirred in ether (100 mL) for several hours and the solid was collected by filtration, washed with ether, and dried to give 1-fluroenylmethoxycarbonyl-N-(2-(tert-butyloxycarbonylaminomethyl)-5-chlorobenzyl)-L-prolinamide as a white crystalline solid (7.8 g; 94%; TLC R$_f$=0.5 (1;1 EtOAc:hexanes); HPLC RT=3.87 min, method A; LC-MS m/z=590).

Step 2. To a stirred solution of 1-fluroenylmethoxycarbonyl-N-(2-(tert-butyloxycarbonylaminomethyl)-5-chlorobenzyl)-L-prolinamide from the previous step (7.0 g, 12 mmol, HPLC RT=3.87 min) in DMF (50 mL) was added piperidine (7.5 mL). At 15 min reaction time, HPLC analysis indicated complete consumption of the starting material with formation of two new closely eluting components (HPLC RT=2.76 min desired product, 2.80 min Fmoc-derived by-product). The solvent and excess piperidine were removed on a rotary evaporator (bath temp 40° C., 0.5 torr). The residue was purified by flash chromatography using a gradient elution of 96:4 to 92:8 to 88:12 CH$_2$Cl$_2$:A (A=95:5 MeOH:NH$_4$OH). L-Prolin-N-(2-(tert-butyloxycarbonylaminomethyl)-5-chlorobenzyl)amide was obtained as a gum (3.9 g, 90%; TLC R$_f$=0.4 (90:10:0.5 CH$_2$Cl$_2$:MeOH:NH$_4$OH; iodine visualization); HPLC RT=2.77 min, method A; LC-MS m/z=368; $^1$H NMR, 400 MHz, CDCl$_3$, 8.04 ppm (br s, 1H), 7.2–7.3 ppm (m, 3H), 5.24 ppm (br s, 1H), 4.4–4.5 ppm (ABX, 2H), 4.28 ppm (d, 2H), 3.80 ppm (dd, J=5.4, 9.4 Hz, 1H), 25 2.9–3.0 ppm (ABXY, 2H), 2.1–2.2 ppm (m, 1H), 1.9–2.0 ppm (m, 1H), 1.7–1.8 ppm (m, 2H), 1.44 ppm (s, 3H)).

Step 3. To a stirred solution of (2R)-2-amino-3,3-dimethylbutyric acid (5.0 g, 38.12 mmol) in 80 mL of 1N sulfuric acid at −10° C. was dropped in slowly a solution of sodium nitrite (5.26 g, 76.23 mmol) dissolved in 25 mL of water. After addition, the reaction was allowed to slowly equilibrate to ambient temperature over 20 h. Sodium chloride (10 g) was added and the solution was extracted twice with 100 mL portions of diethyl ether. The organic layers were separated, combined, dried over anhydrous sodium sulfate, and filtered. The filtrate solvent was removed under reduced pressure. The residue was purified by preprative HPLC using a chiralpak AD column (5 cm×50 cm) using 5% ethanol in 95% hexanes with 0.2% TFA as the mobile phase at a flow rate of 80 mL/min. The product-containing fractions were concentrated in vacuo. (2R)-3,3-Dimethyl-2-hydroxybutyric acid was obtained as an oil that crystallizes on sitting (2.2 g; 44%).

Step 4. To a stirred solution of L-prolin-N-(2-(tert-butyloxycarbonylaminomethyl)-5-chlorobenzyl)amide from step 2 (3.90 g, 10.6 mmol, HPLC RT=2.77 min), (2R)-3,3-dimethyl-R-hydroxybutyric acid from step 3 (1.40 g, 10.6 mmol), and HOBT hydrate (1.68 g, 11 mmol) in DMF (60 mL) was added EDC (2.65 g, 13.8 mmol). Diisopropylethylamine was then added slowly in portions (11.5 mL total) to bring the pH of the solution to 6–7 as measured on wetted E. Merck pH indicator strips. The mixture was stirred at ambient temperature for 6 h, at which time HPLC analysis indicated complete consumption of the proline starting material. Water (10 mL) was added and the solvents were removed under reduced pressure. The residue was partitioned between EtOAc (300 mL) and saturated aqueous NaHCO$_3$ (200 mL). The EtOAc layer was separated, dried over anhydrous MgSO$_4$, and filtered. The filtrate solvent was removed under reduced pressure and the residue was purified by flash chromatography using a gradient elution of 2:1, 4:1, and 1:0 EtOAc:hexanes. 1-((2R)-3,3-dimethyl-2-hydroxybutanoyl)-N-(2-(tert-butyloxycarbonylaminomethyl)-5-chlorobenzyl)-L-prolinamide was obtained as a colorless gum (4.65 g, 91%; TLC R$_f$=0.7 (EtOAc); HPLC RT=3.35 min, method A; LC-MS m/z=482).

Step 5. 1-((2R)-3,3-Dimethyl-2-hydroxybutanoyl)-N-(2-(tert-butyloxycarbonylaminomethyl)-5-chlorobenzyl)-L-prolinamide from the previous step (4.65 g, 9.65 mmol, HPLC RT=3.35 min) was dissolved in CH$_2$Cl$_2$ (15 mL) and cooled with stirring to 0° C. A solution of anhydrous HCl in ether (38 mL of a 1 Molar solution, 38 mmol) was added slowly. The resulting solution was stirred at 0° C. for 10 min, and then at ambient temperature for 20 h. The solid which had formed was collected by filtration and washed with several portions of ether. The solid was purified by preparative reverse-phase HPLC using an acetonitrile:water gradient containing 0.05% concentrated HCl. The product-containing fractions were combined and lyophilized to give the hydrochloride salt of the title compound as a white solid (HPLC RT=2.52 min, method A; LC-MS m/z=382; C, H, N combustion analysis, calculated for C$_{19}$H$_{28}$ClN$_3$O$_3$, 1.0HCl, 1.5H$_2$O, calculated C, 51.24, H, 7.24, N, 9.43, found C, 51.32, H, 7.17, B, 9.33).

EXAMPLE 17

1-((2R)-2-Cyclohexyl-2-hydroxyethanoyl)-N-(2-aminomethyl-5-chlorobenzyl)-L-prolinamide

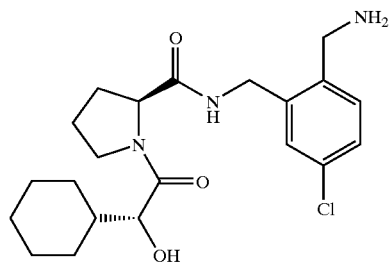

Step 1. To a stirred solution of L-prolin-N-(2-(tert-butyloxycarbonylaminomethyl)-5-chlorobenzyl)amide (1.23 g, 3.32 mmol, 1.0 equiv, HPLC RT=2.77 min), R-hexahydromandelic acid (0.552 g, 3.49 mmol, 1.05 equiv), and HOBT hydrate (0.524 g, 3.32 mmol, 1.0 equiv) in DMF (20 mL) was added EDC (0.855 g, 4.32 mmol, 1.3 equiv). Diisopropylethylamine was then added in portions (0.5 mL total) to bring the pH of the solution to 6–7 as measured on wetted E. Merck pH indicator strips. The mixture was stirred at ambient temperature for 2 h, at which time HPLC analysis indicated complete consumption of the proline starting material. The DMF was removed under reduced pressure and the residue was partitioned between EtOAc (100 mL) and saturated aqueous NaHCO$_3$ (50 mL). The EtOAc layer was separated, dried over anhydrous MgSO$_4$, and filtered. The filtrate solvent was removed under reduced pressure and the residue was purified by flash chromatography using EtOAc as eluant. 1-((2R)-2-Cyclohexyl-2-hydroxyethanoyl)-N-(2-(tert-butyloxycarbonylaminomethyl)-5-chlorobenzyl)-L-prolinamide was obtained as a colorless gum (1.87 g, 90%; TLC R$_f$=0.7 (EtOAc); HPLC RT=3.45 min, method A; LC-MS m/z=508).

Step 2. 1-((2R)-2-Cyclohexyl-2-hydroxyethanoyl)-N-(2-(tert-butyloxycarbonylaminomethyl)-5-chlorobenzyl)-L-prolinamide from the previous step (1.87 g, 3.68 mmol, HPLC RT=3.45 min) was dissolved in EtOAc (150 mL) and cooled with stirring to 0° C. HCl gas was bubbled through the solution for 10 minutes. After 2 hours at 0° C., HPLC analysis indicated complete consumption of the starting material, and the solvent was removed under reduced pressure. The resulting solid was triturated in EtOAc, filtered, and dried in vacuo to give the hydrochloride salt of the title compound as a white solid (TLC R$_f$=0.4 (90:10:0.5 CH$_2$Cl$_2$:MeOH:NH$_4$OH); HPLC RT=2.65 min, method A; LC-MS m/z=408).

EXAMPLE 18

1-((2R)-2-Cyclohexyl-2-(ethoxycarbonylmethylamino)ethanoyl)-N-(2-aminomethyl-5-chlorobenzyl)-L-prolinamide

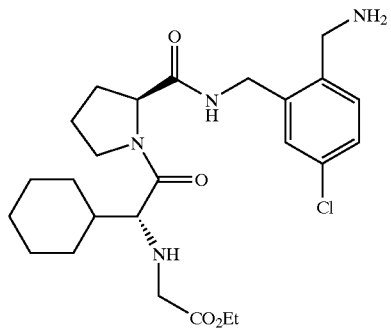

Step 1. To a solution of L-prolin-N-(2-(tert-butyloxycarbonylaminomethyl)-5-chlorobenzyl)amide (0.30 g, 0.82 mmol; HPLC RT=2.77 min), HOBT hydrate (0.13 g, 0.83), and Fmoc-D-cyclohexylglycine (0.30 g, 0.82 mmol, HPLC RT=3.62 min) in DMF (15 mL) was added EDC (0.20 g, 1.0 mmol). To the stirred solution was added DIEA (approximately 0.12 mL) until the solution measured pH 6 on wetted E. Merck pH indicator strips. The mixture was stirred for 18 h at ambient temperature. The solvent was removed under reduced pressure and the residue was partitioned between EtOAc (100 mL) and saturated aqueous sodium bicarbonate solution (50 mL). The organic phase was separated, dried (MgSO$_4$), filtered, and concentrated under reduced pressure. The residue was purified by flash silica gel column chromatography using 2:1 EtOAc:hexanes as eluant. The product-containing fractions were combined and removal of the solvent under reduced pressure gave N-fluorenylmethoxycarbonyl-D-cyclohexylglycyl-N-(2-(tert-butyloxycarbonylaminomethyl)-5-chlorobenzyl)-L-prolinamide as a gum (0.46 g; HPLC RT=4.16 min, method A, LC-MS m/z=715).

Step 2. To a solution of N-fluorenylmethoxycarbonyl-D-cyclohexylglycyl-N-(2-(tert-butyloxycarbonylaminomethyl)-5-chlorobenzyl)-L-prolinamide from the previous step (0.46 g, 0.64 mmol) in DMF (10 mL) was added piperidine (2 mL). The mixture was stirred at ambient temperature for 30 min, then the solvent and excess piperidine were removed under reduced pressure. The residue was purified by flash silica gel column chromatography using a gradient elution of 2% to 4% to 8% A:CH$_2$CL$_2$ (A=95:5 MeOH:NH$_4$OH). The product-containing fractions were combined to give D-cyclohexylglycyl-N-(2-(tert-butyloxycarbonylaninomethyl)-5-chlorobenzyl)-L-prolinamide as an amorphous solid after removal of solvents under reduced pressure (0.28 g; TLC R$_f$=0.5 (95:5:0.25 CH$_2$Cl$_2$:MeOH:NH$_4$OH); HPLC RT=3.07 min, method A; LC-MS m/z=507).

Step 3. To a stirred solution of D-cyclohexylglycyl-N-(2-(tert-butyloxycarbonylaminomethyl)-5-chlorobenzyl)-L-prolinamide from the previous step (0.18 g, 0.35 mmol) in anhydrous THF (6 mL) was added potassium carbonate (0.15 g, 1.1 mmol) and ethyl bromoacetate (0.11 g, 0.66 mmol). The mixture was stirred at ambient temperature for 24 h. The solids were removed by filtration and the filtrate solvent was remove under reduced pressure. The residue was purified by flash silica gel column chromatography using EtOAc as eluant. The product-containing fractions were combined to give N-ethoxycarbonylmethyl-D-cyclohexylglycyl-N-(2-(tert-butyloxycarbonylaminomethyl)-5-chlorobenzyl)-L-prolinamide as an amorphous solid (0.19 g; TLC R$_f$=0.5 (EtOAc); HPLC RT=3.26 min, method A; LC-MS m/z= 593).

Step 4. N-Ethoxycarbonylmethyl-D-cyclohexylglycyl-N-(2-(tert-butyloxycarbonylaminomethyl)-5-chlorobenzyl)-L-prolinamide from the previous step (0.185 g, 0.312 mmol) was dissolved in EtOAc (10 mL) and cooled with stirring to 0° C. Into this solution was bubbled in HCl gas for 5 min. The resulting solution was stirred at 0° C. for 30 min, then concentrated in vacuo. The solid which had formed was triturated with Et$_2$O and collected by filtration and washed with several portions of ether. The HCl salt of the title compound was obtained as a white solid after drying under high vacuum (HPLC RT=2.49 min, method A; LC-MS m/z=493.2; $^1$H NMR, 400 MHz, CD$_3$OD, 7.52 ppm (d, 1H), 7.44 ppm (d, 1H), 7.39 ppm (dd, 1H), 4.54 ppm (d, 1H), 4.46 ppm (m, 1H), 4.39 ppm (d, 1H), 4.3 ppm (q, 2H), 4.24 ppm (m, 2H), 3.9 ppm (s, 2H), 3.76 ppm (m, 1H), 3.63 ppm (m, 1H), 2.5 ppm (m, 1H), 1.7–2.5 ppm (m, 10H), 1.51 ppm (t, 3H), 1.16–1.36 (m, 5H)).

EXAMPLE 19

1-((2R)-2-Carboxymethylamino-2-cyclohexylethanoyl)-N-(2-aminomethyl-5-chlorobenzyl)-L-prolinamide

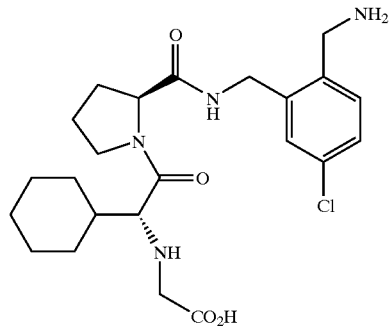

To a stirred solution of N-ethoxycarbonylmethyl-D-cyclohexylglycyl-N-(2-aminomethyl-5-chlorobenzyl)-L-prolinamide (100 mg, 0.203 mmol) in 1:1:1 THF:MeOH:water (20 mL) was added 1N NaOH (0.40 mL, 0.40 mmol). The mixture was stirred at ambient temperature for 2 h, acidified to pH=1 using 1N HCl, then was concentrated in vacuo. The residue was purified by preparative reverse phase HPLC using a gradient of 95:5 to 0:100 (water:CH$_3$CN. 0.1% TFA) over 30 min with a flow rate of 18 ml/min. After concentration of desired fractions in vacuo the residue was triturated with Et$_2$O. The solid was collected by filtration and dried under high vacuum. The TFA salt of the title compound was obtained as a white powder (HPLC RT=2.33 min, method A; LC-MS m/z=465.1; $^1$H NMR, 400 MHz, CD$_3$OD, 7.48 ppm (d, 1H), 7.42 ppm (d, 1H), 7.38 ppm (dd, 1H), 4.56 ppm (d, 1H), 4.46 ppm (q, 1H), 4.33 ppm (d, 1H), 4.23 ppm (m, 3H), 3.74 ppm (m, 1H), 3.69 ppm (s, 2H), 3.62 ppm (m, 1H), 2.28 ppm (m, 1H), 1.78–2.06 ppm (m, 7H), 1.72 ppm (m, 12H), 1.5 ppm (m, 4H)).

EXAMPLE 20

1-((2R)-2-Amino-2-cyclohexylethanoyl)-N-(2-aminomethyl-5-chlorobenzyl)-L-prolinamide

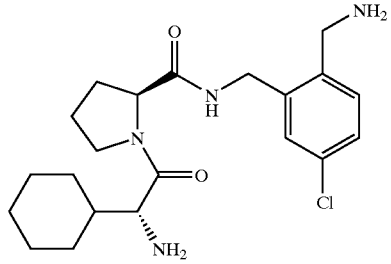

Into a stirred solution of D-cyclohexylglycyl-N-(2-(tert-butyloxycarbonylaminomethyl)-5-chlorobenzyl)-L-prolinamide (0.030 g, 0.059 mmol) in EtOAc (10 mL) at 0° C. was bubbled HCl gas for 5 minutes. The resulting solution was stirred at 0° C. for 30 min, then concentrated in vacuo. The solid which had formed was triturated with Et$_2$O and collected by filtration and washed with several portions of ether. The hydrochloride salt of the title compound was obtained as a white solid after drying under high vacuum (HPLC RT=2.37 min, method A; LC-MS m/z=407.2; $^1$H NMR, 400 MHz, CD$_3$OD, 7.55 ppm (d, 1H), 7.42 ppm (d, 1H), 7.38 ppm (dd, 1H), 4.53 ppm (d, 1H), 4.43 ppm (dd, 1H), 4.38 ppm (d, 1H), 4.24 ppm (s, 2H), 4.04 ppm (d, 1H), 3.86 ppm (m, 1H), 3.64 ppm (m, 1H), 2.24 ppm (m, 1H), 2.0 ppm (m, 3H), 1.82 ppm (m, 4H), 1.7 ppm (m, 2H), 1.12–1.36 (m, 5H)).

EXAMPLE 21

1-((2R)-2-Hydroxy-3-methylbutanoyl)-N-(2-aminomethyl-5-chlorobenzyl)-L-prolinamide

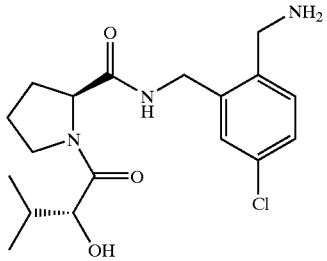

Step 1. To a stirred solution of L-prolin-N-(tert-butyloxycarbonylaminomethyl)-5-chlorobenzyl)amide (0.23 g, 0.62 mmol, HPLC RT=2.77 min), (2R)-2-hydroxy-3-methylbutyric acid (77 mg, 0.65 mm and HOBT hydrate (99 mg, 0.65 mmol) in DMF (4 mL) was added EDC (0.16 g, 0.82 mmol). Diisopropylethylamine was then added in portions (0.1 mL total) to bring the pH of the solution to 6–7 as measured on wetted E. Merck pH indicator strips. The mixture was stirred at ambient temperature for 2 h, at which time HPLC analysis indicated complete consumption of the proline starting material. The DMF was removed under reduced pressure and the residue was partitioned between EtOAc (100 mL) and saturated aqueous NaHCO$_3$ (50 mL). The EtOAc layer was separated, dried over anhydrous MgSO$_4$, and filtered. The filtrate solvent was removed under reduced pressure and the residue was purified by flash chromatography using EtOAc as eluant. 1-((2R)-Hydroxy-3-methylbutanoyl)-N-(2-(tert-butyloxycarbonylaminomethyl)-5-chlorobenzyl)-L-prolinamide was obtained as a colorless gum (0.26 g, 90%; TLC R$_f$=0.7 (EtOAc); HPLC RT=3.21 min, method A; LC-MS m/z=468).

Step 2. 1-((2R)-Hydroxy-3-methylbutanoyl)-N-(2-(tert-butyloxycarbonylaminomethyl)-5-chlorobenzyl)-L-prolinamide from the previous step (0.26 g, 0.56 mmol, HPLC RT=3.21 min) was dissolved in EtOAc (20 mL) and cooled with stirring to 0° C. HCl gas was bubbled through the solution for 10 minutes. After 2 hours at 0° C., HPLC analysis indicated complete consumption of the starting material, and the solvent was removed under reduced pressure. The resulting solid was triturated in EtOAc, filtered, and dried in vacuo to give the hydrochloride salt of the title compound as a white solid (TLC R$_f$=0.3 (90:10:0.5 CH$_2$Cl$_2$:MeOH:NH$_4$OH); HPLC RT=2.38 min, method A; LC-MS m/z=368; $^1$H NMR, 400 MHz, DMSO-d$_6$, ~3.5:1 mixture of rotamers, selected signals: 8.84 ppm (minor) and 8.64 ppm (major) (t, J=6 Hz, 1H), 0.87, 0.83 ppm (major) and 0.74, 0.58 ppm (minor) (two doublets, J=7 Hz, 3H)).

EXAMPLE 22

1-((2S)-2-Hydroxy-2-phenylpropanoyl)-N-(2-aminomethyl-5-chlorobenzyl)-L-prolinamide

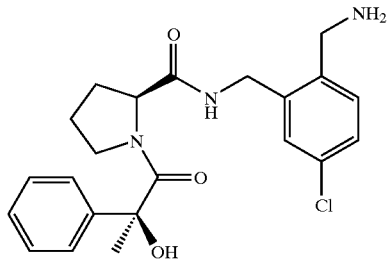

Step 1. To a stirred solution of L-prolin-N-(tert-butyloxycarbonylaminomethyl)-5-chlorobenzyl)amide (90 mg, 0.245 mmol), (2S)-2-hydroxy-2-phenylpropanoic acid (41 mg, 0.245 mmol), and HOBT hydrate (36 mg, 0.269 mmol) in DMF (5 mL) at ambient temperature under nitrogen atmosphere was added EDC (71 mg, 0.37 mmol). The mixture was stirred at ambient temperature for 18 h. The solvent was removed under reduced pressure. The residue was partitioned between EtOAc (100 mL) and saturated aqueous NaHCO$_3$ (100 mL). The EtOAc layer was separated, dried over anhydrous Na$_2$SO$_4$, and filtered. The filtrate solvent was removed under reduced pressure and the residue was purified by flash silica gel chromatography using 2% methanol in dichloromethane as an eluent. 1-((2S)-2-Hydroxy-2-phenyl-propanoyl)-N-(2-(tert-butyloxycarbonylaminomethyl)-5-chlorobenzyl)-L-prolinamide was obtained as a clear colorless oil (0.125 g; HPLC RT=3.48 min, method A; LC-MS m/z=516.2; $^1$H NMR, 400 MHz, CDCl$_3$, 7.4 ppm (d, 2H), 7.2–7.34 ppm (m, 6H), 5.45 ppm (br s, 1H), 5.08 ppm (br s, 1H), 4.24–4.57 ppm (br m, 5H), 3.4 ppm (m, 1H), 3.12 ppm (m, 1H), 2.18 ppm (br s, 1H), 2.04 ppm (m, 1H), 1.9 ppm (m, 1H), 1.8 ppm (m, 1H), 1.72 ppm (s, 3H), 1.56 ppm (m, 1H), 1.45 ppm (s, 9H)).

Step 2. 1-((2S)-2-Hydroxy-2-phenyl-propanoyl)-N-(2-(tert-butyloxycarbonylaminomethyl)-5-chlorobenzyl)-L- prolinamide from the previous step (0.125 g, 0.24 mmol) was dissolved in EtOAc (10 mL) and cooled with stirring to 0° C. Into this solution was bubbled in HCl gas for 5 min. The resulting solution was stirred at 0° C. for 30 min, then concentrated in vacuo. The solid which had formed was triturated with Et$_2$O and collected by filtration and washed with several portions of ether. The hydrochloride salt of the title compound was obtained as a white solid after drying overnight under high vacuum (HPLC RT=2.66 min, method A; LC-MS m/z=416.1; $^1$H NMR, 400 MHz, CD$_3$OD, 7.54 ppm (s, 1H), 7.42 ppm (m, 4H), 7.34 ppm (m, 2H), 7.26 ppm (m, 1H), 4.54 ppm (d, 1H), 4.4 ppm (d, 1H), 4.3 ppm (m, 2H), 3.6 ppm (m, 1H), 3.24 ppm (m, 1H), 2.08 ppm (m, 1H), 1.8 ppm (m, 1H), 1.7 ppm (m, 1H), 1.6 ppm (s, 3H), 1.5 ppm (m, 1H)).

EXAMPLE 23

1-(1-Hydroxycyclopropylcarbonyl)-N-(2-aminomethyl-5-chlorobenzyl)-L-prolinamide

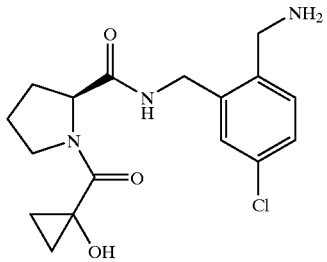

Step 1. To a stirred solution of L-prolin-N-(2-(tert-butyloxycarbonylaminomethyl)-5-chlorobenzyl)amide (109 mg, 0.3 mmol), 1-hydroxycyclopropylcarboxylic acid (33.3 mg, 0.33 mmol), and NMM (33 μL, 0.3 mmol) in DMF (5 mL) at ambient temperature under nitrogen atmosphere was added BOP reagent (157 mg, 0.36 mmol). The mixture was stirred at ambient temperature for 2 h. The solvent was removed under reduced pressure. The residue was partitioned between EtOAc and saturated aqueous NaHCO$_3$. The EtOAc layer was separated, dried over anhydrous Na$_2$SO$_4$, and filtered. The filtrate solvent was removed under reduced pressure and the residue was purified by preparative thick layer silica gel plate chromatography (2000 μM×20 cm×20 cm) developed with 5% MeOH in dichloromethane. Desired bands were removed and eluted with 5% MeOH in dichloromethane. The filtrate solvent was concentrated in vacuo to obtain 1-(1-hydroxycyclopropylcarbonyl)-N-(2-(tert-butyloxycarbonylaminomethyl)-5-chlorobenzyl)-N-prolinamide as a yellow oil (100 mg; HPLC RT=3.01 min, method A; LC-MS m/z=452.1).

Step 2. 1-(1-Hydroxycyclopropylcarbonyl)-N-(2-(tert-butyloxycarbonylaminomethyl)-5-chlorobenzyl)-N-prolinamide from the previous step (0.100 g, 0.22 mmol) was dissolved in EtOAc (10 mL) and cooled with stirring to 0° C. Into this solution was bubbled in HCl gas for 5 min. The resulting solution was stirred at 0° C. for 30 min, then the volume of the reaction was reduced by 50% in vacuo. The solid which had formed was triturated with Et$_2$O and collected by filtration and washed with several portions of ether. The hydrochloride salt of the title compound was obtained as a yellow solid after drying under high vacuum (HPLC RT=2.17 min, method A; LC-MS m/z=352.1; $^1$H NMR, 400 MHz, CD$_3$OD, 7.6 ppm (d, 1H), 7.4 ppm (m, 2H), 4.5 ppm (d, 1H), 4.4 ppm (m, 1H), 4.3 ppm (m, 3H), 4.0 ppm (m, 1H), 3.85 ppm (m, 1H), 1.7–2.2 ppm (br m, 4H), 1.2 ppm (m, 2H), 1.0 ppm (m, 1H), 0.9 ppm (m, 1H).

EXAMPLE 24

1-(3-Ethyl-2-hydroxypentanoyl)-N-(2-aminomethyl-5-chlorobenzyl)-L-prolinamde

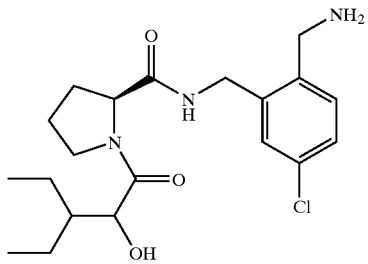

Step 1. A solution of 2-ethyl butyraldehyde (6 g, 60 mmol) in CH$_2$Cl$_2$ (75 mL) was stirred vigorously with a solution of sodium bisulfite (9.4 g, 90 mmol) in water (35 mL). The thick precipitate which had formed was collected by filtration and washed with CH$_2$Cl$_2$ and dried in vacuo. The bisulfite adduct (10 g, 49 mmol) was dissolved in water (60 mL) and to the solution was added sodium cyanide (3.6 g, 73 mmol). The resulting solution was stirred at ambient temperature for 48 h. The mixture was extracted with ether (2×100 mL) and the combined extracts were dried (MgSO$_4$), filtered, and the solvent was removed in vacuo. The residue was purified by flash silica gel column chromatography using a gradient elution of 10%, 12.5%, 15% EtOAc in hexanes. The product-containing fractions were combined to give 1-cyano-2-ethylbutanol as a liquid after removal of the solvents in vacuo (5.0 g; TLC R$_f$=0.4 (9:1 hexanes:EtOAc); 400 MHz $^1$H NMR, CDCl$_3$, 4.51 ppm (dd, 1H), 2.45 ppm (d, 1H), 1.4–1.7 ppm (overlapping m, 5H), 0.98 ppm (overlapping t, 6H)).

Step 2. 1-Cyano-2-ethylbutanol from the previous step (5 g, 39 mmol) was stirred at ambient temperature in 6 N aqueous HCl (50 mL) for 18. The mixture was then warmed to 70° C. and stirred for 6 h. After cooling to ambient temperature, the solution was extracted with CH$_2$Cl$_2$ (2×75 mL). The combined extracts were dried (MgSO$_4$), filtered, and the solvent was removed in vacuo to give 2-hydroxy-3-ethylpentanoic acid as a crystalline solid (4.1 g; 400 MHz $^1$H NMR, CDCl$_3$, 4.35 ppm (d, 1H), 1.68 ppm (m, 1H), 1.49 ppm (m, 2H), 1.36 ppm (m, 2H), 0.98 ppm (t, 3H), 0.93 (t, 3H).

Step 3. To a stirred solution of L-prolin-N-(2-(tert-butyloxycarbonylaminomethyl)-5-chlorobenzyl)amide (171 mg, 0.47 mmol), 2-hydroxy-3-ethylpentanoic acid (68 mg, 0.47 mmol), and NMM (51 μL, 0.47 mmol) in DMF (5 mL) at ambient temperature under nitrogen atmosphere was added BOP reagent (247 mg, 0.56 mmol). The mixture was stirred at ambient temperature for 18 h. The solvent was removed under reduced pressure. The residue was partitioned between EtOAc and saturated aqueous NaHCO$_3$. The EtOAc layer was separated, dried over anhydrous Na$_2$SO$_4$, and filtered. The filtrate solvent was removed under reduced pressure and the residue was purified by preparative thick layer silica gel plate chromatography (2000 μM×20 cm×20 cm) developed with 5% MeOH in dichloromethane. Desired bands were removed and eluted with 5% MeOH in dichloromethane. The filtrate solvent was concentrated in vacuo to obtain 1-(3-ethyl-2-hydroxypentanoyl)-N-(2-(tert-butyloxycarbonylaminomethyl)-5-chlorobenzyl)-L-prolinamide was obtained as a yellow oil (200 mg; HPLC RT=3.45 min, method A; LC-MS m/z=496.1).

Step 4. 1-(3-ethyl-2-hydroxypentanoyl)-N-(2-(tert-butyloxycarbonylaminomethyl)-5-chlorobenzyl)-L-prolinamide from the previous step (0.200 g, 0.4 mmol) was dissolved in EtOAc (30 mL) and cooled with stirring to 0° C. Into this solution was bubbled in HCl gas for 5 min. The resulting solution was stirred at 0° C. for 30 min, then concentrated in vacuo. The residue was purified by preparative reverse phase HPLC using a gradient of 95:5 to 0:100 (water:$CH_3CN$) over 30 min with a flow rate of 18 mL/min. Concentration of desired fractions in vacuo afforded the TFA salts of the individual diastereomers of the title compound as white solids after drying under high vacuum (isomer 2-more polar; HPLC RT=2.58 min, method A; LC-MS m/z=396.2; $^1$H NMR, 400 MHz, $CD_3OD$, 7.49 ppm (d, 1H), 7.42 ppm (d, 1H), 7.38 ppm (dd, 1H), 4.48 ppm (d, 1H), 4.32–4.42 ppm (m, 3H), 4.24 ppm (m, 2H), 3.72 ppm (m, 1H), 3.58 ppm (m, 1H), 2.24 ppm (m, 1H), 2.06 ppm (m, 1H), 1.8–2.0 ppm (m, 2H), 1.55 ppm (m, 1H), 1.4 ppm (m, 3H), 1.26 ppm (m, 1H), 0.96 ppm (t, 3H), 0.82 ppm (t, 3H). Isomer 1-less polar; 22 mg; HPLC RT=2.64 min; LC-MS m/z=396.2; $^1$H NMR, 400 MHz, $CD_3OD$, 7.48 ppm (d, 1H), 7.43 ppm (d, 1H), 7.39 ppm (dd, 1H), 4.6 ppm (d, 1H), 4.22–4.38 ppm (m, 5H), 3.74 ppm (m, 1H), 3.61 ppm (m, 1H), 2.2 ppm (m, 1H), 1.86–2.06 ppm (m, 3H), 1.26–1.56 ppm (m, 6H), 0.96 ppm (t, 3H), 0.82 ppm (t, 3H)).

EXAMPLE 25

1-(2-Cyclopropyl-2-hydroxy-2-(2-pyridyl)ethanoyl)-N-(2-aminomethyl-5-chlorobenzyl)-L-prolinamide

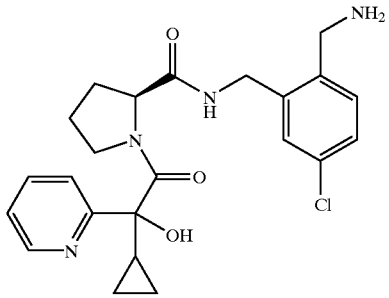

Step 1. To a stirred solution of ethyl 2-(2-pyridyl)-2-oxoacetate (1.0 g, 5.6 mmol) in 10 mL of THF at −78° C. under nitrogen atmosphere was added in 0.92M cyclopropyl magnesium bromide in THF solution (6.7 mL, 7.3 mmol). The reaction was then allowed to equilibrate to 0° C. and stir for 1 h. The reaction was quenched with saturated $NH_4Cl$ solution and partitioned between EtOAc and water. The EtOAc layer was separated, dried over anhydrous $Na_2SO_4$, and filtered. The filtrate solvent was removed under reduced pressure and the residue was purified by flash silica gel chromatography using 1% methanol in dichloromethane as an eluent. After concentration of desired fractions in vacuo ethyl 2-cyclopropyl-2-(2-pyridyl)hydroxyacetate was obtained as a yellow oil (0.9 g; $^1$H NMR, 400 MHz, $CDCl_3$, 8.52 ppm (d, 1H), 7.76 ppm (m, 2H), 7.25 ppm (m, 1H), 5.18 ppm (s, 1H), 4.23 ppm (q, 2H), 1.8 ppm (m, 1H), 1.24 ppm (t, 3H), 0.72 ppm (m, 1H), 0.47 ppm (m, 2H), 0.37 ppm (m, 1H)).

Step 2. To a stirred solution of ethyl 2-cyclopropyl-2-(2-pyridyl)hydroxyacetate from the previous step (0.9 g, 4.0 mmol) in MeOH (10 mL) at ambient temperature was added 1N NaOH (6.0 mL, 6.0 mmol). The resulting solution was stirred at ambient temperature for 18 h, then concentrated in vacuo several times from MeOH. The sodium salt of 2-cyclopropyl-2-(2-pyridyl)hydroxyacetic acid was obtained as a yellow solid (0.79 g; LC-MS m/z=194.0).

Step 3. To a stirred solution of L-prolin-N-(2-(tert-butyloxycarbonylaminomethyl)-5-chlorobenzyl)amide (120 mg, 0.316 mmol), the sodium salt of 2-cyclopropyl-2-(2-pyridyl)hydroxyacetic acid from the previous step (63 mg, 0.326 mmol), and NMM (36 μL, 0.326 mmol) in DMF (5 mL) at ambient temperature under nitrogen atmosphere was added BOP reagent (173 mg, 0.391 mmol). The mixture was stirred at ambient temperature for 3 h. The solvent was removed under reduced pressure. The residue was partitioned between EtOAc (100 mL) and saturated aqueous $NaHCO_3$ (100 mL). The EtOAc layer was separated, dried over anhydrous $Na_2SO_4$, and filtered. The filtrate solvent was removed under reduced pressure and the residue was purified by preparative reverse phase HPLC using a gradient of 95:5 to 0:100 (water:$CH_3CN$ containing 0.1% TFA) over 60 min with a flow rate of 60 mL/min. After concentration of desired fractions in vacuo, the two diastereomers of 1-(2-cyclopropyl-2-(2-pyridyl)hydroxyacetyl)-N-(2-(tert-butyloxycarbonylaminomethyl)-5-chlorobenzyl)-L-prolinamide were obtained as amorphous solids (isomer 1 (less polar) 50 mg; HPLC RT=3.06 min, method A; LC-MS m/z=543.2; $^1$H NMR, 400 MHz, $CDCl_3$, 7.81 ppm (d, 1H), 7.74 ppm (t, 2H), 7.28 ppm (d, 2H), 7.22 ppm (d, 1H), 7.14 ppm (t, 1H), 5.45 ppm (br s, 1H), 5.0 ppm (br s, 1H), 4.8 ppm (d, 1H), 4.6 ppm (dd, 1H), 4.42 ppm (d, 1H), 4.35 ppm (m, 1H), 4.2 ppm (m, 1H), 3.43 ppm (m, 1H), 3.1 ppm (br t, 1H), 2.25 ppm (m, 1H), 2.1 ppm (m, 1H), 1.8 ppm (m, 2H), 1.48 ppm (m, 1H), 1.45 ppm (s, 9H), 1.0 ppm (m, 1H), 0.85 ppm (m, 1H), 0.65 ppm (m, 1H), 0.5 ppm (m, 1H); isomer 2 (more polar)38 mg; HPLC RT=2.99 min, method A; LC-MS m/z=543.2).

Step 4. 1-(2-Cyclopropyl-2-(2-pyridyl)hydroxyacetyl)-N-(2-(tert-butyloxycarbonylaminomethyl)-5-chlorobenzyl)-L-prolinamide from the previous step (more polar isomer, 38 mg, 0.070 mmol) was dissolved in EtOAc (10 mL) and cooled with stirring to 0° C. Into this solution was bubbled in HCl gas for 5 min. The resulting solution was stirred at 0° C. for 30 min. The mixture was concentrated in vacuo and the residue was purified by preparative reverse phase HPLC using a gradient of 95:5 to 0:100 (water:$CH_3CN$, 0.1% TFA) over 60 min with a flow rate of 60 ml/min. After concentration of desired fractions in vacuo the TFA salt of the title compound was obtained as a pale yellow crystalline solid (0.021 g; HPLC RT=2.245 min, method A; LC-MS m/z=443.2).

Step 5. N-(2-cyclopropyl-2-(2-pyridyl)hydroxyacetyl)-L-prolyl-2-(tert-butyloxycarbonylaminomethyl)-5-chlorobenzylamide from the previous step (less polar isomer, 50 mg, 0.092 mmol) was dissolved in EtOAc (10 mL) and cooled with stirring to 0° C. Into this solution was bubbled in HCl gas for 5 min. The resulting solution was stirred at 0° C. for 30 min. The mixture was concentrated in vacuo and the residue was purified by preparative reverse phase HPLC using a gradient of 95:5 to 0:100 (water:$CH_3CN$, 0.1% TFA) over 60 min with a flow rate of 60 mL/min. After concentration of desired fractions in vacuo the TFA salt of the title compound was obtained as

EXAMPLE 26

1-(2-Ethyl-2-hydroxybutanoyl)-N-(2-aminomethyl-5-chlorobenzyl)-L-prolinamide

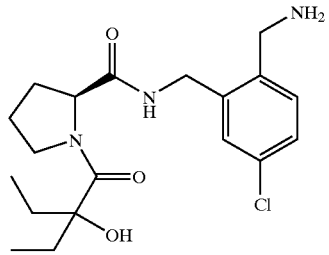

Step 1. To a stirred solution of L-prolin-N-(2-(tert-butyloxycarbonylaminomethyl)-5-chlorobenzyl)amide (100 mg, 0.27 mmol), 2-ethyl-2-hydroxybutanoic acid (36 mg, 0.27 mmol), and NMM (30 µL, 0.27 mmol) in DMF (5 mL) at ambient temperature under nitrogen atmosphere was added BOP reagent (144 mg, 0.326 mmol). The mixture was stirred at ambient temperature for 72 h. The solvent was removed under reduced pressure. The residue was partitioned between EtOAc (100 mL) and saturated aqueous NaHCO$_3$ (100 mL). The EtOAc layer was separated, dried over anhydrous Na$_2$SO$_4$, and filtered. The filtrate solvent was removed under reduced pressure and the residue was purified by preparative reverse phase HPLC using a gradient of 95:5 to 0:100 (water:CH$_3$CN, 0.1% TFA) over 30 min with a flow rate of 18 mL/min. After concentration of desired fractions in vacuo, 1-(2-ethyl-2-hydroxybutanoyl)-N-(2-(tert-butyloxycarbonylaminomethyl)-5-chlorobenzyl)-L-prolinamide was obtained an amorphous solid (55 mg; HPLC RT=3.32 min, method A; LC-MS m/z=482.2; $^1$H NMR, 400 MHz, CDCl$_3$, 7.25 ppm (m, 3H), 7.2 ppm (m, 1H), 7.1 ppm (br s, 1H), 5.45 ppm (br s, 1H), 4.55 ppm (m, 2H), 4.3 ppm (m, 3H), 3.7 ppm (m, 2H), 2.2 ppm (m, 2H), 2.0 ppm (m, 2H), 1.8 ppm (m, 2H), 1.7 ppm (m, 2H), 1.4 ppm (s, 9H), 0.8 ppm (m, 6H)).

Step 2. 1-(2-Ethyl-2-hydroxybutanoyl)-N-(2-(tert-butyloxycarbonylaminomethyl)-5-chlorobenzyl)-L-prolinamide from the previous step (55 mg, 0.11 mmol) was dissolved in EtOAc (10 mL) and cooled with stirring to 0° C. Into this solution was bubbled in HCl gas for 5 min. The resulting solution was stirred at 0° C. for 30 min. The mixture was concentrated in vacuo and the residue was purified by preparative reverse phase HPLC using a gradient of 95:5 to 0:100 (water:CH$_3$CN, 0.1% TFA) over 30 min with a flow rate of 18 mL/min. After concentration of desired fractions in vacuo the TFA salt of the title compound was obtained as an amorphous solid (HPLC RT=2.41 min, method A; LC-MS m/z=382.1; $^1$H NMR, 400 MHz, CD$_3$OD, 7.5 ppm (d, 1H), 7.4 ppm (m, 2H), 4.5 ppm (d, 1H), 4.4 ppm (m, 1H), 4.3 ppm (m, 2H), 4.0 ppm (m, 1H), 3.85 ppm (m, 1H), 1.7–2.2 ppm (br m, 8H), 1.6 ppm (m, 2H), 0.8 ppm (m, 6H)).

EXAMPLE 27

1-((2R)-2-(3-Chlorophenyl)-2-hydroxethanoyl)-N-(2-aminomethyl-5-chlorobenzyl)-L-prolinamide

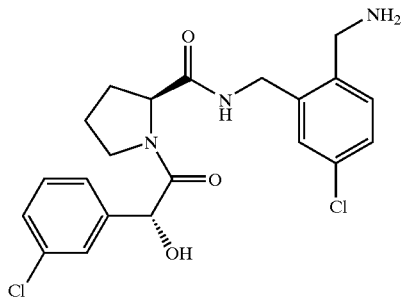

Step 1. To a stirred solution of L-prolin-N-(2-(tert-butyloxycarbonylaminomethyl)-5-chlorobenzyl)amide (100 mg, 0.27 mmol), R-(−)-3-chloromandelic acid (51 mg, 0.27 mmol), and NMM (60 µL, 0.54 mmol) in DMF (5 mL) at ambient temperature under nitrogen atmosphere was added BOP reagent (144 mg, 0.326 mmol). The mixture was stirred at ambient temperature for 18 h. The solvent was removed under reduced pressure. The residue was partitioned between EtOAc (100 mL) and saturated aqueous NaHCO$_3$ (100 mL). The EtOAc layer was separated, dried over anhydrous Na$_2$SO$_4$, and filtered. The filtrate solvent was removed under reduced pressure and the residue was purified by flash silica gel chromatography using 2% methanol in dichloromethane as an eluent. After concentration of desired fractions in vacuo 1-((2R)-2-(3-chlorophenyl)-2-hydroxethanoyl)-N-(2-tert-butuloxyaminomethyl-5-chlorobenzyl)-L-prolinamide was obtained as a yellow oil (110 mg; HPLC RT=3.45 min, method A; LC-MS m/z=536.1; $^1$H NMR, 400 MHz, CDCl$_3$, 8.1 ppm (d, 1H), 7.78 ppm (t, 1H), 7.68 ppm (d, 1H), 7.55 ppm (t, 1H), 7.33 ppm (br s, 1H), 7.3 ppm (m, 1H), 7.22 ppm (m, 2H), 5.48 ppm (br s, 1H), 5.15 ppm (s, 1H), 4.5 ppm (m, 2H), 4.3 ppm (m, 2H), 3.62 ppm (m, 1H), 2.95 ppm (m, 2H), 2.2 ppm (m, 1H), 2.1 ppm (m, 1H), 1.85 ppm (m, 2H), 1.45 ppm (s, 9H)).

Step 2. 1-((2R)-2-(3-Chlorophenyl)-2-hydroxethanoyl)-N-(2-tert-butuloxyaminomethyl-5-chlorobenzyl)-L-prolinamide from the previous step (110 mg, 0.21 mmol) was dissolved in EtOAc (10 mL) and cooled with stirring to 0° C. Into this solution was bubbled in HCl gas for 5 min. The resulting solution was stirred at 0° C. for 30 min. The mixture was concentrated in vacuo and the residue was purified by preparative reverse phase HPLC using a gradient of 95:5 to 0:100 (water:CH$_3$CN, 0.1% TFA) over 30 min with a flow rate of 18 mL/min. After concentration of desired fractions in vacuo the TFA salt of the title compound was obtained as a white powder (HPLC RT=2.68 min, method A; LC-MS m/z=436.0; $^1$H NMR, 400 MHz, CD$_3$OD, 7.5 ppm (d, 1H), 7.44 ppm (m, 3H), 7.34 ppm (m, 3H), 5.34 ppm (s, 1H), 4.2–4.36 ppm (m, 4H), 3.7 ppm (m, 1H), 3.23 ppm (m, 1H), 2.3 ppm (m, 1H), 2.0 ppm (m, 1H), 1.85 ppm (m, 2H), 1.2 ppm (m, 1H)).

a pale yellow crystalline solid (HPLC RT=2.255 min, method A; LC-MS m/z=443.1).

EXAMPLE 28

1-(2-Hydroxy-2-phenyl-3,3,3-trifluoropropanoyl)-N-(2-aminomethyl-5-chlorobenzyl)-L-prolinamide

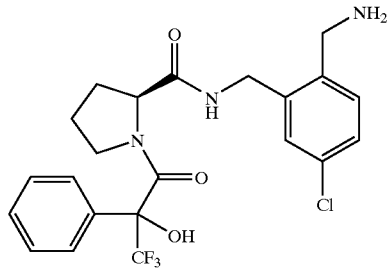

Step 1. To stirred ethyl 2-oxo-phenylacetate (1.0 g, 5.6 mmol) under nitrogen atmosphere at ambient temperature was added trimethyl(trifluoromethyl)silane (1.0 mL, 6.73 mmol) and 1.0 TBAF in THF (6.2 mL, 6.2 mmol). This mixture was stirred at ambient temperature for 72 h. To the reaction was added 5N HCl solution (10 mL) and the mixture was stirred at ambient temperature for 18 h. The mixture was partitioned between $Et_2O$ and water. The $Et_2O$ layer was separated, dried over anhydrous $Na_2SO_4$, and filtered. Crude ethyl 2-phenyl-2-hydroxy-3,3,3-trifluoropropanoate was obtained as a yellow oil (0.9 g; HPLC RT=3.30 min, method A; $^1$H NMR, 400 MHz, $CDCl_3$, 8.2 ppm (d, 1H), 7.78 ppm (m, 1H), 7.4 ppm (m, 3H), 4.4 ppm (m, 2H), 1.35 ppm (t, 3H)).

Step 2. To a stirred solution of ethyl 2-phenyl-2-hydroxy-3,3,3-trifluoropropanoate from the previous step (0.9 g, 0.36 mmol) in EtOH (200 mL) at ambient temperature was added 1N NaOH (6.0 mL, 6.0 mmol). The resulting solution was stirred at ambient temperature for 18 h, then concentrated in vacuo and the resulting solid was triturated with $Et_2O$. The precipitate was collected by filtration to obtain the sodium salt of 2-phenyl-2-hydroxy-3,3,3-trifluoropropanoic acid as a brown solid (0.79 g; HPLC RT=2.76 min, method A).

Step 3. To a stirred solution of L-prolin-N-(2-(tert-butyloxycarbonylaminomethyl)-5-chlorobenzyl)amide (200 mg, 0.544 mmol) and the sodium salt of 2-phenyl-2-hydroxy-3,3,3-trifluoropropanoic acid from the previous step (144 mg, 0.652 mmol) in DMF (5 mL) at ambient temperature under nitrogen atmosphere was added BOP reagent (288 mg, 0.652 mmol). The mixture was stirred at ambient temperature for 72 h. The solvent was removed under reduced pressure and the residue was purified by preparative reverse phase HPLC using a gradient of 95:5 to 0:100 (water:$CH_3CN$, 0.1% TFA) over 60 min with a flow rate of 60 mL/min. After concentration of desired fractions in vacuo the two diastereomers of 1-(2-hydroxy-2-phenyl-3,3,3-trifluoropropanoyl)-N-(2-tert-butyloxycarbonylaminomethyl-5-chlorobenzyl)-L-prolinamide were obtained as amorphous solids (isomer 1 (more polar) 8.5 mg; HPLC RT=3.70 min, method A; LC-MS m/z=570.1; isomer 2 (less polar) 70 mg; HPLC RT=3.57 min, method A; LC-MS m/z=570.1).

Step 4. 1-(2-Hydroxy-2-phenyl-3,3,3-trifluoropropanoyl)-N-(2-tert-butyloxycarbonylaminomethyl-5-chlorobenzyl)-L-prolinamide from the previous step (less polar isomer, 40 mg, 0.070 mmol) was dissolved in EtOAc (30 mL) and cooled with stirring to 0° C. Into this solution was bubbled in HCl gas for 5 min. The resulting solution was stirred at 0° C. for 30 min. The mixture was concentrated in vacuo and the residue was purified by preparative reverse phase HPLC using a gradient of 95:5 to 0:100 (water:$CH_3CN$, 0.1% TFA) over 60 min with a flow rate of 60 mL/min. After concentration of desired fractions in vacuo the TFA salt of the title compound was obtained as a white crystalline solid (8.7 mg; HPLC RT=2.90 min, method A; LC-MS m/z=470.1; $^1$H NMR, 400 MHz, $CD_3OD$, 7.54 ppm (m, 3H), 7.42 ppm (m, 4H), 4.58 ppm (d, 1H), 4.42 ppm (d, 1H), 4.34 ppm (t, 1H), 4.26 ppm (s, 2H), 3.6 ppm (m, 1H), 3.4 ppm (m, 1H), 2.12 ppm (m, 1H), 1.8 ppm (m, 1H), 1.7 ppm (m, 1H), 1.42 (m, 1H)).

Step 5. 1-(2-Hydroxy-2-phenyl-3,3,3-trifluoropropanoyl)-N-(2-tert-butyloxycarbonylaminomethyl-5-chlorobenzyl)-L-prolinamide from step 3 (more polar isomer, 8.5 mg, 0.015 mmol) was dissolved in EtOAc (20 mL) and cooled with stirring to 0° C. Into this solution was bubbled in HCl gas for 5 min. The resulting solution was stirred at 0° C. for 30 min. The hydrochloride salt of the title compound was obtained as a white crystalline solid after concentrating the reaction in vacuo (HPLC RT=2.78 min, method A; LC-MS m/z=470.1; $^1$H NMR, 400 MHz, $CD_3OD$, 7.54 ppm (m, 3H), 7.44 ppm (d, 1H), 7.42 ppm (m, 1H), 4.5 ppm (d, 1H), 4.4 ppm (m, 2H), 4.3 ppm (m, 2H), 3.75 ppm (m, 1H), 2.7 pm (m, 1H), 2.1 ppm (m, 1H), 1.7 ppm (m, 3H)).

EXAMPLE 29

1-(2,2-Diphenyl-2-hydroxyethanoyl)-N-(2-aminomethyl-5-chlorobenzyl)-L-prolinamide

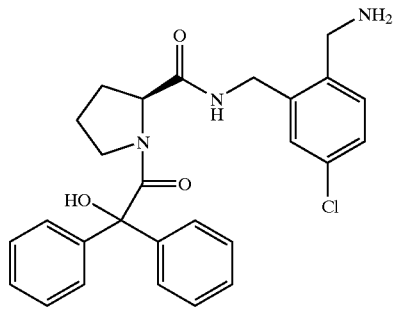

Step 1. To a stirred solution of L-prolin-N-(2-(tert-butyloxycarbonylaminomethyl)-5-chlorobenzyl)amide (0.17 g, 0.45 mmol) in DMF (1 mL) was added benzilic acid (0.23 g, 0.51 mmol), N-methylmorpholine to pH=8 (as measured on wetted E. Merck pH indicator strips), and BOP reagent (0.31 g, 0.70 mmol). After 1 hour of mixing at room temperature, HPLC analysis indicated complete consumption of the starting amine. The mixture was filtered and purified on a preparative HPLC. Pure fractions were pooled and lyophilized to yield 1-(2,2-diphenyl-2-hydroxyethanoyl)-N-(2-tert-butyloxycarbonylaminomethyl-5-chlorobenzyl)-L-prolinamide as a solid (0.23 g, HPLC RT=3.75 min, method A; LC-MS m/z=578).

Step 2. 1-(2,2-Diphenyl-2-hydroxyethanoyl)-N-(2-tert-butyloxycarbonylaminomethyl-5-chlorobenzyl)-L-prolinamide (0.23 g, 0.40 mmol) was dissolved in methyl alcohol (15 mL), cooled to 0 degrees C and saturated with anhydrous HCl gas. The reaction mixed for 3 hours, then the solvent was removed under reduced pressure on a rotary evaporator. The residue was dissolved in DMF and purified on a preparative HPLC. Pure fractions were pooled and lyophilized to yield the trifluoroacetate salt of the title compound as a solid (HPLC; HPLC RT=2.91 min, method A; LC-MS m/z=478).

EXAMPLE 30

1-(2-(4-Carboxyphenyl)-2-hydroxy-2-phenylethanoyl)-N-(2-aminomethyl-5-chlorobenzyl)-L-prolinamide

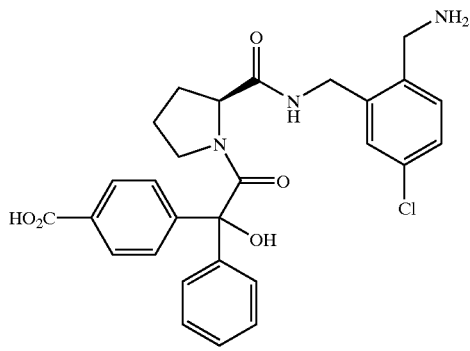

Step 1. To a stirred solution of tert-butyl 4-iodobenzoate (0.304 g, 1.0 mmol) in 10 mL THF at −40° C. was added a solution of isopropylmagnesium bromide (1.05 ml, 1.05 mmol, 1M in THF) dropwise under argon. After stirring for 1 hour at −40° C., ethyl benzoylformate (0.175 ml, 1.1 mmol) was added dropwise and the cold bath allowed to warm to room temperature over a 40 min. period. The reaction was quenched by the addition of an aqueous solution of 20% ammonium chloride. The reaction mixture was extracted twice with ether, the combined organic layers washed with brine, dried over $Na_2SO_4$ and was evaporated to give an oil that was chromatographed on 10 g silica gel using a gradient elution from 0–40% EtOAc in Hexanes. Product containing fractions were combined and concentrated to give (0.078 g, 22%) ethyl (4-tert-butyloxycarbonylphenyl)(hydroxy)phenylacetate as a colorless oil. NMR, 400 MHz (CDCl3) 7.95 ppm (d, J=8.55 Hz, 2H), 7.52 ppm (d, J=8.55 Hz, 2H), 7.30–7.40 ppm (m, 5H), 4.33 ppm (q, J=7.08 Hz, 2H), 4.29 ppm (s, OH, 1H), 1.59 ppm (s, 9H), 1.28 ppm (t, J=7.08 Hz, 3H).

Step 2. To a stirred solution of ethyl(4-tert-butyloxycarbonylphenyl)(hydroxy)phenylacetate from the previous step (78 mg, 0.218 mmol, HPLC RT=2.95 min.) in 2 mL $CH_3OH$ was added 0.3 mL of 1 N NaOH solution. Reaction was stirred at room temperature for 4 hours. HPLC analysis indicated rapid conversion to methyl ester but slow saponification to acid. Added 0.1 mL 1 N NaOH to drive reaction to completion. The solvent was removed on a rotary evaporator and the residue was partitioned between EtOAc (20 mL) and 1 N HCl (5 mL). The organic phase was dried ($MgSO_4$), filtered, and the solvent was removed on a rotary evaporator. (4-tert-butoxycarbonylphenyl)(hydroxy)phenylacetic acid was obtained as a white solid. (62 mg, 87%); HPLC RT=2.53 min, method B. $^1$H NMR, 400 MHz, DMSO-$d_6$, 13.4 ppm (br s, 1H); 7.85 ppm (d, J=7.5 Hz, 2H); 7.50 ppm (d, J=7.32 Hz, 2H); 7.34 ppm (m, 5H); and 1.53 ppm (s, 9H).

Step 3. To a stirred solution of (4-tert-butoxycarbonylphenyl)(hydroxy)phenylacetic acid from the previous step (0.030 g, 0.09 mmol, HPLC RT=2.53 min), L-prolin-N-(2-(tert-butyloxycarbonylaminomethyl)-5-chlorobenzyl)amide (0.037 g, 0.1 mmol) and HOBT hydrate (0.015 g, 0.1 mmol) in DMF (1 mL) was added EDC (0.021 g, 0.1 mmol). Diisopropylethylamine was then added in portions (~0.06 mL total) to bring the pH of the solution to 6–7 as measured on wetted E. Merck pH indicator strips. The mixture was stirred at ambient temperature for 2 days, at which time HPLC analysis indicated complete consumption of the proline starting material. The DMF was removed under reduced pressure and the residue was partitioned between EtOAc (40 mL) and saturated aqueous $NaHCO_3$ (10 mL). The EtOAc layer was separated, dried over anhydrous $MgSO_4$, and filtered. The filtrate solvent was removed under reduced pressure and the oil residue was purified by preparative on a Waters PrepPak using 10–100% $CH_3CN$ in $H_2O$ with 0.1% TFA as eluant over 60 min. Product-containing fractions were combined and the acetonitrile was removed under reduced pressure. The water layer was basicified with saturated aqueous $NaHCO_3$, extracted with 4×20 mL $CH_2Cl_2$, dried over $Na_2SO_4$ and filtered. The filtrate solvent was removed under reduced pressure to give 1-(2-(4-tert-butyloxycarbonylphenyl)-2-hydroxy-2-phenylethanoyl)-N-(2-tert-butyloxycarbonylaminomethyl-5-chlorobenzyl)-L-prolinamide as a white solid. (0.030 g, 46%; HPLC RT=3.25 min, method B; LC-MS M+H= 678).

Step 4. 1-(2-(4-tert-butyloxycarbonylphenyl)-2-hydroxy-2-phenylethanoyl)-N-(2-tert-butyloxycarbonylaminomethyl-5-chlorobenzyl)-L-prolinamide from the previous step (0.017 g, 0.021 mmol, HPLC RT=3.25 min) was dissolved in $CH_2Cl_2$ (2 mL) and cooled with stirring to 0° C. TFA (2 mL) was added. After 2 hours at 0° C., HPLC analysis indicated that the reaction only proceeded half way and also generated a lactone by-product. The reaction was stirred at ambient temperature overnight. The solvent was removed on a rotary evaporator (bath temp 30° C., ~50 torr) and the residue was purified by preparative reverse phase HPLC using 5–95% $CH_3CN$ in $H_2O$ with 0.1% TFA as eluant over 30 min. Product-containing fractions were combined and lyophilized to give the trifluoroacetate salt of the title compound as a white solid. (HPLC RT=1.61 min, method B; LC-MS M+H=521). Mixture of diastereomers, $^1$H NMR, 400 MHz, DMSO-$d_6$, 12.87 ppm (br, s, 1H), 8.55 ppm (s, 1H), 8.07–8.15 ppm (m, 2H), 7.83–7.85 ppm (m, 2H), 7.25–7.83 ppm (m, 7H), 4.34–4.42 ppm (m, 3H), 4.11 ppm (s, 2H), 3.42–3.59 ppm (m, 2H), 2.04–2.08 ppm (m, 1H), 1.75 ppm (m, 1H), 1.63–1.65 ppm (m, 2H).

EXAMPLE 31

1-(2,5-Dimethyl-2-hydroxy-3-hexynoyl)-N-(2-aminomethyl-5-chlorobenzyl)-L-prolinamide

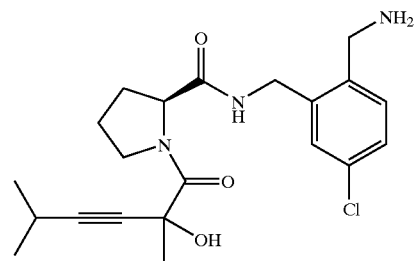

Step 1. To a solution of 3-methylbut-1-yne (0.5 g, 0.73 mmol), in dry THF (12 mL) was added dropwise at 0° C. a solution of n-butyllithium in hexane (1.6 N solution, 4.57 mL, 0.73 mmol). After being stirred for 0.25 h at 0° C., the solution was cooled at −78° C. and transferred dropwise by cannulation into a solution of ethyl pyruvate (0.80 mL, 0.73 mmol) in dry THF (12 mL) at −78° C. The resulting solution was stirred at −78° C. for 0.5 hr and quenched by the addition of saturated aqueous NH₄Cl (10 mL). The mixture was extracted twice with Et₂O (100 mL). The combined organic layers were washed with brine, dried over anhydrous MgSO₄, and filtered. The filtrate solvent was removed on a rotary evaporator to give ethyl 2-hydroxy-2,5-dimethyl-3-hexynoate as a clear oil (0.85 g, 63%). LC-MS M+H=185. ¹H NMR, 400 MHz, CDCl3, 4.26–4.32 ppm (m, 2H); 3.38 ppm (s, 1H); 2.53–2.58 ppm (m, 1H); 1.63 ppm (s, 3H); 1.32 ppm (t, J=7.14 Hz, 3H); and 1.15 ppm (d, J=6.96 Hz 6H).

Step 2. To a stirred solution of ethyl 2-hydroxy-2,5-dimethyl-3-hexynoate from the previous step (0.35 g, 1.9 mmol) in 2 mL THF was added H₂O (2 mL) and 1 N NaOH solution (2 mL). The reaction was stirred at ambient temperature for 3 h. The mixture was acidified with 1N HCl (2 mL) and extracted twice with Et₂O (10 mL). The organic layers were washed with brine, dried over anhydrous MgSO₄, and filtered. The filtrate solvent was removed on a rotary evaporator to give 2-hydroxy-2,5-dimethy-3-hexynoic acid as a white solid (0.272 g, 92%). ¹H NMR, 400 MHz, CDCl3, 4.81 ppm (br, s, 1H); 2.56–2.62 ppm (m, 1H); 1.70 ppm (s, 3H); 1.17 ppm (d, J=3.18 Hz, 6H).

Step 3. To a stirred solution of ethyl 2-hydroxy-2,5-dimethyl-3-hexynoic acid from the previous step (0.033 g, 0.21 mmol), L-prolin-N-(2-(tert-butyloxycarbonylaminomethyl)-5-chlorobenzyl)amide (0.080 g, 0.22 mmol) and HOBT hydrate (0.088 g, 0.24 mmol) in DMF (3 mL) was added EDC (0.032 g, 0.24 mmol). Diisopropylethylamine was then added in portions (~0.15 mL total) to bring the pH of the solution to 6–7 as measured on wetted E. Merck pH indicator strips. The mixture was stirred at ambient temperature for 2 days, at which time HPLC analysis indicated complete consumption of the proline starting material. The DMF was removed under reduced pressure and the residue was partitioned between EtOAc (40 mL) and saturated aqueous NaHCO₃ (10 mL). The EtOAc layer was separated, dried over anhydrous MgSO₄, and filtered. The filtrate solvent was removed under reduced pressure and the oil residue was purified by preparative reverse-phase HPLC using a Waters PrepPak column and a gradient of 5–95% CH₃CN:H₂O with 0.1% TFA as eluant over 60 min. The product-containing fractions were combined and lyophilized to give 1-(2,5-dimethyl-2-hydroxy-3-hexynoyl)-N-(2-tert-butyloxycarbonylaminomethyl-5-chlorobenzyl)-L-prolinamide as a white solid. (72 mg, 68%; HPLC RT=2.61 min, method B; LC-MS M+H= 506). ¹H NMR, 400 MHz, DMSO-d₆, 8.22 ppm (d, J=15.9 Hz, 2H); 7.17–7.32 ppm (m, 2H); 4.25–4.30 ppm (m, 2H), 4.06 ppm (s, 2H); 3.69–3.73 ppm (m, 1H); 2.51–2.56 ppm (m, 1H); 2.07–2.09 ppm (m, 2H); 1.91–1.94 ppm (m, 2H); 1.68–1.78 ppm (m, 2H); 1.45 ppm, (d, J=7.69 Hz, 3H); 1.35 ppm (s, 9H); 1.04–1.08 ppm, (m, 6H).

Step 4. 4-(2,5-Dimethyl-2-hydroxy-3-hexynoyl)-N-(2-tert-butyloxycarbonylaminomethyl-5-chlorobenzyl)-L-prolinamide from the previous step (0.035 g, 0.07 mmol, HPLC RT=2.61 min) was dissolved in CH₂Cl₂ (2 mL) and cooled with stirring to 0° C. TFA (2 mL) was added. After 2 hours at 0° C., HPLC analysis indicated reaction was complete. Solvent was removed on a rotary evaporator and the glassy material was treated with EtOAc and 2 drops of 4M HCl in dioxane solution. The solvents were removed on a rotary evaporator and the residue was triturated in Et₂O to give the hydrochloride salt of the title compound as a white solid. HPLC RT=1.42 min, method B; LC-MS M+H=406, 408. Mixture of diastereomers ¹H NMR, 400 MHz, DMSO-d₆, selected signals: 8.50 ppm and 8.31 ppm (m, 1H), 7.41 ppm (m, 2H), 1.46 ppm (d, J=10.7 Hz, 3H), 1.07 ppm (s, 6H).

EXAMPLE 32

1-(N-(2-Carboxy-2-propyl)-D-phenylglycyl)-N-(2-aminomethyl-5-chlorobenzyl)-L-prolinamide

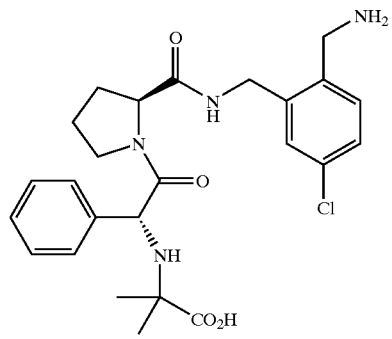

Step 1. To a stirred solution of S-methyl mandelate (1.66 g, 10 mmol) in 50 mL of dichloromethane at −78° C. under Ar was added trifluoromethanesulfonic anhydride (1.85 mL, 11 mmol), 2,6-lutidine (1.34 mL, 11.5 mmol) and t-butyl 2-aminoisobutyrate (2.39 g, 15 mmol). After stirring at −78° C. for 30 min, the cold bath was allowed to expire overnight. The reaction mixture was partitioned between water and CH₂Cl₂, the aqueous layer extracted with CH₂Cl₂, the combined organic layers washed with brine, dried over Na₂SO₄ and the solvents removed to give an oil that contained the desired triflate plus lutidine by NMR analysis. This material was dissolved in 5 mL DMF, and t-butyl 2-aminoisobutyrate (2.02 g, 12.7 mmol) and potassium carbonate (1.38 g, 10 mmol) were added. The solution was heated to 80° C. for 4 days under Ar. The reaction mixture was partitioned between ethyl acetate and water, the aqueous layer extracted with ethyl acetate, the combined organic layers washed with brine, dried over Na₂SO₄ and solvents removed to give a yellow oil that was purified by preparative reversed phase HPLC (50 mL/min, gradient elution 95:5 to 35:65 0.1% TFA H₂O:CH₃CN over 1 h). After assaying the fractions by LC-MS, the fractions containing product were concentrated, basicified with 10% Na₂CO₃, a extracted with two portions of ethyl acetate, the combined organic layers washed with brine, dried over Na₂SO₄ and solvents removed to give methyl (N-(2t-butyloxycarbonylisopropyl)-S-phenylglycinate (782 mg) as a colorless oil: ¹H NMR, 300 MHz, CDCl3, 7.44 (dd, J=8.3, 1.7 Hz, 2H), 7.26–7.35(m, 3H), 4.35 (s, 1H), 3.67 (s, 3H), 1.43 (s, 9H), 1.30 (s, 3H), 1.15 (s, 3H). M+H= 308.5.

Step 2. To a stirred solution of methyl (N-(2-t-butyloxycarbonylisopropyl)-S-phenylglycinate (307 mg, 1.0 mmol) in 10 mL methanol under Ar was added 2.0 mL of 1M aqueous NaOH dropwise. After stirring for 3.5 h, added an additional 1.0 mL of 1M NaOH and stirred for another 3.5 h. The reaction mixture was concentrated at reduced pressure, quenched with 5 mL of 1M citric acid, extracted with two portions of EtOAc, the combined organic layers washed with water, brine, dried over Na₂SO₄ and concentrated at reduced pressure to give 180 mg of (N-(2-t-butyloxycarbonylisopropyl)-S-phenylglycine as a colorless oil: M+H=294.5.

Step 3. To a stirred solution of L-prolin-N-(2-(tert-butyloxycarbonylaminomethyl)-5-chlorobenzyl)amide (50 mg, 0.135 mmol), (N-(2-t-butyloxycarbonylisopropyl)-S-phenylglycine (43 mg, 0.145 mmol), and HOBT hydrate (20 mg, 0.145 mmol) in DMEF (1.5 mL) was added EDC (28 mg, 0.145 mmol). The mixture was stirred at ambient temperature overnight, at which time HPLC analysis indicated complete consumption of the proline starting material. After diluting with water and $Na_2CO_3$, the reaction mixture was extracted with three portions of $CHCl_3$. The organic layer was dried over $Na_2SO_4$ and concentrated at reduced pressure to give 86 mg of a colorless oil. M+H=643.5.

Step 4. 1-(N-(2-tert-Butyloxycarbonyl-2-propyl)-D-phenylglycyl)-N-(2-tert-butyloxycarbonylaminomethyl-5-chlorobenzyl)-L-prolinamide from the previous step (86 mg, 0.134 mmol) was dissolved in $CH_2Cl_2$ (5 mL) and treated with 5 mL trifluoroacetic acid at ambient temperature. After stirring for 4.5 h, the reaction mixture was concentrated at reduced pressure and purified by preparative HPLC, Waters C-18 Delta Prep, 95:5 to 50:50 0.1% TFA water:$CH_3CN$ over 1 h. The fractions were assayed by HPLC, combined, concentrated and lyophilized to give the TFA salt of the title compound as a colorless solid: $^1H$ NMR, 400 MHz, DMSO-$d_6$, 3:2 mixture of rotamers, selected signals: 8.64 ppm (br s, 1H), 8.20 (br s, 2H), 1.49 & 1.42(s, 3H, minor), 1.46 & 1.36 (s, 3H, major). M+H= 487.5.

EXAMPLE 33

1-((2R,3R)-3-(3-Carboxyphenyl)-3-(2-pyridyl)-2-hydroxypropanoyl)-N-(2-aminomethyl-5-chlorobenzyl)-L-prolinamide

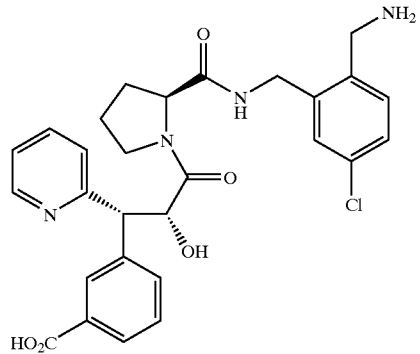

Step 1: To a cooled (0° C.) slurry of NaH (0.979 g, 24.5 mmol) in THF (15 mL) was added triethylphosphonoacetate (4.9 mL, 24.5 mmol). The cooling bath was removed and the mixture was stirred until everything had dissolved. The solution was cooled to 0° C. and tert-butyl 3-formylbenzoate (3.89 g, 24.5 mmol, ref. Syn. Comm., 29, pp. 3401–3407, 1999) was added in THF (40 mL) dropwise over 5 min. The cooling bath was removed and after 2 hours, the reaction was complete as judged by TLC. Saturated aqueous $NaHCO_3$ was added and extracted with ether. The organic layer was washed with brine, dried over $MgSO_4$, filtered, and the solvent was removed under reduced pressure. The residue was chromatographed on a 110 g ISCO column using 0–25% EtOAc:hexanes over 40 min. Product fractions were combined and was solvent removed under reduced pressure to give ethyl (2E)-3-[3-(tert-butoxycarbonyl)phenyl]prop-2-enoate as a thick oil (3.44 g, 76%). TLC $R_f$=0.3 (1:4 EtOAc:hexanes, UV visualization); HPLC RT=3.00 min, method A; $^1H$ NMR, 400 MHz, $CDCl_3$, 8.14, (s, 1H); 7.97–8.04, (m, 1H); 7.71, (d, J=16 Hz, 1H); 7.64–7.68, (m, 1H); 7.44, (t, J=8 Hz, 1H); 6.50 (d, J=16 Hz, 1H); 4.28, (q, J=5 Hz, 2H); 1.51 (s, 9H); 1.36, (t, J=5 Hz, 3H).

Step 2: To a stirred solution of ethyl (2E)-3-[3-(tert-butoxycarbonyl)phenyl]prop-2-enoate from the previous step (3.44 g, 12.4 mmol) in EtOH (30 mL), was added 1N NaOH (15 mL, 15 mmol) and the mixture was stirred for 2 hours. The reaction was concentrated under reduced pressure to ~20 mL, acidified with 10% aqueous citric acid and extracted with 2×100 mL EtOAc. The organic layer was washed with brine, dried over $MgSO_4$, filtered and the solvent removed under reduced pressure to give (2E)-3-[3-(tert-butoxycarbonyl)phenyl]prop-2-enoic acid as an oil which solidified on standing (3.1 g, 100%). HPLC RT=2.43 min, method B; $^1H$ NMR, 400 MHz, $CDCl_3$, 8.16, (s, 1H); 8.03 (d, J=8 Hz, 1H); 7.81, (d, J=16 Hz, 1H); 7.70, (d, J=8 Hz, 1H); 7.47 (t, J=8 Hz, 1H); 6.52 (d, J=16 Hz, 1H); 1.62 (s, 9H).

Step 3: To a stirred solution of (2E)-3-[3-(tert-butoxycarbonyl)phenyl]prop-2-enoic acid from the previous step (0.186 g, 0.749 mmol) in THF (3 mL) was added triethylamine (0.110 mL, 0.787 mmol) and the mixture was cooled to −20° C. Pivaloyl chloride (0.0969 mL, 0.787 mmol) was added and then the reaction mixture was stirred at −20° C. for 15 min, warmed to 0° C. and stirred for 40 min. Meanwhile, to a cooled (−78° C.) solution of (R)-4-benzyl-2-oxazolidinone (0.305 g, 1.72 mmol) in THF (5 mL), was added nBuLi (1.1 mL, 1.6M in hexanes) dropwise and the mixture was stirred for 30 min. The slurry was warmed to 0° C. and added via cannula into the anion solution. After one hour, the reaction was quenched by the addition of 10 mL 20% aqueous $NH_4Cl$ solution, warmed to room temperature and extracted with 2×50 mL ether. The organic layer was washed with saturated aqueous $NaHCO_3$ and brine, dried over $MgSO_4$, filtered, and the solvent removed under reduced pressure, and chromatographed on a 4" 25 mm $SiO_2$ column using 18% EtOAc:hexanes. The clean fractions were combined and the solvent was removed under reduced pressure to give tert-butyl 3-{(1E)-3-[(4R)-4-benzyl-2-oxo-1,3-oxazolidin-3-yl]-3-oxoprop-1-enyl}benzoate as an oil (0.273 g, 89%). TLC $R_f$=0.3 (1:4 EtOAc:hexanes, UV visualization); HPLC RT=2.9 min, method B; M+H=408.

Step 4: To a 1.0 M solution of isopropylmagnesium chloride (1.0 mL, 2.08 mmol) in THF was added 2-bromopyridine (0.198 mL, 2.08 mmol) and the mixture was stirred for 1.5 hours. This dark solution, at 0° C., was quickly added to a cooled (−40° C.) solution of CuBr.DMS complex (0.206 g, 1.01 mmol) in THF (2 mL) and dimethylsulfide (1 mL), and the resulting mixture was stirred at −40° C. for 10 min, then placed in an ice bath. Tert-butyl 3-{(1E)-3-[(4R)-4-benzyl-2-oxo-1,3-oxazolidin-3-yl]-3-oxoprop-1-enyl}benzoate from the previous step, dissolved in THF (2 mL), was added dropwise and the mixture was stirred for 1.5 hours. The reaction was quenched with 20% aqueous $NH_4Cl$ solution, the dimethylsulfide was removed under reduced pressure and the mixture was partitioned between EtOAc and $H_2O$. The layers were separated, the water layer was extracted with EtOAc, and the combined organics were washed with $H_2O$ and brine, dried over $MgSO_4$, filtered, and the solvent was removed under reduced pressure. The residue was chromatographed on a 10 g ISCO column using 0–40% EtOAc/hexanes over 40 min. The lower diastereomer was combined to give tert-butyl 3-{(1R)-3-[(4R)-4-benzyl-2-oxo-1,3-oxazolidin-3-yl]-3-oxo-1-pyridin-2-ylpropyl}benzoate as an oil (0.12 g, 37%). Absolute chirality was assigned based on literature precedent. TLC $R_f$=0.3 (1:1 EtOAc:hexanes, UV visualization); HPLC RT=2.1 min, method B; M+H=488.

Step 5: To a cooled solution (−78° C.) of sodium hexamethyldisilazide (0.38 mL, 0.38 mmol) in THF (0.5 mL) was added tert-butyl 3-{(1R)-3-[(4R)-4-benzyl-2-oxo-1,3-oxazolidin-3-yl]-3-oxo-1-pyridin-2-ylpropyl}benzoate from the previous step (0.153 g, 0.314 mmol) in THF (1 mL) dropwise and stirred for 45 min. 2-(Phenysulfonyl)-3-phenyloxaziridine (0.167 g, 0.629 mmol) dissolved in THF (0.5 mL) was added to cold solution and the mixture was stirred for 10 min. Camphorsulfonic acid, dissolved in THF (2 mL), was quickly added and the bath was removed. The reaction was warmed to room temperature, diluted with saturated aqueous NaHCO$_3$, extracted with EtOAc, washed with saturated aqueous NaHCO$_3$ and brine, dried over MgSO$_4$, filtered, and the solvent removed under reduced pressure. The residue was chromatographed on a 35 g ISCO column using 0–50% EtOAc/hexanes over 40 min and the lowest spot fractions were combined and the solvent removed under reduced pressure to give an oil. This oil was purified by preparative HPLC on a Waters PrepPak using 10% to 100% CH$_3$CN/H$_2$O with 0.1% TFA as eluant over 60 min. The product-containing fractions were combined and the acetonitrile was removed under reduced pressure. The remaining aqueous solution was basicified with saturated aqueous NaHCO$_3$, extracted with 4×20 mL CH$_2$Cl$_2$, dried over Na$_2$SO$_4$ and filtered. The filtrate solvent was removed under reduced pressure to give tert-butyl 3-{(1R,2R)-3-[(4R)-4-benzyl-2-oxo-1,3-oxazolidin-3-yl]-2-hydroxy-3-oxo-1-pyridin-2-ylpropyl}benzoate as an oil (0.068 g, 43%). TLC $R_f$=0.3 (1:1 EtOAc:hexanes, UV visualization); HPLC RT=2.61 min, method B; M+H=503.

Step 6. To a cooled (0° C.) solution of tert-butyl 3-{(1R,2R)-3-[(4R)-4-benzyl-2-oxo-1,3-oxazolidin-3-yl]-2-hydroxy-3-oxo-1-pyridin-2-ylpropyl}benzoate from the previous step (0.068 g, 0.135 mmol) in THF (2 mL), was added 35% hydrogen peroxide (0.061 mL, 0.541 mmol) dropwise, then 1.0M LiOH (0.271 mL, 0.271 mmol) in H$_2$O (0.4 mL). The reaction was stirred for 1.5 hours, at which time HPLC indicated incomplete reaction so additional 35% hydrogen peroxide (0.030 mL, 0.271 mmol) and 1.0M LiOH (0.135 mL, 0.135 mmol) in H$_2$O (0.2 mL) were added and stirring continued for 1 hour. HPLC analysis showed complete consumption of starting material. The mixture was quenched with 10% aqueous Na$_2$SO$_3$ (1 mL) and saturated aqueous NaHCO$_3$ (1 mL), diluted with H$_2$O (20 mL), and washed with 2×20 mL CH$_2$Cl$_2$. The aqueous layer was acidified with 10% aqueous citric acid, extracted with 2×30 mL CH$_2$Cl$_2$, dried over MgSO$_4$, filtered, and the solvent removed under reduced pressure to give (2R,3R)-3-[3-(tert-butoxycarbonyl)phenyl]-2-hydroxy-3-pyridin-2-ylpropanoic acid as a yellow oil (0.020 g, 43%). TPLC RT=1.44 min, method B; M+H=344.

Step 7. To a stirred solution of L-prolin-N-(2-(tert-butyloxycarbonylaminomethyl)-5-chlorobenzyl)amide (0.026 g, 0.07 mmol), (2R,3R)-3-[3-(tert-butoxycarbonyl)phenyl]-2-hydroxy-3-pyridin-2-ylpropanoic acid from step 6 (20 mg, 0.058 mmol), and HOBT hydrate (12 mg, 0.087 mmol) in DMF (1 mL) was added EDC (0.017 g, 0.087 mmol). Diisopropylethylamine (0.0122 mL, 0.07 mmol) was added and the mixture was stirred at ambient temperature for 3 days, at which time HPLC analysis indicated complete consumption of the proline starting material. The DMF was removed under reduced pressure and the residue was partitioned between EtOAc (50 mL) and 10% aqueous Na$_2$CO$_3$ (20 mL). The EtOAc layer was separated, dried over anhydrous MgSO$_4$, and filtered. The filtrate solvent was removed under reduced pressure and the residue was purified by preparative HPLC on a Waters PrepPak using 10% to 100% CH$_3$CN:H$_2$O with 0.1% TFA as eluant over 60 min. The product-containing fractions were combined and the acetonitrile was removed under reduced pressure. The remaining aqueous solution was basicified with saturated aqueous NaHCO$_3$, extracted with 4×20 mL CH$_2$Cl$_2$, dried over Na$_2$SO$_4$ and filtered. The filtrate solvent was removed under reduced pressure to give 1-((2R,3R)-3-(3-tert-butyloxycarbonylphenyl)-3-(2-pyridyl)-2-hydroxypropanoyl)-N-(2-tert-butyloxycarbonylaminomethyl-5-chlorobenzyl)-L-prolinamide an oil (0.018 g, 45%). HPLC RT=2.54 min, method B; LC-MS M+H=693, 695.

Step 8. 1-((2R,3R)-3-(3-tert-Butyloxycarbonylphenyl)-3-(2-pyridyl)-2-hydroxypropanoyl)-N-(2-tert-butyloxycarbonylaminomethyl-5-chlorobenzyl)-L-prolinamide from the previous step (0.018 g, 0.026 mmol, HPLC RT=2.54 min) was dissolved in EtOAc (1 mL) and cooled with stirring to 0° C. HCl/EtOAc (3.55M, 1.5 mL) was added. After 2 hours at 0° C., the bath was removed and stirred overnight. HPLC analysis indicated completion and the solvent was removed under reduced pressure. The residue was purified on a Waters PrepPak using 10% to 100% CH$_3$CN/H$_2$O with 0.1% TFA as eluant over 60 min. The product-containing fractions were combined and lyophilized to give the trifluoroacetate salt of the title compound. HPLC RT=1.1 min, method B; LC-MS m+h=537, 539; $^1$H NMR, 400 MHz, DMSO-d$_6$, 12.85, (br s, 1H); 8.5, (d, J=4 Hz, 1H); 8.42, (t, J=5.8 Hz, 1H); 8.03–8.23, (m, 3H); 7.98, (s, 1H); 7.76–7.78 (m, 1H); 7.65–7.68 (m, 2H); 7.37–7.46 (m, 4H); 7.24–7.26 (m, 1H); 7.19–7.22, (m, 1H); 5.13 (d, J=10 Hz, 1H); 4.51, (d, J=10 Hz, 1H); 4.34–4.39 (m, 1H); 4.23–4.29, (m, 1H); 4.05–4.12, (m, 2H); 3.93–3.97, (m, 1H); 3.58–3.71 (m, 2H); 1.82–1.99 (m, 2H); 1.66–1.82 (m, 2H).

EXAMPLE 34

1-((9-Hydroxy-9H-fluoren-9-yl)carbonyl)-N-(2-aminomethyl-5-chlorobenzyl)-L-prolinamide

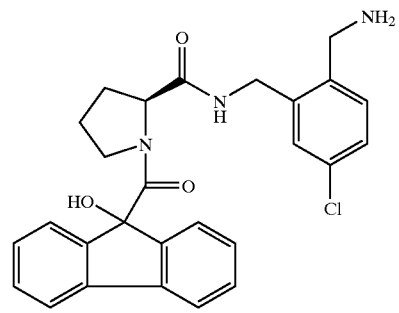

Step 1. To a solution of 9-hydroxy-9-fluorene carboxylic acid (5.04 g, 22.3 mmol) in N,N-dimethylformamide (30 mL), cooled to 0° C. under nitrogen, was added (O-7-azabenzotriazol-1-y)-1,1,3,3-tetramethyluronium hexafluorophosphate, (9.32 g, 24.5 mmol), L-proline benzyl ester hydrochloride (5.93 g, 24.5 mmol), and N,N-diisopropylethylamine (8.5 mL, 48.8 mmol). The mixture was stirred at 0° C. for 3 hours, then concentrated and purified on silica gel (ethyl acetate-hexane, 1:2) to give 9-hydroxy-9-fluorenylcarbonyl-L-proline benzyl ester. HPLC=96%, R.T.=3.7 min, method A; M+1=414.1.

Step 2. A mixture of 9-hydroxy-9-fluorenylcarbonyl-L-proline benzyl ester (3.8 g, 9.3 mmol) from step 1 above and 10% palladium on carbon (390 mg) in ethyl acetate (100 mL) was stirred under an atmosphere of hydrogen (balloon pressure) for 24 hours. The mixture was filtered through celite and concentrated in vacuo to give 9-hydroxy-9-fluorenylcarbonyl-L-proline. HPLC=90%, R.T.=2.97 min, method A; M+1=324.1; $^1$H NMR (CD$_3$OD) 7.78–7.75 (m, 2H), 7.47–7.32 (m, 6H), 4.49–4.45 (q, 1H), 2.42–2.30 (m, 2H), 2.01–1.94 (m, 1H), 1.78–1.71 (m, 1H), 1.58–1.41 (m, 2H).

Step 3. A solution of 9-hydroxy-9-fluorenylcarbonyl-L-proline (1.8 g, 5.6 mmol) from step 2 above, 2-tert-butoxycarbonylaminomethyl-5-chlorobenzylamine (1.8 g, 6.8 mmol), N-methylmorpholine (12 drops), and benzotriazol-1-yloxy-tris(dimethylamino)phosphonium hexafluorophosphate (3.0 g, 6.7 mmol) in N,N-dimethylformamide (25 mL) was stirred at ambient temperature for 24 hours, concentrated in vacuo, and purified on silica gel (ethyl acetate-hexane, 1:2) to give 1-((9-hydroxy-9H-fluoren-9-yl)carbonyl)-N-(2-tert-butyloxycarbonylaminomethyl-5-chlorobenzyl)-L-prolinamide. HPLC=99%, R.T.=3.69 min, method A; M+1=576.2.

Step 4. A solution of 1-((9-hydroxy-9H-fluoren-9-yl)carbonyl)-N-(2-tert-butyloxycarbonylaminomethyl-5-chlorobenzyl)-L-prolinamide (1.4 g, 2.4 mmol) from step 3 above in methanol (40 mL) was cooled to 0° C. and saturated with anhydrous HCl gas. After stirring for one hour at 0° C., the mixture was concentrated in vacuo and purified on a reverse phase C18 HPLC column to give the TFA salt of the title compound as a solid. HPLC RT=2.83 min, method A; M+1=476.1; combustion analysis for C$_{27}$H$_{26}$ClN$_3$O$_3$, 1.25 TFA, 1.00 water; calculated C: 55.67, H: 4.63, N: 6.60; found C: 55.64, H: 4.60, N: 6.70; $^1$H NMR (CDCl$_3$) δ 8.44–8.27 (s, 3H), 7.67–7.64 (m, 2H), 7.43–7.19 (m, 6H), 4.81–4.75 (m, 1H) 4.45–4.42 (m, 1H), 4.15–3.99 (m, 3H), 2.39–2.26 (m, 2H), 2.02–1.83 (m, 1H), 1.76–1.68 (m, 1H), 1.65–1.54 (m, 1H), 1.46–1.37 (m, 1H).

EXAMPLE 35

N-(1-(9-Hydroxy-9H-fluoren-9-ylcarbonyl)azetidin-2S-ylcarbonyl)-5-chlorobenzylamine

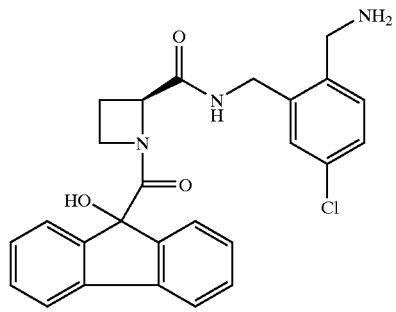

Step 1. To a stirred solution of N-Fmoc-L-azetidine carboxylic acid (0.15 g, 0.45 mmol) in dimethylformamide (1 mL) was added HOBT hydrate (0.081 g, 0.60 mmol), EDC (0.13 g, 0.70 mmol), diisopropylethylamine to pH=7 and 2-(tert-butyloxycarbonylaminomethyl)-5-chlorobenzylamine (0.14 g, 0.53 mmol). After 1.5 hours, the reaction mixture was evaporated in vacuo and purified on a silica gel column using ethyl acetate:hexane (1:1, 3:1) as mobile phase to obtain 1-(N-(fluorenylmethoxycarbonyl)-azetidin-2S-yl-carbonylaminomethyl)-2-(tert-butyloxycarbonylaminomethyl)-5-chlorobenzene (0.20 g, HPLC RT=3.83 min, method A).

Step 2. 1-(N-(Fluorenylmethoxycarbonyl)azetidin-2S-yl-carbonylaminomethyl)-2-(tert-butyloxycarbonylaminomethyl)-5-chlorobenzene from the previous step (0.20 g, 0.34 mmol) was dissolved in dimethylformamide (2 mL) and then piperidine (1.0 mL, 10.2 mmol) was added. The mixture was stirred at room temperature for 30 minutes. The solvent was evaporated in vacuo and the residue was purified on silica gel using a methylene chloride to methanol mixture (98:2, 90:10) as mobile phase to yield 1-(azetidin-2S-yl-carbonylaminomethyl)-2-(tert-butyloxycarbonylaminomethyl)-5-chlorobenzene (0.11 g, HPLC RT=2.82 min, method A).

Step 3. To a stirred solution of 1-(azetidin-2S-yl-carbonylaminomethyl)-2-(tert-butyloxycarbonylaminomethyl)-5-chlorobenzene from the previous step (0.11 g, 0.31 mmol) in dimethylformamide (1 mL) was added 9-hydroxyfluorene-9-carboxylic acid (0.08 g, 0.34 mmol), HOAT (0.10 g, 0.74 mmol), EDC (0.11 g, 0.58 mmol) and N-methylmorpholine to pH=7. After 3 hours, the reaction was evaporated in vacuo and partitioned between ethyl acetate and water. The organic layer was washed 3 times with water, stripped dry on a rotary evaporator and vacuum dried to yield 1-(N-(9-hydroxy-9-fluorenylcarbonyl)azetidin-2S-yl-carbonylaminomethyl)-2-(tert-butyloxycarbonylaminomethyl)-5-chlorobenzene (HPLC RT=3.57 min, method A).

Step 4. 1-(N-(9-Hydroxy-9-fluorenylcarbonyl)azetidin-2S-yl-carbonylaminomethyl)-2-(tert-butyloxycarbonylaminomethyl)-5-chlorobenzene from the previous step was dissolved in methyl alcohol (10 mL) and cooled to 0 degrees Centigrade. The solution was saturated with anhydrous HCl gas and allowed to stir for 1.5 hours. The mixture was evaporated in vacuo, dissolved in dimethylformamide and purified on a preparative reverse-phase HPLC using an acetonitrile:water (0.1% TFA) gradient. Pure fractions were combined and lyophilized to give the TFA salt of the title compound as a solid (HPLC RT=2.73 min, method A; LC-MS m/z= 462).

EXAMPLE 36

N-(1-(9-Hydroxy-9H-fluoren-9-ylcarbonyl)-N-cyclopropylglycin-N-(2-aminomethyl-5-chlorobenzyl)amide

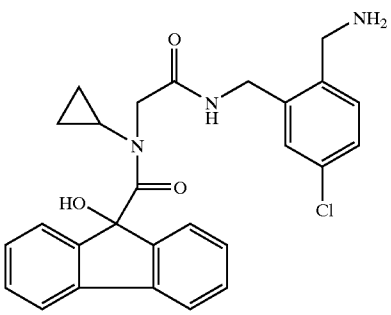

Step 1. To a stirred solution of 2-(tert-butyloxycarbonylaminomethyl)-5-chlorobenzylamine (0.52 g, 1.93 mmol) in dichloromethane (2 mL) was added diisopropylethylamine (0.34 mL, 1.95 mmol) and the solution was cooled to −78° C. Bromoacetyl bromide (0.19 mL, 2.12 mmol) was added slowly and after the addition was complete, the temperature was raised to 0° C. The reaction was complete in 15 min based on the disappearance of starting amine on silica gel TLC a 95:5 mixture of dichloromethane to methanol as mobile phase. The solvent was removed on a rotary evaporator to yield N-(2-(tert-butyloxycarbonylaminomethyl-5-chlorobenzyl)bromoacetamide (0.75 g).

Step 2. To a stirred solution of N-(2-(tert-butyloxycarbonylaminomethyl-5-chlorobenzyl) bromoacetamide (0.75 g, 1.92 mmol.) in DMF (2 mL) was added cyclopropylamine (1.3 mL, 19.3 mmol). The reaction was complete in 1 hour based on the disappearance of starting material on silica gel TLC (95:5, dichloromethane to methyl alcohol as the mobile phase). The solvent was removed on a rotary evaporator and the residue was purified on a silica gel column using a 95:5 mixture of dichloromethane to methyl alcohol as mobile phase. Pure fractions were combined and evaporated in vacuo to yield the liquid N-cyclopropylglycin-N-(2-(tert-butyloxycarbonylaminomethyl-5-chlorobenzyl)amide (0.67 g, 96% pure by HPLC; HPLC RT=2.76 min, method A; LC-MS m/z=368).

Step 3. N-cyclopropylglycin-N-(2-(tert-butyloxycarbonylaminomethyl-5-chlorobenzyl)amide (0.22 g, 0.59 mmol) from the previous step was dissolved in DMF (0.8 mL) and dichloromethane (1.2 mL). To the solution was added 9-hydroxy-9-fluorene carboxylic acid (0.15 g, 0.65 mmol), HOAT (0.18 g, 1.35 mmol), EDC (0.18 g, 0.92 mmol) and N-methylmorpholine to pH=7.5 (based on wetted E Merck indicator strips). The reaction continued 24 hours and then was filtered and purified on a preparative reverse phase HPLC using an acetonitrile:water gradient containing 0.1% TFA. Pure fractions were combined and lyophilized to yield the solid N-(1-(9-hydroxy-9H-fluoren-9-ylcarbonyl)-N-cyclopropylglycin-N-(2-tert-butlyoxycarbonylaminomethyl-5-chlorobenzyl) amide (0.090 g, HPLC RT=3.73 min, method A; LC-MS m/z=576).

Step 4. N-(1-(9-hydroxy-9H-fluoren-9-ylcarbonyl)-N-cyclopropylglycin-N-(2-tert-butlyoxycarbonylaminomethyl-5-chlorobenzyl)amide (0.090 g, 0.15 mmol) from the previous step was dissolved in trifluoroacetic acid (1 mL) and dichloromethane (5 mL) and stirred at room temperature for 1 hour. No starting material remained based on HPLC analysis so the solvents were removed on a rotary evaporator and the residue was purified on a preparative reverse phase HPLC using an acetonitrile:water gradient containing 0.1% TFA to yield a solid TFA salt of the title compound (HPLC RT=2.89 min, method A; LC-MS m/z=476).

EXAMPLE 37

1-((9-Hydroxy-9H-fluoren-9-yl)carbonyl)-N-(2-(1-amino-2-hydroxyethyl)-5-chlorobenzyl)-prolinamide

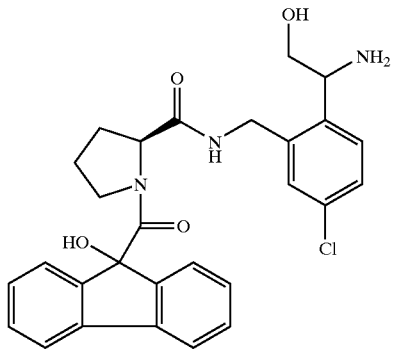

Step 1. (S)-N-(2-{[tert-butyl(dimethyl)silyl]oxy}ethylidene)-2-methylpropane-2-sulfinamide was prepared from (S)-(−)-2-methyl-2-propanesulfinamide and (tert-butyldimethylsilyloxy)acetaldehyde essentially according to the procedure of Barrow, J. C.; Ngo, P. L. *Tetrahedron Lett.* 2000, PAGES.

Step 2. To a stirred solution of (5-chloro-2-iodophenyl) methanol (626 mg, 2.3 mmol, 1 eq) in anhydrous THF (14 mL) at 0° C. was added sodium hydride (160 mg, 4.0 mmol, 1.7 eq) in one portion. The mixture was stirred at 0° C. for 5 min, then at room temperature for 5 min and was then cooled to −78° C. A 2.5 M solution of n-butylllithium in hexanes (2.0 mL, 5.0 mmol, 2.1 eq) was added dropwise. The resulting yellow mixture was stirred at −78° C. for 10 min and was then transferred via wide-bore cannula to a cold (−78° C.) solution of (S)-N-(2-{[tert-butyl(dimethyl)sily]oxy}ethylidene)-2-methylpropane-2-sulfinamide (647 mg, 2.3 mmol, 1.0 eq) in anhydrous THF (2.3 mL). The reaction was quenched at −78° C. after 30 min by the addition of saturated aqueous NH₄Cl. The mixture was stirred at room temperature for 15 min and was then partitioned between EtOAc and brine. The layers were separated and the aqueous layer extracted twice with EtOAc. The combined organic extracts were washed with brine, dried over Na₂SO₄ and concentrated to a light yellow oil. Purification by normal phase MPLC (40 mm column, 30 min gradient 10:85:5 to 70:25:5 EtOAc:hexanes:CH$_2$Cl$_2$) afforded separation of the two diastereomeric of N-{2-{tert-butyl(dimethyl)silyl}oxy}-1-[4-chloro-2-(hydroxymethyl)phenyl]ethyl}-2-methylpropane-2-sulfinamide: Diastereomer A (213 mg, >96% diastereomeric purity by LCMS, LCMS RT=2.73 min): $^1$H NMR (400 MHz, CDCl$_3$): δ 7.42–7.28 (m, 3H), 4.84–4.79 (m, 2H), 4.67–4.62 (m, 1H), 4.32 (s, 1H), 3.80–3.69 (m, 2H), 3.09 (br s, 1H), 1.21 (s, 9H), 0.90 (s, 9H), 0.07 (s, 3H), 0.00 (s, 3H). LCMS (M+H)=420.4. Diastereomer B (63 mg, 80% diastereomeric purity by LCMS, LCMS RT=2.68 min): $^1$H NMR (400 MHz, CDCl$_3$): δ 7.44–7.31 (m, 3H), 4.82–4.67 (m, 3H), 4.01–3.98 (m, 1H), 3.92 (br s, 1H), 3.85–3.78 (m, 1H), 3.67 (br s, 1H), 1.23 (s, 9H), 0.85 (s, 9H), 0.02 (s, 3H), 0.00 (s, 3H). LCMS (M+H)=420.4.

Step 3. To a solution of diastereomer A of N-{2-{tert-butyl(dimethyl)silyl}oxy}-1-[4-chloro-2-(hydroxymethyl)phenyl]ethyl}-2-methylpropane-2-sulfinamide (prepared as above, 195 mg, 0.46 mmol, 1 eq) in anhydrous THF (2.5 mL) at 0° C. under argon atmosphere was added DPPA (110 μL, 0.51 mmol, 1.1 eq) and DBU (73 μL, 0.49 mmol, 1.05 eq). The mixture was stirred at room temperature for 3 h and was then heated to 60° C. for 2.5 h. The mixture was cooled to room temperature and partitioned between EtOAc and brine. The layers were separated and the aqueous layer was extracted with EtOAc. The combined organic extracts were washed successively with 10% aqueous citric acid, saturated aqueous NaHCO$_3$ and brine. The organic layer was dried over MgSO$_4$, filtered and concentrated to a yellow oil. Purification by silica gel chromatography (isocratic elution with 3:1 hexanes:EtOAc) afforded diastereomer A of N-(1-[2-(azidomethyl)-4-chlorophenyl]-2-{[tert-butyl(dimethyl)silyl]oxy}ethyl-2-methylpropane-2-sulfinamide as a clear oil. (139 mg, 67%). $^1$H NMR (400 MHz, CDCl$_3$): δ 7.42–7.40 (m, 1H), 7.35–7.32 (m, 1H), 7.26 (s, 1H), 4.70 (dd, J=4.2, 9.2 Hz, 1H), 4.54 (d, J=13.7 Hz, 1H), 4.44 (d, J=13.7 Hz, 1H), 4.34 (br s, 1H), 3.80 (dd, J=4.2, 10.1 Hz, 1H), 3.64 (apparent t, J=9.9 Hz, 1H), 1.21 (s, 9H), 0.92 (s, 9H), 0.10 (s, 3H), 0.08 (s, 3H). LCMS RT=3.28 min, (M+H)=445.2. Diastereomer B (63 mg, 0.15 mmol) from Step 2 above was also subjected to these reaction conditions to afford the crude azide as an orange oil. Silica gel chromatography (gradient elution 4:1 to 3:1 hexanes:EtOAc) afforded the pure diastereomer B of the azide (separated from traces of diastereomer A of the azide derived from diastereomer A of the alcohol which was present in the starting material) as a clear oil. (20 mg, 30%). $^1$H NMR (400 MHz, CDCl$_3$): δ 7.52–7.49 (m, 1H), 7.40–7.30 (m, 2H), 4.67 (dd, J=5.6, 10.0 Hz, 1H), 4.50 (s, 2H), 4.05 (d, J=4.0 Hz, 1H), 3.92–3.82 (m, 2H), 1.23 (s, 9H), 0.88 (s, 9H), 0.04 (s, 3H), 0.01 (s, 3H). LCMS RT=3.07 min, (M+H)=445.3.

Step 4. To a solution of diastereomer A of N-(1-[2-(azidomethyl)-4-chlorophenyl]-2-{[tert-butyl(dimethyl)silyl]oxy}ethyl-2-methylpropane-2-sulfinamide (from the previous step, 136 mg, 0.31 mmol, 1 eq) in THF (5.6 mL) at room temperature was added triphenylphosphine (160 mg, 0.61 mmol, 2.0 eq). Water (111 μL) was added after 20 min and the reaction mixture was then heated at 55° C. for 6 h. The mixture was then stirred at room temperature overnight. The solvent was removed in vacuo and the residue was purified by silica gel chromatography (gradient elution 100% EtOAc to 9:1 EtOAc:MeOH to 9:1:0.5 EtOAc:MeOH:NH$_4$OH) to afford diastereomer A of N-(1-[2-(aminomethyl)-4-chlorophenyl]-2-{[tert-butyl(dimethyl)silyl]oxy}ethyl)-2-methylpropane-2-sulfinamide as a nearly colorless oil. (123 mg, 96%). $^1$H NMR (400 MHz, CDCl$_3$): δ 7.37–7.34 (m, 2H), 7.25–7.22 (m, 1H), 4.80 (dd, J=4.4, 9.2 Hz, 1H), 4.35 (br s, 1H), 4.04 (d, J=14.4 Hz, 1H), 3.86 (d, J=14.0 Hz, 1H), 3.79 (dd, J=4.4, 10.0 Hz, 1H), 3.62 (apparent t, J=10.0 Hz, 1H), 1.64 (br s, 2H), 1.21 (s, 9H), 0.91 (s, 9H), 0.08 (s, 3H), 0.07 (s, 3H). LCMS RT=1.93 min. LCMS (M+H)=419.4. Diastereomer B of the azide (20 mg, 0.05 mmol) was also subjected to these reaction conditions (heated overnight at 60° C.) to afford the crude amine as a light pink oil. Silica gel chromatography (gradient elution 100% EtOAc to 9:1:1 EtOAc:MeOH:NH$_4$OH) afforded diastereomer B of the title compound as a pale yellow oil (17 mg). Some triphenylphosphine oxide co-eluted with the product. $^1$H NMR (400 MHz, CDCl$_3$): δ 7.40–7.35 (m, 2H), 7.31–7.29 (m, 1H), 4.78 (t, J=6.0 Hz, 1H), 4.42 (br s, 1H), 4.06–3.95 (m, 3H), 3.86 (dd, J=6.0, 10.0 Hz, 1H), 1.25 (s, (H), 0.87 (s, 9H), 0.05 (s, 3H), 0.02 (s, 3H). LCMS RT=1.76 min, (M+H)=419.3.

Step 5. A mixture of diastereomer A of N-(1-[2-(aminomethyl)-4-chlorophenyl]-2-{[tert-butyl(dimethyl)silyl]oxy}ethyl)-2-methylpropane-2-sulfinamide (from the previous step, 67 mg, 0.16 mmol, 1.07 eq), 1-[(9-hydroxy-9H-fluoren-9-yl)carbonyl]-L-proline (48 mg, 0.15 mmol, 1.0 eq (43 mg, 0.22 mmol, 1.5 eq), triethylamine (22 μL, 0.16 mmol, 1.07 eq) and HOAt (10 mg, 0.08 mmol, 0.5 eq) in anhydrous DMF (1 mL) was stirred at room temperature overnight. Most of the DMF was removed in vacuo and the residue was purified by silica gel chromatography (isocratic elution, 1:1 EtOAc:hexanes) to afford diastereomer A of N-(2-{2-{[tert-butyl(dimethylsilyl)oxy}-1-[(tert-butylsulfinyl)amino]ethyl}-5-chlorobenzyl)-1-[(9-hydroxy-9H-fluoren-9-yl)carbonyl]-L-prolinamide as a white solid (66 mg, 61%). $^1$H NMR (400 MHz, CDCl$_3$): δ 7.66–7.64 (m, 2H), 7.44–7.00 (m, 9H), 5.91 (m, 1H), 4.71–4.58 (m, 3H), 4.40 (m, 1H), 4.35 (br s, 1H), 3.75 (dd, J=4.4, 10.3 Hz, 1H), 3.67 (apparent t, J=9.7 Hz, 1H), 2.38–2.28 (m, 2H), 2.02 (m, 1H), 1.81 (m, 1H), 1.65 (m, 1H), 1.45 (m, 1H), 1.23 (s, 9H), 0.91 (s, 9H), 0.08 (s, 3H), 0.00 (s, 3H). LCMS RT=3.05 min, (M+H)=724.6. Diastereomer B of the amine (17 mg from previous step) was coupled and purified under similar conditions to afford diastereomer B of N-(2-{2-{[tert-butyl(dimethylsilyl)oxy}-1-[(tert-butylsulfinyl)amino]ethyl}-5-chlorobenzyl)-1-[(9-hydroxy-9H-fluoren-9-yl)carbonyl]-L-prolinamide a a pale yellow oil (20 mg) which still contained traces of triphenylphosphine oxide from the previous step. LCMS RT=3.01 min, (M+H)=724.6.

Step 6. To a solution of diastereomer A of N-(2-{2-{[tert-butyl(dimethylsilyl)oxy}-1-[(tert-butylsulfinyl)amino]ethyl}-5-chlorobenzyl)-1-[(9-hydroxy-9H-fluoren-9-yl)carbonyl]-L-prolinamide (66 mg, 0.09 mmol, 1 eq) in absolute MeOH (3 mL) at 0° C. was added a 2M solution of HCl in diethyl ether (683 μL, 1.3 mmol, 15 eq). The mixture was allowed to warm to room temperature while stirring overnight. The solvent was removed in vacuo to afford a yellow oil. Purification by reverse phase HPLC afforded diastereomer A of the title compound as a white film. (35 mg, TFA salt, 62%). $^1$H NMR (500 MHz, CD$_3$OD): δ 8.4 (m, 1H), 7.78 (dd, J=4.0, 7.5 Hz, 2H), 7.56–7.54 (m, 2H), 7.49–7.44 (m, 3H), 7.39–7.26 (m, 4H), 4.71–4.68 (m, 2H), 4.37 (dd, J=5.0, 8.0 Hz, 1H), 4.28 (d, J=15.0 Hz, 1H), 4.05 (dd, J=4.5, 12.0 Hz, 1H), 3.85 (dd, J=8.5, 12.0 Hz, 1H), 2.46–2.39 (m, 2H), 2.00–1.93

(m, 1H), 1.69–1.57 (m, 2H), 1.47–1.38 (m, 1H). LCMS RT=1.31 min, (M+H)=506.4. Diastereomer B of N-(2-{2-{[tert-butyl(dimethylsilyl)oxy}-1-[(tert-butylsulfinyl)amino]ethyl}-5-chlorobenzyl)-1-[(9-hydroxy-9H-fluoren-9-yl)carbonyl]-L-prolinamide (20 mg) was similarly deprotected and purified to afford diastereomer B of the title compound as a nearly colorless oil. ¹H NMR (500 MHz, CD₃OD): δ 7.79 (dd, J=3.5, 7.5 Hz, 2H), 7.57–7.55 (m, 2H), 7.49–7.45 (m, 3H), 7.38–7.32 (m, 4H), 4.83 (dd, J=5.5, 15.0 Hz, 1H), 4.74 (dd, J=4.5, 7.5 Hz, 1H), 4.33 (dd, J=5.8, 8.3 Hz, 1H), 4.13 (d, J=15.0 Hz, 1H), 3.92 (dd, J=4.3, 12.0 Hz, 1H), 3.82 (dd, J=8.0, 12.0 Hz, 1H), 2.41–2.38 (m, 2H), 2.00–1.93 (m, 1H), 1.70–1.60 (m, 2H), 1.44–1.40 (m, 1H). LCMS RT=1.33 min, (M+H)=506.4.

EXAMPLE 38

1-((9-Hydroxy-9H-fluoren-9-yl)carbonyl)-N-(2-(2-hydroxyethylaminomethyl)-5-chlorobenzyl)-prolinamide

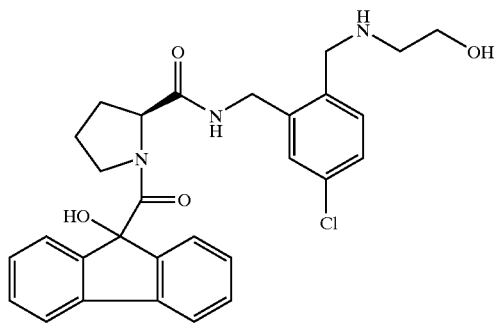

The TFA salt of 1-((9-hydroxy-9H-fluoren-9-yl)carbonyl)-N-(2-aminomethyl-5-chlorobenzyl)-L-prolinamide (0.074 g, 0.12 mmol) was dissolved in dimethylformamide (0.2 mL). To the solution was added diisopropylethylamine (0.046 mL, 0.26 mmol) and (2-bromoethoxy)-tert-butyldimethylsilane (0.028 mL, 0.13 mmol). The reaction was heated to 98 degrees in a pressure vessel for one hour. The mixture was then filtered and purified on a preparative HPLC. Pure fractions were combined and lyophilized to yield the trifluoroacetate salt of the title compound as a solid (HPLC RT=2.84 min, method A; LC-MS m/z=520).

EXAMPLE 39

1-((9-Hydroxy-9H-fluoren-9-yl)carbonyl)-N-(2-(bis-(N-2-hydroxyethyl)aminomethyl)-5-chlorobenzyl)-prolinamide

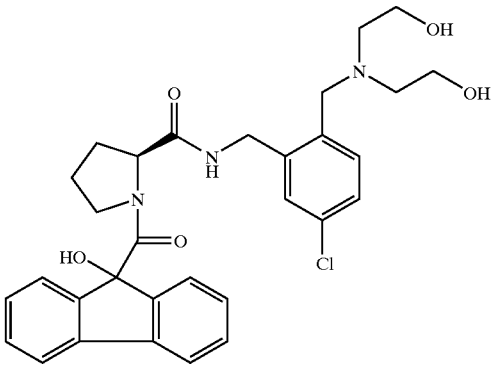

The TFA salt of the title compound was also obtained from the reaction and purification as described in the previous example (HPLC RT=2.9 min, method A; LC-MS m/z=564).

EXAMPLE 40

1-((9-Hydroxy-9-H-fluoren-9-yl)carbonyl)-N-(5-chloro-2-((3-hydroxyazetidin-1-yl)methyl)benzyl)-L-prolinamide

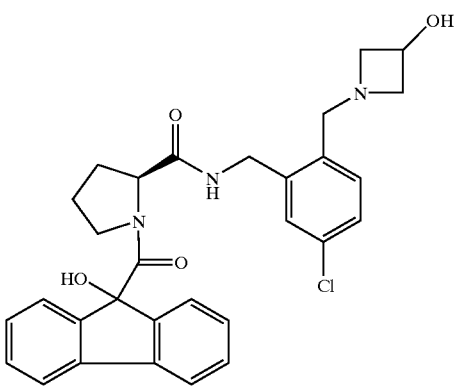

Step 1. DIEA (3.57 mL, 20.50 mmol) was added to a stirred mixture of 3-hydroxyazetidine hydrochloride (1.00 g, 9.11 mmol) and 2-bromomethyl-5-chlorobenzonitrile (2.10 g, 9.11 mmol) in CH₂Cl₂ (75 mL). After 16 h the reaction mixture was concentrated and the residue was partitioned between ether and 1N HCl. The aqueous layer was washed with ether, made neutral with NaHCO₃, saturated with NaCl and extracted into CH₂Cl₂. The organic layer was dried (Na₂SO₄) and evaporated to give 5-chloro-2-[(3-hydroxyazetidin-1-yl)methyl]benzonitrile (1.67 g) as a gum: ¹H NMR (CDCl₃, 400 MHz) δ 3.03 (m, 2H), 3.68 (m, 2H), 4.49 (t, J=6.2 Hz, 1H), 7.46 (d, J=8.6 Hz, 1H), 7.53 (d,d, J=2.2, 6.2 Hz, 1H), 7.60 (d, J=2.0 Hz, 1H).

Step 2. 1M LAH in ether (11.25 mL, 11.25 mmol) was added to a stirred solution of 5-chloro-2-[(3-hydroxyazetidin-1-yl)methyl]benzonitrile (1.67 g, 7.50 mmol) in THF (70 mL) at 0° C. After 1 h the reaction was quenched with EtOAc (5 ml) and concentrated. The residue was stirred with ether (150 mL) and this was then treated successively with water (0.43 mL), 15% NaOH (0.43 mL) and water (1.29 mL). After stirring for 15 min the mixture was filtered and evaporated to give 5-Chloro-2-[(3-hydroxyazetidin-1-yl)methyl]benzylamine (1.19 g) as a gum: $^1$H NMR (CDCl$_3$, 400 MHz) δ 2.99 (m, 2H), 3.64 (m, 2H), 3.75 (s, 2H), 4.38 (d, J=5.3 Hz, 2H), 4.50 (m, 1H), 7.13 (d, J=8.0 Hz, 1H), 7.21 (dd, J=2.2, 9.7 Hz, 1H), 7.35 (d, J=2.2 Hz, 1H).

Step 3. EDC (1.51 g, 7.87 mmol) was added to a stirred mixture of 5-chloro-2-[(3-hydroxyazetidin-1-yl)methyl]benzylamine (1.19 g, 5.25 mmol), N-Boc-L-proline (1.13 g, 5.25 mmol) and HOAT (0.36 g, 2.62 mmol) in DMF (9 mL). After 16 h the mixture was concentrated and the residue was partitioned between EtOAc and 10% NaHCO$_3$. The organic layer was washed with water and brine, dried (Na$_2$SO$_4$) and evaporated. The residue was partitioned between EtOAc and 1M citric acid. The aqueous layer was made neutral with NaHCO$_3$ and was extracted into CH$_2$Cl$_2$. The organic layer was evaporated and the residue was purified by chromatography on silica (ammonia saturated CHCl$_3$/MeOH, 95:5) to give N-{5-chloro-2-[(3-hydroxyazetidin-1-yl)methyl]benzyl}-1-(tert-butoxycarbonyl)-L-prolinamide (210 mg) as a glass: MS: 424.5 (M+1).

Step 4. TFA (3 mL) was added to a stirred solution of N-{5-chloro-2-[(3-hydroxyazetidin-1-yl)methyl]benzyl}-1-(tert-butoxycarbonyl)-L-prolinamide (210 mg, 0.49 mmol) in CH$_2$Cl$_2$ (6 mL) at 0° C. After 90 min the solution was concentrated and the residue was partitioned between CH$_2$Cl$_2$ and 10% NaHCO$_3$. The aqueous layer was saturated with NaCl and then extracted with more CH$_2$Cl$_2$. The combined organic layers were washed with brine, dried over (Na$_2$SO$_4$) and then evaporated. The reside was purified by chromatography on silica (ammonia saturated CHCl$_3$/MeOH, 93:7) to give N-{5-chloro-2-[(3-hydroxyazetidin-1-yl)methyl]benzyl}-L-prolinamide (55.8 mg) as a glass: $^1$H NMR (CDCl$_3$, 400 MHz) δ 1.71 (m, 2H), 1.93 (m, 1H), 2.16 (m, 1H), 2.92 (m, 2H), 3.05 (m, 2H), 3.39 (m, 2H), 3.61 (dd, J=12.3, 20.7 Hz, 2H), 3.72 (dd, J=6.4, 8.6 Hz, 2H), 4.28–4.46 (m, 3H), 7.12 (d, J=8.1 Hz), 7.19 (dd, J=2.2, 8.1 Hz), 7.36 (d, J=2.0 Hz, 1H), 9.09 (br s, 1H).

Step 5. EDC (49.5, 0.26 mmol) was added to a stirred mixture of N-{5-chloro-2-[(3-hydroxyazetidin-1-yl)methyl]benzyl}-L-prolinamide (55.8 mg, 0.17 mmol), 9-hydroxy-9-H-fluoren-9-ylcarboxylic acid (40.9 mg, 0.18 mmol) and HOAT (11.7 mg, 0.086 mmol) in DMF (1.25 mL). After 16 h the mixture was concentrated and the residue was partitioned between EtOAc and 10% NaHCO$_3$. The organic layer was washed with water and brine, dried (Na$_2$SO$_4$) and evaporated. The residue was purified by chromatography on silica (ammonia saturated CHCl$_3$/MeOH, 98:2) to give the title compound as a glass: HRMS (FAB) calcd C$_{30}$H$_{31}$ClN$_3$O$_4$ (M+1) 554.1817, found 554.1855.

EXAMPLE 41

1-((9-Hydroxy-9-H-fluoren-9-yl)carbonyl)-N-(5-chloro-2-(((2,2-difluoroethyl)amino)methyl)benzyl-L-prolinamide

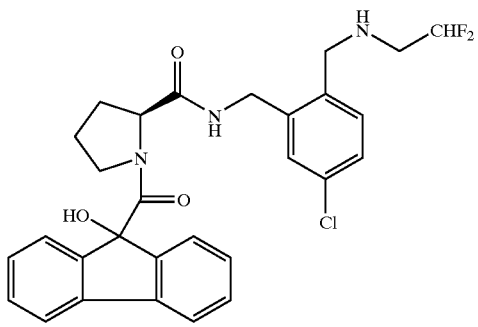

Step 1. To a solution of 1-((9-hydroxy-9H-fluoren-9-yl)carbonyl)-N-(2-aminomethyl-5-chlorobenzyl)-L-prolinamide (65 mg, 0.14 mmol) in anhydrous toluene (1.0 mL) at 0° C. was added difluoroacetaldehyde ethylhemiacetal (20 mg, 0.16 mmol, 1.1 eq). The mixture was heated to 100° C. under nitrogen atmosphere for 40 min and was then treated with MgSO$_4$. Heating was continued for another 2 h. The mixture was then cooled to room temperature and diluted with CH$_2$Cl$_2$. The solution was dried over MgSO$_4$, filtered and concentrated to an orange oil which yielded N-(5-chloro-2-{[(2,2-difluoroethylidene)amino]-methyl}benzyl-1-[(9-hydroxy-9-H-fluoren-9-yl)carbonyl]-L-prolinamide as a foam on prolonged drying under high vacuum. (66 mg, 90%).

Step 2. To a solution of N-(5-chloro-2-{[(2,2-difluoroethylidene)amino]methyl}benzyl-1-[(9-hydroxy-9-H-fluoren-9-yl)carbonyl]-L-prolinamide (from the previous step, 66 mg, 0.12 mmol) in absolute MeOH (2.0 mL) at 0° C. was added sodium borohydride (9.0 mg, 0.24 mmol, 2.0 eq). The solution was stirred overnight while warming to room temperature. More sodium borohydride (12 mg, 0.32 mmol) was added and the mixture was stirred for an additional 2 h, at which point no further change was observed by LCMS. The solvent was removed in vacuo and the residue partitioned between EtOAc and saturated aqueous NH$_4$Cl. The layers were separated and the aqueous layer was extracted with EtOAc. The combined organic layers were washed with brine, dried over Na$_2$SO$_4$ and concentrated to a tan foam. Purification by reverse phase HPLC afforded the title compound as an oil which solidified to a tan foam under high vacuum. 1H NMR (400 MHz, CD$_3$OD): δ 7.77 (d, J=7.7 Hz, 2H), 7.56–7.28 (m, 9H), 6.34 (tt, J=3.5, 54 Hz, 1H), 4.87–4.35 (m, 5H), 3.74–3.60 (m, 2H), 2.40–2.35 (m, 2H), 2.00–1.90 (m, 1H), 1.64–1.57 (m, 2H), 1.56–1.38 (m, 1H). LCMS (M+H)=540.3. LCMS RT=1.83 min.

EXAMPLE 42

1-((4-Aza-9-hydroxy-9H-fluoren-9-yl)carbonyl)-N-(2-aminomethyl-5-chlorobenzyl)-L-prolinamide

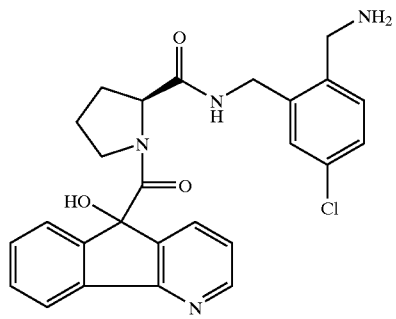

Step 1. To a solution of 2-chloro-3-cyanopyridine (4.06 g, 29.3 mmol) in toluene (60 mL) was added phenylboronic acid (5.4 g, 43.9 mmol), potassium carbonate (6.1 g, 44.1 mmol) and tetrakis(triphenylphosphine)palladium (1.7 g, 1.5 mmol). The mixture was refluxed under nitrogen for 24 hours, then the solvent was removed under reduced pressure. The residue was purified on a silica gel column using 100% $CH_2Cl_2$ then 99:1 $CH_2Cl_2$:MeOH as mobile phase. Pure fractions were combined and dried in vacuo to yield the solid 2-phenyl-3 cyanopyridine (5.0 g, HPLC RT=2.98 min, method A; LC-MS m/z=181).

Step 2. 2-Phenyl-3-cyanopyridine (5.0 g, 27.9 mmol) from the previous step was dissolved in concentrated hydrochloric acid (140 mL) and refluxed for 6 days until no starting material was evident by HPLC. The solvent was evaporated in vacuo to yield the HCl salt of 2-phenyl-3-pyridine carboxylic acid as a solid (7.97 g, HPLC RT=1.08 min, method A; LC-MS m/z=200) $^1$H NMR, 400 MHz, $CD_3OD$, 9.03 ppm (d, 1H), 8.97–8.95 ppm (m, 1H), 8.18–8.14 ppm (m, 1H), 7.68–7.62 ppm (m, 5H).

Step 3. 2-Phenyl-3-pyridine carboxylic acid (7.97 g, 40.0 mmol) and polyphosphoric acid (162.2 g) were combined and heated slowly to 200 degrees C with mixing until the starting material was consumed (7 h). Then the mixture was cooled to 140 degrees, poured carefully over crushed ice and allowed to mix for 5 hours. The product was extracted with dichloromethane (4×200 mL). The combined organic phases were dried ($MgSO_4$), filtered, and the solvent was removed under reduced pressure to give 4-azafluorenone as a pale yellow solid (4.7 g, HPLC RT=2.91 min, method A; LC-MS m/z=182; $^1$H NMR, 400 MHz, $CD_3OD$, 8.62–8.60 ppm (m, 1H), 7.98 ppm (d, 1H), 7.87 ppm (d, 1H), 7.74–7.68 ppm (m, 2H), 7.54–7.52 ppm (m, 1H), 7.39–7.35 ppm (m, 1H)).

Step 4. To a stirred solution of 4-azafluorenone (4.7 g, 25.9 mmol) from the previous step in dichloromethane (50 mL) was added zinc iodide (0.81 g, 2.5 mmol) and trimethylsilylcyanide (31 mL, 233 mmol). The mixture was heated to reflux until the 4-azafluorenone was consumed as determined by HPLC (24 h). The mixture was then blown dry with nitrogen to yield 4-aza-9-trimethylsiloxy-9-cyanofluorene which was used without further purification (HPLC RT=3.71 min, method A; LC-MS m/z=281).

Step 5. The crude 4-aza-9-trimethylsiloxy-9-cyanofluorene from the previous step was immediately dissolved in methyl alcohol (40 mL) and cooled to 0 degrees. The solution was saturated with HCl gas and allowed to mix until the starting material was consumed as judged by HPLC analysis (4 h). The solvent was removed under reduced pressure and the residue was partitioned between CH2Cl2 and saturated aqueous NaHCO3. The organic phase was separated and evaporated under reduced pressure. The residue was purified on silica gel using 95:5 dichloromethane:MeOH as eluant. 4-Aza-9-hydroxyfluorene-9-carboxylic acid methyl ester was obtained as a solid (4.4 g, HPLC RT=2.08 min, method A; LC-MS m/z=242).

Step 6. To a stirred solution of 4-aza-9-hydroxyfluorene-9-carboxylic acid methyl ester from the previous step (4.4 g, 18.1 mmol) in isopropyl alcohol (100 mL) was added hydrazine (2.84 mL, 90.5 mmol) and the mixture was heated to reflux under nitrogen for 16 h. The solvent was evaporated in vacuo and the crude product was purified on silica gel (90:10 mixture of dichloromethane to methanol used as eluant) to yield 4-aza-9-hydroxyfluorene-9-carboxylic acid hydrazide as a solid (2.2 g, HPLC RT=0.65 min, method A; LC-MS m/z=242).

Step 7. 4-Aza-9-hydroxyfluorene-9-carboxylic acid hydrazide from the previous step (1.67 g, 6.9 mmol) was dissolved in dimethylformamide (10 mL) and cooled to −20 degrees. To the solution was added HCl saturated tetrahydrofuran to pH<2 (as measured on wetted E. Merck pH indicator strips), followed by amylnitrite (0.9 mL, 6.9 mmol) and stirring was continued until all of the starting hydrazide was converted to the acyl azide (HPLC RT=2.28 min, method A). The pH of the solution was adjusted to 6.5 with diisopropylethylamine, and L-prolin-N-(2-(tert-butyloxycarbonylaminomethyl)-5-chlorobenzyl)amide (2.54 g, 6.9 mmol) was added. The pH of the solution was then adjusted to 8 with by the addition of more diisopropylethylamine. The reaction was warmed to 0° C. and stirred for 24 h. The solvent was removed under reduced pressure and the residue was partitioned between EtOAc and saturated aqueous NaHCO3. The organic phase was dried (MgSO4), filtered, and the solvent was removed under reduced pressure. The residue was purified on a silica gel column (gradient elution of 98:2 to 95:5 to 93:7 $CH_2Cl_2$:MeOH). Pure fractions were combined and dried to give N-(4-aza-9-hydroxy-9-fluorenylcarbonyl)-N-(2-(tert-butyloxycarbonylaminomethyl)-5-chlorobenzyl)-L-prolinamide (3.4 g, TLC $R_f$=0.4 (95:5 $CH_2Cl_2$:MeOH); HPLC RT=3.1 min, method A; LC-MS m/z=577).

Step 8. To a stirred solution of N-(4-aza-9-hydroxy-9-fluorenylcarbonyl)-N-(2-(tert-butyloxycarbonylaminomethyl)-5-chlorobenzyl)-L-prolinamide (3.4 g, 5.9 mmol) in dichloromethane (6 mL) was added trifluoroacetic acid (2 mL). The mixture was stirred at room temperature for 1.5 hours and then evaporated to dryness in vacuo. The residue was purified on a preparative reverse phase HPLC using an acetonitrile:water gradient containing 0.1% TFA. The resulting mixture of diastereomers was then separated using a Chiralpak AD column, 5×50 cm, 35:65 A:B (A=0.1% diethylamine in hexanes, B=ethanol) as the mobile phase with a flow rate of 60 mL/min. Each diastereomer was then purified again by preparative reverse phase HPLC using an acetonitrile:water gradient containing 0.1% TFA. Product-containing fractions were combined and lyophilized to give the TFA salt of each diastereomer of the title compound as a solid. First eluting diastereomer: HPLC RT=2.347 min, method A; LC-MS m/z=477; RT=5.7 min on a Chiralpak AD column, 250×4.6 mm, 35:65 A:B (A=0.1% diethylamine in hexanes, B=ethanol) as the mobile phase with a flow rate of 1.5 mL/min); $^1$H NMR, 400 MHz, $CDCl_3$, 8.63 ppm (d, 1H), 8.52 ppm (s, 2H), 8.41 ppm (d, 1H), 8.02 ppm (d, 1H), 7.70 ppm (d, 1H), 7.54–7.51 ppm (m, 2H), 7.39 ppm (d, 1H), 7.35 ppm (d, 1H), 7.33–7.27 ppm (s, 1H), 7.22 ppm (m, 1H), 4.91–4.85 ppm (m, 1H), 4.45–4.42 ppm (m, 1H), 4.19–4.09 ppm (m, 1H), 4.03–3.99 ppm (d, 1H), 2.44–2.36 ppm (m, 2H), 1.97–1.88 ppm (m, 1H), 1.80–1.70 ppm (m, 1H), 1.68–1.63 ppm (m, 1H), 1.53–1.45 ppm (m, 1H). Second eluting diastereomer: 0.45 g, HPLC RT=2.349 min, method A; LC-MS m/z=477; RT=7.9 min on a Chiralpak AD column, 250×4.6 mm, 35:65 A:B (A=0.1% diethylamine in hexanes, B=ethanol) as the mobile phase with a flow rate of 1.5 mL/min); $^1$H NMR, 400 MHz, CDCl$_3$, 8.66–8.65 ppm (d, 1H), 8.52–8.51 ppm (s, 2H), 8.10 ppm (d, 1H), 7.76 ppm (d, 1H), 7.57–7.54 ppm (m, 1H), 7.47–7.40 ppm (m, 2H), 7.37–7.26 ppm (m, 4H), 4.88–4.83 ppm (m, 1H), 4.47–4.44 ppm (m, 1H), 4.23–4.00 ppm (m, 2H), 2.32–2.17 ppm (m, 2H), 2.01–1.92 ppm (m, 1H), 1.76–1.63 (m, 2H), 1.61–1.45 ppm (m, 1H).

EXAMPLE 43

1-((4-Oxidoaza-9-hydroxy-9H-fluoren-9-yl)carbonyl)-N-(2-aminomethyl-5-chlorobenzyl)-L-prolinamide

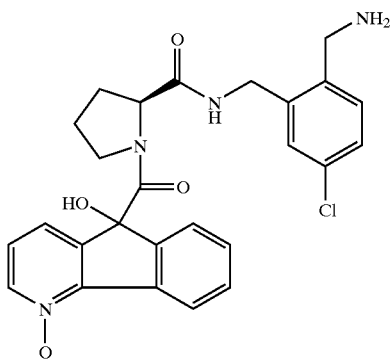

Step 1. A stirred solution of 1-((4-aza-9-hydroxy-9H-fluoren-9-yl)carbonyl)-N-(2-tert-butyloxycarbonylaminomethyl-5-chlorobenzyl)-L-prolinamide (0.11 g, 0.19 mmol) in dichloromethane (2 mL) was cooled to 0 degrees Centigrade and 3-chloroperoxybenzoic acid (0.054 g, 0.31 mmol) was added. The solution was stirred at 0 degrees for 24 hours. The solvent was evaporated in vacuo and the residue was purified by preparative reverse-phase HPLC using an acetonitrile:water (0.1% TFA) gradient. Pure fractions were combined and lyophilized to yield 1-((4-oxidoaza-9-hydroxy-9H-fluoren-9-yl)carbonyl)-N-(2-tert-butyloxycarbonylaminomethyl-5-chlorobenzyl)-L-prolinamide as a solid (0.52 g, HPLC RT=3.13 min, method A; LC-MS m/z=593).

Step 2. 1-((4-Oxidoaza-9-hydroxy-9H-fluoren-9-yl)carbonyl)-N-(2-tert-butyloxycarbonylaminomethyl-5-chlorobenzyl)-L-prolinamide from the previous step (0.52 g, 0.087 mmol) was dissolved in dichloromethane (4 mL) and trifluoroacetic acid (2 mL) was added. The solution was stirred at room temperature for one hour and evaporated in vacuo. The residue was dissolved in dimethylformamide and purified on a preparative reverse-phase HPLC using an acetonitrile:water (0.1% TFA) gradient. Product-containing fractions were combined and lyophilized to yield the trifluoroacetate salt of the title compound as a solid (HPLC RT=2.31 min, method A; LC-MS m/z=493).

EXAMPLE 44

1-((4-Aza-7-chloro-9-hydroxy-9H-fluoren-9-yl)carbonyl)-N-(2-antinomethyl-5-chlorobenzyl)-L-prolinamide

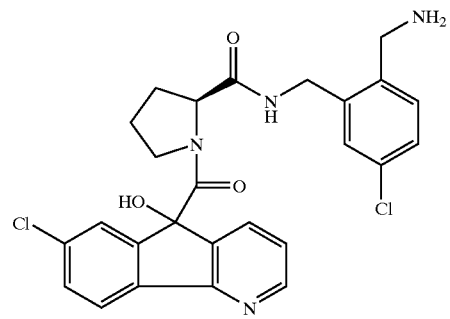

Step 1. To a solution of methyl 2-bromonicotinate (5.6 g, 25.9 mmol) in toluene (140 mL) was added 4-chlorophenylboronic acid (6.1 g, 38.9 mmol), potassium carbonate (5.4 g, 39 mmol), and tetrakis(triphenylphosphine) palladium (1.53 g. 1.3 mmol). The mixture was heated to reflux for 3.5 hours, evaporated in vacuo and then purified on a silica gel column using a 1:4 mixture of ethyl acetate:hexane as mobile phase. Pure fractions were combined and the solvent was removed in vacuo to yield methyl 2-(4-chlorophenyl)nicotinate (6.0 g, HPLC RT=3.04 min, method A; LC-MS m/z=248).

Step 2. To a solution containing methyl 2-(4-chlorophenyl)nicotinate from the previous step (6.0 g, 24.2 mmol) in methyl alcohol (30 mL) was added 1N sodium hydroxide (29 mL). The mixture was stirred at room temperature overnight then neutralized with 1N hydrochloric acid (29 mL), evaporated in vacuo and dried overnight to yield the solid 2-(4-chlorophenyl)nicotinic acid (7.3 g, Theo. Yield=5.65 g, balance is NaCl; HPLC RT=2.17 min; LC-MS m/z=234).

Step 3. 2-(4-Chlorophenyl)nicotinic acid from the previous step (7.3 g, 31.4 mmol) was added to polyphosphoric acid (157.7 g) and the mixture was slowly heated to 200 degrees centigrade with stirring. After 8 hours the mixture was cooled to 140 degrees and slowly poured over crushed ice and stirred for 48 hours. The solid was collected by filtration, washed with water, and dried in vacuo to give 4-aza-7-chlorofluorenone (4.2 g; HPLC RT=3.34 min, method A; LC-MS m/z=216; $^1$H NMR, 400 MHz, CD$_3$OD, 8.62 ppm (d, 1H), 8.00 ppm (d, 1H), 7.99–7.84 ppm (m, 1H), 7.69–7.67 ppm (m, 2H), 7.40–7.37 ppm (m, 1H)).

Step 4. To a stirred solution of 4-aza-7-chlorofluorenone from the previous step (4.1 g, 19.2 mmol) in acetonitrile (50 mL) was added 10% by weight of zinc iodide (0.46 g) and trimethylsilylcyanide (18 mL, 134.6 mmol). The mixture was stirred at room temperature for 2 hours then refluxed until the starting ketone was absent by HPLC (24 h). Upon completion, the mixture was blown dry with nitrogen, dissolved in methyl alcohol (40 mL), cooled to 0 degrees and saturated with anhydrous HCl gas. After 1.5 hours, the mixture was evaporated in vacuo and partitioned between dichloromethane and 5% sodium bicarbonate solution. The organic phase was dried (MgSO4), filtered, and evaporated in vacuo. The residue was purified on a silica gel column using 95:5 dichloromethane to methyl alcohol as mobile phase. The dried pure fractions yielded 4-aza-7-chloro-9-hydroxyfluoren-9-carboxylic acid methyl ester as a solid (4.8 g, HPLC RT=2.55 min, method A; LC-MS m/z=276).

Step 5. 4-Aza-7-chloro-9-hydroxyfluoren-9-carboxylic acid methyl ester (4.8 g, 17.4 mmol) was dissolved in hydrazine (20 mL) and the mixture was stirred at room temperature for 2 hours. The mixture was evaporated in vacuo and the resulting solid was suspended in dichloromethane, filtered, washed with dichloromethane, and dried in vacuo to yield 4-aza-7-chloro-9-hydroxyfluorene-9-carboxylic acid hydrazide as a powder (3.8 g, HPLC RT=1.75 min, method A; LC-MS m/z=276).

Step 6. 4-Aza-7-chloro-9-hydroxyfluorene-9-carboxylic acid hydrazide from the previous step (0.72 g, 2.6 mmol) was dissolved in dimethylformamide (7 mL) and cooled to –20 degrees. HCl saturated tetrahydrofuran was then added to pH<2 (as measured on wetted E. Merck pH indicator strips), followed by amylnitrite (0.4 mL, 2.9 mmol). The mixture was stirred for several hours until the hydrazide had been completely consumed (acyl azide HPLC RT=2.78 min; LC-MS m/z=287). The pH of the solution was adjusted to 6.5 with diisopropylethylamine and L-prolin-N-(2-(tert-butyloxycarbonylaminomethyl)-5-chlorobenzyl)amide (1.0 g, 2.8 mmol) was added. The pH of the solution was adjusted to 8 with the addition of more diisopropylethylamine. The reaction was stirred at –20 degrees for 3 hours and then warmed to room temperature and allowed to stir for 5 days. The solvent was removed on a rotary evaporator and the residue was purified on a silica gel column (95:5 dichloromethane to methanol). Pure fractions were combined and the solvent was removed under reduced pressure give 1-((4-aza-7-chloro-9-hydroxy-9H-fluoren-9-yl)carbonyl)-N-(2-tert-butyloxycarbonylaminomethyl-5-chlorobenzyl)-L-prolinamide (0.42 g, HPLC RT=3.39 min, method A; LC-MS m/z=611).

Step 7. To a stirred solution of give 1-((4-aza-7-chloro-9-hydroxy-9H-fluoren-9-yl)carbonyl)-N-(2-tert-butyloxycarbonylaminomethyl-5-chlorobenzyl)-L-prolinamide from the previous step (0.42 g, 0.7 mmol) in dichloromethane (6 mL) was added trifluoroacetic acid (2 mL). The mixture was stirred at room temperature for 1.5 hours. The solvents were evaporated in vacuo and the residue was purified by preparative reverse-phase HPLC using an acetonitrile:water (0.1% TFA) gradient to give the title compound as a mixture of diastereomers. The diastereomers were separated by preparative reverse-phase HPLC using an ammonium bicarbonate buffered mobile phase: Deltapak C18 100A column, 40×100 mm, 3 in series, a gradient of 95:5 A:B to 5:95 A:B over 60 min (A=0.1% ammonium bicarbonate in water) and (B=acetonitrile), with a flow rate of 50 mL/min. The individual diastereomers were each then repurified by preparative reverse-phase HPLC using an acetonitrile:water (0.1% TFA) gradient, giving TFA salts of the title compound as solids after lyophilization. First eluting diastereomer (HPLC RT=2.58 min, method A; LC-MS m/z=511); $^1$H NMR, 400 MHz CD$_3$OD, 8.58 ppm (d, 1H), 7.94 ppm (d, 1H), 7.83 ppm (m, 1H), 7.56 ppm (m, 1H), 7.50 ppm (s, 2H), 7.42 ppm (m, 2H), 7.38–7.35 ppm (m, 1H), 4.60 ppm (d, 1H), 4.43–4.39 ppm (m, 1H), 4.32 ppm (s, 1H), 4.28 ppm (s, 1H), 4.27 ppm (s, 1H), 2.67–2.63 ppm (m, 2H), 2.08–1.99 ppm (m, 1H), 1.74–1.61 ppm (m, 2H), 1.59–1.54 ppm (m, 1H). Second eluting diastereomer (0.08 g, HPLC RT=2.60 min, method A; LC-MS m/z=511); $^1$H NMR, 400 MHz CD$_3$OD, 8.59 ppm (d,1H), 7.95 ppm (d, 1H), 7.80 ppm (d, 1H), 7.60–7.57 ppm (m, 1H), 7.52–7.46ppm (m, 2H), 7.44–7.41 ppm (m, 2H), 7.39–7.36 ppm (m, 1H), 4.61 ppm (d, 1H), 4.44–4.41 ppm (m, 1H), 4.30 ppm (s, 1H), 4.27 ppm (s, 2H), 2.71–2.60 ppm (m, 1H), 2.59–2.54 ppm (m, 1H), 2.11–2.02 ppm (m, 1H), 1.72–1.56 ppm (m, 3H).

EXAMPLE 45

1-((2-Aza-9-hydroxy-9H-fluoren-9-yl)carbonyl)-N-(2-aminomethyl-5-chlorobenzyl)-L-prolinamide

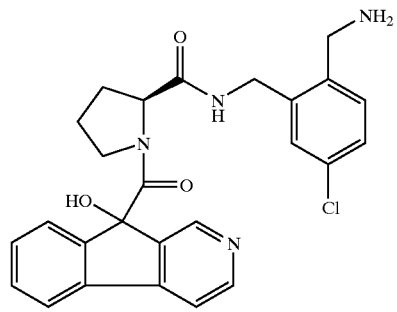

Step 1. Methyl nicotinate (3.9 g, 28.5 mmol) and copper iodide (0.27 g, 1.4 mmol) were dissolved in tetrahydrofuran (48 mL) and cooled to –20° C. under nitrogen. To the stirred solution was added methyl sulfide (14.7 mL, 199.5 mmol) followed by dropwise addition of phenylchloroformate (3.6 mL, 28.5 mmol). The resulting mixture was stirred for 15 min, then phenylmagnesium bromide 1.0 M in THF (28.5 mL) was added dropwise. After 30 minutes, the reaction was complete as judged by HPLC. The reaction was allowed to warm to room temperature and quenched with aqueous 20% ammonium chloride solution (160 mL) and partitioned with ethyl ether. The ether layer was washed with a 1:1 mixture of 20% aq. NH$_4$Cl and NH$_4$OH, water, brine, and then dried over anhydrous magnesium sulfate. The ether layer was then filtered and the ether was removed under reduced pressure to yield the crude dihydropyridine as a viscous oil (9.2 g, HPLC RT=3.83 min, method A; LC-MS m/z=336).

Step 2. The crude dihydropyridine from Step 1 (9.2 g, 27.5 mmol) was combined with sulfur (0.88 g, 27.5 mmol) and dissolved in decahydronaphthalene (100 mL). The mixture was refluxed under a nitrogen atmosphere for 24 hours. The mixture was cooled to room temperature, diluted with ethyl ether (300 mL) and extracted with 4×100 mL portions of cold 10% hydrochloric acid. The acid portions were combined with dichloromethane (400 mL), made basic with 10% sodium hydroxide solution and extracted with dichloromethane. The organic extracts were dried over anhydrous magnesium sulfate, filtered and the solvent was removed under reduced pressure to yield the crude methyl 4-phenylnicotinate (4.8 g). The crude material was purified on silica gel using a 1:2 mixture of ethyl acetate to hexane as mobile phase. Methyl 4-phenylnicotinate as a colorless oil (3.8 g, HPLC RT=2.57 min, method A; LC-MS m/z=214; $^1$H NMR, 400 MHz, CDCl$_3$, 9.03 ppm (s, 1H), 8.73–8.68 ppm (d, 1H), 7.47–7.42 ppm (m, 3H), 7.36–7.31 ppm (m, 3H), 3.70 ppm (s, 3H).

Step 3. To a solution containing methyl 4-phenylnicotinate (3.8 g, 17.8 mmol) from the previous step in methyl alcohol (20 mL) was added 1 N sodium hydroxide (21.4 mL). The mixture was stirred at room temperature for 6 hours, neutralized with 1 N hydrochloric acid, evaporated in vacuo and dried overnight to yield the solid 4-phenylnicotinic acid (4.7 g, Theo. Yield=3.6 g, balance is NaCl); HPLC RT=1.80 min, method A; LC-MS m/z= 200; $^1$H NMR, 400 MHz, CD$_3$OD, 8.91 ppm (s, 1H), 8.66 ppm (d, 1H), 7.48 ppm (d, 1H), 7.46–7.41 ppm (m, 5H).

Step 4. 4-Phenylnicotinic acid (4.7 g, 23.8 mmol) from the previous step was suspended in polyphosphoric acid (160.3 g) and slowly heated to 200° C. with stirring. After 5 hours, the mixture was cooled to 140° C. and slowly poured over crushed ice and stirred for 24 hours. The mixture was then neutralized to pH=4 with 50% sodium hydroxide solution and extracted 3 times with dichloromethane. The dichloromethane extracts were combined and the solvent was removed under reduced pressure to yield the yellow solid of 2-azafluorenone (3.1 g, HPLC RT=2.16 min, method A; LC-MS m/z=182), $^1$H NMR, 400 MHz, CHCl$_3$, 8.72 ppm (s, 1H), 8.75 ppm (d, 1H), 7.75 ppm (d, 1H), 7.65 ppm (d, 1H), 7.62–7.55 ppm (m, 1H), 7.51–7.46 ppm (m, 2H).

Step 5. To a stirred solution of 2-azafluorenone (3.1 g, 17.2 mmol) from the previous step in acetonitrile (40 mL) was added 10% by weight of zinc iodide (0.33 g) and trimethylsilylcyanide (16 mL, 120.2 mmol). The mixture was stirred for 2 hours at room temperature then refluxed for 48 hours. Additional amounts of zinc iodide and trimethylsilylcyanide were added following the above procedure until conversion to the cyanohydrin was complete. Upon completion, the mixture was blown to dryness with nitrogen, dissolved in methyl alcohol (40 mL), cooled to 0° C. and saturated with anhydrous HCl gas. After stirring overnight, the mixture was evaporated in vacuo and partitioned between dichloromethane and 5% sodium bicarbonate solution. The dichloromethane layer was evaporated in vacuo and the residue was purified on a silica gel column using a 98:2 mixture of dichloromethane to methyl alcohol as mobile phase. 2-Aza-9-hydroxy-9-fluorene carboxylic acid methyl ester was obtained as a solid (1.3 g, HPLC RT=2.06 min, method A; LC-MS m/z=242), ), $^1$H NMR, 400 MHz, CHCl$_3$, 8.67–8.65 ppm (m, 2H), 7.75 ppm (d, 1H), 7.57 ppm (d, 1H), 7.51–7.44 ppm (m, 3H), 4.50 ppm (s, 1H), 3.64 ppm (s, 3H).

Step 6. 2-Aza-9-hydroxy-9-fluorene carboxylic acid methyl ester (1.3 g, 5.3 mmol) from the previous step was dissolved in hydrazine (13 mL) and the resulting solution was stirred at room temperature for 2 hours. Excess hydrazine was evaporated in vacuo and the solid was dried in vacuo overnight to yield the 2-aza-9-hydroxy-9-fluorene-carboxyhydrazide (1.4 g, HPLC RT=0.8 min, method A; LC-MS m/z=242), ), $^1$H NMR, 400 MHz, CD$_3$OD, 8.58 ppm (s, 1H), 8.55 ppm (d, 1H), 7.9–7.85 ppm (m, 1H), 7.78 ppm (d, 1H), 7.59–7.54 ppm (m, 1H), 7.52–7.47 ppm (m, 2H).

Step 7. 2-Aza-9-hydroxy-9-fluorene-carboxyhydrazide (1.17 g, 4.85 mmol) was dissolved in dimethylformamide (10 mL) and cooled to −20° C. under nitrogen. HCl saturated tetrahydrofuran was then added to pH<2 (as measured on wetted E. Merck pH indicator strips), followed by amylnitrite (0.7 mL, 4.85 mmol) and stirring was continuued until all of the starting hydrazide was converted to the azide (as determined by HPLC and LC-MS). The pH was adjusted to 6.0 with diisopropylethylamine and L-prolin-N-(2-(tert-butyloxycarbonylaminomethyl)-5-chlorobenzyl)amide (1.5 g, 4.08 mmol) was added. The pH was adjusted to 8 with diisopropylethylamine and the reaction was stirred at 0° C. for 48 hours. The solvent was removed on a rotary evaporator and the residue was purified on a silica gel column using 99:1 then 95:5 mixture of dichloromethane to methanol as mobile phase. Pure fractions were combined and the solvent was removed in vacuo to give 1-((2-aza-9-hydroxy-9H-fluoren-9-yl)carbonyl)-N-(2-tert-butyloxycarbonylaminomethyl-5-chlorobenzyl)-L-prolinamide as a solid (0.27 g, HPLC RT=2.75 min, method A; LC-MS m/z=577).

Step 8. To a stirred solution of 1-((2-aza-9-hydroxy-9H-fluoren-9-yl)carbonyl)-N-(2-tert-butyloxycarbonylaminomethyl-5-chlorobenzyl)-L-prolinamide (0.27 g, 0.47 mmol) from the previous step in dichloromethane (4 mL) was added trifluoroacetic acid (2 mL). The solution was stirred at room temperature for 1.5 hours and the solvents were removed in vacuo. The residue was purified by preparative reverse phase HPLC using an acetonitrile:water gradient containing 0.1% TFA to give the title compound as a mixture of diastereomers. A second preparative reverse phase HPLC separation using an acetonitrile:water gradient containing ammonium acetate in the mobile phase was employed to obtain the two diastereomers of the title compound. Each diastereomer was subjected to preparative reverse phase HPLC using an acetonitrile:water gradient containing 0.1% TFA to obtain, after lyophilization, solid TFA salts of the title compound. First eluting diastereomer (HPLC RT=2.25 min, method A; LC-MS m/z=477); second eluting diastereomer (0.034 g, HPLC RT=2.28 min, method A; LC-MS m/z=477).

EXAMPLE 46

3-Ethylprolyl-N-(2-aminomethyl-5-chlorobenzyl)-L-prolinamide

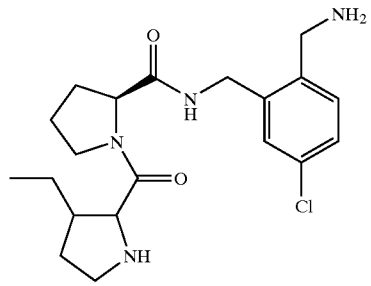

Step 1. The procedure for the preparation of trans-3-ethyl-D,L-proline as described in U.S. Pat. No. 4,060,603; Nov. 29, 1977 was followed, with the following modifications: 4-ethyl-5,5-dicarboethoxy-2-pyrroline (LCMS RT=1.47 min. LCMS (M+H)=242.5) was not distilled, but carried on without purification. Following acidification of the hydrolyzed product using 4 N HCl, the aqueous layer was extracted three times with EtOAc. By LCMS analysis, the desired product remained in the aqueous layer which was then concentrated in vacuo to give trans-3-ethyl-D,L-proline as an orange solid.

Step 2. To a stirred solution of trans-3-ethyl-D,L-proline (1.61 g, 11.2 mmol) from the previous step in H$_2$O (11.3 mL), 1 N NaOH (12.4 mL), and dioxane (22.5 mL) at 0° C. was added Boc anhydride (2.70 g, 12.4 mmol) in portions. The reaction was allowed to warm to room temperature and stirred for 72 h. The solvent was removed in vacuo. The residue was taken up in H$_2$O and acidified to pH 2 using 1 N HCl. The aqueous layer was extracted with EtOAc. The organic layer was washed with brine, dried (Na$_2$SO$_4$), and concentrated to give 1-(tert-butoxycarbonyl)-3-ethyl-D,L-proline as a brown solid. LCMS (M+H)=244.6; LCMS RT=1.64 min. $^1$H NMR (CD$_3$OD, 400 MHz): δ 4.25–4.14 (m, 1H), 3.87–3.78 (m, 1H), 3.61–3.49 (m, 1H), 3.43–3.38 (m, 1H), 2.16–2.01 (m, 2H), 1.38 (s, 9H), 1.02–0.92 (m, 3H).

Step 3. A mixture of crude 1-(tert-butoxycarbonyl)-3-ethyl-D,L-proline (73 mg, 0.30 mmol) from the previous step, N-(2-{[(tert-butoxycarbonyl)amino]methyl}-5-chlorobenzyl)-L-prolinamide (111 mg, 0.30 mmol), HOAT (20 mg, 0.15 mmol), and EDC (87 mg, 0.45 mmol) was stirred at room temperature under N$_2$. Two additional equivalents of 1-(tert-butoxycarbonyl)-3-ethyl-D,L-proline were added and the reaction monitored for completeness by LCMS. The diastereomers of 1-(tert-butoxycarbonyl)-3-ethylprolyl-N-(2-{[(tert-butoxycarbonyl)amino]methyl}-5-chlorobenzyl)-L-prolinamide were separated by reverse phase HPLC (30 min gradient elution with 95:5 H$_2$O/0.1% TFA:CH$_3$CN/ 0.1% TFA to 5:95 H$_2$O/0.1% TFA:CH$_3$CN/0.1% TFA). Diastereomer A: LCMS retention time=2.48 min. LCMS (M+H)=593.5. Diastereomer B: LCMS retention time= 2.62 min. LCMS (M+H)=593.2.

Step 4. To a stirred solution of diastereomer A of 1-(tert-butoxycarbonyl)-3-ethylprolyl-N-(2-{[(tert-butoxycarbonyl)amino]methyl}-5-chlorobenzyl)-L-prolinamide (34 mg, 0.06 mmol) from the previous step in dioxane (2.0 mL) at ambient temperature was added an excess of 4.0 N solution of HCl in dioxane. The reaction was monitored for completeness by LCMS. The solvent was removed in vacuo to give the HCl salt of 3-ethyl-L-prolyl-N-[2-(aminomethyl)-5-chlorobenzyl]-L-prolinamide as a pale yellow oil. LCMS RT=0.74 min. LCMS (M+H)=393.3. $^1$H NMR (CD$_3$OD, 400 MHz): δ 8.93 (m, 1H), 7.51 (s, 1H), 7.42–7.37 (m, 2H), 4.54–4.47 (m, 2H), 4.41–4.31 (m, 2H), 4.23 (s, 2H), 3.78–3.70 (m, 1H), 3.64–3.52 (m, 1H), 3.50–3.45 (m, 1H), 3.44–3.34 (m, 1H), 2.43 (br m, 1H), 2.34–2.27 (m, 1H), 2.16–1.67 (br m, 6H), 1.53–1.45 (m, 1H), 1.03 (t, J=7.4 Hz, 3H). Diastereomer B (37 mg, 0.06 mmol) was deprotected in similar fashion to afford the HCl salt of 3-ethyl-L-prolyl-N-[2-(aminomethyl)-5-chlorobenzyl]-L-prolinamide as a yellow oil. LCMS RT=0.73 min. LCMS (M+H)=393.3. $^1$H NMR (CD$_3$OD, 400 MHz): δ 8.95 (m, 1H), 7.52 (s, 1H), 7.43–7.40 (m, 2H), 4.55 (d, J=15.6 Hz, 1H), 4.44 (dd, J=3.2 Hz, 8.8 Hz, 1H), 4.37 (d, J=15.2 Hz, 1H), 4.31 (d, J=4.8 Hz, 1H), 4.25 (s, 2H), 3.84–3.81 (m, 1H), 3.66–3.59 (m, 1H), 3.57–3.46 (m, 1H), 3.42–3.35 (m, 1H), 2.41–2.38 (m, 1H), 2.31–1.84 (m, 6H), 1.71–1.66 (m, 1H), 1.56–1.50 (m, 1H), 1.04 (t, J=7.4 Hz, 3H).

EXAMPLE 47

3,3-Dimethylprolyl-N-(2-aminomethyl-5-chlorobenzyl)-L-prolinamide

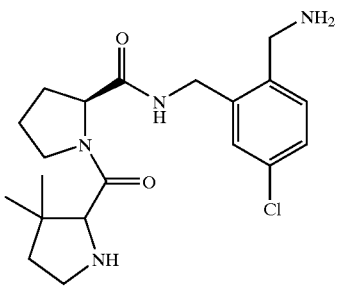

Step 1. The procedure for the preparation of 3,3-dimethyl-D,L-proline as described in U.S. Pat. No. 4,060,603; Nov. 29, 1977, was followed, with the following modifications: the intermediate 2,2-dicarboethoxy-3,3-dimethylpyrrolidine was chromatographed on a silica gel column eluting with 50% EtOAc/hexanes. LCMS RT=1.41 min. LCMS (M+H)=242.5. $^1$H NMR (CDCl$_3$, 400 MHz): δ 4.23–4.16 (m, 4H), 3.16–3.12 (m, 2H), 1.97–1.94 (m, 2H), 1.30–1.26 (m, 6H). Acid hydrolysis as described in U.S. Pat. No. 4,060,603 afforded 3,3-dimethyl-D,L-proline as a brown solid which was used without further purification. $^1$H NMR (CD$_3$OD, 400 MHz): δ 3.97 (s, 1H), 3.40 (m, 2H), 2.00 (m, 2H), 1.37 (s, 3H), 1.07 (s, 3H).

Step 2. 3,3-Dimethyl-D,L-proline (1.00 g, 6.98 mmol) from the previous step was Boc protected according to the above procedure given in Step 2 of Example 46. Silica gel chromatography (gradient elution with 30% EtOAc/ hexanes—100% EtOAc—5% AcOH/EtOAc) afforded 1-(tert-butoxycarbonyl)-3,3-dimethyl-D,L-proline as a brown solid. LCMS RT=1.56 min. LCMS (M+H)=244.1. $^1$H NMR (CD$_3$OD, 400 MHz): δ 3.81 and 3.78 (m, rotamers, 1H), 3.50 (m, 1H), 3.40 (m, 1H), 1.85 (m, 1H), 1.62 (m, 1H), 1.45 and 1.42 (s, Boc rotamers, 9H), 1.16 (s, 3H), 1.07 (s, 3H).

Step 3. 1-(tert-Butoxycarbonyl)-3,3-dimethylprolyl-N-(2-{ [(tert-butoxycarbonyl)amino]methyl}-5-chlorobenzyl)-L-prolinamide was prepared as a mixture of diastereomers from 1-(tert-butoxycarbonyl)-3,3-dimethyl-D,L-proline (73 mg, 0.30 mmol) and L-prolin-N-(2-{[(tert-butoxycarbonyl)amino]methyl}-5-chlorobenzyl)amide (111 mg, 0.30 mmol) essentially according to the EDC coupling procedure described in Step 3 of Example 46. The diastereomeric products were separated by reverse phase HPLC as described in Step 3 of Example 46. Diastereomer A: LCMS RT=2.44 min. LCMS (M+H)= 593.4. Diastereomer B: LCMS RT=2.58 min. LCMS (M+H)=593.5.

Step 4. To a stirred solution of diastereomer A of 1-(tert-butoxycarbonyl)-3,3-dimethylprolyl-N-(2-{[(tert-butoxycarbonyl)amino]methyl}-5-chlorobenzyl)-L-prolinamide from the previous step in approximately 1 mL CH$_2$Cl$_2$ at room temperature was added an excess of TFA (0.5 mL). The reaction was determined to be complete by LCMS after 2 h. The solvent was removed in vacuo to afford the TFA salt of the title compound as a colorless oil. Diastereomer A: LCMS RT=0.71 min; LCMS (M+H)=393.1. $^1$H NMR (CD$_3$OD, 500 MHz): δ 7.51 (d, J=2.0 Hz, 1H), 7.42 (d, J=8.3 Hz, 1H), 7.35 (dd, J=2.0, 8.0 Hz, 1H), 4.53 (d, J=15.4 Hz, 1H), 4.51–4.48 (m, 1H), 4.35–4.28 (m, 2H), 4.24 (s, 2H), 3.83–3.79 (m, 1H), 3.62–3.57 (m, 1H), 3.51–3.45 (m, 1H), 3.42–3.35 (m, 1H), 2.31–2.27 (m, 1H), 2.14–2.09 (m, 1H), 2.00–1.85 (m, 4H), 1.35 (s, 3H), 1.07 (s, 3H). Diastereomer B was deprotected in similar fashion to afford the TFA salt of the title compound as a colorless oil: LCMS RT=0.71 min; LCMS (M+H)=393.0. $^1$H NMR (CD$_3$OD, 500 MHz): δ 7.49 (d, J=2.0 Hz, 1H), 7.42 (d, J=8.3 Hz, 1H), 7.38 (dd, J=2.0, 8.3 Hz, 1H), 4.56 (d, J=15.4 Hz, 1H), 1H), 4.42 (dd, J=3.9, 8.5 Hz, 1H), 4.34–4.30 (m, 2H), 4.24 (s, 2H), 3.82–3.80 (m, 1H), 3.65–3.63 (m, 1H), 3.52–3.49

(m, 1H), 3.40–3.38 (m, 1H), 2.29–2.27 (m, 1H), 2.07–1.94 (m, 5H), 1.34 (s, 3H); HRMS (FT/ICR) M+H: 393.2076.

EXAMPLE 48

3-Phenylprolyl-N-(2-aminomethyl-5-chlorobenzyl)-L-prolinamide

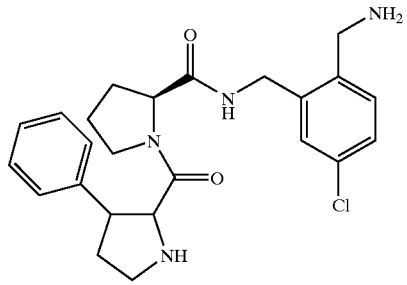

Step 1. Diethyl-3-phenylpyrrolidine-2,2-dicarboxylate was prepared from cinnamaldehyde (1.22 mL, 9.70 mmol) essentially according to the procedure described in U.S. Pat. No. 4,060,603 for the preparation of 2,2-dicarboethoxy-3,3-dimethyl-pyrrolidine. The resulting yellow oil was used in the next step without purification. LCMS RT=1.26 min. LCMS (M+H)=292.1.

Step 2. 3-Phenyl-D,L-proline was prepared from diethyl-3-phenylpyrrolidine-2,2-dicarboxylate (2.82 g, 9.70 mmol) essentially according to the procedure described in U.S. Pat. No. 4,060,603 for the preparation of 3,3-dimethyl-D,L-proline from 2,2-dicarboethoxy-3,3-dimethylpyrrolidine. The product was isolated as a brown oil. LCMS RT=0.62 min. LCMS (M+H)=191.9. $^1$H NMR (CD$_3$OD, 400 MHz): δ 7.36–7.28 (m, 5H), 4.60 (d, J=9.2 Hz, 1H), 3.97 (apparent q, J=8.4 Hz, 1H), 3.77–3.71 (m, 1H), 3.48–3.41 (m, 1H), 2.58–2.50 (m, 1H), 2.43–2.33 (m, 1H).

Step 3. 3-Phenyl-D,L-proline (1.85 g, 9.70 mmol) from the previous step was Boc protected according to the procedure described in Step 2 of Example 46. The product was purified by silica gel chromatography (70% EtOAc/hexanes) to give 1-(tert-butoxycarbonyl)-3-phenyl-dl-proline as an orange solid. $^1$H NMR (CDCl$_3$, 400 MHz): δ 7.52–7.17 (m, 5H), 4.60 and 4.48(rotamers, d, J=8.8 Hz, 1H), 3.90–3.66 (m, 2H), 3.50–3.40 (m, 1H), 2.62–2.48 (m, 1H), 2.21–2.12 (m, 1H), 1.48 and 1.40 (rotamers of Boc group, s, 9H).

Step 4. 1-(tert-Butoxylcarbonyl)-3-phenylprolyl-N-(2-{[(tert-butoxycarbonyl)amino]methyl}-5-chlorobenzyl)-L-prolinamide was prepared as a mixture of diastereomers from 1-(tert-Butoxycarbonyl)-3-phenyl-D,L-proline (88 mg, 0.30 mmol) from the previous step and L-prolin-N-(2-{[(tert-butoxycarbonyl)amino]methyl}-5-chlorobenzyl)amide (111 mg, 0.30 mmol) essentially according to the EDC coupling procedure described in Step 3 of Example 46. The diastereomeric products separated under the following analytical conditions: Chiralcel OD (250×4.6 m) column eluting with A/B 85/15 where A=hexane/0.1% diethylamine and B=ethanol, with detection at 220 nm and flow rate of 1.0 mL/min. Under these conditions, the early peak elutes at 4.87 min. and later peak at 8.51 min. The products were separated on preparative scale using these conditions. Diastereomer A: LCMS RT=2.72 min. LCMS (M+H)=641.2. Diastereomer B: LCMS RT=2.75 min. LCMS (M+H)=641.0

Step 5. To a stirred solution of diastereomer A of 1-(tert-butoxylcarbonyl)-3-phenylprolyl-N-(2-{[(tert-butoxycarbonyl)amino]methyl}-5-chlorobenzyl)-L-prolinamide (60 mg, 0.09 mmol) from the previous step in approx. 2 mL MeOH at room temperature was added excess of a solution of 1.0 M HCl in ether. The reaction was monitored for completeness by LCMS. The solvent was removed in vacuo to give the HCl salt of the title compound as a white solid. LCMS RT=0.94 min. LCMS (M+H)=441.1. $^1$H NMR (CD$_3$OD, 500 MHz): δ 7.50–7.23 (m, 8H), 4.58–4.51 (m, 1H), 4.41–4.24 (m, 3H), 4.08–3.96 (m, 1H), 3.80–3.74 (m, 1H), 3.49–3.43 (m, 1H), 3.39–3.31 (m, 3H), 3.05–2.92 (m, 1H), 2.57–2.37 (m, 2H), 2.06–1.64 (m, 2H), 1.56–1.26 (m, 2H). Diastereomer B (73 mg, 0.11 mmol) was deprotected in similar fashion to afford the HCl salt of the title compound as a white solid. LCMS RT=0.98 min. LCMS (M+H)=441.2. $^1$H NMR (CD$_3$OD, 400 MHz): δ 8.90 (m, 1H), 7.49–7.32 (m, 8H), 4.49 (d, J=15.6 Hz, 1H), 4.31 (d, J=15.6 Hz, 1H), 4.23 (s, 2H), 4.02–3.95 (m, 1H), 3.90–3.87 (m, 1H), 3.79–3.75 (m, 1H), 3.48–3.30 (m, 2H), 3.13–3.03 (m, 1H), 2.91–2.85 (m, 1H), 2.50–2.43 (m, 1H), 2.39–2.28 (m, 1H), 1.73–1.59 (m, 3H), 1.18–1.12 (m, 1H).

EXAMPLE 49

D-Homoprolyl-N-(2-aminomethyl-5-chlorobenzyl)-L-prolinamide

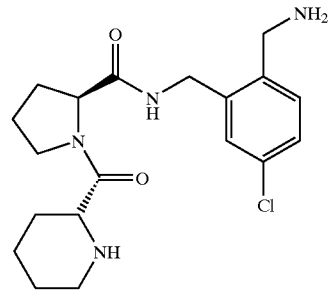

Step 1. A mixture of Boc-D-Homopro-OH (0.50 g, 2.18 mmol), L-proline benzyl ester hydrochloride (0.53 g, 2.18 mmol), HOAT (148 mg, 1.09 mmol), EDC (0.63 g, 3.27 mmol), and Et$_3$N (0.30 mL, 2.18 mmol) in DMF (5.0 mL) was stirred at room temperature under N$_2$ for 4 h. The solvent was removed in vacuo and the remaining yellow residue was taken up in EtOAc and washed with saturated aqueous K$_2$CO$_3$. The aqueous layer was extracted with EtOAc. The combined organic extracts were washed with brine, dried over Na$_2$SO$_4$, and concentrated. Silica gel chromatography (50% EtOAc/hexanes) afforded Boc-D-homoprolyl-L-proline benzyl ester as a colorless oil. LCMS RT=2.40 min. LCMS (M+H)=417.3. $^1$H NMR (CDCl$_3$, 400 MHz, spectrum considerably broadened due to rotamers): δ 7.36–7.31 (m, 5H), 5.25–5.16 (m, 1H), 5.11–5.08 (m, 1H), 4.96 and 4.80 (rotamers, br m, 1H), 4.53 (br m, 1H), 3.84–3.81 (br m, 1H), 3.61–3.51 (br m, 2H), 3.20–2.90 (br m, 1H), 2.23–2.20 (m, 1H), 1.98–1.86 (m, 3H), 1.58–1.36 (br m, 15H).

Step 2. A mixture of Boc-D-homoprolyl-L-proline benzyl ester (0.84 g, 2.02 mmol) from the previous step and 10% palladium on carbon (80 mg) in EtOAc (29.0 mL) was stirred under a balloon atmosphere of H$_2$. After several hours, the reaction was filtered through Celite and the filter cake was washed with MeOH. The filtrate was concentrated in vacuo to give Boc-D-homoprolyl-L-proline as a white solid. LCMS RT=1.57 min. LCMS (M+H)=327.1. $^1$H NMR (CD$_3$OD, 400 MHz): δ 4.64–4.62 (m, 1H), 4.36 (br m, 1H), 3.90–3.51 (br m, 4H), 2.25–2.21 (m, 2H), 1.98–1.93 (m, 4H), 1.70–1.55 (m, 4H), 1.46 and 1.44 (Boc rotamers, s, 9H).

Step 3. A mixture of Boc-D-homoprolyl-L-proline (97 mg, 0.3 mmol) from the previous step, 2-(tert-butyloxycarbonylaminomethyl)-5-chlorobenzylamine (81 mg, 0.3 mmol), HOAT (20 mg, 0.15 mmol), and EDC (86 mg, 0.45 mmol) in DMF (1.5 mL) was stirred under N$_2$ at room temperature overnight. The solvent was removed in vacuo and the residue was purified by silica gel chromatography (5% MeOH/CHCl$_3$) to afford Boc-D-homoprolyl-N-(2-{[(tert-butoxycarbonyl)amino]methyl}-5-chlorobenzyl)-L-prolinamide compound as a yellow oil. LCMS RT=2.49 min. LCMS (M+H)=579.5.

Step 4. To a stirred solution of Boc-D-homoprolyl-N-(2-{[(tert-butoxycarbonyl)amino]methyl}-5-chlorobenzyl)-L-prolinamide from the previous step in approx. 2 mL CH$_2$Cl$_2$ at room temperature was added excess TFA (0.5 mL). After 2 h, the solvent was removed in vacuo and the residue was purified by reverse phase HPLC to afford the bis-TFA salt of the title compound as a colorless oil. LCMS RT=0.60 min. LCMS (M+H)=379.6. $^1$H NMR (CD$_3$OD, 500 MHz): δ 7.47 (d, J=1.5 Hz, 1H), 7.42 (d, J=8.3 Hz, 1H), 7.34 (dd, J=1.7, 8.0 Hz, 1H), 4.51 (d, J=15.4 Hz, 1H), 4.39 (dd, J=3.4, 9.0 Hz, 1H), 4.34 (d, J=15.1 Hz, 1H), 4.24 (s, 2H), 4.16 (m, 1H), 3.82–3.78 (m, 1H), 3.61–3.56 (m, 1H), 3.42–3.40 (m, 1H), 3.10–3.08 (m, 1H), 2.26–2.19 (m, 2H), 2.07–1.86 (m, 5H), 1.79–1.58 (m, 3H).

EXAMPLE 50

1-(3,3,-Diphenylpropanoyl)-N-(2-aminomethyl-5-chlorobenzyl)-L-prolinamide

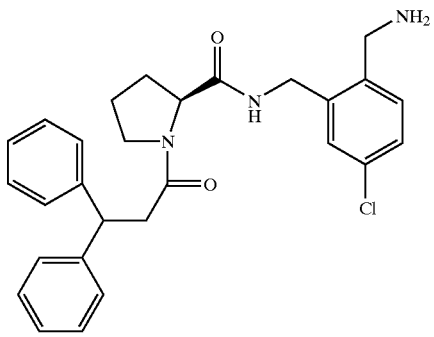

Step 1. To a stirred solution of L-prolin-N-(2-(tert-butyloxycarbonylaminomethyl)-5-chlorobenzyl)amide (0.030 g, 0.082 mmol), 3,3-diphenylpropanoic acid (20 mg, 0.090 mmol), and HOBT hydrate (13 mg, 0.098 mmol) in DMF (1 mL) was added EDC (0.023 g, 0.122 mmol). Diisopropylethylamine (0.0142 mL, 0.082 mmol) was added and the mixture was stirred at ambient temperature for 3 hours, at which time HPLC analysis indicated complete consumption of the proline starting material. The DMF was removed under reduced pressure and the residue was partitioned between EtOAc (50 mL) and 1N HCl. The EtOAc layer was separated, washed with water, 10% aqueous Na$_2$CO$_3$ and brine, dried over anhydrous MgSO$_4$, and filtered. The filtrate solvent was removed under reduced pressure and the residue was purified by chromatography on a 10 g ISCO column using 10–100% EtOAc/hexanes over 40 min. The product-containing fractions were combined and the solvents were removed under reduced pressure to give N-(2-{[(tert-butoxycarbonyl)amino]methyl}-5-chlorobenzyl)-1-(3,3-diphenylpropanoyl)-L-prolinamide as an oil (0.050 g, 99%). HPLC RT=2.9 min, Method B; LC-MS M+H=576, 578.

Step 2. N-(2-{[(tert-butoxycarbonyl)amino]methyl}-5-chlorobenzyl)-1-(3,3-diphenylpropanoyl)-L-prolinamide from the previous step (0.050 g, 0.082 mmol, HPLC RT=2.9 min) was dissolved in EtOAc (2 mL) and cooled with stirring to 0° C. HCl/EtOAc (3.55M, 1.5 mL) was added. Remove bath and stir for 2 hours. HPLC analysis indicated completion and the solvent was removed under reduced pressure. The residue was triturated with Et$_2$O and filtered to give the hydrochloride salt of the title compound as a solid. HPLC RT=1.84 min, Method B; LC-MS M+H=476, 478; $^1$H NMR, 400 MHz, DMSO-d$_6$, 8.40, (t, J=6 Hz, 1H); 8.16, (br s, 2H); 7.40–7.44, (m, 4H); 7.10–7.32 (m, 9H); 4.48–4.52 (m, 1H); 4.30–4.31, (m, 2H); 4.15–4.17 (m, 1H); 4.07 (s, 2H); 3.58–3.60 (m, 1H); 3.48–3.51 (m, 1H); 2.94, (dd, J=5, 16 Hz, 1H); 1.72–1.99 (m, 5H).

HPLC Method A:
  Stationary Phase: Hewlett-Packard Zorbax SB-C8 column
    75×4.6 mm, 3.5 micron
  Mobile Phase: A=H$_2$O containing 0.1% by volume TFA
    B=CH$_3$CN containing 0.1% by volume TFA
    Gradient: 95:5 A:B to 0:100 A:B over 4.5 minutes
    Flow Rate: 3.0 mL/min
  UV Detection at 215 nm HPLC Method B:
  Stationary Phase: Waters Xterra RP18 column
    50×4.6 mm, 3.5 micron
  Mobile Phase: A=H$_2$O containing 0.1% by volume H$_3$PO$_4$
    B=CH$_3$CN
    Gradient: 95:5 A:B to 5:95 A:B over 4.0 minutes
    Flow Rate: 4.0 mL/min
  UV Detection at 215 nm LC-MS HPLC Method:
  Stationary Phase: YMC Pro C18 5 micron 120 Å 3.0×50 mm
  Mobile Phase: A=H$_2$O containing 0.05% by volume TFA
    B=CH$_3$CN containing 0.0425% by volume TFA
    Gradient: 92:8 A:B to 100:0 A:B over 3.6 minutes
    Flow Rate: 1.5 to 2.0 mL/min over 3.6 min
  UV Detection at 215 nm
  Electrospray ionization for mass detector.

EXAMPLE 51 tert-Butyl 2-[2-(Aminomethyl)phenyl]ethylcarbamate

Step A. 2-Bromomethylphenylacetic Acid:
To a solution of 97.0 g (0.646 mol) o-tolylacetic acid in 1.75 L carbon tetrachloride was added 115.0 g (0.646 mol) N-bromosuccinimide and 3.4 g (0.021 mol) 2,2'-azobisisobutyronitrile. The mixture was heated at reflux under a nitrogen atmosphere for 4 h. After the mixture was cooled to 0–5° C. for 30 min, the solids were removed by filtration and washed with a small portion of carbon tetrachloride. This solid was triturated with water (0.8 L), collected on a filter, and washed with 500 mL of water to give 2-bromomethylphenylacetic acid. The filtrate was concentrated to a volume of 150 ml, and the resulting slurry cooled to 0–5° C. for 30 min. A second batch of product was obtained.

Step B. 2-Bromomethylphenylacetic Acid t-Butyl Ester:

To a solution of 80 g (0.349 mol) 2-bromomethylphenylacetic acid in 700 mL 1,4-dioxane in a 2 L heavy-walled flask was added 84 mL (1.571 mol) concentrated sulfuric acid at ambient temperature.

The reaction mixture was chilled to −15° C., and 580 mL isobutylene was condensed directly into the reaction vessel. The sealed pressure flask was shaken mechanically at room temperature for 4 h (the pressure inside the flask rises to ca. 20 psi during this step). The mixture was carefully quenched by slowly pouring it into a 0–5° C. stirred mixture of 1.2 L tert-butyl methyl ether and 336 g (4.0 mol) solid sodium bicarbonate before slow dilution with 1.2 L ice-water. The separated organic phase was washed with 0.8 L brine, dried with sodium sulfate, filtered concentrated in vacuo to give an oil, which was used without further purification.

Step C. 2-Azidomethylphenylacetic Acid t-Butyl Ester:

To a solution of crude 2-bromomethylphenylacetic acid t-butyl ester (0.349 mol) in 600 mL DMF was added 34.1 g (0.524 mol) sodium azide and the mixture stirred at 65° C. for 3 h. After cooling to ambient temperature, the mixture was diluted with 1.2 L ethyl acetate. The organic layer was washed with water (3×800 mL), dried over sodium sulfate, filtered and concentrated in vacuo to give the titled compound as a yellow oil. This material was used without further purification.

Step D. tert-Butyl [2-(Aminomethyl)phenyl]acetate Oxalate Salt:

To a solution of 78.0 g (0.312 mol) 2-azidomethylphenylacetic acid t-butyl ester in 1.36 L THF was added 7.8 g (50% water wet) 5% Pd on C and the mixture shaken mechanically in a 2 L heavy-walled flask under $H_2$ at 45 psi for 2 h. The catalyst was removed by filtration through a bed of celite, rinsing with 250 mL THF. To the filtrate was added a solution of 31.25 g (0.347 mol) oxalic acid in 500 mL methyl tert-butyl ether, and the resultant suspension stirred at room temperature for 30 min. The solid was collected on a filter and washed with 300 mL methyl tert-butyl ether (the filtration was very slow, requiring about 3 hours). Drying under reduced pressure at 60° C. for 18 h gave 42.4 g (39% overall from 2-bromomethylphenylacetic acid) tert-butyl [2-(aminomethyl)phenyl]acetate oxalate salt as a white powder. The product is unstable as the free base, and will cyclize to the amide over several hours at room temperature.

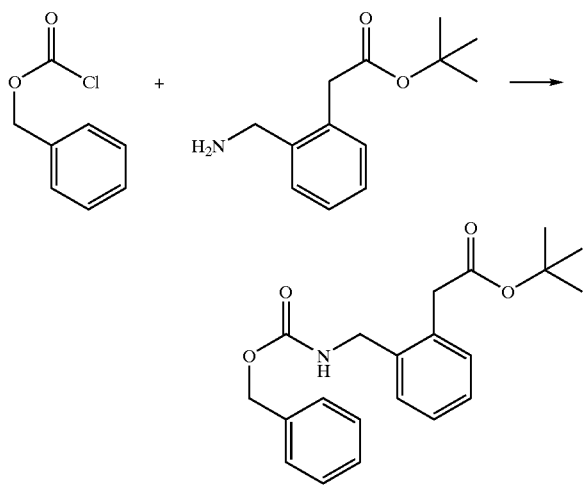

Step E. tert-Butyl [2-({[(Benzyloxy)carbonyl]amino}methyl)phenyl]acetate:

To a solution of 3.0 g (9.64 mmol) tert-butyl [2-(aminomethyl)phenyl]acetate in 100 mL methylene chloride cooled to 0° C. was added 0.825 ml (5.78 mmol) benzyl chloroformate followed by 1.47 g (12.05 mmol) of 4-dimethylaminopyridine and a second 0.825 ml (5.78 mmol) portion of benzyl chloroformate. After 30 min the reaction was washed with 10% potassium hydrogen sulfate (aq) (2×3 mL), water (1×30 mL), and brine (1×30 mL), dried over sodium sulfate, filtered and concentrated to dryness in vacuo. The resulting crude oil (3.69 g) was flash chromatographed on silica gel (15% ethyl acetate in hexane) to give tert-butyl [2-({[(benzyloxy)carbonyl]amino}methyl) phenyl]acetate as a colorless oil: $^1$H NMR (CDCl$_3$, 400 MHz): δ 7.38–7.30 (m, 5H), 7.28–7.21 (m, 4H), 5.40 (br s, 1H), 5.12 (s, 2H), 4.40 (d, 2H, J=5.5 Hz), 3.61 (s, 2H), 1.41 (s, 9H); MS (Electrospray): M+Na=378.1; TLC R$_f$=0.30 (15% ethyl acetate in hexane).

Step F. Benzyl 2-(2-Hydroxyethyl)benzylcarbamate:

To a solution of 3.15 g (8.86 mmol) tert-butyl [2({[(benzyloxy)carbonyl]amino}methyl)phenyl]acetate in 32 mL of THF cooled to 0° C. and under a nitrogen atmosphere was added dropwise 6.65 mL of a 2.0M lithium borohydride solution in THF over 30 min. After stirring overnight at room temperature, the reaction was cooled in an ice bath and treated with 10% potassium hydrogen sulfate (aq) portionwise until fizzing subsided and extracted with ethyl acetate (3×). The organic extracts were combined, washed with brine (1×), dried over sodium sulfate, filtered and concentrated to dryness in vacuo to give 2.58 g of a crude light yellow oil. Flash chromatography on silica gel (linear gradient from 5 to 40% ethyl acetate in hexane) gave benzyl 2-(2-hydroxyethyl)benzyl carbamate as a colorless oil: $^1$H NMR (CDCl$_3$, 400 MHz): δ 7.37–7.19 (m, 9H), 5.44 (br s, 1H), 5.12 (s, 2H), 4.42 (d, 2H, J=5.2 Hz), 3.90–3.82 (br t, 2H), 2.95–2.88 (br t, 2H, J=5.2 Hz); MS (Electrospray): M+Na=308.1; TLC R$_f$=0.28 (40% ethyl acetate in hexane).

Step G. 2-[2-({[(Benzyloxy)carbonyl]amino}methyl) phenyl]ethyl Methanesulfonate:

To a solution of 1.06 g (3.72 mmol) benzyl 2-(2-hydroxyethyl)benzyl carbamate in 10 mL of methylene chloride cooled to 0° C. was added 0.570 mL (4.09 mmol) of triethylamine followed by 0.316 mL (4.09 mmol) of methanesulfonyl chloride. After stirring overnight at room temperature, the reaction was flash chromatographed directly on silica gel (40% ethyl acetate in hexane) to give 2-[2-({[(benzyloxy)carbonyl]amino}methyl)phenyl]ethyl methanesulfonate as a colorless oil: $^1$H NMR (CDCl$_3$, 400 MHz): δ 7.38–7.21 (m, 9H), 5.21 (br s 1H), 5.13 (s, 2H), 4.45–4.38 (m, 4H), 3.12 (br, t, 2H, J=6.7 Hz), 2.84 (s, 3H); MS (Electrospray): M+Na=386.0; TLC R$_f$=0.35 (40% ethyl acetate in hexane).

Step H. Benzyl 2-(2-Azidoethyl)benzylcarbamate:

To a solution of 1.15 g (3.16 mmol) of 2-[2-({ [(benzyloxy)carbonyl]amino}methyl)phenyl]ethyl methanesulfonate in 8.0 mL of DMF was added 0.411 g (6.33 mmol) of sodium azide. After stirring at room temperature overnight, an additional 0.205 g (3.15 mmol) of sodium azide was added and the reaction warmed to 40° C. for 4 h. The reaction was cooled to room temperature, treated with saturated sodium carbonate (aq) and extracted with ethyl acetate (3×). The organic extracts were combined, washed with water (1×) and brine (1×), dried over sodium sulfate and concentrated to dryness in vacuo to give 1.2 g of a crude oil. Flash chromatography on silica gel (20% ethyl acetate in hexane) gave benzyl 2-(2-azidoethyl)benzylcarbamate as a colorless oil: $^1$H NMR (CDCl$_3$, 400 MHz): δ 7.39–7.20 (m, 9H), 5.14 (s, 2H), 5.05 (br s, 1H), 4.42 (d, 2H, J=5.6 Hz), 3.56–3.49 (t, 2H, J=7.0 Hz), 2.97–2.91 (t, 2H, J=7.0 Hz); MS (Electrospray): M+Na=333.1; TLC R_f=0.32 (20% ethyl acetate in hexane).

Step I. Benzyl 2-(2-Aminoethyl)benzylcarbamate:

To a solution of 904 mg (2.91 mmol) benzyl 2-(2-azidoethyl)benzyl carbamate in 40.0 mL THF containing 4.0 mL water was added 1.53 g (5.28 mmol) triphenylphosphine and the reaction stirred at room temperature overnight. The THF was removed in vacuo and the residual aqueous phase extracted with methylene chloride (3×). The organics were combined, washed with brine (1×), dried over sodium sulfate, filtered and concentrated to dryness in vacuo. Flash chromatography on silica gel (linear gradient from 160/10/1 to 114/10/1 of methylene chloride/methanol/concentrated ammonium hydroxide) gave benzyl 2-(2-aminoethyl) benzylcarbamate as a colorless oil: $^1$H NMR (CDCl$_3$, 400 MHz): δ 7.38–7.17 (m, 9H), 6.14 (br s, 1H), 5.12 (s, 2H), 4.41 (d, 2H, J=4.5 Hz), 3.01–3.95 (t, 2H, J=6.7 Hz), 2.82–2.75 (t, 2H, J=6.7 Hz); MS (Electrospray): M+H= 285.1; TLC R_f=0.18 (160/10/1 of methylene chloride/methanol/concentrated ammonium hydroxide).

Step J. Benzyl 2-{2-[(tert-Butoxycarbonyl)amino] ethyl}benzylcarbamate:

To a solution of 584 mg (2.05 mmol) benzyl 2-(2-aminoethyl)benzyl carbamate in 6.0 mL of methylene chloride at 0° C. was added a 3.0 mL methylene chloride solution of 493 mg (2.26 mmol) di-tert-butyldicarbonate. The reaction was stirred 0.5 h at 0° C. and then warmed to room temperature for 2 h. Flash chromatography of the reaction directly onto silica gel (6% diethylether in methylene chloride) gave benzyl 2-{2-[(tert-butoxycarbonyl)amino] ethyl}benzylcarbamate as a colorless oil: $^1$H NMR (CDCl$_3$, 400 MHz): δ 7.38–7.15 (m, 9H), 5.56 (br s, 1H), 5.13 (s, 2H), 4.67 (br s 1H), 4.41 (d, 2H, J=5.8 Hz), 3.34–3.27 (m, 2H), 2.88–2.80 (br t, 2H, J=7.0 Hz), 1.42 (s, 9H); MS (Electrospray): M+Na=407.1; TLC R_f=0.42 (5% diethyl ether in methylene chloride).

Step K. tert-Butyl 2-[2-(Aminomethyl)phenyl] ethylcarbamate:

To a solution of 750 mg (1.95 mmol) benzyl 2-{2-[(tert-butoxycarbonyl)amino]ethyl}benzylcarbamate in 6.0 mL absolute ethanol was added 150 mg of 10% palladium on carbon catalyst. A balloon of hydrogen was bubbled into the stirring suspension at room temperature over 2 h. The reaction was filtered through celite and the filter pad washed with fresh absolute ethanol (2×). The filtrate was concentrated to dryness in vacuo to give tert-butyl 2-[2-(aminomethyl)phenyl]ethylcarbamate as a colorless oil: $^1$H NMR (CDCl$_3$, 400 MHz): δ 7.31–7.19 (m, 4H), 5.68 (br s, 1H), 3.90 (s, 2H), 3.41–3.34 (br m, 2H), 2.90–2.83 (br t, 2H, J=6.8 Hz), 1.41 (s, 9H); MS (Electrospray): M+NH=251; TLC R_f=0.24 (160/10/1 of methylene chloride/methanol/concentrated ammonium hydroxide).

EXAMPLE 52 tert-Butyl 2-[2-(Aminomethyl)-4-chlorophenyl] ethylcarbamate

Step A: 2-(tert-Butoxycarbonyl)-7-chloro-3,4-dihydro-2H-isoquinolin-1-one

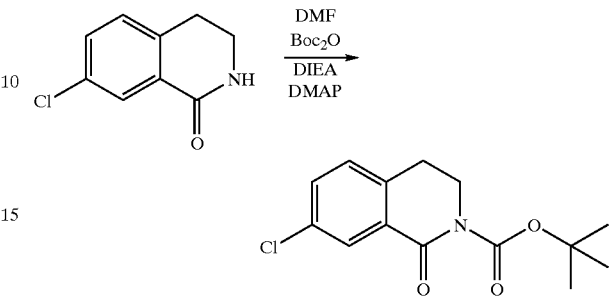

Into a stirred solution of 7-chloro-3,4-dihydroisoquinolin-1-one (11.6 g, 12.6 mMol) in 50 mL of anhydrous N,N-dimethylformamide under inert atmosphere at ambient temperature was added diisopropylethylamine (17.0 mL, 95.8 mMol, 1.5 eq), di-tert-butyl dicarbonate (15.33 g, 70.26 mMol, 1.1 eq), and a catalytic amount of 4-(dimethylamino) pyridine. This was stirred at ambient temperature for 2 hours, concentrated in vacuo, then partitioned between methylene chloride and water. The organics were dried (Na$_2$SO$_4$) and concentrated in vacuo. The residue was purified by flash silica gel chromatography using methylene chloride as an eluent. Desired fractions were concentrated in vacuo to afford 2-(tert-butoxycarbonyl)-7-chloro-3,4-dihydro-2H-isoquinolin-1-one (2) as a clear colorless oil (hplc rt=3.55 min, method A; mass spec m/z=282.1).

Step B: 2-(tert-Butoxycarbonylaminoethyl)-5-chlorobenzyl Alcohol

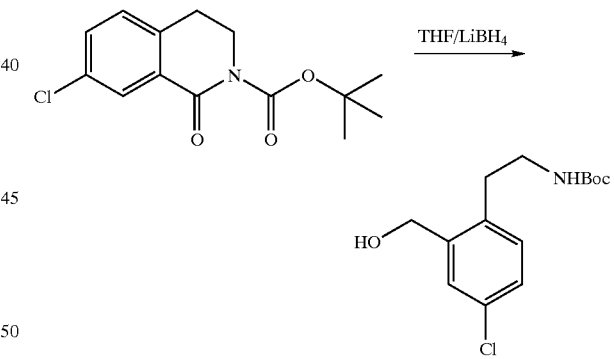

Into a stirred solution of 2-(tert-butoxycarbonyl)-7-chloro-3,4-dihydro-2H-isoquinolin-1-one (18.4 g, 64.38 mMol) in 50 mL of anhydrous tetrahydrofuran under inert atmosphere at 0° C. was added 2.0M LiBH4 in tetrahydrofuran (64.38 mL, 128.76 mMol, 2 eq). This was stirred at 0° C. for 1.5 hours, quenched with saturated ammonium chloride solution, then partitioned between ethyl acetate and water. The organics were dried(Na$_2$SO$_4$) and concentrated in vacuo. This afforded 2-(tert-butoxycarbonylaminoethyl)-5-chlorobenzyl alcohol as a clear colorless oil (hplc rt=3.21 min, method A; mass spec m/z=286.2).

Step C. tert-Butyl 2-[2-Azidomethyl)-4-chlorophenyl] ethylcarbamate:

To a solution of 649 mg (2.27 mmol) tert-butyl 2-[4-chloro-2-(hydroxymethyl)phenyl]ethylcarbamate in 5.0 mL THF at 0° C. was added 0.674 mL (3.13 mmol) of diphenylphosphoryl azide (DPPA) and 0.468 mL (3.63 mmol) of 1,8-diazabicyclo[5.4.0]undec-7-ene (DBU) and the reaction stirred at 0° C. for 10 min, then at room temperature. After 3 h the reaction was treated with saturated sodium carbonate (aq) and extracted with ethyl acetate (3×). The organic extracts were combined, washed with brine (1×), dried over sodium sulfate, filtered and concentrated to dryness in vacuo to give 963 mg of a crude oil. Flash chromatography on silica gel (15% ethyl acetate in hexane) gave tert-butyl 2-[2-azidomethyl)-4-chlorophenyl]ethylcarbamate as a colorless oil: $^1$H NMR (DMSO-d6, 400 MHz): δ 7.44 (d, 1H, J=1.8 Hz), 7.36 (dd, 1H, J=2.0 and 8.2 Hz), 7.26 (d, 1H, J=8.1 Hz), 6.92 (br t, 1H, J5.5 Hz), 4.53 (s, 2H), 3.10 (dt, 2H, J=6.3 and 7.6 Hz), 2.73 (t, 2H, J=7.3 Hz), 1.36 (s, 9H); MS (Electrospray): M+Na 333.0; TLC $R_f$=0.32 (15% ethyl acetate in hexane), Step D. tert-Butyl 2-[2-(Aminomethyl)-4-chlorophenyl] ethylcarbamate:

To a solution of 629 mg (2.02 mmol) tert-butyl 2-[2-azidomethyl)-4-chlorophenyl]ethylcarbamate in 30.0 mL THF containing 3.1 mL water was added 1.06 g (4.053 mmol) triphenylphosphine and the reaction stirred at room temperature overnight. The THF was removed in vacuo and the residual aqueous phase extracted with methylene chloride (3×). The organics were combined, washed with brine (1×), dried over sodium sulfate, filtered and concentrated to dryness in vacuo. Flash chromatography on silica gel (linear gradient from 266/10/1 to 200/10/1 of methylene chlorid/methanol/concentrated ammonium hydroxide) gave tert-butyl 2-[2-(aminomethyl)-4-chlorophenyl]ethylcarbamate as a colorless oil: $^1$H NMR (DMSO-d$_6$, 400 MHz): δ 7.45 (d, I1H, J=1.7 Hz), 7.18 (dd, 1H, J=2.1 and 8.2 Hz), 7.12 (d, 1H), J=8.2 Hz), 7.01 (br t, 1H, J=5.2 Hz), 3.73 (s, 2H), 3.07 (dt, 2H, J=6.5 and 7.3 Hz), 2.68 (t, 2H, J=7.4 Hz), 1.36 (s, 9H); MS (Electrospray): M+H=285.1; TLC $R_f$=0.33 (160/10/1 of methylene chloride/methanol/concentrated ammonium hydroxide).

EXAMPLE 53 tert-Butyl 2-(Aminomethyl)benzylcarbamate

Step A. 2-(Azidomethyl)benzonitrile:

To a solution of 90 g (459 mmol) 2-cyanobenzylbromide in 600 mL THF was added in one portion a solution of 36 g (553 mmol) sodium azide in 100 mL water. The two phase mixture was stirred at 23° C. for 18 hr. The THF layer was separated from the lower water layer and used in the next step without further purification.

Step B. tert-Butyl 2-Cyanobenzylcarbamate:

To the THF layer from the previous step was diluted to a volume of 1.6 L, divided into two equal portions and each hydrogenated at 45 psi in a Parr pressure bottle containing 6 g of 5% palladium on carbon (50% water by weight). A 5–10° C. exotherm was observed within 30 min and shaking continued a total of 1.5 hr. The individual batches were filtered through celite, washed 2× with 100 mL fresh THF and the filtrates combined into a single portion. To the amine mixture without concentration (Caution: attempts to concentrate the solution resulted in a large exotherm and the batch turned black) was added 87.5 mL (381 mmol) of di-tert-butyl dicarbonate neat. After 2 hr the THF was removed in vacuo and flushed with 250 mL of 15% ethyl acetate in hexane. The semi-solid was slurried in 250 mL of 15% ethyl acetate and filtered. The filtrate was concentrated in vacuo, diluted with 10% ethyl acetate in hexane (175 mL), cooled to 0° C. and filtered to give tert-butyl 2-cyanobenzylcarbamate as a gray solid.

Step C. tert-Butyl 2-(Aminomethyl)benzylcarbamate Hemisulfate:

To a 3 L, 3 neck flask fitted with a thermocouple, a condenser and nitrogen inlet was added 3 g (23 mmol) of cobaltous chloride, then 1200 mL of THF followed by 59 g (254 mmol) of tert-butyl 2-cyanobenzylcarbamate and 600 mL of ice-water. To the light pink solution at 15° C. was added 26 g (684 mmol) of sodium borohydride in portions as follows. The initial 3 g of sodium borohydride resulted in a vigorous hydrogen gas evolution and formation of a black suspension. The batch temperature reached 35° C. within 2 hr, and was maintained at this temperature with a heating mantle. Additional sodium borohydride and cobaltous chloride were added as needed to drive the reaction to completion. Typically, 2×7.5 g of additional sodium borohydride and 2×1 g portions of cobaltous chloride were added at 12 hour intervals. Once complete, the layers were allowed to settle and the clear upper THF layer was decanted from the black aqueous layer. The aqueous layer was washed with 750 mL fresh THF, the two THF layers combined and filtered through a pad of celite. The orange-yellow filtrate was concentrated to about 300 mL in vacuo, resulting in water layer with the product as an oily lower layer. The mixture was extracted with 2×250 mL ethyl acetate and the combined extracts reacted with 24 g (200 mmol) of solid sodium hydrogensulfate. A solid formed immediately, and the slurry was stirred for 30 min, filtered and washed with 2×100 mL ethyl acetate to give 62 g of a white powder. The powder was slurried in 175 mL water, cooled to 0° C., filtered, washed with 2×40 mL cold water and the solid dried in a vacuum oven at 55° C. for 24 hr to give tert-butyl 2-(aminomethyl)benzylcarbamate hemisulfate salt as a white powder.

EXAMPLE 54 tert-Butyl 2-(Aminomethyl)-4-chlorobenzylcarbamate

Step A. 2-Bromo-5-chlorobenzoate

Through a solution of 2-bromo-chlorobenzoic acid (11 g, 46.7 mmol) in methanol (250 ml) was bubbled HCl gas. The reaction was allowed to warm to room temperature and stirred overnight. The reaction mixture is concentrated in vacuo to give an orange oil, which is purified by flash chromatography (silica gel, hexane) to give the title compound as a colorless oil.

1H NMR (CDCl$_3$, 400MHz): δ 7.78 (d, 1H, J=2.6 Hz); 7.59 (d, 1H, J=12.81 Hz); 7.30 (dd, 1H, J=8.6, 2.5 Hz); 3.94 (s, 3H).

Step B. Methyl 5-Chloro-2-cyanobenzoate

To a solution of methyl 2-bromo-5-chlorobenzoate (1.15 g, 4.6 mmol) in degassed DMF was added zinc cyanide (282 mg, 2.40 mmol) and palladium tetrakis triphenylphosphine (100 mg, 0.086 mmol) and the reaction is stirred at 90C over night. The reaction was partitioned between ethyl acetate and water. The organic was concentrated in vacuo and purified by flash chromatography eluting a gradient to 10 to 25% ethyl acetate in hexane yielding a white solid (methyl 5-chloro-2-cyanobenzoate).

H NMR (CDCl$_3$, 400 MHz): δ 8.13 (d, 1H, J=1.83 Hz); 3.09 (d, 1H, J=8.24 Hz); 7.29 (dd, 1H, J=8.34, 2.10 Hz); 4.02 (s, 3H).

Step, C. [2-(Aminomethyl)-5-chlorophenyl]methanol

To LAH (1 M/Et$_2$O, 104.4 ml, 104.4 mmol) in anhydrous THF (300 ml) at 0C was added methyl 5-chloro-2-cyanobenzoate (9.28 g, 0.512 mmol) maintaining the temperature below 20 C. After one half hour, quenched at 0C with water (3.97 ml), NaOH (1N, 11.9 ml, 11.9 mmol) and water (3.97 ml). A precipitate was filtered out and washed with THF. The filtrate was concentrated in vacuo and was used immediately in the next step.

H NMR (CDCl₃, 400 MHz): δ 7.17–7.36 (m, 3H); 4.60 (s, 2H); 3.98 (s, 2H);

Step D. tert-Butyl 4-Chloro-2-(hydroxymethyl)benzylcarbamate

To a solution of [2-(aminomethyl)-5-chlorophenyl]methanol in dichloromethane (200 ml), was added di-tert-butyl-dicarbonate (11.38 g, 52.18 mmol) at room temperature. After one hour, the reaction was partitioned. The organic layer was concentrated in vacuo and purified by flash chromatography eluting a gradient of ethyl acetate/hexane which gave a brown oil, which was taken up in dichloromethane (500 ml) and treated with activated charcoal yielding a pink solid.

H NMR (CDCl₃, 400 MHz): 7.36 (s, 1H); 7.2–7.5 (m, 2H); 4.69 (b s, 2H); 4.32 (d, 2H, J=6.04 Hz); 1.43 (s, 9H).

Step E. tert-Butyl 2-(Azidomethyl)-4-chlorobenzylcarbamate

To a solution of tert-butyl 4-chloro-2-(hydroxymethyl)benzylcarbamate (10 g, 36.8 mmol) in anhydrous THF (100 ml) was added DPPA (8.3 ml, 38.6 mmol) and DBU (5.79 ml, 38.6 mmol). The mixture was stirred overnight and then was partitioned between ethyl acetate and water. The organic layer was washed with brine, and was concentrated in vacuo to a crude oil (14.6 g). Purification was accomplished by silica gel chromatography, eluting a gradient of ethyl acetate-hexane (10, 15, 20, 25, 50%) to give tert-butyl 2-(aminomethyl)-4-chlorobenzylcarbamate.

H NMR (CDCl₃, 400 MHz): δ 7.25–7.39 (m, 3H); 4.41 (s, 2H), 4.32 (d, 2H, J=5.86 Hz); 1.45 (s, 9H).

Step F. tert-Butyl 2-(Aminomethyl)-4-chlorobenzylcarbamate

To a solution of tert-butyl 2-(azidomethyl)-4-chlorobenzylcarbamate (10.9 g, 36.73 mmol) in THF (60 ml) and water (6 ml) was added triphenylphospine (10.59 g, 40.40 mmol). The reaction was heated to 65 C and stirred overnight at room temperature. The reaction was concentrated in vacuo and flashed with 4% (10% NH4OH/MeOH)/dichlor-omethane. A second purification using silica gel column chromatography with a careful gradient of 3 to 5% (10% NH4OH/MeOH)/dichloro methane gave the title compound.

H NMR (CDCl₃, 400 MHz) δ 7.21–7.52 (m, 3H); 4.32 (b d, 2H); 3.90 (s, 2H); 1.44 (s, 9H).

EXAMPLE 55

D-Phenylalanyl-N-[2-(ammoniomethyl)-5-chlorobenzyl]-L-prolinamide bis(Hydrochloride)

Step A: N-(tert-Butoxyacetyl)-D-phenylalanyl-N-(2-{[(tert-butoxycarbonyl)amino]methyl}-5-chlorobenzyl)-L-prolinamide To a solution of tert-Butyl 2-(aminomethyl)-4-chlorobenzylcarbamate (0.14 mmol, 37 mg), EDC (0.21 mmol, 40 mg), and Boc-D-Phe-Pro-OH (0.14 mmol, 50 mg), in 0.5 mL dimethylformamide, was added HOAT (0.15 mmol, 21 mg). The solution was stirred overnight and purified by prep HPLC to give N-(tert-Butoxyacetyl)-D-phenylalanyl-N-(2-{[(tert-butoxycarbonyl)amino]methyl}-5-chlorobenzyl)-L-prolinamide. Mass Spec ES (M+1)= 615.2.

Step B: D-Phenylalanyl-N-[2-(ammoniomethyl)-5-chlorobenzyl]-L-prolinamide bis(Hydrochloride)

HCl gas was bubbled through a 0° C. solution of N-(tert-Butoxyacetyl)-D-phenylalanyl-N-(2-{[(tert-butoxycarbonyl)amino]methyl}-5-chlorobenzyl)-L-prolinamide (0.073 mmol, 45 mg) in 0.500 mL ethylacetate for 2 min. Let stir 1 h and concentrated in vaccuo to give D-Phenylalanyl-N-[2-(ammoniomethyl)-5-chlorobenzyl]-L-prolinamide bis(hydrochloride). Mass Spec ES (M+1)= 415.1.

The following examples were prepared by procedures similar to that described above for EXAMPLE 55 using the products of Examples 51–54 and an appropriate carboxylic acid.

EXAMPLE 56

D-Phenylalanyl-N-[2-(ammoniomethyl)benzyl]-L-prolinamide bis(Trifluoroacetate)

Mass Spec ES (M+1)=381.1.

EXAMPLE 57

D-Phenylalanyl-N-[2-(2-ammonioethyl)benzyl]-L-prolinamide bis(Hydrochloride)

Mass Spec ES (M+1)=395.2.

EXAMPLE 58

D-Phenylalanyl-N-[2-(2-ammonioethyl)-5-chlorobenzyl]-L-prolinamide bis(Hydrochloride)

Mass Spec ES (M+1)=429.1.

EXAMPLE 59

3-Pyridinium-2-yl-D-alanyl-N-[2-(2-ammonioethyl)-5-chlorobenzyl]-L-prolinamide Trichloride Step A.
N-(tert-Butoxycarbonyl)-3-pyridin-2-yl-L-alanyl-L-proline To a solution of 1.0 g (3.8 mmol) N-(tert-butoxycarbonyl)-3-pyridin-2-yl-L-alanine in 7 ml DMF was added 0.62 g (3.8 mmol) methyl L-prolinate hydrochloride, 0.52 mL (3.8 mmol) triethylamine, 0.51 g (0.38 mmol) HOAt, and 1.1 g (5.7 mmol) EDC. After 3 h at room temperature, the reaction mixture was diluted with 300 ml EtOAc, washed with 200 ml each of saturated NaHCO₃ solution, water, and ml brine. The organic layer was dried over Na₂SO₄, filtered and concentrated in vacuo. Purification by automated flash chromatography (ISCO combiflash, 70 g silica gel, linear gradient 50–100% EtOAc:hexane 30 min then 2–10% MeOH/EtOAc at 60 mL/min) afforded 0.9 g N-(tert-butoxycarbonyl)-3-pyridin-2-yl-L-alanyl-L-proline of which 0.44 g (1.2 mmol) was dissolved in 7 mL MeOH. To this was added 1.2 mL (1.2 mmol, 1M aqueous solution) LiOH and the reaction mixture stirred 6 hours, then another 0.12 mL (0.12 mmol, 1M aqueous solution) portion of LiOH was added and the reaction mixture stirred an additional 16 hrs before addition of 0.12 mL conc. HCl (1.44 mmol, 12M aqueous solution) was added and the reaction concentrated to a foam. ¹H NMR (CD₃OD, 400 MHz) δ 8.47 (m, 1H); 7.78 (m, 1H); 7.34 (m, 2H,); 4.31 (dd, 1H, J=4.21, 8.8 Hz); 3.78 (br m, 1H); 3.54 (br m, 1H); 3.17 (dd, 1H, J=6.23 and 13.5 Hz); 3.02 (m, 2H); 2.3–1.8 (br m, 4H); 1.35 (s, 9H); electrospray mass spectrum 364.

Step B.
3-Pyridinium-2-yl-D-alanyl-N-[2-(2-ammonioethyl)-5-chlorobenzyl]-L-prolinamide Trichloride:

The title compound is prepared using a similar procedure as described for the synthesis of EXAMPLE 55 Step B: ¹H NMR (DMSO-d₆, 400 MHz): δ 8.84 (t, 1H, J=5.8 Hz), 8.72–8.62 (br m, 4H), 8.12–8.00 (br m, 4H), 7.54 (d, 2H, J=7.9 Hz ), 7.33–7.19 (m, 4H), 4.58 (br s, 11H), 4.40–4.20 (m, 3H), 3.88–3.80 (m, 2H), 3.43–3.28 (m, 3H), 2.96 (br s, 4H), 1.90–1.75 (br m, 2H); MS (Electrospray): M+H=430.2; TLC: R$_f$=0.13 (80/10/1 of methylene chloride/methanol/concentrated ammonium hydroxide).

EXAMPLE 60

N-[2-(Aminomethyl)-5-chlorobenzyl]-1-[(9-hydroxy-9H-fluoren-9-yl)carbonyl]prolinamide Step A.
9-Hydroxy-9-fluorenylcarbonyl-L-proline Benzyl Ester To a solution of 9-hydroxy-9-fluorene carboxylic acid (5.04 g, 22.3 mmol) in N,N-dimethylformamide (30 mL), cooled to 0° C. under nitrogen, was added (O-7-azabenzotriazol-1-y)-1,1,3,3-tetramethyluronium hexafluorophosphate (HATU), (9.32 g, 24.5 mmol), L-proline-benzyl ester hydrochloride (5.93 g, 24.5 mmol), and N,N-diisopropylethylamine (8.5 mL, 48.8 mmol). The mixture was stirred at 0° C. for 3 hours, then concentrated and purified on silica gel (ethyl acetate-hexane, 1:2) to give 9-hydroxy-9-fluorenylcarbonyl-L-proline benzyl ester. HPLC=96%, R.T.=3.7 min; M+1=414.1.

Step B.
9-Hydroxy-9-fluorenylcarbonyl-L-proline

A mixture of 9-hydroxy-9-fluorenylcarbonyl-L-proline benzyl ester (3.8 g, 9.3 mmol) from step 1 above and 10% palladium on carbon (390 mg) in ethyl acetate (100 mL) was stirred under an atmosphere of hydrogen (balloon pressure) for 24 hours. The mixture was filtered through celite and concentrated in vacuo to give 9-hydroxy-9-fluorenylcarbonyl-L-proline. HPLC=90%, R.T.=2.97 min; M+1=324.1; $^1$H NMR (CD$_3$OD) 7.78–7.75 (m, 2H), 7.47–7.32 (m, 6H), 4.49–4.45 (q, 1H), 2.42–2.30 (m, 2H), 2.01–1.94 (m, 1H), 1.78–1.71 (m, 1H), 1.58–1.41 (m, 2H).

Step C.
9-Hydroxy-9-fluorenylcarbonyl-L-prolyl-2-tert-butyloxycarbonylaminomethyl-5-chlorobenzylamide A solution of 9-hydroxy-9-fluorenylcarbonyl-L-proline (1.8 g, 5.6 mmol) from step 2 above, 2-tert-butoxycarbonylaminomethyl-5-chlorobenzylamine (1.8 g, 6.8 mmol), N-methylmorpholine (12 drops), and benzotriazol-1-yloxy-tris(dimethylamino) phosphonium hexafluorophosphate (3.0 g, 6.7 mmol) in N,N-dimethylformamide (25 mL) was stirred at ambient temperature for 24 hours, concentrated in vacuo, and purified on silica gel (ethyl acetate-hexane, 1:2) to give 9-hydroxy-9-fluorenylcarbonyl-L-prolyl-2-tert-butyloxycarbonylaminomethyl-5-chlorobenzylamide. HPLC=99%, R.T.=3.69 min; M+1=576.2.

Step D.
9-Hydroxy-9-fluorenylcarbonyl-L-prolyl-2-aminomethyl-5-chlorobenzylamide A solution of 9-hydroxy-9-fluorenylcarbonyl-L-prolyl-2-tert-butyloxycarbonylaminomethyl-5-chlorobenzylamide (1.4 g, 2.4 mmol) from step 3 above in methanol (40 mL) was cooled to 0° C. and saturated with anhydrous HCl gas. After stirring for one hour at 0° C., the mixture was concentrated in vacuo and purified on a reverse phase C18 HPLC column to give the TFA salt of 9-hydroxy-9-fluorenylcarbonyl-L-prolyl-2-aminomethyl-5-chlorobenzylamide. HPLC=99%, R.T.=2.83 min; M+1=476.1; combustion analysis for C$_{27}$H$_{26}$ClN$_3$O$_3$, 1.25 TFA, 1.00 water; calculated C: 55.67, H: 4.63, N: 6.60; found C: 55.64, H: 4.60, N: 6.70; 1H NMR (CDCl$_3$) δ 8.44–8.27 (s, 3H), 7.67–7.64 (m, 2H), 7.43–7.19 (m, 6H), 4.81–4.75 (m, 1H) 4.45–4.42 (m, 1H), 4.15–3.99 (m, 3H), 2.39–2.26 (m, 2H), 2.02–1.83 (m, 1H), 1.76–1.68 (m, 1H), 1.65–1.54 (m, 1H), 1.46–1.37 (m, 1H).

HPLC Method
Mobile Phase:
gradient: 95:5 to 0:100 A:B over 4.5 minutes; A=water with 0.1% TFA, B=acetonitrile with 0.1% TFA; flow rate: 3.0 mL/min.

Stationary Phase: Zorbax C8 column, 4.5 mm ID×7.5 cm; 3.5 micron

EXAMPLE 61

Step 1. To a stirred solution of 2-(tert-butyloxycarbonylaminomethyl)-5-chlorobenzylamine (3.80 g, 14.1 mmol, HPLC RT=2.63 min), Fmoc-L-Proline (4.98 g, 14.8 mmol, HPLC RT=3.26 min), and HOBT hydrate (2.15 g, 14.1 mmol) in DMF (25 mL) was added EDC (3.51 g, 18.3 mmol). The pH of the solution was slowly raised to pH 6 (as measured on wetted E. Merck pH indicator strips) by the gradual addition of diisopropylethylamine (~2 mL), At 2 hours reaction time, HPLC analysis indicated complete consumption of the benzylamine starting material. The solvent was removed on a rotary evaporator (bath temp 30° C., ~0.5 torr) and the residue was partitioned between EtOAc (100 mL) and water (50 mL). The organic phase was dried (MgSO$_4$), filtered, and the solvent was removed on a rotary evaporator (bath temp 30° C., ~50 torr). The residue was purified by flash chromatography using a gradient elution of 1:1 to 3:1 EtOAc:hexanes. N-Fluroenylmethoxycarbonyl-L-prolyl-2-(tert-butyloxycarbonylaminomethyl)-5-chlorobenzylamide was obtained as a gum (TLC Rf=0.5 (1;1 EtOAc:hexanes, UV visualization); HPLC RT=3.87 min; LC-MS m/z= 590).

Step 2. To a stirred solution of N-fluroenylmethoxycarbonyl-L-prolyl-2-(tert-butyloxycarbonylaminomethyl)-5-chlorobenzylamide from the previous step (7.0 g, 12 mmol, HPLC RT=3.87 min) in DMF (50 mL) was added piperidine (7.5 mL). At 15 min reaction time, HPLC analysis indicated complete consumption of the Fmoc-Proline derivative with formation of two new closely eluting components (HPLC RT=2.76 min desired product, 2.80 min Fmoc by-product). The solvent and excess piperidine were removed on a rotary evaporator (bath temp 40° C., ~0.5 torr). The residue was purified by flash chromatography using a gradient elution of 96:4 to 92:8 to 88:12 CH$_2$Cl$_2$:A (A=95:5 MeOH:NH$_4$OH). N-L-Prolyl-2-(tert-butyloxycarbonylaminomethyl)-5-chlorobenzylamide was obtained as a gum (TLC Rf=0.4 (90:10:0.5 CH$_2$Cl$_2$:MeOH:NH$_4$OH; iodine visualization); HPLC RT=2.77 min; LC-MS m/z=368; 1H NMR, 400 MHz, CDCl$_3$, 8.04 ppm (br s, 1H), 7.2–7.3 ppm (m, 3H), 5.24 ppm (br s, 1H), 4.4–4.5 ppm (ABX, 2H), 4.28 ppm (d, 2H), 3.80 ppm (dd, J=5.4,9.4 Hz, 1H), 2.9–3.0 ppm (ABXY, 2H), 2.1–2.2 ppm (m, 1H), 1.9–2.0 ppm (m, 1H), 1.7–1.8 ppm (m, 2H), 1.44 ppm (s, 3H)).

Step 3. To a stirred solution of L-prolyl-2-(tert-butyloxycarbonylaminomethyl)-5-chlorobenzylamide from the previous step (0.23 g, 0.62 mmol, HPLC RT=2.77 min), 2R-hydroxy-3-methylbutyric acid acid (77 mg, 0.65 mmol), and HOBT hydrate (99 mg, 0.65 mmol) in DMF (4 mL) was added EDC (0.16 g, 0.82 mmol). Diisopropylethylamine was then added in portions (~0.1 mL total) to bring the pH of the solution to 6–7 as measured on wetted E. Merck pH indicator strips. The mixture was stirred at ambient temperature for 2 h, at which time HPLC analysis indicated complete consumption of the proline starting material. The DMF was removed under reduced pressure and the residue was partitioned between EtOAc (100 mL) and saturated aqueous NaHCO$_3$ (50 mL). The EtOAc layer was separated, dried over anhydrous MgSO$_4$, and filtered. The filtrate solvent was removed under reduced pressure and the residue was purified by flash chromatography using EtOAc as eluant. N-(2R-Hydroxy-3-methylbutanoyl)-L-prolyl-2-(tert-butyloxycarbonylaminomethyl)-5-chlorobenzylamide was obtained as a colorless gum (TLC Rf=0.7 (EtOAc); HPLC RT=3.21 min; LC-MS m/z=468).

Step 4. N-(2R-Hydroxy-3-methylbutanoyl)-L-prolyl-2-(tert-butyloxycarbonylaminomethyl)-5-chlorobenzylamide from the previous step (0.26 g, 0.56 mmol, HPLC RT=3.21 min) was dissolved in EtOAc (20 mL) and cooled with stirring to 0° C. HCl gas was bubbled through the solution for 10 minutes. After 2 hours at 0° C., HPLC analysis indicated complete consumption of the starting material, and the solvent was removed under reduced pressure. The resulting solid was triturated in EtOAc, filtered, and dried in vacuo to give the hydrochloride salt of N-(2R-hydroxy-3-methylbutanoyl)-L-prolyl-2-aminomethyl-5-chlorobenzylamide as a white solid (TLC Rf=0.3 (90:10:0.5 CH$_2$Cl$_2$:MeOH:NH$_4$OH); HPLC RT=2.38 min; LC-MS m/z=368; 1H NMR, 400 MHz, DMSO-d6, ~3.5:1 mixture of rotamers, selected signals: 8.84 ppm (minor) and 8.64 ppm (major) (t, J=6 Hz, 1H), 0.87, 0.83 ppm (major) and 0.74, 0.58 ppm (minor) (two doublets, J=7 Hz, 3H)).

HPLC Conditions:
  Stationary Phase: Hewlett-Packard Zorbax SB-C8 column 75×4.6 mm, 3.5 micron
  Mobile Phase: A=H$_2$O containing 0.1% by volume TFA; B=CH$_3$CN containing 0.1% by volume TFA
  Gradient: 95:5 A:B to 0:100 A:B over 4.5 minutes
  Flow Rate: 3.0 mL/min
  UV Detection at 215 nm

EXAMPLE 62

N-(2R-Hydroxy-3,3-dimethylbutanoyl)-L-prolyl-2-aminomethyl-5-chlorobenzylamide

Step I. To a stirred solution of 2-(tert-butyloxycarbonylaminomethyl)-5-chlorobenzylamine (3.80 g, 14.1 mmol, HPLC RT=2.63 min), Fmoc-L-Proline (4.98 g, 14.8 mmol, HPLC RT=3.26 min), and HOBT hydrate (2.15 g, 14.1 mmol) in DMF (25 mL) was added EDC (3.51 g, 18.3 mmol). The pH of the solution was slowly raised to pH 6 (as measured on wetted E. Merck pH indicator strips) by the gradual addition of diisopropylethylamine (~2 mL). At 2 hours reaction time, HPLC analysis indicated complete consumption of the benzylamine starting material. The solvent was removed on a rotary evaporato (bath temp 30° C., ~0.5 torr) and the residue was partitioned between EtOAc (100 mL) and water (50 mL). The organic phase was dried (MgSO$_4$), filtered, and the solvent was removed on a rotary evaporator (bath temp 30° C., ~50 torr). The residue was purified by flash chromatography using a gradient elution of 1:1 to 3:1 EtOAc:hexanes. N-Fluroenylmethoxycarbonyl-L-prolyl-2-(tert-butyloxycarbonylaminomethyl)-5-chlorobenzylamide was obtained as a gum (TLC R$_f$=0.5 (1;1 EtOAc:hexanes, UV visualization); HPLC RT=3.87 min; LC-MS m/z=590).

Step 2. To a stirred solution of N-fluroenylmethoxycarbonyl-L-prolyl-2-(tert-butyloxycarbonylaminomethyl)-5-chlorobenzylamide from the previous step (7.0 g, 12 mmol, HPLC RT=3.87 min) in DMF (50 mL) was added piperidine (7.5 mL). At 15 min reaction time, HPLC analysis indicated complete consumption of the Fmoc-Proline derivative with formation of two new closely eluting components (HPLC RT=2.76 min desired product, 2.80 min Fmoc by-product). The solvent and excess piperidine were removed on a rotary evaporator (bath temp 40° C., ~0.5 torr). The residue was purified by flash chromatography using a gradient elution of 96:4 to 92:8 to 88:12 CH$_2$Cl$_2$:A (A=95:5 MeOH:NH$_4$OH). N-L-Prolyl-2-(tert-butyloxycarbonylaminomethyl)-5-chlorobenzylamide was obtained as a gum (TLC R$_f$=0.4 (90:10:0.5 CH$_2$Cl$_2$:MeOH:NH$_4$OH; iodine visualization); HPLC RT=2.77 min; LC-MS m/z=368; $^1$H NMR, 400 MHz, CDCl$_3$, 8.04 ppm (br s, 1H), 7.2–7.3 ppm (m, 3H), 5.24 ppm (br s, 1H), 4.4–4.5 ppm (ABX, 2H), 4.28 ppm (d, 2H), 3.80 ppm (dd, J=5.4, 9.4 Hz, 1H), 2.9–3.0 ppm (ABXY, 2H), 2.1–2.2 ppm (m, 1H), 1.9–2.0 ppm (m, 1H), 1.7–1.8 ppm (m, 2H), 1.44 ppm (s, 3H)).

Step 3. To a stirred solution of L-prolyl-2-(tert-butyloxycarbonylaminomethyl)-5-chlorobenzylamide from the previous step (3.90 g, 10.6 mmol, HPLC RT=2.77 min), 2R-hydroxy-3,3-dimethylbutyric acid acid (1.40 g, 10.6 mmol), and HOBT hydrate (1.68 g, 11 mmol) in DMF (60 mL) was added EDC (2.65 g, 13.8 mmol). Diisopropylethylamine was then added slowly in portions (1.5 mL total) to bring the pH of the solution to 6–7 as measured on wetted E. Merck pH indicator strips. The mixture was stirred at ambient temperature for 6 h, at which time HPLC analysis indicated complete consumption of the proline starting material. Water (10 mL) was added and the solvents were removed under reduced pressure. The residue was partitioned between EtOAc (300 mL) and saturated aqueous NaHCO$_3$ (200 mL). The EtOAc layer was separated, dried over anhydrous MgSO$_4$, and filtered. The filtrate solvent was re moved under reduced pressure and the residue was purified by flash chromatography using a gradient elution of 2:1, 4:1, and 1:0 EtOAc:hexanes. N-(2R-Hydroxy-3,3-dimethylbutanoyl)-L-prolyl-2-(tert-butyloxycarbonylaminomethyl)-5-chlorobenzylamide was obtained as a colorless gum (TLC R$_f$=0.7 (EtOAc); HPLC RT=3.35 min; LC-MS m/z=482).

Step 4. N-(2R-Hydroxy-3,3-dimethylbutanoyl)-L-prolyl-2-(tert-butyloxycarbonylaminomethyl)-5-chlorobenzylamide from the previous step (4.65 g, 9.65 mmol, HPLC RT=3.35 min) was dissolved in CH$_2$Cl$_2$ (15 mL) and cooled with stirring to 0° C. A solution of anhydrous HCl in ether (38 mL of a 1 Molar solution, 38 mmol) was added slowly. The resulting solution was stirred at 0° C. for 10 min, and then at ambient temperature for 20 h. The solid which had formed was collected by filtration and washed with several portions of ether. The solid was purified by preparative reverse-phase HPLC using an acetonitrile:water gradient containing 0.05% concentrated HCl. The product-containing fractions were combined and lyophilized to give the hydrochloride salt of N-(2R-hydroxy-3,3-dimethylbutanoyl)-L-prolyl-2-aminomethyl-5-chlorobenzylamide as a white solid (HPLC RT=2.52 min; LC-MS m/z=382; C, H, N combustion analysis, calculated for C$_{19}$H$_{28}$ClN$_3$O$_3$, 1.0 HCl, 1.5 H$_2$O, calculated C, 51.24, H, 7.24, N, 9.43, found C, 51.32, H, 7.17, N, 9.33).

HPLC Conditions:
- Stationary Phase: Hewlett-Packard Zorbax SB-C8 column; 75×4.6 mm, 3.5 micron
- Mobile Phase: A=$H_2O$ containing 0.1% by volume TFA; B=$CH_3CN$ containing 0.1% by volume TFA; Gradient: 95:5 A:B to 0:100 A:B over 4.5 minutes; Flow Rate: 3.0 mL/min
- UV Detection at 215 nm Typical tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

In Vitro Assay For Determining Proteinase Inhibition

Assays of human α-thrombin and human trypsin were performed by the methods substantially as described in Thrombosis Research, Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM $CaCl_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM) and bovine trypsin ($K_m$=125 μM). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate benzyloxycarbonyl-Gly-Pro-Arg-7-amino-4-trifluoromethylcoumarin (Z-GPR-afc, Lewis S. D. et al. (1998) J. Biol. Chem. 273, pp. 4843–4854) ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration <0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i=1+[I]/K_i$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

EXAMPLE 63

Tablet Preparation

Tablets containing 25.0, 50.0, and 100.0 mg., respectively, of the following active compounds are prepared as illustrated below (compositions A–C). Active I is compound D-Phenylalanyl-N-[2-(ammoniomethyl)-5-chlorobenzyl]-L-prolinamide bis(hydrochloride).

| | Amount-(mg) | | |
|---|---|---|---|
| Component | A | B | C |
| Active I | 25 | 50 | 100 |
| Microcrystalline cellulose | 37.25 | 100 | 200 |
| Modified food corn starch | 37.25 | 4.25 | 8.5 |
| Magnesium stearate | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 64

Tablet Preparation

Exemplary compositions of compound D-Phenylalanyl-N-[2-(ammoniomethyl)-5-chlorobenzyl]-L-prolinamide bis (hydrochloride) (Active I) tablets are shown below:

| Component | 0.25 mg | 2 mg | 10 mg | 50 mg |
|---|---|---|---|---|
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation via Direct Compression

Active I, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation via Dry Granulation

Alternatively, a dry powder blend is compacted under modest forces and remilled to afford granules of specified particle size. The granules are then mixed with magnesium stearate and tabletted as stated above.

EXAMPLE 65

Intravenous Formulations

Intravenous formulations of compound D-Phenylalanyl-N-[2-(ammoniomethyl)-5-chlorobenzyl]-L-prolinamide bis (hydrochloride) (Active I) were prepared according to general intravenous formulation procedures.

| Component | Estimated range |
| --- | --- |
| Active I | 0.12–0.50 mg |
| D-glucuronic acid* | 0.5–5 mg |
| Mannitol NF | 50–53 mg |
| 1 N Sodium Hydroxide | q.s. pH 3.9–4.1 |
| Water for injection | q.s. 1.0 mL |

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:
1. A compound of the general formula

1)

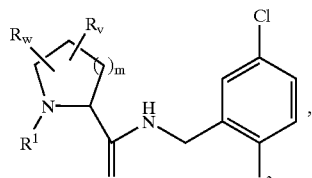

2)

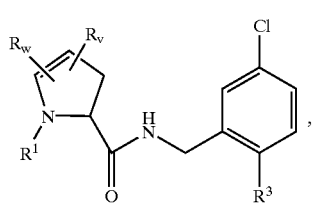

3)

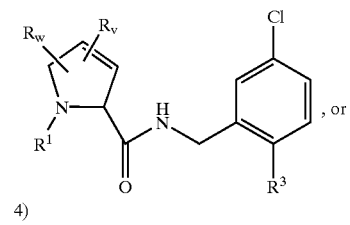

, or

4)

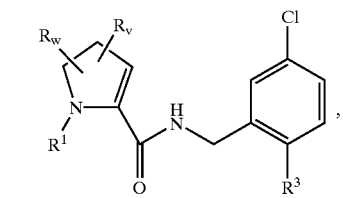

, or a pharmaceutically acceptable salt thereof, wherein m is 1;

$R_w$ and $R_v$ are independently selected from the group consisting of hydrogen, $C_{1-4}$ alkyl, and halogen;

$R_t$ is $C_{1-6}$ alkyl or $C_{3-7}$ cycloalkyl;

$R^1$ is selected from the group consisting of

1)

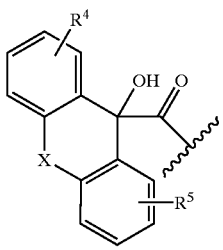

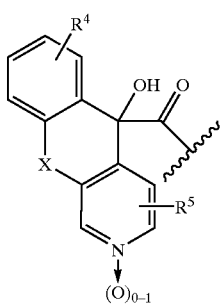

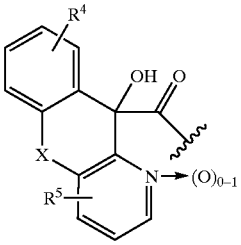

wherein $R^4$ and $R^5$ are independently selected from the group consisting of hydrogen, halogen, $C_{1-4}$ alkoxy, $C_{1-6}$ alkyl, —OH, and cyano, and X is a bond, O, or S, and 2) 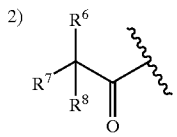

wherein $R^6$ is selected from the group consisting
  a) hydrogen,
  b) $C_{1-6}$ alkyl,
  c) —OH,
  d) —$NR^{24}R^{25}$, where $R^{24}$ and $R^{25}$ are independently hydrogen, or $C_{1-6}$ alkyl unsubstituted or substituted with one or more of —OH, —COOH, $C_{3-7}$ cycloalkyl, or $COOR^{17}$, where $R^{17}$ is $C_{1-6}$ alkyl,
  e) $NHC(O)OR^{18}$,
  f) $NHC(O)R^{18}$,
  g) $NHC(O)NHR^{18}$,
  h) $NHSO_2R^{18}$,
  i) $NHC(O)NH_2$, and
  j) NHCN,
    wherein $R^{18}$ is selected from the group consisting of $C_{1-6}$ alkyl, aryl, and $C_{3-7}$ cycloalkyl;

$R^7$ and $R^8$ are independently selected from the group consisting of
  a) hydrogen,
  b) —$CF_3$,
  c) $C_{1-6}$ alkyl,
  d) phenyl, unsubstituted or substituted with $C_{1-6}$ alkyl, $COOR^{26}$ or halogen, where $R^{26}$ is $C_{1-6}$ alkyl or hydrogen, e) 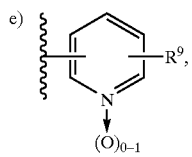

f) $C_{3-7}$ cycloalkyl, g) 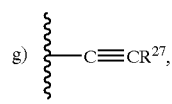

where $R^{27}$ is $C_{1-6}$ alkyl or $C_{3-7}$ cycloalkyl, h) 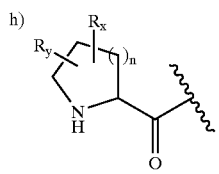

wherein $R_x$ and $R_y$ are independently selected from the group consisting of hydrogen, $C_{1-6}$ alkyl, $C_{3-7}$ cycloalkyl, unsubstituted phenyl or phenyl substituted with halogen, $C_{1-4}$ alkyl, OH, or $C_{1-4}$ alkoxy, and
  wherein n is 0, 1, 2 or 3,
  i) $C_{1-6}$ alkyl substituted with one or two of the group consisting of i) $C_{3-7}$ cycloalkyl, either unsubstituted or substituted with $C_{1-4}$ alkyl,
    ii) —COOH,
    iii) —OH, iv) 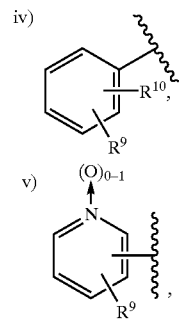

v) 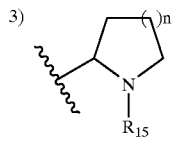

wherein $R^9$ and $R^{10}$ are independently selected from the group consisting of
      aa) hydrogen,
      bb) halogen,
      cc) $C_{1-4}$ alkoxy,
      dd) $C_{1-4}$ alkyl,
      ee) hydroxy,
      ff) $CF_3$,
      gg) cyano,
      hh) $COOR^{28}$, where $R^{28}$ is $C_{1-4}$ alkyl or hydrogen;

or $R^7$ and $R^8$ are joined to form a $C_{3-7}$ carbocyclic ring which is unsubstituted or independently substituted with one or two $C_{1-6}$ alkyl groups;

$R^3$ is selected from the group consisting of
  1) —$C(R^{11})(R^{12})C(R^{13})(R^{14})N(R^{15})(R^{16})$,
  2) —$C(R^{13})(R^{14})N(R^{15})(R^{16})$, and

3)

where n is 0, 1 or 2,
wherein
  $R^{11}$ and $R^{12}$ are independently selected from the group consisting of
    a) hydrogen,
    b) F,
    c) $C_{1-4}$ alkyl,
    d) $CF_3$,
    e) $CHF_2$,
    f) $C_{3-7}$ cycloalkyl,
      or $R^{11}$ and $R^{12}$ together form a 3–7 membered carbocyclic ring,
  $R^{13}$ and $R^{14}$ are independently selected from the group consisting of
    a) hydrogen,
    b) $C_{1-4}$ alkyl
    c) —$CF_3$,
    d) —$CHF_2$,
    e) —$CH_2OH$,
    f) $C_{3-6}$ cycloalkyl,
      or $R^{13}$ and $R^{14}$ together form a 3–7 membered carbocyclic ring,
  $R^{15}$ and $R^{16}$ are independently selected from the group consisting of a) hydrogen,
b) C$_{1-6}$ alkyl, unsubstituted or substituted with —OH, C$_{3-7}$ cycloalkyl, or C(O)OR$^{19}$, wherein R$^{19}$ is selected from the group consisting of hydrogen and C$_{1-6}$ alkyl,
c) C$_{3-7}$ cycloalkyl, and
d) —C(O)R$^{20}$, wherein R$^{20}$ is selected from the group consisting of —OR$^{21}$ and —NHR$^{21}$, and wherein R$^{21}$ is hydrogen, C$_{1-6}$ alkyl or benzyl,
or R$^{15}$ and R$^{16}$ are joined to form a 4–7 membered heterocyclic ring which is unsubstituted or substituted with hydroxyl or halogen.

2. A compound of claim 1, or a pharmaceutically acceptable salt thereof, wherein the compound has the formula

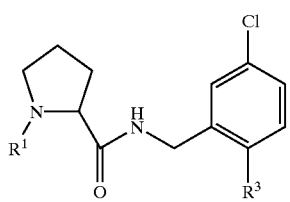

and R$^3$ is —C(R$^{11}$)(R$^{12}$)C(R$^{13}$)(R$^{14}$)N(R$^{15}$)(R$^{16}$) or —C(R$^{13}$)(R$^{14}$)N(R$^{15}$)(R$^{16}$).

3. A compound of claim 2, or a pharmaceutically acceptable salt thereof, wherein R$^3$ is —C(R$^{11}$)(R$^{12}$)C(R$^{13}$)(R$^{14}$)N(R$^{15}$)(R$^{16}$).

4. A compound of claim 3, or a pharmaceutically acceptable salt thereof, wherein R$^3$ is —C(R$^{11}$)(R$^{12}$)C(R$^{13}$)(R$^{14}$)NH$_2$.

5. A compound of claim 4, or a pharmaceutically acceptable salt thereof, wherein R$^3$ is —CH$_2$CH$_2$NH$_2$, —CH$_2$CH(CHF$_2$)NH$_2$, or —CH$_2$CH(CF$_3$)NH$_2$.

6. A compound of claim 5, or a pharmaceutically acceptable salt thereof, wherein
x is a bond;
R$^6$ is hydrogen, —OH, —CH$_3$ or —NH$_2$;
R$^7$ is hydrogen, —CH$_3$, phenyl, 3-chlorophenyl, cyclopropyl or —CH$_2$CH$_3$; and
R$_8$ is phenyl, 3-chlorophenyl, cyclohexyl, —CH$_3$, —CF$_3$, —CH$_2$CH$_3$, —CH(CH$_3$)$_2$, —CH(CH$_3$)(CH$_2$CH$_3$), —C(CH$_3$)$_3$, 2-pyridyl, 3-pyridyl,

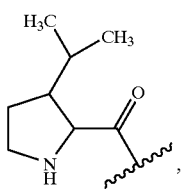

or C$_{1-6}$ alkyl substituted with

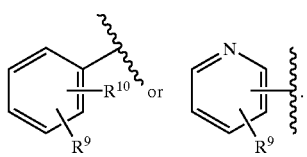

7. A compound of claim 6, or a pharmaceutically acceptable salt thereof, wherein R$^9$ is hydrogen or Cl and R$^{10}$ is hydrogen.

8. A compound of claim 7, or a pharmaceutically acceptable salt thereof, wherein R$^1$ is selected from the group consisting of

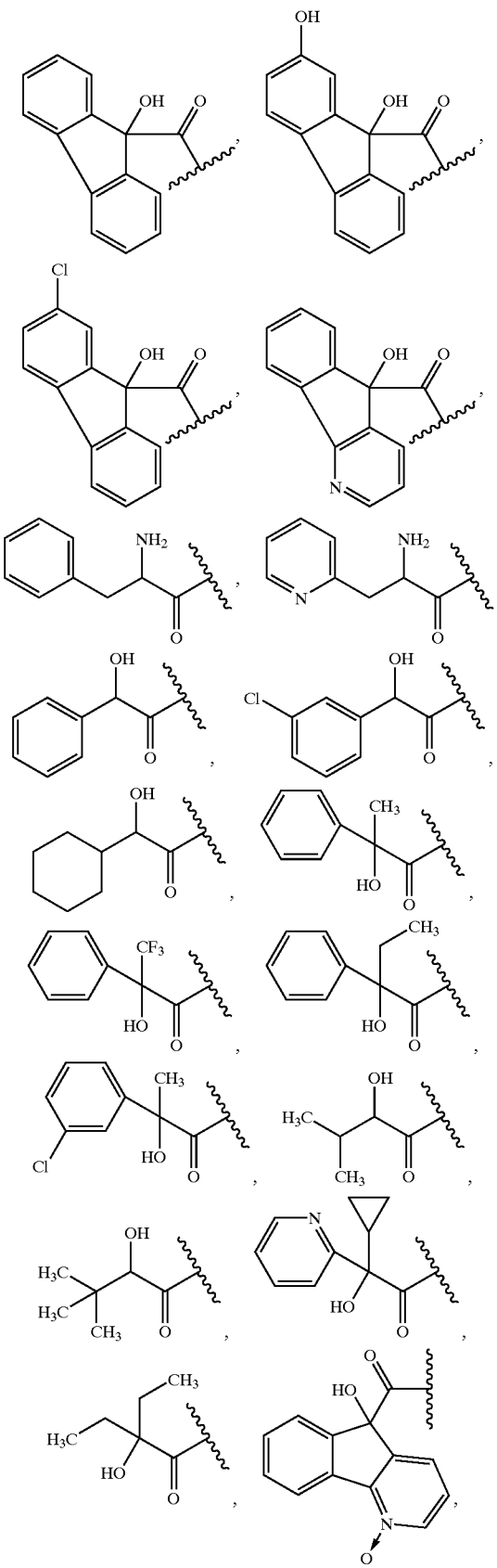

-continued
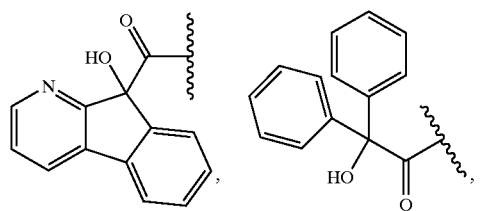
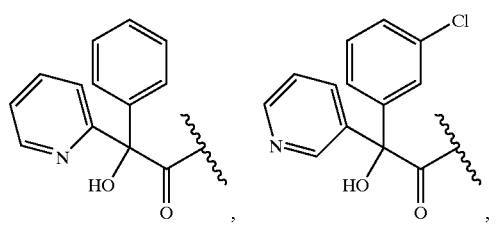
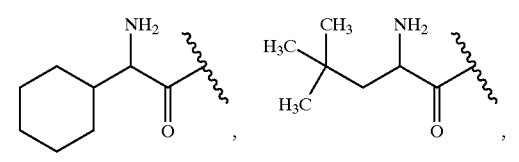
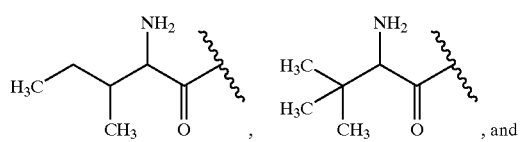
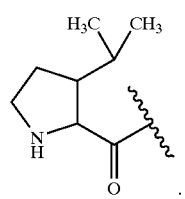
9. A compound of claim 8, or a pharmaceutically acceptable salt thereof, selected from the group consisting of
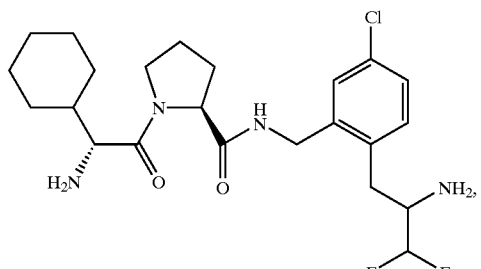
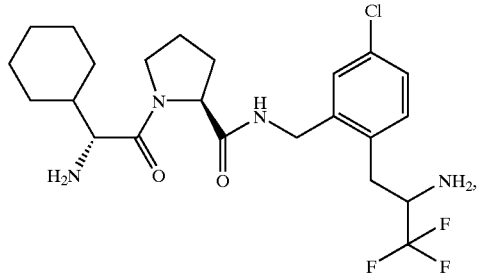
-continued
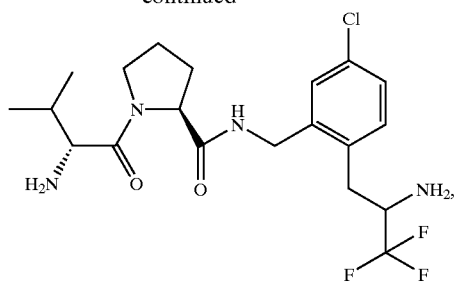
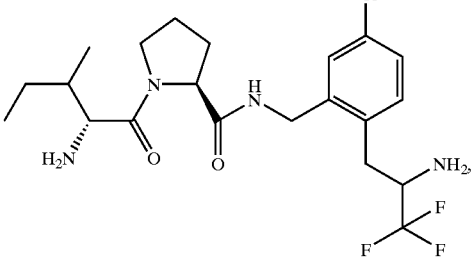
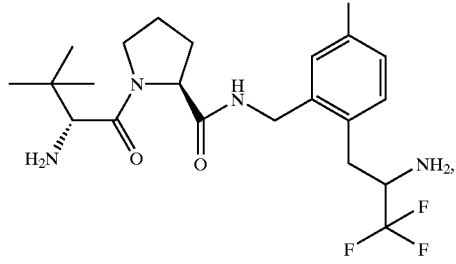
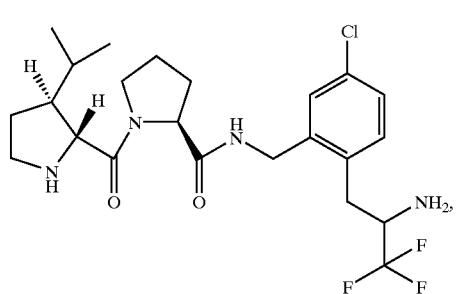
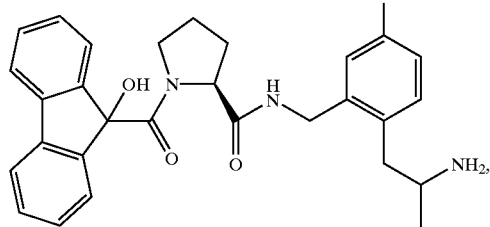
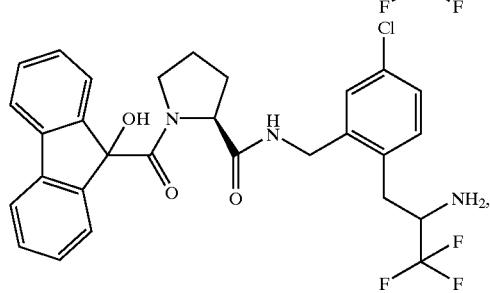

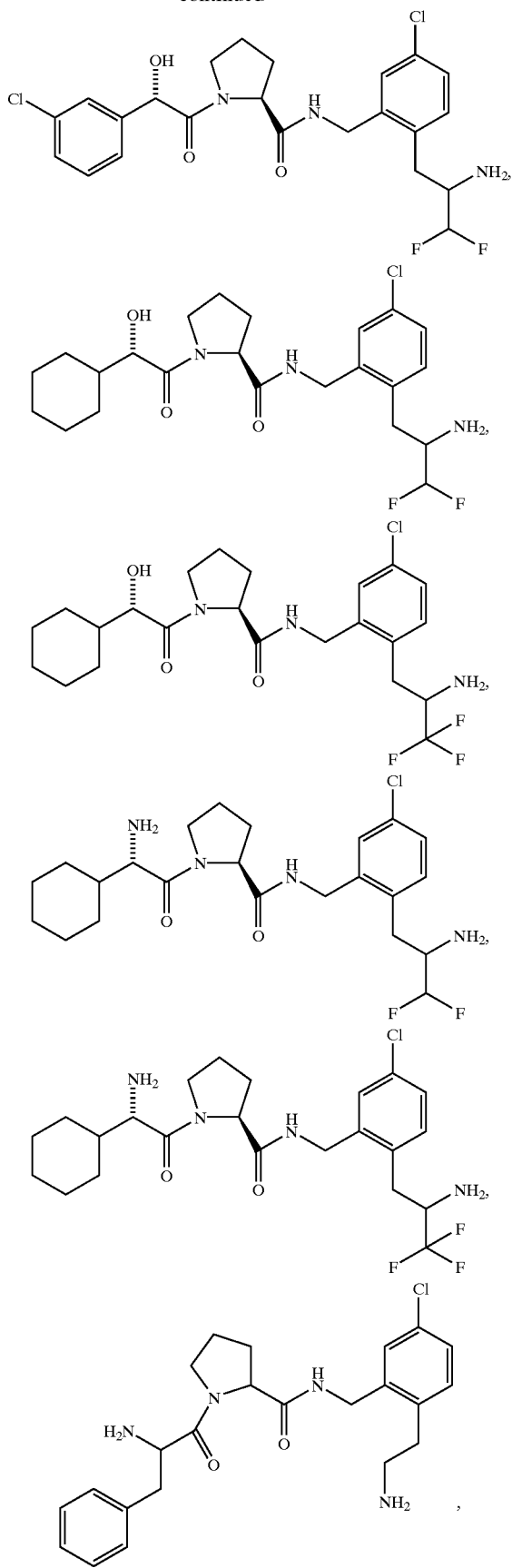

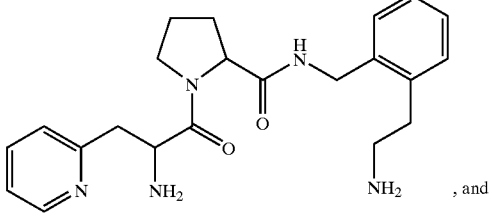

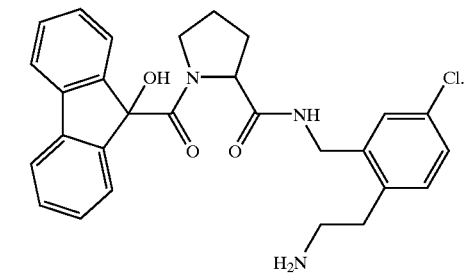

10. A compound of claim 2, or a pharmaceutically acceptable salt thereof, wherein $R^3$ is —C($R^{13}$)($R^{14}$)N($R^{15}$)($R^{16}$).

11. A compound of claim 10, or a pharmaceutically acceptable salt thereof, wherein $R^3$ is —CH$_2$N($R^{15}$)($R^{16}$), —CH(CHF$_2$)N($R^{15}$)($R^{16}$), —CH(CH$_2$OH)N($R^{15}$)($R^{16}$), or —CH(CH$_3$)N($R^{15}$)($R^{16}$).

12. A compound of claim 11, or a pharmaceutically acceptable salt thereof, wherein $R^3$ is —CH$_2$NH$_2$, —CH$_2$NHC(O)OC(CH$_3$)$_3$, —CH(CHF$_2$)NH$_2$, —CH(CH$_2$OH)NH$_2$, or —CH(CH$_3$)NH$_2$.

13. A compound of claim 12, or a pharmaceutically acceptable salt thereof, wherein x is a bond;

$R^6$ is hydrogen, —OH or —NH$_2$;

$R^7$ is hydrogen, —CH$_3$, phenyl, 3-chlorophenyl, cyclopropyl or —CH$_2$CH$_3$; and $R_8$ is phenyl, 3-chlorophenyl, cyclohexyl, —CH$_3$, —CF$_3$, —CH$_2$CH$_3$, —CH$_2$C(CH$_3$)$_3$, 2-pyridyl, 3-pyridyl, or $C_{1-6}$ alkyl substituted with

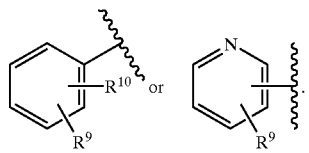

14. A compound of claim 13, or a pharmaceutically acceptable salt thereof, wherein $R^9$ is hydrogen or Cl and $R^{10}$ is hydrogen.

15. A compound of claim 14, or a pharmaceutically acceptable salt thereof, wherein $R^1$ is selected from the group consisting of

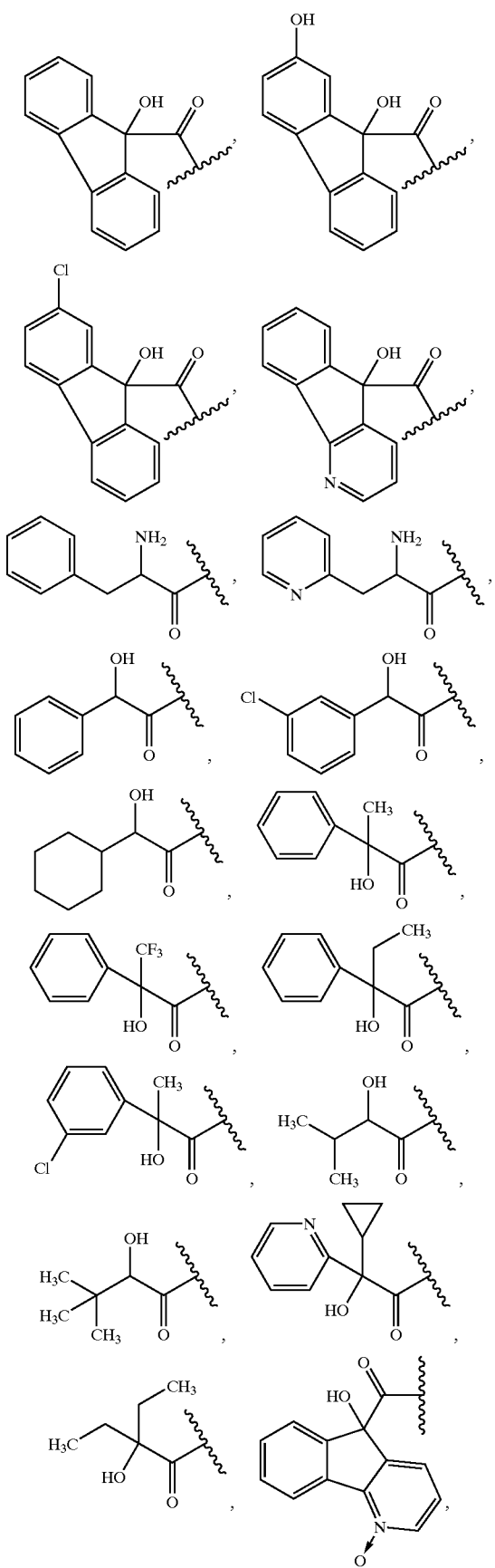
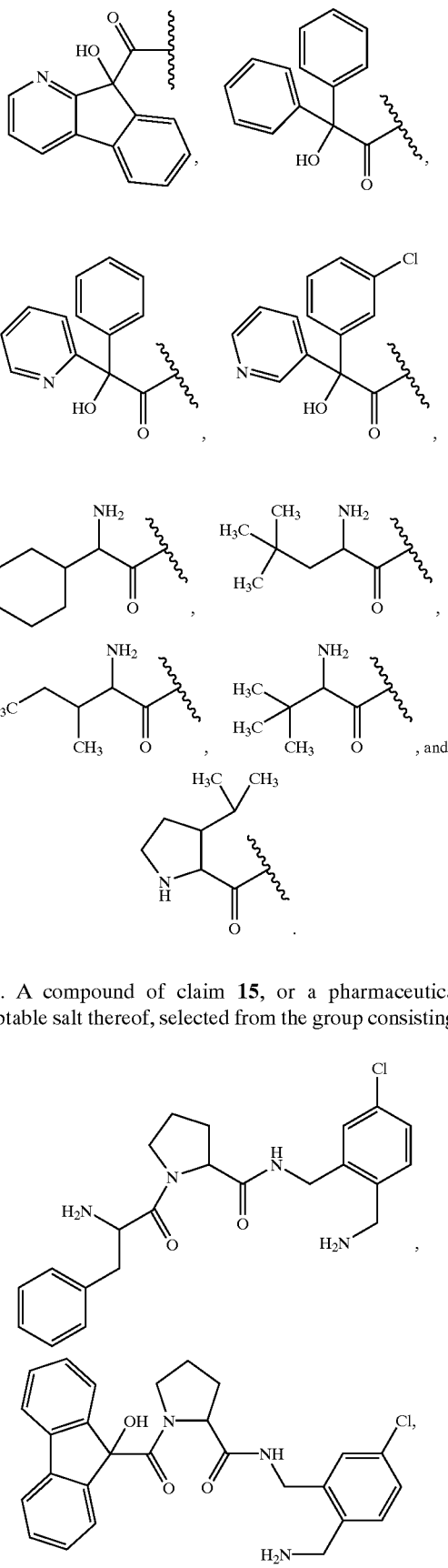
16. A compound of claim 15, or a pharmaceutically acceptable salt thereof, selected from the group consisting of

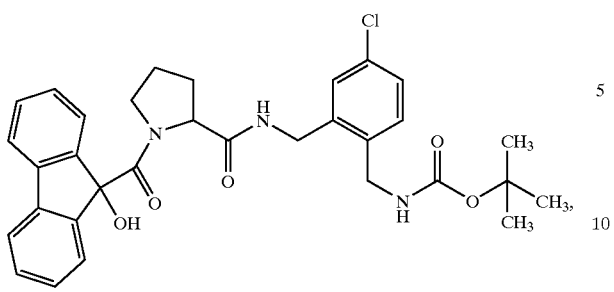
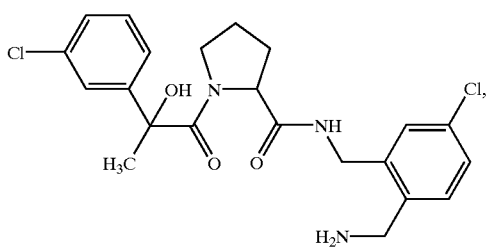
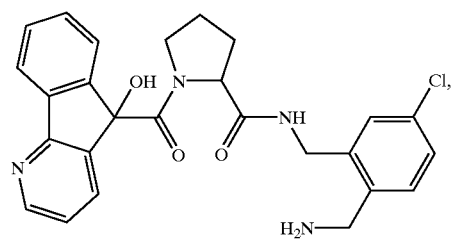
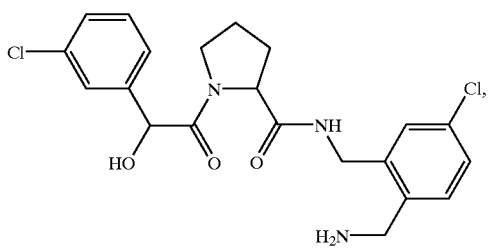
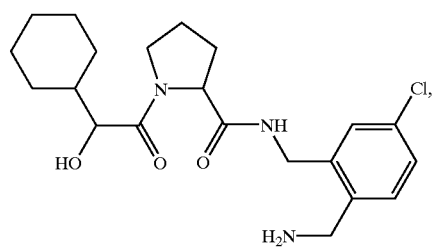
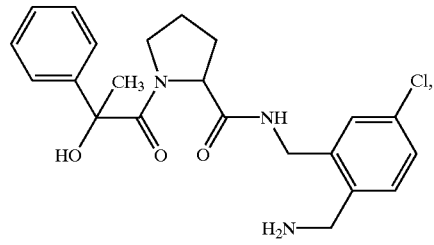
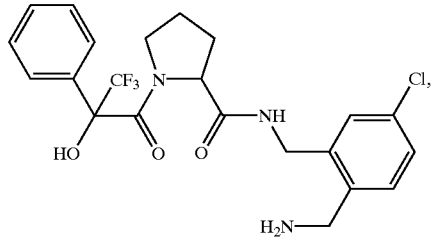
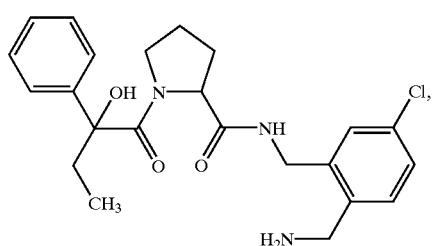
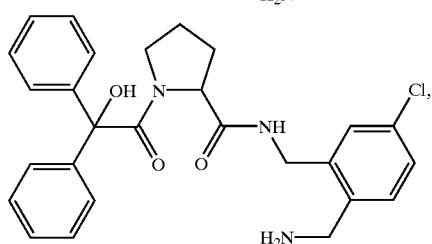
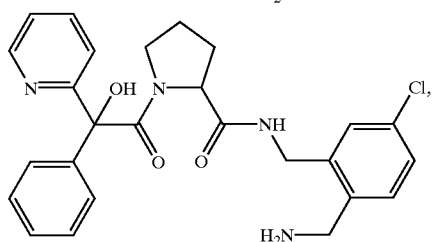
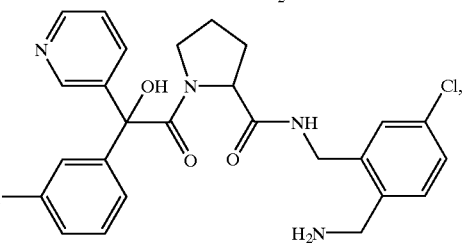
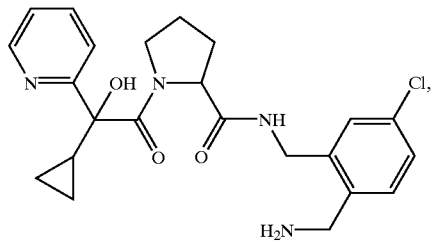
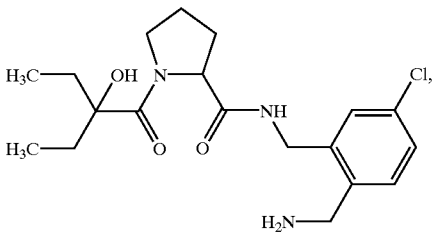

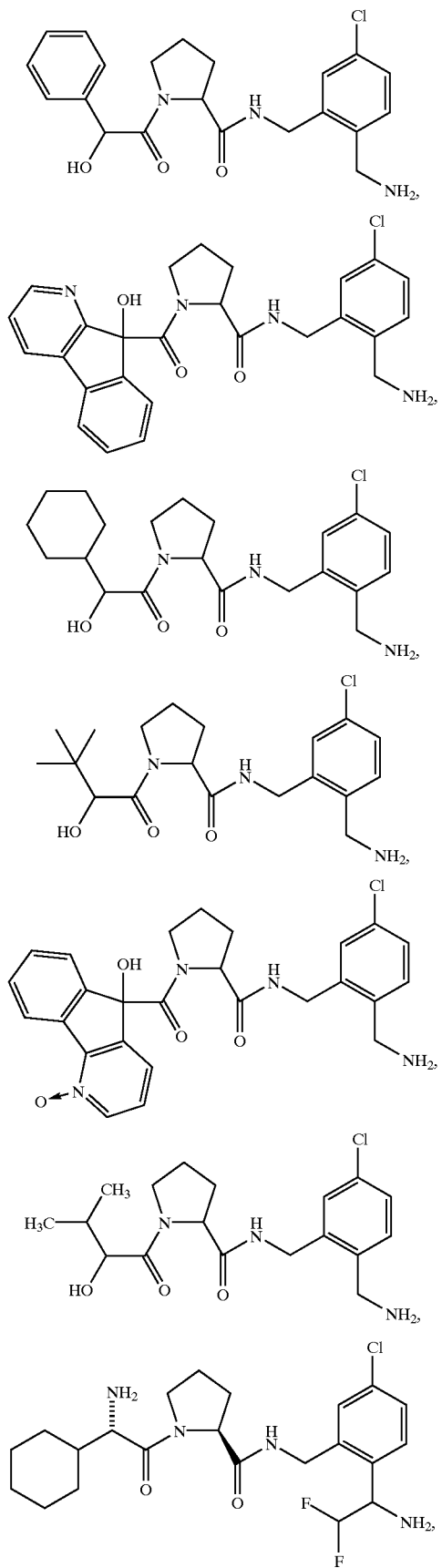
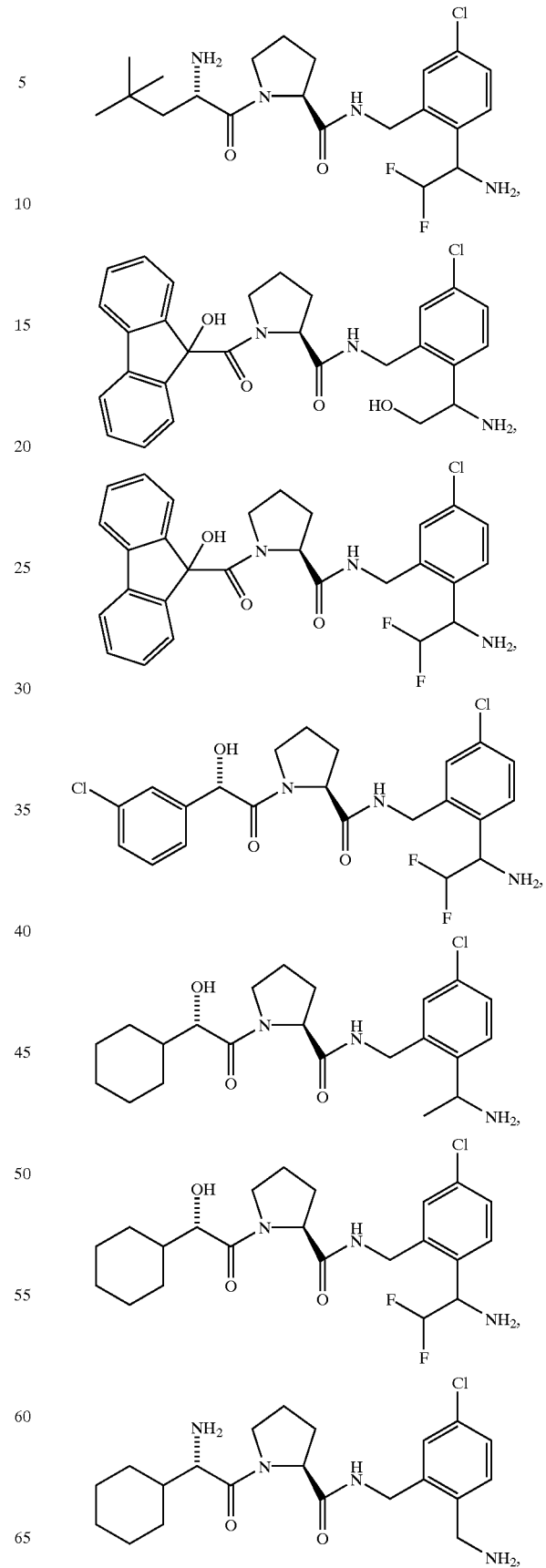

-continued

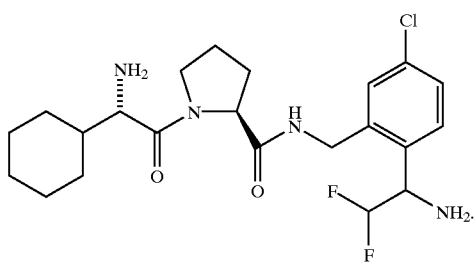

17. A compound of claim 16, or a pharmaceutically acceptable salt thereof, selected from the group consisting of

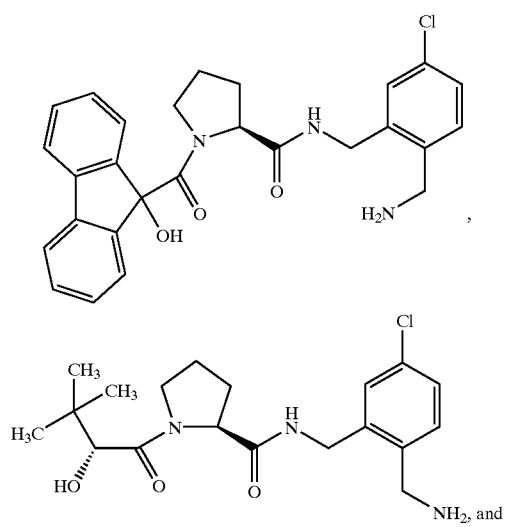

-continued

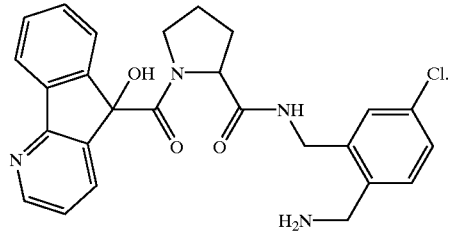

18. A pharmaceutical composition comprising a compound of claim 1 and a pharmaceutically acceptable carrier.

19. A method for inhibiting thrombus formation in a patient comprising administering to the patient a therapeutically effective amount of a compound of claim 1.

20. A method for inhibiting formation of blood platelet aggregates in a patient comprising administering to the patient a therapeutically effective amount of a compound of claim 1.

21. A method for treating or preventing venous thromboembolism and pulmonary embolism in a mammal comprising administering to the mammal a therapeutically effective amount of a compound of claim 1.

22. A method for treating or preventing deep vein thrombosis in a mammal comprising administering to the mammal a therapeutically effective amount of a compound of claim 1.

23. A method for treating or preventing thromboembolic stroke in humans and other mammals comprising administering to the mammal a therapeutically effective amount of a compound of claim 1.

* * * * *